US009085599B2

(12) United States Patent
Or et al.

(10) Patent No.: US 9,085,599 B2
(45) Date of Patent: Jul. 21, 2015

(54) 2'ALLENE-SUBSTITUTED NUCLEOSIDE DERIVATIVES

(75) Inventors: Yat Sun Or, Watertown, MA (US); Jun Ma, Belmont, CA (US); Guoqiang Wang, Belmont, MA (US); In Jong Kim, Lexington, MA (US); Jiang Long, Wayland, MA (US); Yao-Ling Qiu, Andover, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 427 days.

(21) Appl. No.: 13/422,268

(22) Filed: Mar. 16, 2012

(65) Prior Publication Data

US 2012/0237480 A1 Sep. 20, 2012

Related U.S. Application Data

(60) Provisional application No. 61/453,286, filed on Mar. 16, 2011.

(51) Int. Cl.

| | |
|---|---|
| *A61K 31/706* | (2006.01) |
| *C07H 19/12* | (2006.01) |
| *C07H 19/173* | (2006.01) |
| *C07H 19/044* | (2006.01) |
| *C07H 19/10* | (2006.01) |
| *C07H 19/11* | (2006.01) |
| *C07H 19/06* | (2006.01) |
| *A61K 38/55* | (2006.01) |
| *A61K 45/06* | (2006.01) |
| *A61K 31/7056* | (2006.01) |
| *A61K 31/7068* | (2006.01) |
| *A61K 31/7072* | (2006.01) |
| *A61K 31/7076* | (2006.01) |
| *A61K 31/708* | (2006.01) |

(52) U.S. Cl.

CPC .............. *C07H 19/06* (2013.01); *A61K 31/706* (2013.01); *A61K 31/708* (2013.01); *A61K 31/7056* (2013.01); *A61K 31/7068* (2013.01); *A61K 31/7072* (2013.01); *A61K 31/7076* (2013.01); *A61K 38/55* (2013.01); *A61K 45/06* (2013.01)

(58) Field of Classification Search

CPC . C07H 19/06; A61K 31/7056; A61K 31/706; A61K 38/55; A61K 31/7072; A61K 31/7076; A61K 31/708; A61K 31/7068; A61K 31/426

USPC ........ 514/43, 45–47, 49–52; 536/26.2, 26.11, 536/26.12, 26.13, 26.14, 26.7, 26.8, 27.13, 536/27.6, 27.81, 28.3, 28.5, 28.52, 28.53, 536/28.54

See application file for complete search history.

(56) References Cited

U.S. PATENT DOCUMENTS

| | | | |
|---|---|---|---|
| 5,750,806 | A | 5/1998 | Brocker et al. |
| 7,247,621 | B2 | 7/2007 | Hong et al. |
| 7,438,920 | B1 | 10/2008 | Kim et al. |
| 7,589,077 | B2 | 9/2009 | Kumar et al. |
| 8,163,707 | B2 | 4/2012 | Qiu et al. |
| 8,263,575 | B2 | 9/2012 | McGuigan et al. |
| 8,575,119 | B2 | 11/2013 | Wang et al. |
| 2010/0074889 | A1 | 3/2010 | Qiu et al. |
| 2010/0074890 | A1 | 3/2010 | Hagel et al. |
| 2011/0257122 | A1 | 10/2011 | Sofia et al. |
| 2013/0078217 | A1 | 3/2013 | Wang et al. |
| 2013/0315864 | A1 | 11/2013 | Or et al. |

FOREIGN PATENT DOCUMENTS

WO 2010030858 A1 3/2010

OTHER PUBLICATIONS

Wolff, Manfred E. "Burger's Medicinal Chemistry, 5ed, Part I", John Wiley & Sons, 1995, pp. 975-977.*

Banker, G.S. et al, "Modern Pharmaceutics,3ed.", Marcel Dekker, New York, 1996, pp. 451 and 596.*

The Merck Manual, 1992, pp. 183-189.*

Li, et al. Synthesis of 2'-C-Branched Nucleosides, Organic Preparations and Procedures International, 42:191-283 (2010).

Hayashi, et al., "Adenallene and cytallene: Acyclic nucleoside analogues that inhibit replication and cytopathic effect of human immunodeficiency virus in vitro," Proceedings of the National Academy of Science, 85:6127-6131,1988.

International Search Report for PCT/US12/29381, dated Jun. 28, 2012.

* cited by examiner

*Primary Examiner* — Ganapathy Krishnan

(74) *Attorney, Agent, or Firm* — Edgar W. Harlan; Carolyn S. Elmore, Esq.; Elmore Patent Law Group, P.C.

(57) ABSTRACT

The present invention relates to 2'-allene-substituted nucleoside derivatives of the general formula (I):

(I)

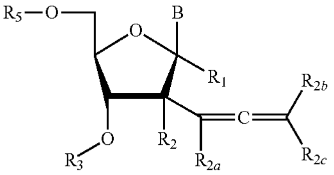

As well as pharmaceutical compositions comprising such compounds and methods to treat or prevent an HIV infection, HBV infection, HCV infection or abnormal cellular proliferation, comprising administering said compounds or compositions. In addition, the present invention includes processes for the preparation of such compounds, and the related β-D and β-L-nucleoside derivatives.

21 Claims, No Drawings

2'ALLENE-SUBSTITUTED NUCLEOSIDE DERIVATIVES

RELATED APPLICATIONS

This application claims the benefit of U.S. Provisional Application No. 61/453,286 filed on Mar. 16, 2011. The entire teachings of the above application are incorporated herein by reference.

TECHNICAL FIELD

The present invention relates generally to compounds and pharmaceutical compositions useful as antiviral and antiproliferative agents. Specifically, the present invention relates to nucleoside derivatives with 2'-allenic substitution and methods for their preparation and use.

BACKGROUND OF THE INVENTION

Synthetic nucleosides such as 5-iodouracil and 5-fluorouracil have been used for the treatment of cancer for many years. Since the 1980's, synthetic nucleosides have also been a focus of interest for the treatment of HIV and hepatitis.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). In 1985, it was reported that the synthetic nucleoside 3'-azido-3'-deoxythymidine (AZT) inhibits the replication of human immunodeficiency virus. Since then, a number of other synthetic nucleosides, including 2',3'-dideoxyinosine (DDI), 2',3'-dideoxycytidine (DDC), and 2',3'-dideoxy-2',3'-didehydrothymidine (D4T), have been proven to be effective against HIV. After cellular phosphorylation to the 5'-triphosphate by cellular kinases, these synthetic nucleosides are incorporated into a growing strand of viral DNA, causing chain termination due to the absence of the 3'-hydroxyl group. They can also inhibit the viral enzyme reverse transcriptase.

The success of various synthetic nucleosides in inhibiting the replication of HIV in vivo or in vitro has led a number of researchers to design and test nucleosides that substitute a heteroatom for the carbon atom at the 3'-position of the nucleoside. European Patent Publication No. 0,337,713 and U.S. Pat. No. 5,041,449, assigned to BioChem Pharma, Inc., disclose 2-substituted-4-substituted-1,3-dioxolanes that exhibit antiviral activity. U.S. Pat. No. 5,047,407 and European Patent Publication No. 0,382,526, also assigned to BioChem Pharma, Inc., disclose that a number of 2-substituted-5-substituted-1,3-oxathiolane nucleosides have antiviral activity, and specifically report that 2-hydroxymethyl-5-(cytosin-1-yl)-1,3-oxathiolane (referred to below as BCH-189) has approximately the same activity against HIV as AZT, with little toxicity.

It has also been disclosed that cis-2-hydroxymethyl-5-(5-fluorocytosin-1-yl)-1,3-oxathiolane ("FTC") has potent HIV activity. Schinazi, et al., "Selective Inhibition of Human Immunodeficiency viruses by Racemates and Enantiomers of cis-5-Fluoro-1-[2-(Hydroxymethyl)-1,3-Oxathiolane-5-yl]-Cytosine" Antimicrobial Agents and Chemotherapy, November 1992, 2423-2431. See also U.S. Pat. Nos. 5,210,085; 5,814,639; and 5,914,331.

Another virus that causes a serious human health problem is the hepatitis B virus (referred to below as "HBV"). HBV is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended or indefinite period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome, which accounts for why HBV infection is common among patients with AIDS or AIDS related complex. However, HBV is more contagious than HIV.

Both FTC and 3TC exhibit activity against HBV. Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" Antimicrobial Agents and Chemotherapy, December 1992, pp. 2686-2692; and Cheng, et al., Journal of Biological Chemistry, Volume 267(20), pp. 13938-13942 (1992). Other compounds that exhibit activity against HBV in humans include Clevudine or CLV (L-FMAU) (Pharmasset, Inc. under license from The University of Georgia Research Foundation and Yale University), and L-dT and L-dC (Idenix Pharmaceuticals, Inc.).

HCV is the major causative agent for post-transfusion and for sporadic non A, non B hepatitis (Alter, H. J. (1990) *J. Gastro. Hepatol.* 1:78-94; Dienstag, J. L. (1983) *Gastro* 85:439-462). Despite improved screening, HCV still accounts for at least 25% of the acute viral hepatitis in many countries (Alter, H. J. (1990) supra; Dienstag, J. L. (1983) supra; Alter M. J. et al. (1990a) *J.A.M.A.* 264:2231-2235; Alter M. J. et al (1992) *N. Engl. J. Med.* 327:1899-1905; Alter, M. J. et al. (1990b) *N. Engl. J. Med.* 321:1494-1500). Infection by HCV is insidious in a high proportion of chronically infected (and infectious) carriers who may not experience clinical symptoms for many years. The high rate of progression of acute infection to chronic infection (70-100%) and liver disease (>50%), its world-wide distribution and lack of a vaccine make HCV a significant cause of morbidity and mortality. Currently, there are three types of interferon and a combination of interferon and ribavirin used to treat hepatitis C. Selection of patients for treatment may be determined by biochemical, virologic, and when necessary, liver biopsy findings, rather than presence or absence of symptoms.

Interferon is given by injection, and may have a number of side effects including flu-like symptoms including headaches, fever, fatigue, loss of appetite, nausea, vomiting, depression and thinning of hair. It may also interfere with the production of white blood cells and platelets by depressing the bone marrow. Periodic blood tests are required to monitor blood cells and platelets. Ribavirin can cause sudden, severe anemia, and birth defects so women should avoid pregnancy while taking it and for 6 months following treatment. The severity and type of side effects differ for each individual. Treatment of children with HCV is not currently approved but is under investigation. While 50-60% of patients respond to treatment initially, lasting clearance of the virus occurs in only about 10-40% of patients. Treatment may be prolonged and given a second time to those who relapse after initial treatment. Re-treatment with bioengineered consensus interferon alone results in elimination of the virus in 58% of patients treated for one year. Side effects occur but the medication is usually well tolerated. Combined therapy (interferon and ribavirin) shows elimination of the virus in 47% after 6 months of therapy. Side effects from both drugs may be prominent.

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is now the second leading cause of death in the United States. Over 8,000,000 persons in the United States have been diagnosed with cancer, with 1,208,000 new diagnoses expected in 1994. Over 500,000 people die annually from the disease in this country.

Cancer is not fully understood on the molecular level. It is known that exposure of a cell to a carcinogen such as certain viruses, certain chemicals, or radiation, leads to DNA alteration that inactivates a "suppressive" gene or activates an "oncogene." Suppressive genes are growth regulatory genes, which upon mutation, can no longer control cell growth. Oncogenes are initially normal genes (called prooncongenes) that by mutation or altered context of expression become transforming genes. The products of transforming genes cause inappropriate cell growth. More than twenty different normal cellular genes can become oncongenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three means of therapies: surgery, radiation and chemotherapy. Surgery involves the bulk removal of diseased tissue. While surgery is sometimes effective in removing tumors located at certain sites, for example, in the breast, colon and skin, it cannot be used in the treatment of tumors located in other areas, such as the backbone, or in the treatment of disseminated neoplastic conditions such as leukemia.

Chemotherapy involves the disruption of cell replication or cell metabolism. It is used most often in the treatment of leukemia, as well as breast, lung, and testicular cancer.

There are five major classes of chemotherapeutic agents currently in use for the treatment of cancer: natural products and their derivatives; anthacyclines; alkylating agents; antiproliferatives (also called antimetabolites); and hormonal agents. Chemotherapeutic agents are often referred to as antineoplastic agents.

The alkylating agents are believed to act by alkylating and cross-linking guanine and possibly other bases in DNA, arresting cell division. Typical alkylating agents include nitrogen mustards, ethyleneimine compounds, alkyl sulfates, cisplatin and various nitrosoureas. A disadvantage with these compounds is that they not only attack malignant cells, but also other cells which are naturally dividing, such as those of bone marrow, skin, gastrointestinal mucosa, and fetal tissue.

Antimetabolites are typically reversible or irreversible enzyme inhibitors, or compounds that otherwise interfere with the replication, translation or transcription of nucleic acids.

Several synthetic nucleosides have been identified that exhibit anticancer activity. A well known nucleoside derivative with strong anticancer activity is 5-fluorouracil. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation and edema. Derivatives of 5-fluorouracil with anti-cancer activity have been described in U.S. Pat. No. 4,336,381, and in Japanese patent publication Nos. 50-50383, 50-50384, 50-64281, 51-146482, and 53-84981.

U.S. Pat. No. 4,000,137 discloses that the peroxidate oxidation product of inosine, adenosine or cytidine with methanol or ethanol has activity against lymphocytic leukemia.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites" *Cancer Medicine, Chapter XV*-1, 3rd Edition, Edited by J. Holland, et al., Lea and Febigol, publishers.

5-Azacytidine is a cytidine analog that is primarily used in the treatment of acute myelocytic leukemia and myelodysplastic syndrome.

2-Fluoroadenosine-5'-phosphate (Fludara, also referred to as FaraA) is one of the most active agents in the treatment of chronic lymphocytic leukemia. The compound acts by inhibiting DNA synthesis. Treatment of cells with F-araA is associated with the accumulation of cells at the Gl/S phase boundary and in S phase; thus, it is a cell cycle S phase-specific drug. Incorporation of the active metabolite, F-araATP, retards DNA chain elongation. F-araA is also a potent inhibitor of ribonucleotide reductase, the key enzyme responsible for the formation of dATP.

2-Chlorodeoxyadenosine is useful in the treatment of low grade B-cell neoplasms such as chronic lymphocytic leukemia, non-Hodgkins' lymphoma, and hairy-cell leukemia.

In light of the fact that acquired immune deficiency syndrome, AIDS-related complex, hepatitis B virus and hepatitis C virus have reached epidemic levels worldwide, and have tragic effects on the infected patient, there remains a strong need to provide new effective pharmaceutical agents to treat these diseases that have low toxicity to the host. Further, there is a need to provide new antiproliferative agents.

Therefore, it is an object of the present invention to provide a method and composition for the treatment of human patients or other host animals infected with HIV.

It is another object of the present invention to provide a method and composition for the treatment of human patients infected with hepatitis B or C.

It is a further object of the present invention to provide new antiproliferative agents.

It is still another object of the present invention to provide a new process for the preparation of 2'-allene-substituted nucleoside derivatives of the present invention.

SUMMARY OF THE INVENTION

The present invention includes β-D and β-L-nucleoside derivatives, pharmaceutical compositions comprising such compounds, as well as methods to treat or prevent an HIV infection, HBV infection, HCV infection or abnormal cellular proliferation, comprising administering said compounds or compositions. In addition, the present invention includes processes for the preparation of such compounds, and the related β-D and β-L-nucleoside derivatives.

The compounds of the invention are 2'-allene-substituted nucleoside derivatives of the general formula (I):

(I)

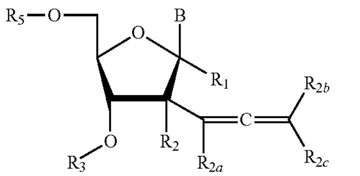

or the β-L enantiomer thereof, or a pharmaceutically acceptable salt, ester, stereoisomer, tautomer, solvate, prodrug, or combination thereof, wherein:

$R_1$ is selected from the group consisting of:
1) hydrogen;
2) —CN;
3) halogen;
4) —$N_3$; and
5) Substituted or unsubstituted —$C_1$-$C_8$ alkyl;

$R_{2a}$, $R_{2b}$ and $R_{2c}$ are each independently selected from the group consisting of: hydrogen, halogen, and substituted or unsubstituted —$C_1$-$C_8$ alkyl;

$R_2$ is selected from the group consisting of:
1) halogen;
2) —CN;
3) —$N_3$; and
4) $OR_6$; where $R_6$ is selected from the group consisting of: hydrogen, hydroxy protecting group, —C(O)$R_D$, —C(O)$OR_7$, and —C(O)$NR_{8a}R_{8b}$; wherein $R_7$ is selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic; $R_{8a}$ and $R_{8b}$ are each independently selected from the group consisting of: hydrogen and $R_7$; or alternatively $R_{8a}$ and $R_{8b}$ taken together with the nitrogen atom to which they are attached form a heterocyclic ring;

$R_3$ is $R_6$; or alternatively $R_2$ is —$OR_6$ and $R_3$ and $R_6$ together form a group selected from: —C(Me)$_2$-, —C($CH_2$)$_4$—, —CH(Ph)-, —CH(OMe)- and —P(O)(OH)—.

B is selected from the group consisting of: substituted or unsubstituted aryl, substituted or unsubstituted heteroaryl, and substituted or unsubstituted heterocyclic; preferably a heterocycle containing at least one nitrogen atom.

$R_5$ is selected from the group consisting of:
1) hydrogen;
2) $R_6$;
3) —P(O)($OR_{7a}$)($OR_{7b}$); wherein $R_{7a}$ and $R_{7b}$ are each independently selected from the group consisting of a) hydrogen; b) unsubstituted or substituted —$C_1$-$C_8$ alkyl;
4) —P(O)($OR_{7a}$)—O—P(O)($OR_{7b}$)($OR_{7c}$); wherein $R_{7a}$ and $R_{7b}$ are previously defined; $R_{7c}$ is selected from the group consisting of a) hydrogen; b) unsubstituted or substituted —$C_1$-$C_8$ alkyl;
5) —P(O)($OR_{7a}$)—O—P(O)($OR_{7b}$)—O—P(O)($OR_{7c}$)($OR_{7d}$); wherein $R_{7a}$, $R_{7b}$ and $R_{7c}$ are previously defined; $R_{7d}$ is selected from the group consisting of a) hydrogen; b) unsubstituted or substituted —$C_1$-$C_8$ alkyl;

6)

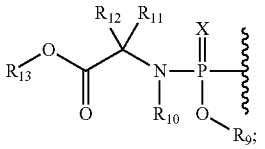

where X is O or S; $R_9$ is $R_7$ wherein $R_7$ is previously defined; $R_{10}$, $R_{11}$ and $R_{12}$ are each independently selected from the group consisting of: a) hydrogen; b) unsubstituted or substituted —$C_1$-$C_8$ alkyl; alternatively, (c) $R_{11}$ is hydrogen, and $R_{12}$ and $R_{10}$ are taken together with the atoms to which they are attached to form a heterocyclic ring; or d) $R_{11}$ and $R_{12}$ are taken together with the carbon atom to which they are attached to form a ring; and $R_{13}$ is hydrogen or $R_7$, wherein $R_7$ is previously defined; and

7)

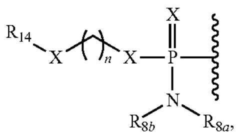

where X is O or S; n is 1-4; $R_{8a}$ and $R_{8b}$ are as previously defined; $R_{14}$ is hydrogen or —(CO)—$R_7$, wherein $R_7$ is as previously defined.

Or, $R_5$ and $R_3$ are taken together to form

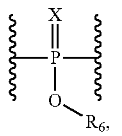

where X is O or S; and $R_6$ is as previously defined.

In another embodiment, the present invention provides a pharmaceutical composition comprising a therapeutically effective amount of a compound or combination of compounds of the present invention, or a pharmaceutically acceptable salt form, prodrug, salt of a prodrug, stereoisomer, tautomer, solvate, or combination thereof, in combination with a pharmaceutically acceptable carrier or excipient.

In yet another embodiment, the present invention provides a method of inhibiting the replication of an RNA or DNA containing virus comprising contacting said virus with a therapeutically effective amount of a compound or a combination of compounds of the present invention, or a pharmaceutically acceptable salt, prodrug, salt of a pro drug, stereoisomer, tautomer, solvate, or combination thereof. Particularly, this invention is directed to methods of inhibiting the replication of HIV, HBV and HCV.

In still another embodiment, the present invention provides a method of treating or preventing infection caused by an RNA or DNA-containing virus comprising administering to a patient in need of such treatment a therapeutically effective amount of a compound or combination of compounds of the present invention, or a pharmaceutically acceptable salt form, prodrug, salt of a prodrug, stereoisomer, or tautomer, solvate, or combination thereof. Particularly, this invention is directed to methods of treating or preventing infection caused by HIV, HBV and HCV.

Yet another embodiment of the present invention provides the use of a compound or combination of compounds of the present invention, or a therapeutically acceptable salt form, prodrug, salt of a prodrug, stereoisomer or tautomer, solvate, or combination thereof, as defined hereinafter, in the preparation of a medicament for the treatment or prevention of infection caused by RNA or DNA-containing virus, specifically HIV, HBV and HCV.

DETAILED DESCRIPTION OF THE INVENTION

In a first embodiment of the present invention is a compound of Formula (I) as illustrated above, or a pharmaceutically acceptable salt, ester or prodrug thereof.

In a second embodiment of the present invention is the β-L enantiomer of 2'-allene-substituted nucleoside derivative represented by formula (II), or pharmaceutically acceptable salt or prodrug thereof:

(II)

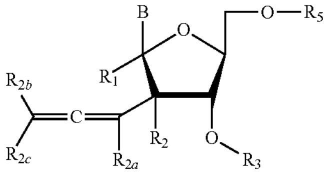

wherein $R_1$, $R_2$, $R_{2a}$, $R_{2b}$, $R_{2c}$, $R_3$, $R_5$, B are as previously defined.

In a particular embodiment of the present invention is a β-D 2'-allene-substituted nucleoside derivatives represented by formula (III), or its β-L enantiomer, or pharmaceutically acceptable salt or prodrug thereof:

(III)

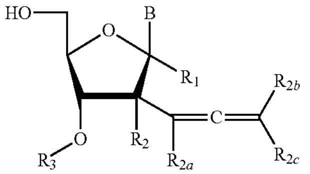

wherein $R_1$, $R_2$, $R_{2a}$, $R_{2b}$, $R_{2c}$, $R_3$, B are as previously defined. Illustrative structures of formula (III) can be represented, but not limited, by formula (III-1~III-24) and the β-L enantiomers thereof:

(III-1)

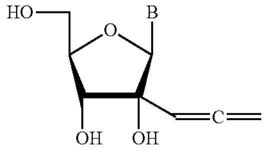

(III-2)

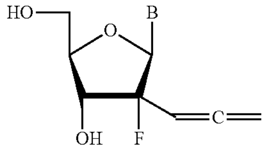

(III-3)

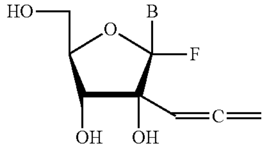

(III-4)

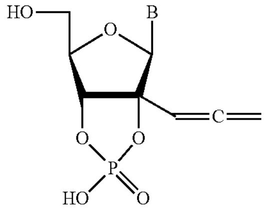

(III-5)

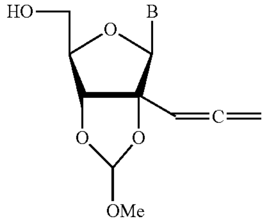

(III-6)

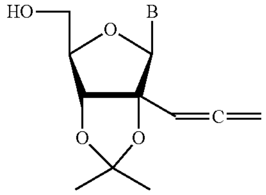

-continued
(III-7)
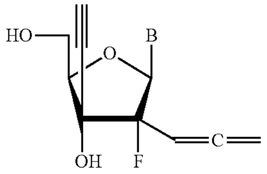
(III-8)
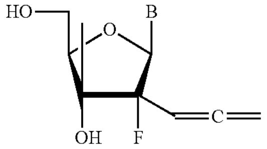
(III-9)
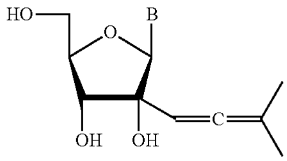
(III-10)
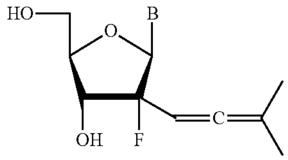
(III-11)
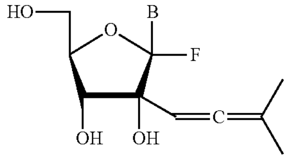
(III-12)
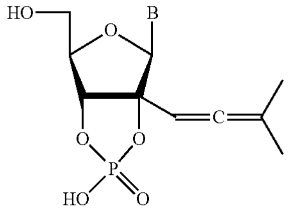
(III-13)
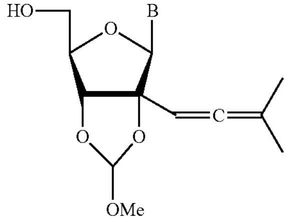
(III-14)
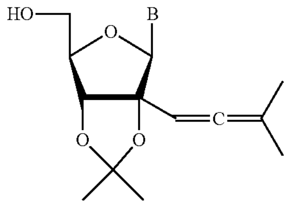
-continued
(III-15)
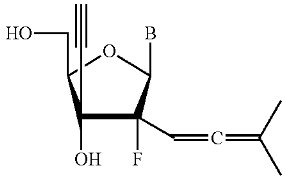
(III-16)
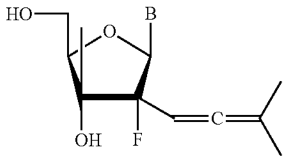
(III-17)
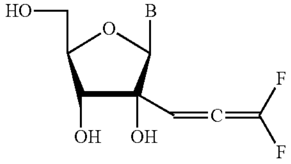
(III-18)
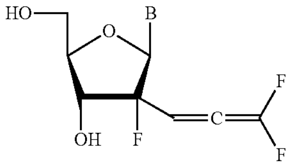
(III-19)
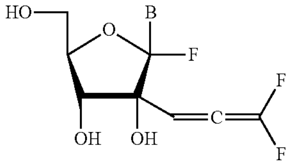
(III-20)
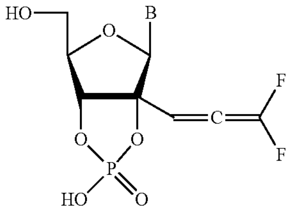
(III-21)
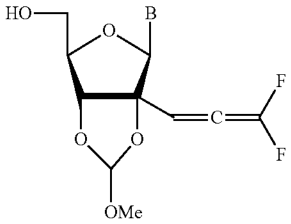
(III-22)
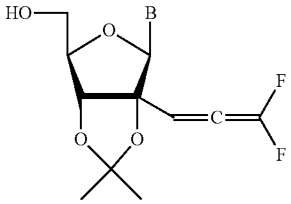

-continued (III-23)

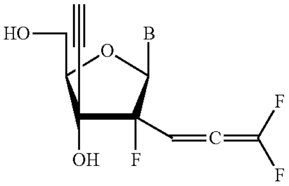

(III-24)

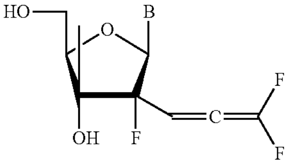

wherein B is as previously defined;

In another particular embodiment of the present invention is a β-D 2'-allene-substituted nucleoside diester derivatives represented by formula (IV), or its β-L enantiomer, or pharmaceutically acceptable salt or prodrug thereof:

(IV)

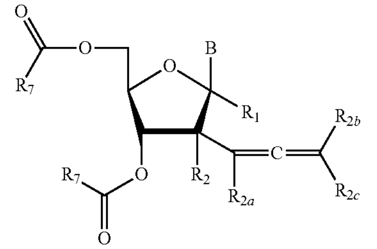

wherein $R_1$, $R_2$, $R_{2a}$, $R_{2b}$, $R_{2c}$, $R_7$, and B are as previously defined.

In another particular embodiment of the present invention is a β-D 2'-allene-substituted nucleoside phosphonamidate derivative represented by formula (V), or its β-L enantiomer, or a pharmaceutically acceptable salt or prodrug thereof:

(V)

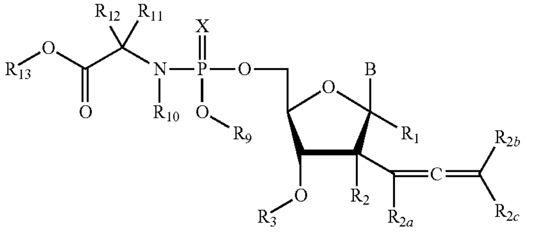

wherein $R_1$, $R_2$, $R_{2a}$, $R_{2b}$, $R_{2c}$, $R_3$, $R_7$, $R_9$, $R_{10}$, $R_{11}$, $R_{12}$, $R_{13}$, and B are as previously defined. X is O or S.

Illustrative structures of formula (V) can be represented, but not limited, by formula (V-1~V-12):

(V-1)

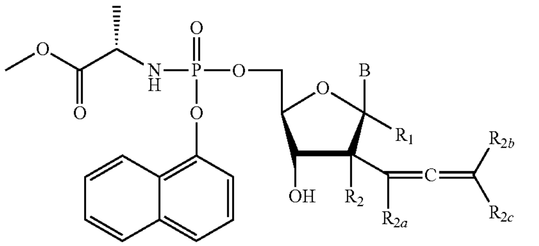

(V-2)

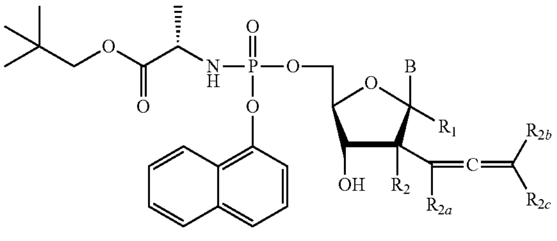

(V-3)

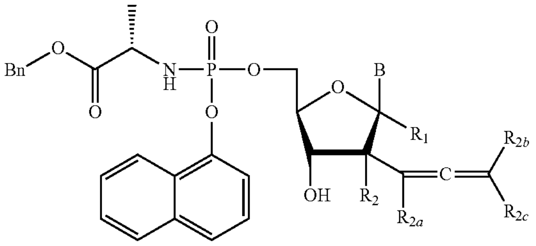

(V-4)

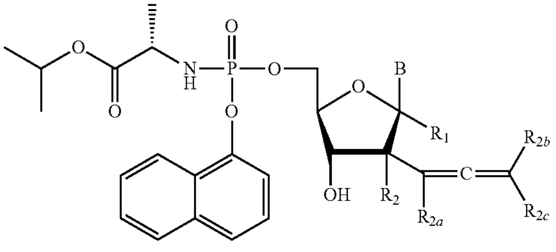

(V-5)

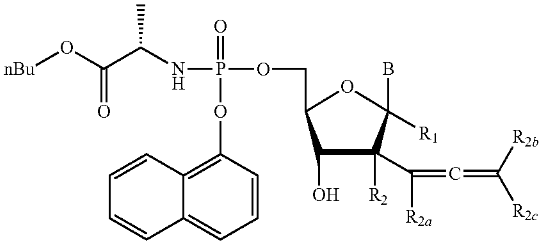

(V-6)

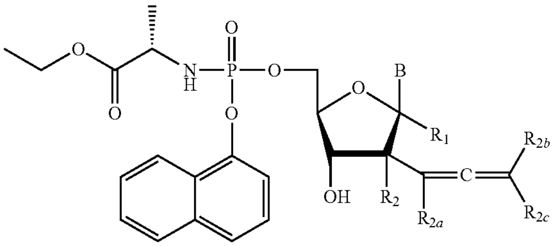

-continued (V-7)

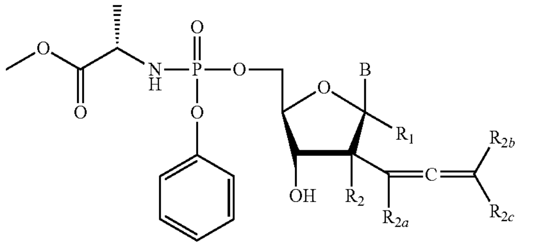

(V-8)

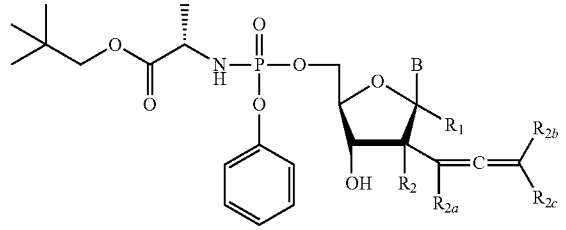

(V-9)

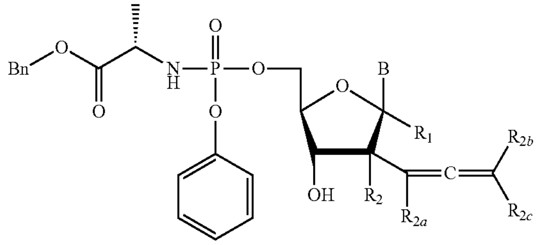

(V-10)

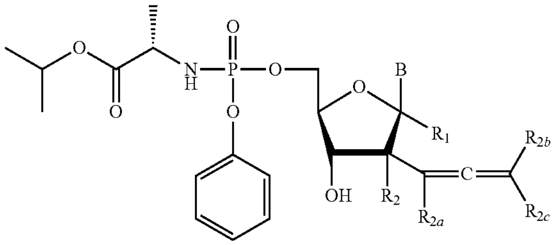

(V-11)

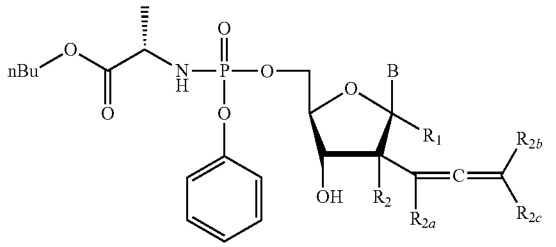

(V-12)

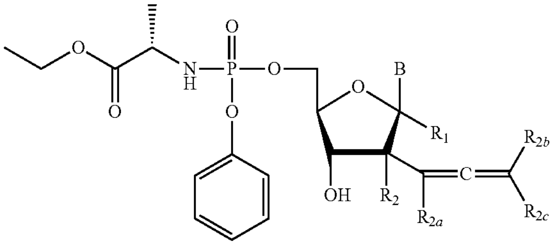

wherein $R_1$, $R_2$, $R_{2a}$, $R_{2b}$, $R_{2c}$, and B are as previously defined.

In another particular embodiment of the present invention is a β-D 2'-allene-substituted nucleoside phosphate derivative represented by formula (VI), or its β-L enantiomer, or a pharmaceutically acceptable salt or prodrug thereof:

(VI)

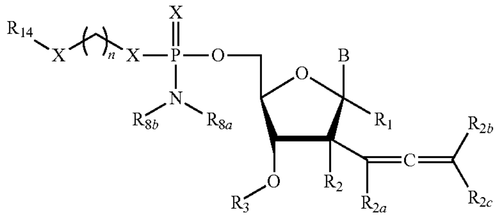

wherein $R_1$, $R_2$, $R_{2a}$, $R_{2b}$, $R_{2c}$, $R_3$, $R_{8a}$, $R_{8b}$, $R_{14}$, and B are as previously defined. X is O or S. n is 1~4.

In still another particular embodiment of the present invention is a β-D 2'-allene-substituted nucleoside phosphate derivative represented by formula (VII), or its β-L enantiomer, or a pharmaceutically acceptable salt or prodrug thereof:

(VII)

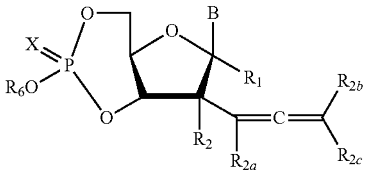

wherein $R_1$, $R_2$, $R_{2a}$, $R_{2b}$, $R_{2c}$, $R_6$, and B are as previously defined. X is O or S.

In yet another particular embodiment of the present invention is a β-D 2'-allene-substituted nucleoside derivative represented by formula (I), or its β-L enantiomer, or pharmaceutically acceptable salt or prodrug thereof, with B at each occurrence is an optionally substituted aryl, heteroaryl, or heterocyclic; preferably a heterocycle moiety containing at least one nitrogen, most preferably a pyrimidinyl, purinyl group or the like of the general formula of (B1) and (B2):

(B1)

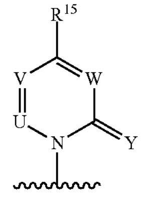

(B2)

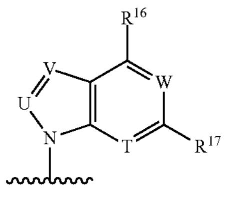

wherein:

Y is selected from a group consisting of: O, S, $NR_{8a}$, $NC(O)R_7$, $NC(O)OR_7$ and $NC(O)NR_{8a}R_{8b}$;

T, U, V and W are independently N or $CR_{18}$; wherein $R_{18}$ is selected from a group consisting of: hydrogen, halogen, —CN, —$C(O)R_7$, —$C(O)NR_{8a}R_{8b}$, —$NO_2$, —$N_3$, —$OR_7$, —$SR_7$, —$NR_{8a}R_{8b}$, —$OC(O)R_7$, —$OC(O)OR_7$, —$NHC(O)R_7$, —$NHC(O)OR_7$ and —$NHC(O)NR_{8a}R_{8b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, substituted or unsubstituted —$C_2$-$C_8$ alkynyl;

$R^{15}$, $R^{16}$ and $R^{17}$ at each occurrence are independently selected from a group consisting of: hydrogen, halogen, —CN, —$C(O)R_7$, —$C(O)NR_{8a}R_{8b}$, —$NO_2$, —$N_3$, —$OR_7$, —$SR_7$, —$NR_{8a}R_{8b}$, —$OC(O)R_7$, —$OC(O)OR_7$, —$NHC(O)R_7$, —$NHC(O)OR_7$ and —$NHC(O)NR_{8a}R_{8b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, substituted or unsubstituted —$C_2$-$C_8$ alkynyl.

Illustrative structures of B are represented by formula (B1a~B1r), (B2a~B2o), and (B3a~B3j):

(B1a)

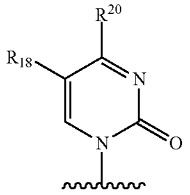

(B1b)

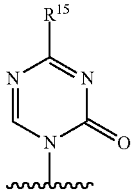

(B1c)

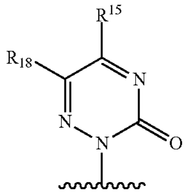

(B1d)

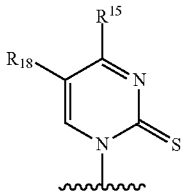

-continued (B1e)

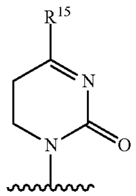

(B1f)

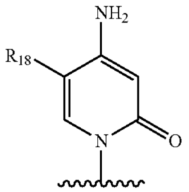

(B1g)

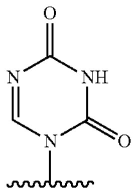

(B1h)

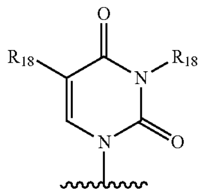

(B1i)

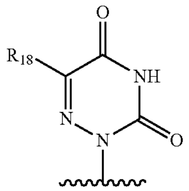

(B1j)

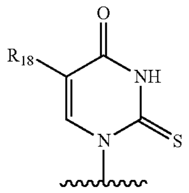

(B1k)

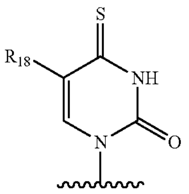

(B1l)

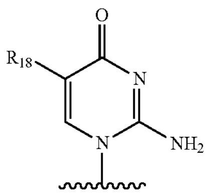

-continued
(B1m)
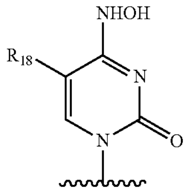
(B1n)
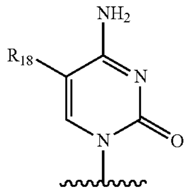
(B1o)
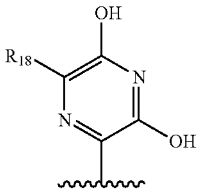
(B1p)
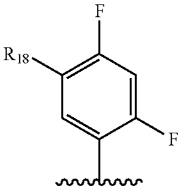
(B1q)
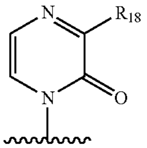
(B1r)
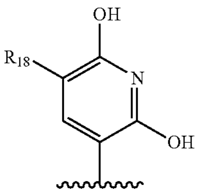
(B2a)
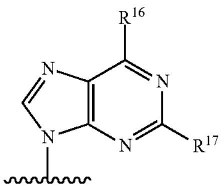
(B2b)
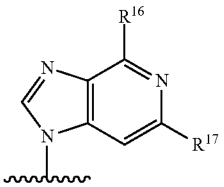
-continued
(B2c)
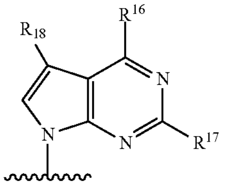
(B2d)
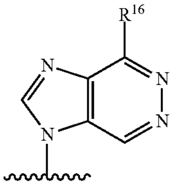
(B2e)
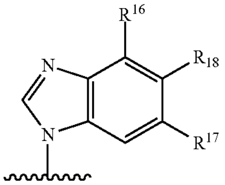
(B2f)
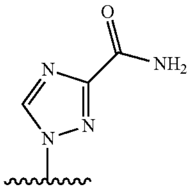
(B2g)
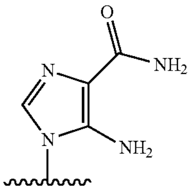
(B2h)
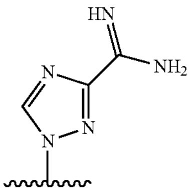
(B2i)
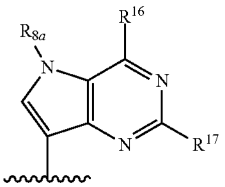
(B2j)
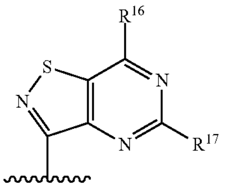

-continued
(B2k)
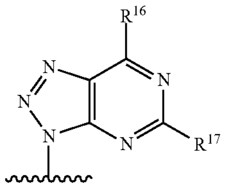
(B2l)
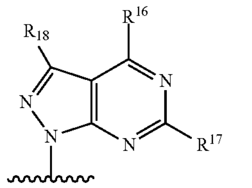
(B2m)
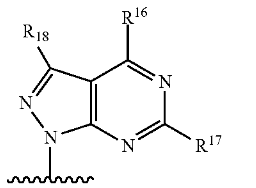
(B2n)
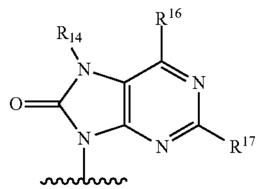
(B2o)
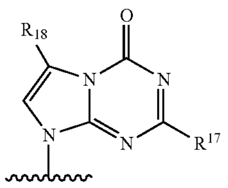
(B1a)
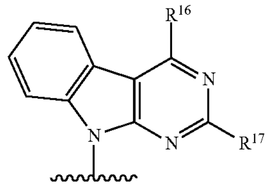
(B3b)
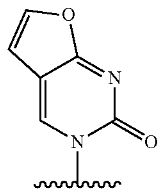
(B3c)
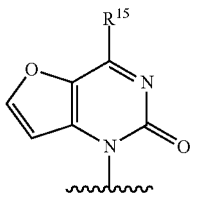
-continued
(B3d)
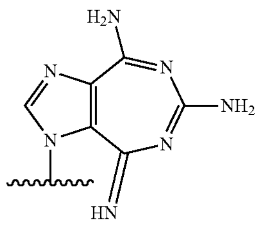
(B3e)
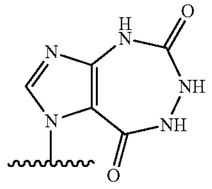
(B3f)
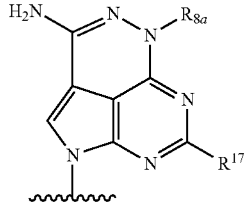
(B3g)
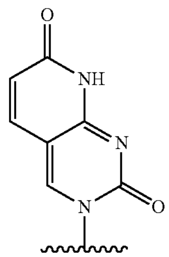
(B3h)
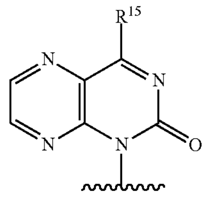
(B3i)
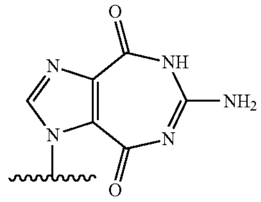
(B3j)
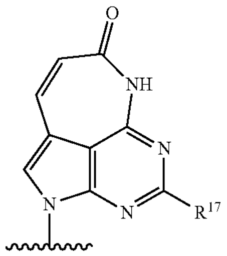
wherein $R_{8a}$, $R_{18}$, $R^{15}$, $R^{16}$ and $R^{17}$ are as previously defined.

Representative compounds of the invention include, but are not limited to, the following compounds illustrated in Table 1 to Table 5.

Compounds in Table 1 are represented by Formula (III-1) wherein $R_2$, $R_{2a}$, $R_{2b}$, $R_{2c}$, and B are delineated for each example in Table 1.

TABLE 1

(III-1)

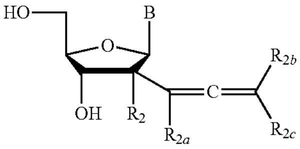

| Example# | $R_{2a}$ | $R_{2b}$ | $R_{2c}$ | $R_2$ | B |
|---|---|---|---|---|---|
| 1 | H | H | H | OH | 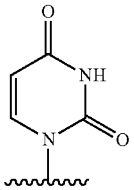 [SMILES: *n1ccc(=O)[nH]c1=O] |
| 2 | H | H | H | F | 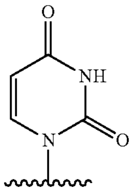 [SMILES: *n1ccc(=O)[nH]c1=O] |
| 3 | H | Me | Me | OH | 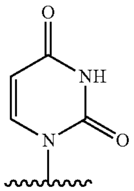 [SMILES: *n1ccc(=O)[nH]c1=O] |
| 4 | H | Me | Me | F | 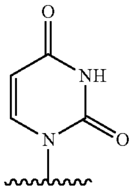 [SMILES: *n1ccc(=O)[nH]c1=O] |
| 5 | H | F | F | OH | 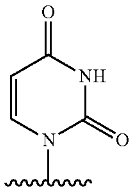 [SMILES: *n1ccc(=O)[nH]c1=O] |
| 6 | H | F | F | F | 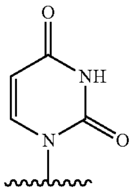 [SMILES: *n1ccc(=O)[nH]c1=O] |

TABLE 1-continued (III-1)

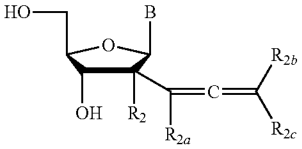

| Example# | $R_{2a}$ | $R_{2b}$ | $R_{2c}$ | $R_2$ | B |
|---|---|---|---|---|---|
| 7 | H | H | H | OH | 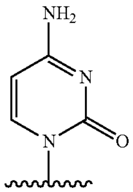 |
| 8 | H | H | H | F | 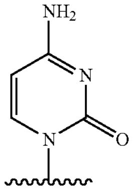 |
| 9 | H | Me | Me | OH | 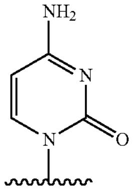 |
| 10 | H | Me | Me | F | 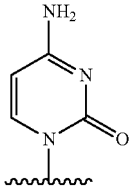 |
| 11 | H | F | F | OH | 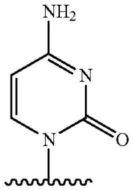 |
| 12 | H | F | F | F | 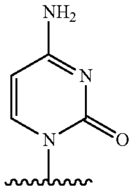 |
| 13 | H | H | H | OH | 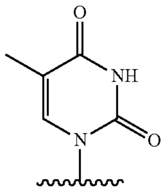 [SMILES: *n1cc(C)c(=O)[nH]c1=O] |

TABLE 1-continued
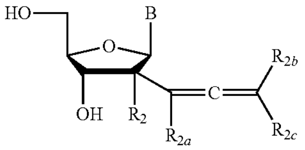
(III-1)
| Example# | $R_{2a}$ | $R_{2b}$ | $R_{2c}$ | $R_2$ | B |
|---|---|---|---|---|---|
| 14 | H | H | H | F | 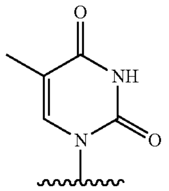 [SMILES: *n1cc(C)c(=O)[nH]c1=O] |
| 15 | H | Me | Me | OH | 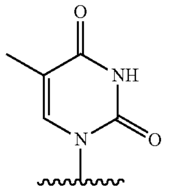 |
| 16 | H | Me | Me | F | 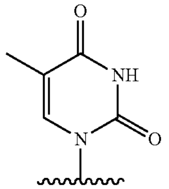 [SMILES: *n1cc(C)c(=O)[nH]c1=O] |
| 17 | H | F | F | OH | 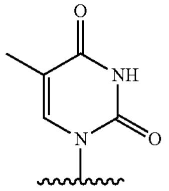 |
| 18 | H | F | F | F | 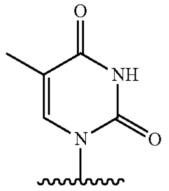 [SMILES: *n1cc(C)c(=O)[nH]c1=O] |
| 19 | H | H | H | OH | 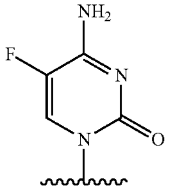 |
| 20 | H | H | H | F | 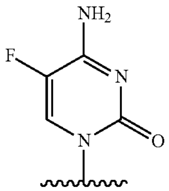 |
TABLE 1-continued
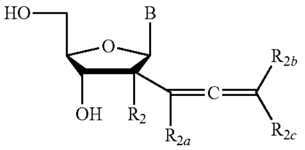
(III-1)
| Example# | $R_{2a}$ | $R_{2b}$ | $R_{2c}$ | $R_2$ | B |
|---|---|---|---|---|---|
| 21 | H | Me | Me | OH | 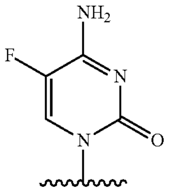 |
| 22 | H | Me | Me | F | 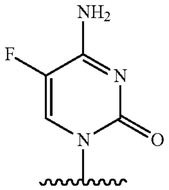 |
| 23 | H | F | F | OH | 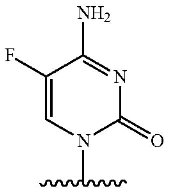 |
| 24 | H | F | F | F | 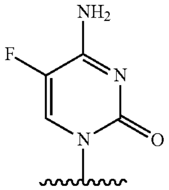 |
| 25 | H | H | H | OH | 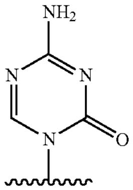 [SMILES: *n1cnc(N)nc1=O] |
| 26 | H | H | H | F | 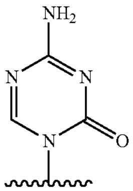 [SMILES: *n1cnc(N)nc1=O] |
| 27 | H | Me | Me | OH | 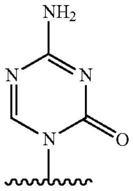 [SMILES: *n1cnc(N)nc1=O] |

TABLE 1-continued
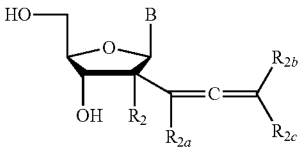
(III-1)
| Example# | $R_{2a}$ | $R_{2b}$ | $R_{2c}$ | $R_2$ | B |
|---|---|---|---|---|---|
| 28 | H | Me | Me | F | 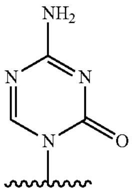 |
| 29 | H | F | F | OH | 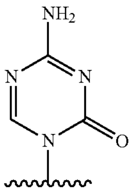 [SMILES: *n1cnc(N)nc1=O] |
| 30 | H | F | F | F | 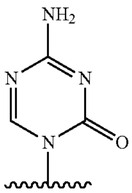 [SMILES: *n1cnc(N)nc1=O] |
| 31 | H | H | H | OH | 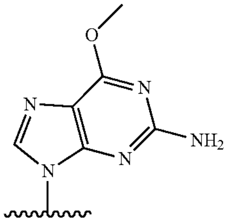 [SMILES: *n1cnc2c(OC)nc(N)nc21] |
| 32 | H | H | H | F | 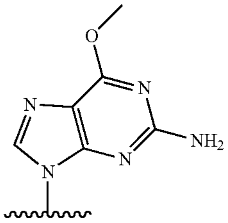 [SMILES: *n1cnc2c(OC)nc(N)nc21] |
| 33 | H | Me | Me | OH | 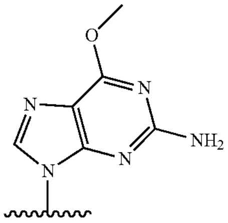 [SMILES: *n1cnc2c(OC)nc(N)nc21] |
TABLE 1-continued
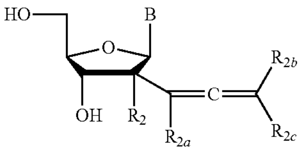
(III-1)
| Example# | $R_{2a}$ | $R_{2b}$ | $R_{2c}$ | $R_2$ | B |
|---|---|---|---|---|---|
| 34 | H | Me | Me | F | 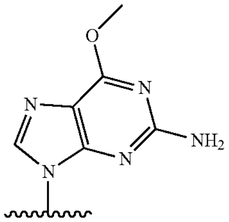 [SMILES: *n1cnc2c(OC)nc(N)nc21] |
| 35 | H | F | F | OH | 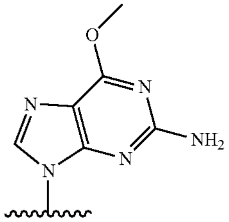 [SMILES: *n1cnc2c(OC)nc(N)nc21] |
| 36 | H | F | F | F | 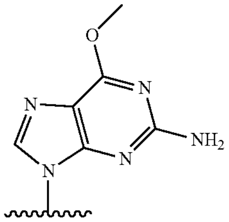 [SMILES: *n1cnc2c(OC)nc(N)nc21] |
| 37 | H | H | H | OH | 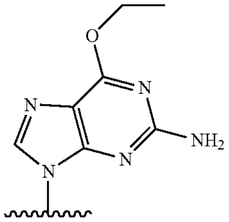 [SMILES: *n1cnc2c(OCC)nc(N)nc21] |
| 38 | H | H | H | F | 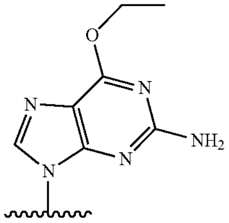 [SMILES: *n1cnc2c(OCC)nc(N)nc21] |
| 39 | H | Me | Me | OH | 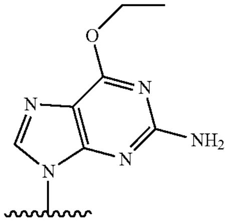 [SMILES: *n1cnc2c(OCC)nc(N)nc21] |

TABLE 1-continued
(III-1)
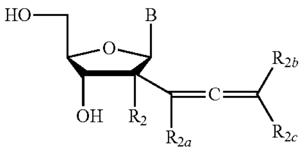
| Example# | $R_{2a}$ | $R_{2b}$ | $R_{2c}$ | $R_2$ | B |
|---|---|---|---|---|---|
| 40 | H | Me | Me | F | 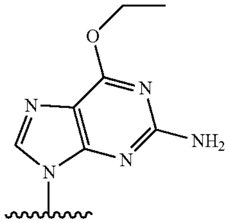 [SMILES: *n1cnc2c(OCC)nc(N)nc21] |
| 41 | H | F | F | OH | 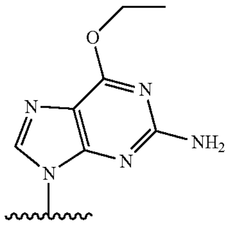 [SMILES: *n1cnc2c(OCC)nc(N)nc21] |
| 42 | H | F | F | F | 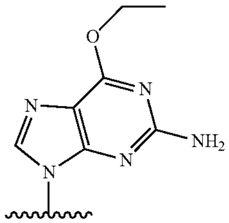 [SMILES: *n1cnc2c(OCC)nc(N)nc21] |
| 43 | H | H | H | OH | 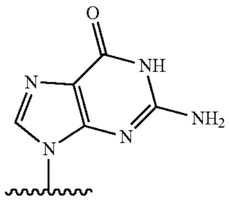 [SMILES: *n1cnc2c(=O)[nH]c(N)nc21] |
| 44 | H | H | H | F | 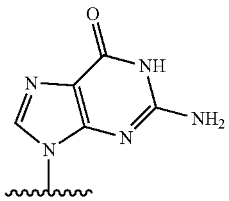 [SMILES: *n1cnc2c(=O)[nH]c(N)nc21] |
| 45 | H | Me | Me | OH | 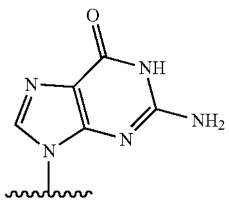 [SMILES: *n1cnc2c(=O)[nH]c(N)nc21] |
TABLE 1-continued
(III-1)
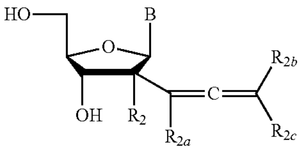
| Example# | $R_{2a}$ | $R_{2b}$ | $R_{2c}$ | $R_2$ | B |
|---|---|---|---|---|---|
| 46 | H | Me | Me | F | 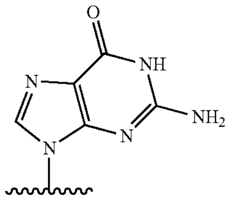 [SMILES: *n1cnc2c(=O)[nH]c(N)nc21] |
| 47 | H | F | F | OH | 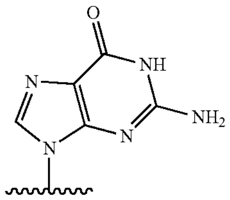 [SMILES: *n1cnc2c(=O)[nH]c(N)nc21] |
| 48 | H | F | F | F | 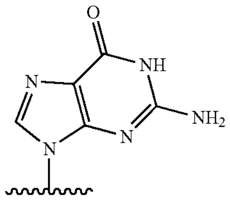 [SMILES: *n1cnc2c(=O)[nH]c(N)nc21] |
| 49 | H | H | H | OH | 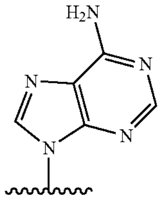 |
| 50 | H | H | H | F | 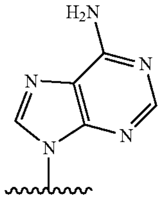 [SMILES: *n1cnc2c(N)ncnc21] |
| 51 | H | Me | Me | OH | 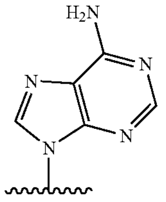 [SMILES: *n1cnc2c(N)ncnc21] |

TABLE 1-continued
(III-1)
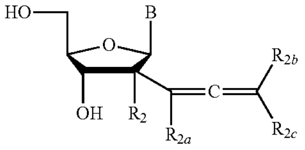
| Example# | $R_{2a}$ | $R_{2b}$ | $R_{2c}$ | $R_2$ | B |
|---|---|---|---|---|---|
| 52 | H | Me | Me | F | 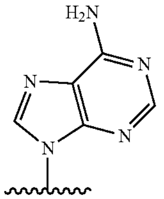 [SMILES: *n1cnc2c(N)ncnc21] |
| 53 | H | F | F | OH | 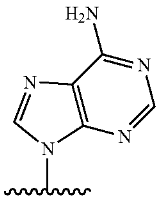 [SMILES: *n1cnc2c(N)ncnc21] |
| 54 | H | F | F | F | 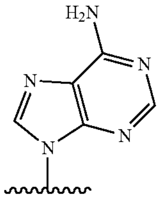 [SMILES: *n1cnc2c(N)ncnc21] |
| 55 | H | H | H | OH | 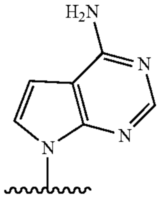 [SMILES: *n1ccc2c(N)ncnc21] |
| 56 | H | H | H | F | 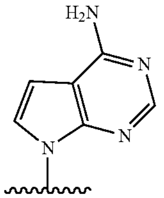 [SMILES: *n1ccc2c(N)ncnc21] |
| 57 | H | Me | Me | OH | 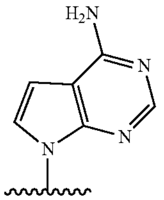 [SMILES: *n1ccc2c(N)ncnc21] |
TABLE 1-continued
(III-1)
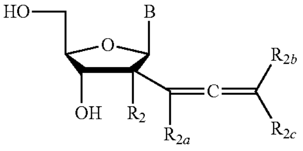
| Example# | $R_{2a}$ | $R_{2b}$ | $R_{2c}$ | $R_2$ | B |
|---|---|---|---|---|---|
| 58 | H | Me | Me | F | 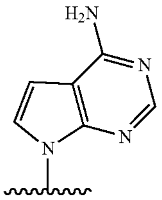 |
| 59 | H | F | F | OH | 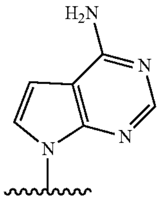 [SMILES: *n1ccc2c(N)ncnc21] |
| 60 | H | F | F | F | 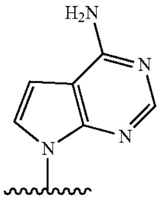 [SMILES: *n1ccc2c(N)ncnc21] |
Compounds in Table 2 are represented by Formula (IV-1) wherein $R_2$, $R_7$, $R_{2a}$, $R_{2b}$, $R_{2c}$, and B are delineated for each example in Table 2.
TABLE 2
(IV-1)
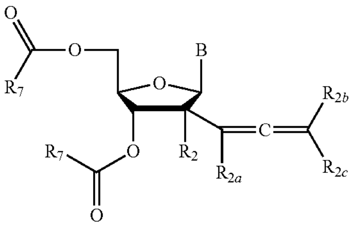
| Example# | $R_{2a}$ | $R_{2b}$ | $R_{2c}$ | $R_2$ | $R_7$ | B |
|---|---|---|---|---|---|---|
| 61 | H | H | H | OH | i-Pr | 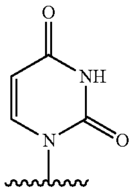 [SMILES: *n1ccc(=O)[nH]c1=O] |

TABLE 2-continued
(IV-1)
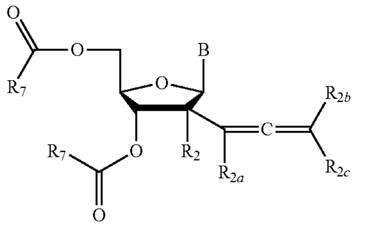
| Example# | $R_{2a}$ | $R_{2b}$ | $R_{2c}$ | $R_2$ | $R_7$ | B |
|---|---|---|---|---|---|---|
| 62 | H | H | H | F | i-Pr | 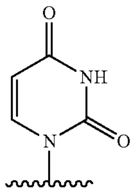 [SMILES: *n1ccc(=O)[nH]c1=O] |
| 63 | H | Me | Me | OH | i-Pr | 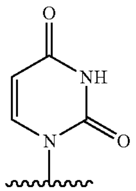 [SMILES: *n1ccc(=O)[nH]c1=O] |
| 64 | H | Me | Me | F | i-Pr | 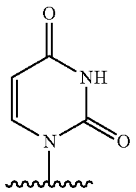 [SMILES: *n1ccc(=O)[nH]c1=O] |
| 65 | H | F | F | OH | i-Pr | 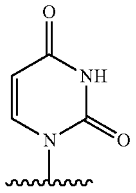 [SMILES: *n1ccc(=O)[nH]c1=O] |
| 66 | H | F | F | F | i-Pr | 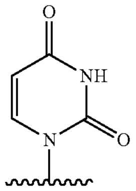 [SMILES: *n1ccc(=O)[nH]c1=O] |
| 67 | H | H | H | OH | i-Pr | 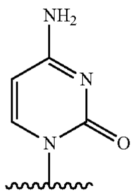 |
TABLE 2-continued
(IV-1)
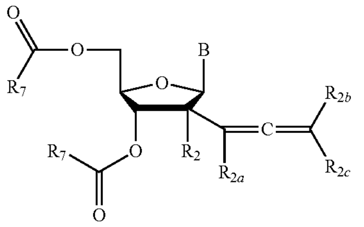
| Example# | $R_{2a}$ | $R_{2b}$ | $R_{2c}$ | $R_2$ | $R_7$ | B |
|---|---|---|---|---|---|---|
| 68 | H | H | H | F | i-Pr | 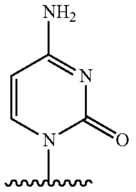 |
| 69 | H | Me | Me | OH | i-Pr | 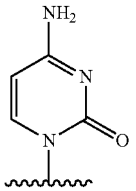 [SMILES: *n1ccc(N)nc1=O] |
| 70 | H | Me | Me | F | i-Pr | 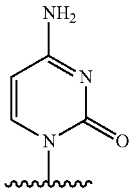 |
| 71 | H | F | F | OH | i-Pr | 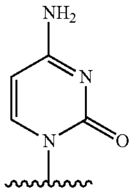 |
| 72 | H | F | F | F | i-Pr | 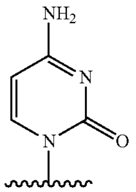 |
| 73 | H | H | H | OH | i-Pr | 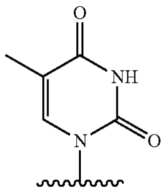 [SMILES: *n1cc(C)c(=O)[nH]c1=O] |

TABLE 2-continued
(IV-1)
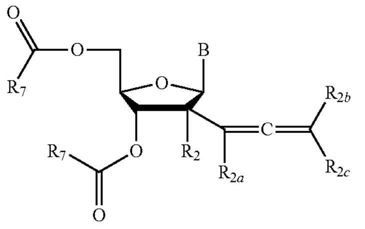
| Example# | $R_{2a}$ | $R_{2b}$ | $R_{2c}$ | $R_2$ | $R_7$ | B |
|---|---|---|---|---|---|---|
| 74 | H | H | H | F | i-Pr | 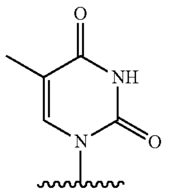 [SMILES: *n1cc(C)c(=O)[nH]c1=O] |
| 75 | H | Me | Me | OH | i-Pr | 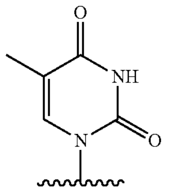 [SMILES: *n1cc(C)c(=O)[nH]c1=O] |
| 76 | H | Me | Me | F | i-Pr | 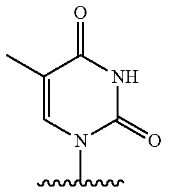 [SMILES: *n1cc(C)c(=O)[nH]c1=O] |
| 77 | H | F | F | OH | i-Pr | 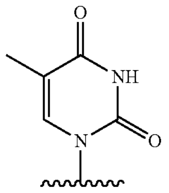 [SMILES: *n1cc(C)c(=O)[nH]c1=O] |
| 78 | H | F | F | F | i-Pr | 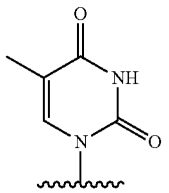 |
| 79 | H | H | H | OH | i-Pr | 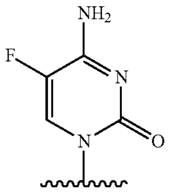 |
TABLE 2-continued
(IV-1)
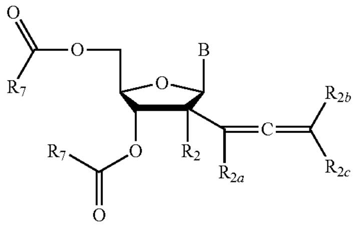
| Example# | $R_{2a}$ | $R_{2b}$ | $R_{2c}$ | $R_2$ | $R_7$ | B |
|---|---|---|---|---|---|---|
| 80 | H | H | H | F | i-Pr | 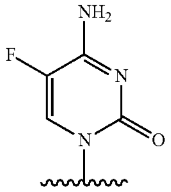 |
| 81 | H | Me | Me | OH | i-Pr | 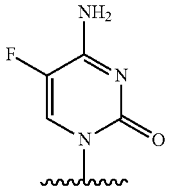 |
| 82 | H | Me | Me | F | i-Pr | 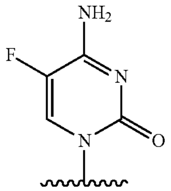 |
| 83 | H | F | F | OH | i-Pr | 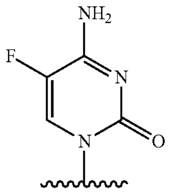 |
| 84 | H | F | F | F | i-Pr | 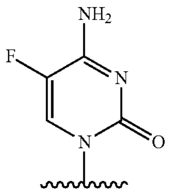 |
| 85 | H | H | H | OH | i-Pr | 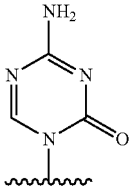 [SMILES: *n1cnc(N)nc1=O] |

TABLE 2-continued
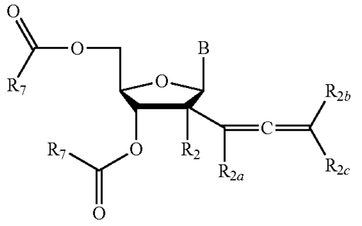
(IV-1)
| Example# | $R_{2a}$ | $R_{2b}$ | $R_{2c}$ | $R_2$ | $R_7$ | B |
|---|---|---|---|---|---|---|
| 86 | H | H | H | F | i-Pr | 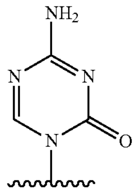 |
| 87 | H | Me | Me | OH | i-Pr | 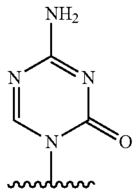 |
| 88 | H | Me | Me | F | i-Pr | 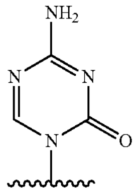 |
| 89 | H | F | F | OH | i-Pr | 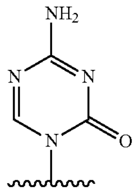 [SMILES: *n1cnc(N)nc1=O] |
| 90 | H | F | F | F | i-Pr | 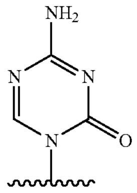 |
| 91 | H | H | H | OH | i-Pr | 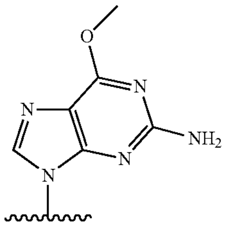 [SMILES: *n1cnc2c(OC)nc(N)nc21] |
TABLE 2-continued
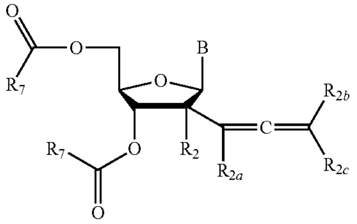
(IV-1)
| Example# | $R_{2a}$ | $R_{2b}$ | $R_{2c}$ | $R_2$ | $R_7$ | B |
|---|---|---|---|---|---|---|
| 92 | H | H | H | F | i-Pr | 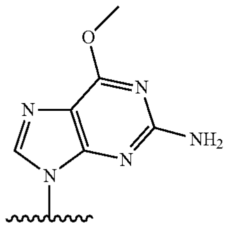 |
| 93 | H | Me | Me | OH | i-Pr | 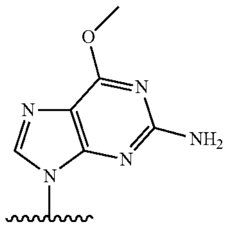 [SMILES: *n1cnc2c(OC)nc(N)nc21] |
| 94 | H | Me | Me | F | i-Pr | 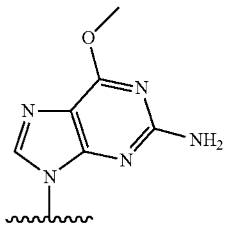 [SMILES: *n1cnc2c(OC)nc(N)nc21] |
| 95 | H | F | F | OH | i-Pr | 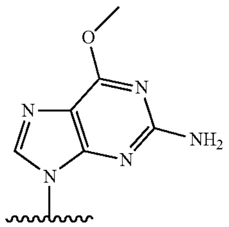 [SMILES: *n1cnc2c(OC)nc(N)nc21] |
| 96 | H | F | F | F | i-Pr | 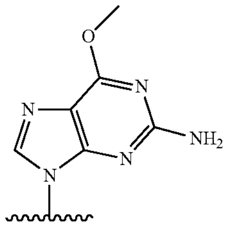 |

TABLE 2-continued
(IV-1)
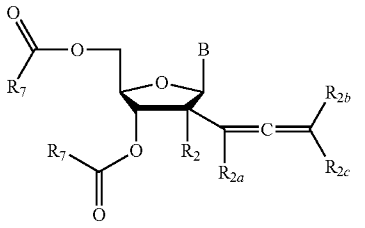
| Example# | $R_{2a}$ | $R_{2b}$ | $R_{2c}$ | $R_2$ | $R_7$ | B |
|---|---|---|---|---|---|---|
| 97 | H | H | H | OH | i-Pr | 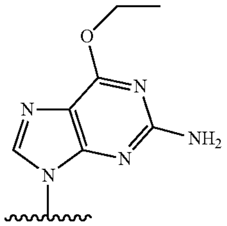 [SMILES: *n1cnc2c(OCC)nc(N)nc21] |
| 98 | H | H | H | F | i-Pr | 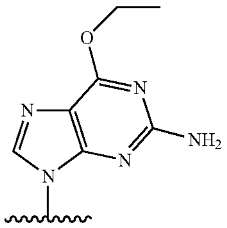 [SMILES: *n1cnc2c(OCC)nc(N)nc21] |
| 99 | H | Me | Me | OH | i-Pr | 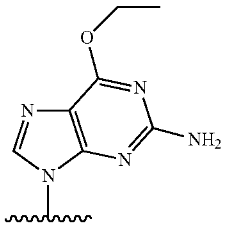 [SMILES: *n1cnc2c(OCC)nc(N)nc21] |
| 100 | H | Me | Me | F | i-Pr | 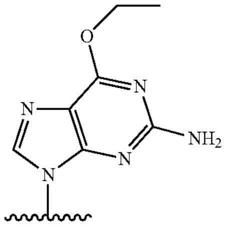 [SMILES: *n1cnc2c(OCC)nc(N)nc21] |
| 101 | H | F | F | OH | i-Pr | 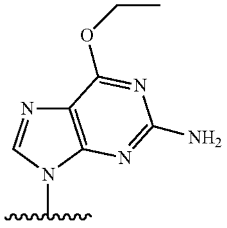 [SMILES: *n1cnc2c(OCC)nc(N)nc21] |
TABLE 2-continued
(IV-1)
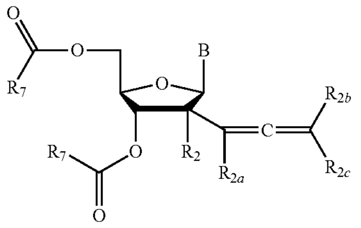
| Example# | $R_{2a}$ | $R_{2b}$ | $R_{2c}$ | $R_2$ | $R_7$ | B |
|---|---|---|---|---|---|---|
| 102 | H | F | F | F | i-Pr | 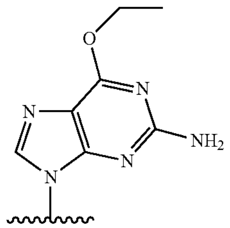 [SMILES: *n1cnc2c(OCC)nc(N)nc21] |
| 103 | H | H | H | OH | i-Pr | 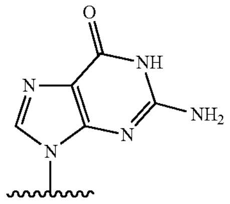 [SMILES: *n1cnc2c(=O)[nH]c(N)nc21] |
| 104 | H | H | H | F | i-Pr | 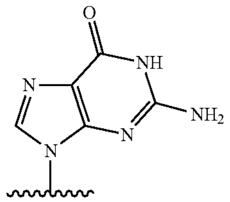 [SMILES: *n1cnc2c(=O)[nH]c(N)nc21] |
| 105 | H | Me | Me | OH | i-Pr | 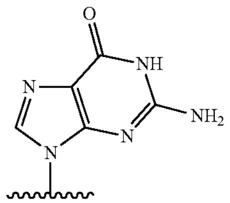 [SMILES: *n1cnc2c(=O)[nH]c(N)nc21] |
| 106 | H | Me | Me | F | i-Pr | 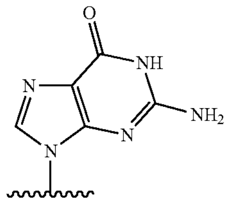 [SMILES: *n1cnc2c(=O)[nH]c(N)nc21] |
| 107 | H | F | F | OH | i-Pr | 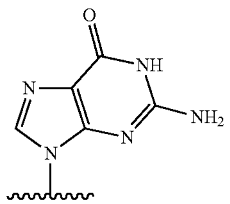 [SMILES: *n1cnc2c(=O)[nH]c(N)nc21] |

TABLE 2-continued
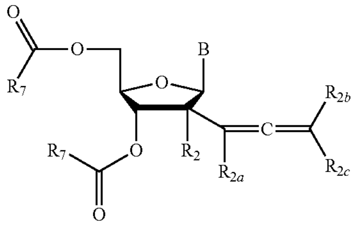
(IV-1)
| Example# | $R_{2a}$ | $R_{2b}$ | $R_{2c}$ | $R_2$ | $R_7$ | B |
|---|---|---|---|---|---|---|
| 108 | H | F | F | F | i-Pr | 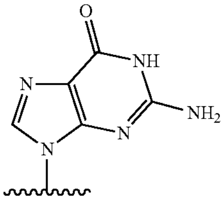 [SMILES: *n1cnc2c(=O)[nH]c(N)nc21] |
| 109 | H | H | H | OH | i-Pr | 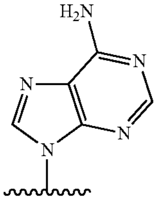 |
| 110 | H | H | H | F | i-Pr | 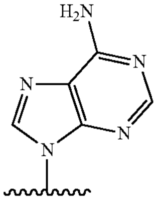 [SMILES: *n1cnc2c(N)ncnc21] |
| 111 | H | Me | Me | OH | i-Pr | 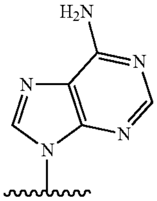 [SMILES: *n1cnc2c(N)ncnc21] |
| 112 | H | Me | Me | F | i-Pr | 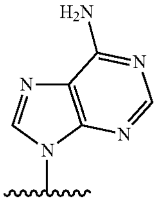 |
| 113 | H | F | F | OH | i-Pr | 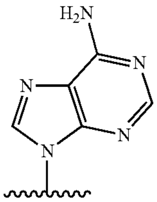 [SMILES: *n1cnc2c(N)ncnc21] |
TABLE 2-continued
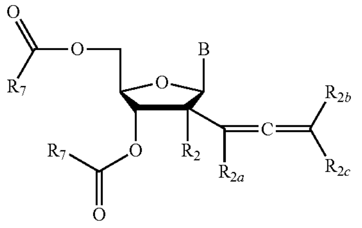
(IV-1)
| Example# | $R_{2a}$ | $R_{2b}$ | $R_{2c}$ | $R_2$ | $R_7$ | B |
|---|---|---|---|---|---|---|
| 114 | H | F | F | F | i-Pr | 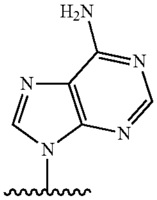 [SMILES: *n1cnc2c(N)ncnc21] |
| 115 | H | H | H | OH | i-Pr | 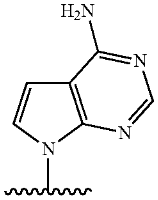 [SMILES: *n1ccc2c(N)ncnc21] |
| 116 | H | H | H | F | i-Pr | 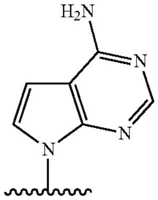 |
| 117 | H | Me | Me | OH | i-Pr | 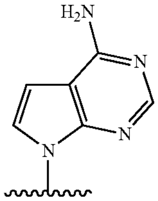 [SMILES: *n1ccc2c(N)ncnc21] |
| 118 | H | Me | Me | F | i-Pr | 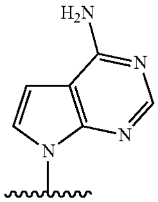 [SMILES: *n1ccc2c(N)ncnc21] |
| 119 | H | F | F | OH | i-Pr | 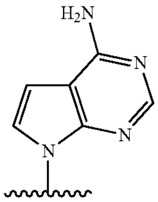 [SMILES: *n1ccc2c(N)ncnc21] |

TABLE 2-continued
(IV-1)
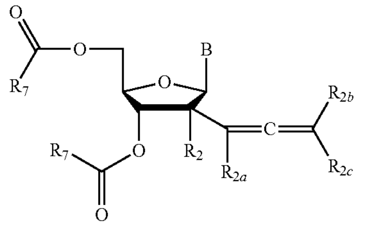
| Example# | $R_{2a}$ | $R_{2b}$ | $R_{2c}$ | $R_2$ | $R_7$ | B |
|---|---|---|---|---|---|---|
| 120 | H | F | F | F | i-Pr | 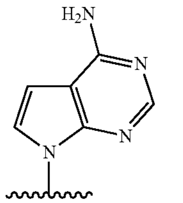 [SMILES: *n1ccc2c(N)ncnc21] |
| 121 | H | H | H | OH | Et | 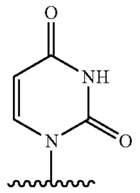 [SMILES: *n1ccc(=O)[nH]c1=O] |
| 122 | H | H | H | F | Et | 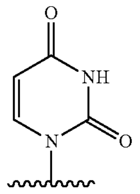 [SMILES: *n1ccc(=O)[nH]c1=O] |
| 123 | H | Me | Me | OH | Et | 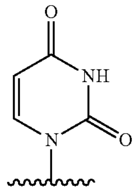 [SMILES: *n1ccc(=O)[nH]c1=O] |
| 124 | H | Me | Me | F | Et | 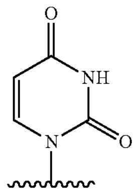 [SMILES: *n1ccc(=O)[nH]c1=O] |
| 125 | H | F | F | OH | Et | 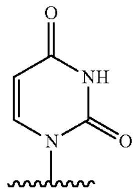 [SMILES: *n1ccc(=O)[nH]c1=O] |
TABLE 2-continued
(IV-1)
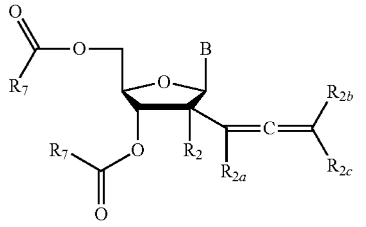
| Example# | $R_{2a}$ | $R_{2b}$ | $R_{2c}$ | $R_2$ | $R_7$ | B |
|---|---|---|---|---|---|---|
| 126 | H | F | F | F | Et | 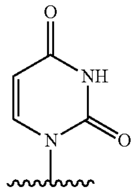 [SMILES: *n1ccc(=O)[nH]c1=O] |
| 127 | H | H | H | OH | Et | 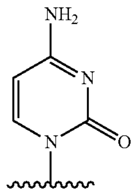 |
| 128 | H | H | H | F | Et | 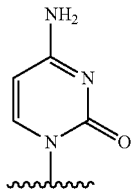 |
| 129 | H | Me | Me | OH | Et | 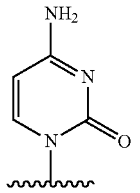 |
| 130 | H | Me | Me | F | Et | 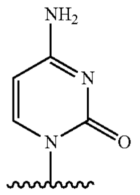 |
| 131 | H | F | F | OH | Et | 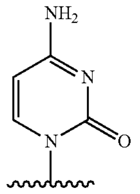 |

TABLE 2-continued
(IV-1)
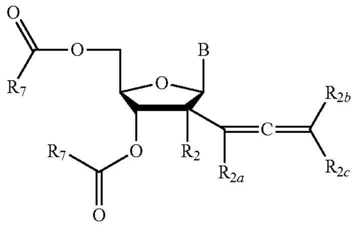
| Example# | $R_{2a}$ | $R_{2b}$ | $R_{2c}$ | $R_2$ | $R_7$ | B |
|---|---|---|---|---|---|---|
| 132 | H | F | F | F | Et | 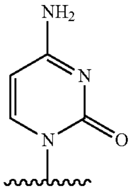 |
| 133 | H | H | H | OH | Et | 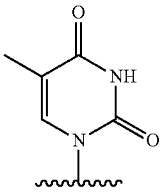 [SMILES: *n1cc(C)c(=O)[nH]c1=O] |
| 134 | H | H | H | F | Et | 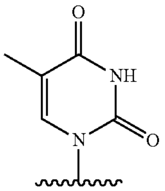 [SMILES: *n1cc(C)c(=O)[nH]c1=O] |
| 135 | H | Me | Me | OH | Et | 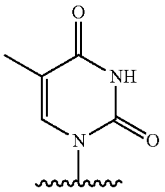 |
| 136 | H | Me | Me | F | Et | 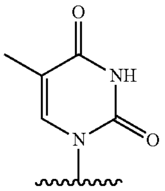 [SMILES: *n1cc(C)c(=O)[nH]c1=O] |
| 137 | H | F | F | OH | Et | 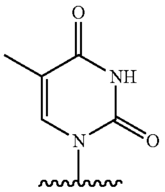 [SMILES: *n1cc(C)c(=O)[nH]c1=O] |
TABLE 2-continued
(IV-1)
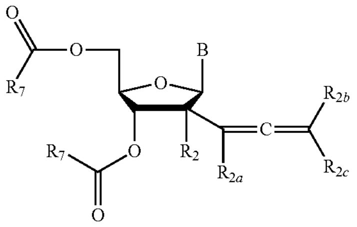
| Example# | $R_{2a}$ | $R_{2b}$ | $R_{2c}$ | $R_2$ | $R_7$ | B |
|---|---|---|---|---|---|---|
| 138 | H | F | F | F | Et | 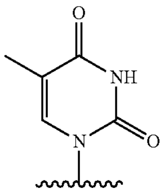 [SMILES: *n1cc(C)c(=O)[nH]c1=O] |
| 139 | H | H | H | OH | Et | 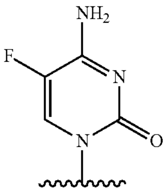 |
| 140 | H | H | H | F | Et | 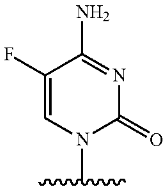 |
| 141 | H | Me | Me | OH | Et | 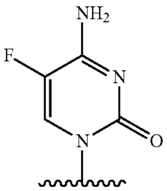 |
| 142 | H | Me | Me | F | Et | 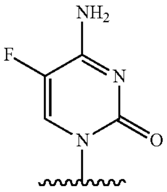 |
| 143 | H | F | F | OH | Et | 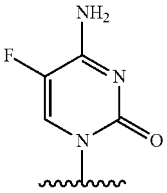 |

TABLE 2-continued
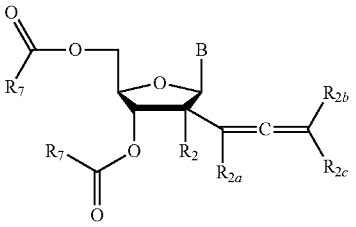
(IV-1)
| Example# | $R_{2a}$ | $R_{2b}$ | $R_{2c}$ | $R_2$ | $R_7$ | B |
|---|---|---|---|---|---|---|
| 144 | H | F | F | F | Et | 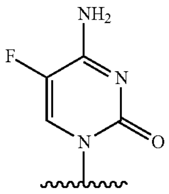 |
| 145 | H | H | H | OH | Et | 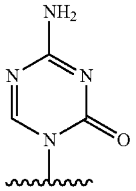 |
| 146 | H | H | H | F | Et | 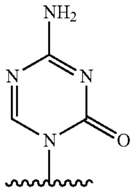 |
| 147 | H | Me | Me | OH | Et | 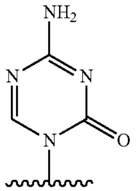 [SMILES: *n1cnc(N)nc1=O] |
| 148 | H | Me | Me | F | Et | 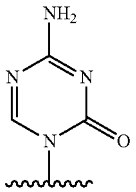 |
| 149 | H | F | F | OH | Et | 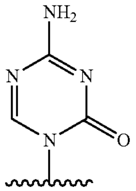 |
TABLE 2-continued
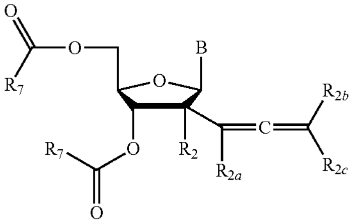
(IV-1)
| Example# | $R_{2a}$ | $R_{2b}$ | $R_{2c}$ | $R_2$ | $R_7$ | B |
|---|---|---|---|---|---|---|
| 150 | H | F | F | F | Et | 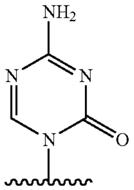 [SMILES: *n1cnc(N)nc1=O] |
| 151 | H | H | H | OH | Et | 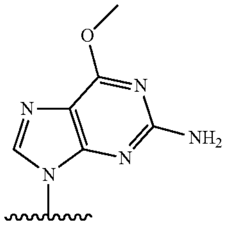 |
| 152 | H | H | H | F | Et | 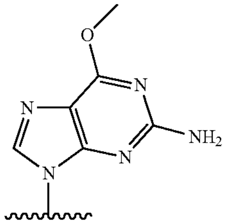 [SMILES: *n1cnc2c(OC)nc(N)nc21] |
| 153 | H | Me | Me | OH | Et | 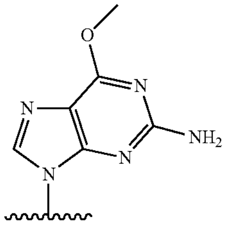 [SMILES: *n1cnc2c(OC)nc(N)nc21] |
| 154 | H | Me | Me | F | Et | 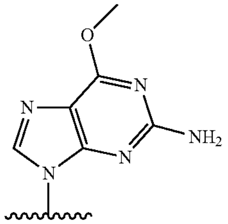 [SMILES: *n1cnc2c(OC)nc(N)nc21] |

TABLE 2-continued
(IV-1)
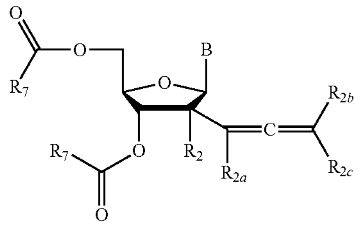
| Example# | $R_{2a}$ | $R_{2b}$ | $R_{2c}$ | $R_2$ | $R_7$ | B |
|---|---|---|---|---|---|---|
| 155 | H | F | F | OH | Et | 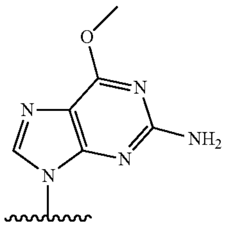 [SMILES: *n1cnc2c(OC)nc(N)nc21] |
| 156 | H | F | F | F | Et | 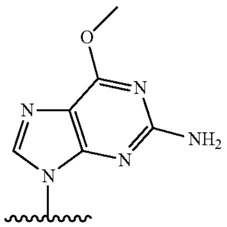 [SMILES: *n1cnc2c(OC)nc(N)nc21] |
| 157 | H | H | H | OH | Et | 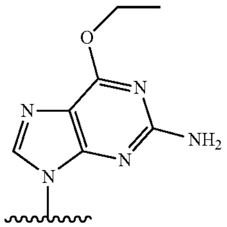 [SMILES: *n1cnc2c(OCC)nc(N)nc21] |
| 158 | H | H | H | F | Et | 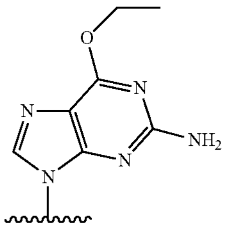 [SMILES: *n1cnc2c(OCC)nc(N)nc21] |
| 159 | H | Me | Me | OH | Et | 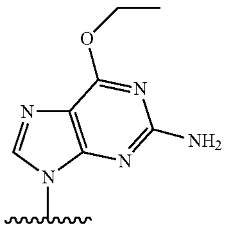 [SMILES: *n1cnc2c(OCC)nc(N)nc21] |
TABLE 2-continued
(IV-1)
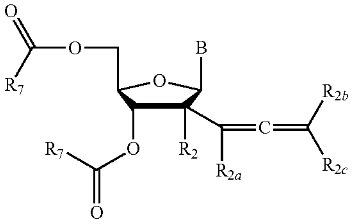
| Example# | $R_{2a}$ | $R_{2b}$ | $R_{2c}$ | $R_2$ | $R_7$ | B |
|---|---|---|---|---|---|---|
| 160 | H | Me | Me | F | Et | 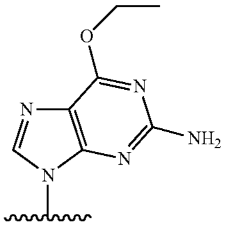 [SMILES: *n1cnc2c(OCC)nc(N)nc21] |
| 161 | H | F | F | OH | Et | 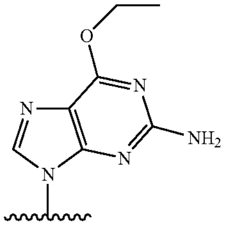 [SMILES: *n1cnc2c(OCC)nc(N)nc21] |
| 162 | H | F | F | F | Et | 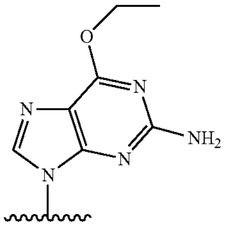 [SMILES: *n1cnc2c(OCC)nc(N)nc21] |
| 163 | H | H | H | OH | Et | 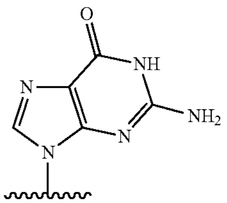 [SMILES: *n1cnc2c(=O)[nH]c(N)nc21] |
| 164 | H | H | H | F | Et | 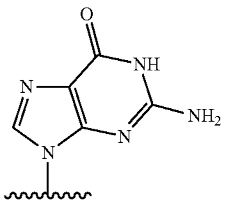 [SMILES: *n1cnc2c(=O)[nH]c(N)nc21] |
| 165 | H | Me | Me | OH | Et | 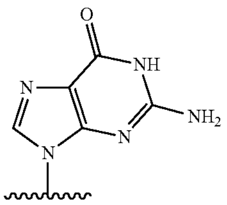 [SMILES: *n1cnc2c(=O)[nH]c(N)nc21] |

TABLE 2-continued
(IV-1)
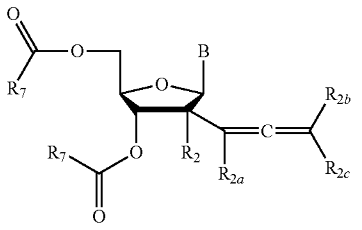
| Example# | $R_{2a}$ | $R_{2b}$ | $R_{2c}$ | $R_2$ | $R_7$ | B |
|---|---|---|---|---|---|---|
| 166 | H | Me | Me | F | Et | 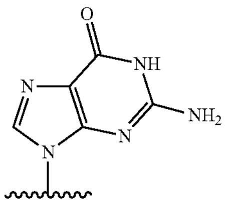 [SMILES: *n1cnc2c(=O)[nH]c(N)nc21] |
| 167 | H | F | F | OH | Et | 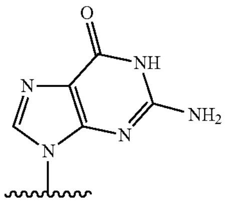 [SMILES: *n1cnc2c(=O)[nH]c(N)nc21] |
| 168 | H | F | F | F | Et | 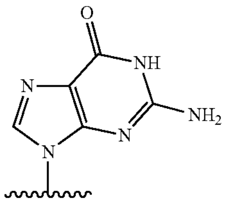 [SMILES: *n1cnc2c(=O)[nH]c(N)nc21] |
| 169 | H | H | H | OH | Et | 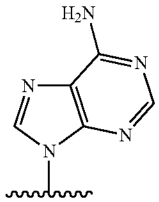 |
| 170 | H | H | H | F | Et | 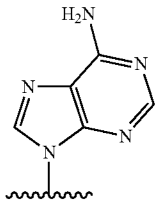 |
| 171 | H | Me | Me | OH | Et | 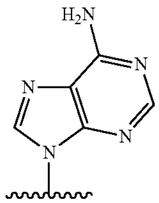 [SMILES: *n1cnc2c(N)ncnc21] |
TABLE 2-continued
(IV-1)
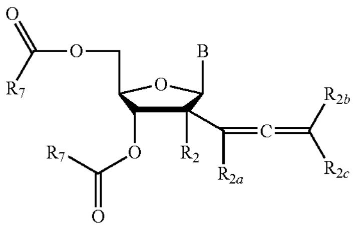
| Example# | $R_{2a}$ | $R_{2b}$ | $R_{2c}$ | $R_2$ | $R_7$ | B |
|---|---|---|---|---|---|---|
| 152 | H | Me | Me | F | Et | 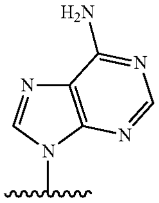 [SMILES: *n1cnc2c(N)ncnc21] |
| 173 | H | F | F | OH | Et | 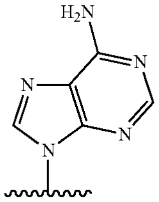 [SMILES: *n1cnc2c(N)ncnc21] |
| 174 | H | F | F | F | Et | 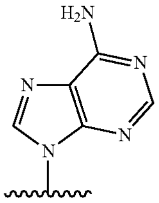 [SMILES: *n1cnc2c(N)ncnc21] |
| 175 | H | H | H | OH | Et | 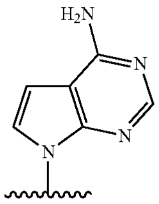 [SMILES: *n1ccc2c(N)ncnc21] |
| 176 | H | H | H | F | Et | 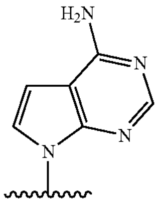 [SMILES: *n1ccc2c(N)ncnc21] |
| 177 | H | Me | Me | OH | Et | 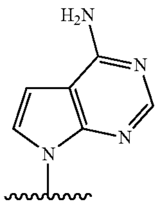 [SMILES: *n1ccc2c(N)ncnc21] |

TABLE 2-continued
(IV-1)
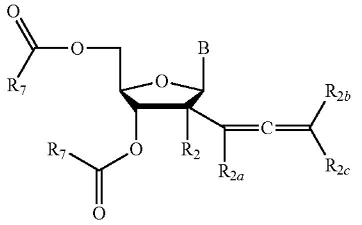
| Example# | $R_{2a}$ | $R_{2b}$ | $R_{2c}$ | $R_2$ | $R_7$ | B |
|---|---|---|---|---|---|---|
| 178 | H | Me | Me | F | Et | 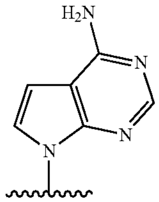 [SMILES: *n1ccc2c(N)ncnc21] |
| 179 | H | F | F | OH | Et | 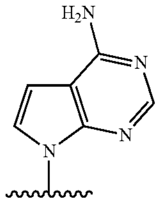 [SMILES: *n1ccc2c(N)ncnc21] |
| 180 | H | F | F | F | Et | 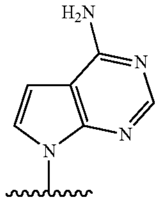 [SMILES: *n1ccc2c(N)ncnc21] |
| 181 | H | H | H | OH | i-Bu | 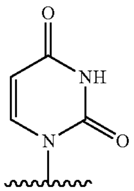 [SMILES: *n1ccc(=O)[nH]c1=O] |
| 182 | H | H | H | F | i-Bu | 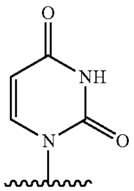 [SMILES: *n1ccc(=O)[nH]c1=O] |
| 183 | H | Me | Me | OH | i-Bu | 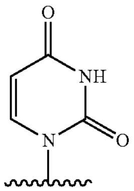 [SMILES: *n1ccc(=O)[nH]c1=O] |
TABLE 2-continued
(IV-1)
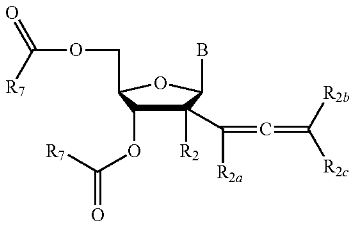
| Example# | $R_{2a}$ | $R_{2b}$ | $R_{2c}$ | $R_2$ | $R_7$ | B |
|---|---|---|---|---|---|---|
| 184 | H | Me | Me | F | i-Bu | 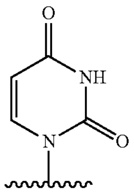 |
| 185 | H | F | F | OH | i-Bu | 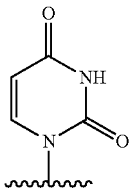 [SMILES: *n1ccc(=O)[nH]c1=O] |
| 186 | H | F | F | F | i-Bu | 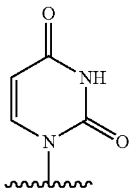 [SMILES: *n1ccc(=O)[nH]c1=O] |
| 187 | H | H | H | OH | i-Bu | 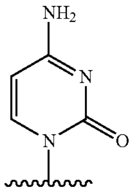 |
| 188 | H | H | H | F | i-Bu | 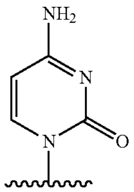 |
| 189 | H | Me | Me | OH | i-Bu | 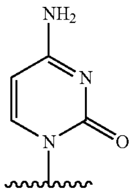 [SMILES: *n1ccc(N)nc1=O] |

TABLE 2-continued
(IV-1)
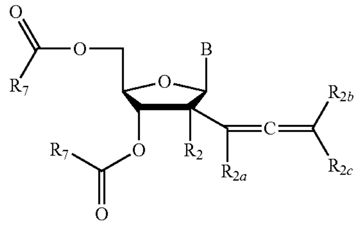
| Example# | $R_{2a}$ | $R_{2b}$ | $R_{2c}$ | $R_2$ | $R_7$ | B |
|---|---|---|---|---|---|---|
| 190 | H | Me | Me | F | i-Bu | 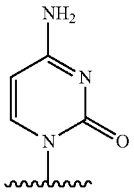 |
| 191 | H | F | F | OH | i-Bu | 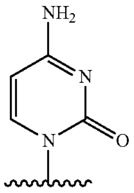 |
| 192 | H | F | F | F | i-Bu | 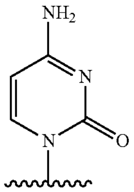 |
| 193 | H | H | H | OH | i-Bu | 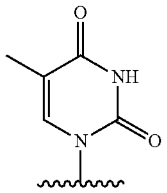 [SMILES: *n1cc(C)c(=O)[nH]c1=O] |
| 194 | H | H | H | F | i-Bu | 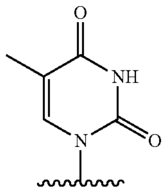 [SMILES: *n1cc(C)c(=O)[nH]c1=O] |
| 195 | H | Me | Me | OH | i-Bu | 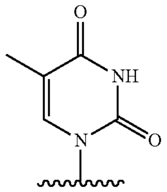 [SMILES: *n1cc(C)c(=O)[nH]c1=O] |
TABLE 2-continued
(IV-1)
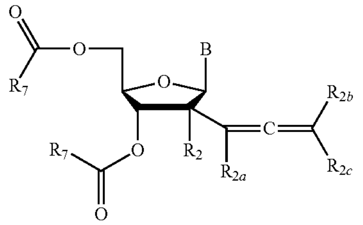
| Example# | $R_{2a}$ | $R_{2b}$ | $R_{2c}$ | $R_2$ | $R_7$ | B |
|---|---|---|---|---|---|---|
| 196 | H | Me | Me | F | i-Bu | 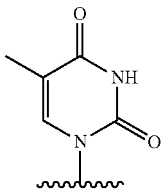 [SMILES: *n1cc(C)c(=O)[nH]c1=O] |
| 197 | H | F | F | OH | i-Bu | 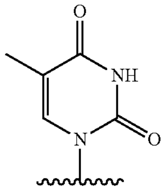 [SMILES: *n1cc(C)c(=O)[nH]c1=O] |
| 198 | H | F | F | F | i-Bu | 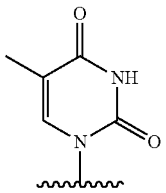 [SMILES: *n1cc(C)c(=O)[nH]c1=O] |
| 199 | H | H | H | OH | i-Bu | 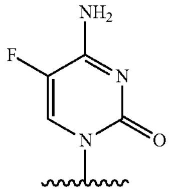 |
| 200 | H | H | H | F | i-Bu | 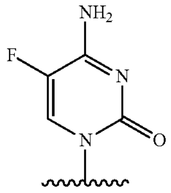 |
| 201 | H | Me | Me | OH | i-Bu | 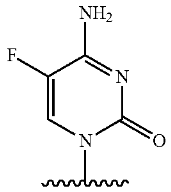 |

TABLE 2-continued
(IV-1)
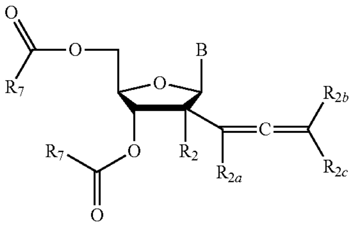
| Example# | $R_{2a}$ | $R_{2b}$ | $R_{2c}$ | $R_2$ | $R_7$ | B |
|---|---|---|---|---|---|---|
| 202 | H | Me | Me | F | i-Bu | 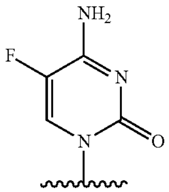 |
| 203 | H | F | F | OH | i-Bu | 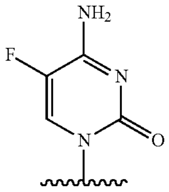 |
| 204 | H | F | F | F | i-Bu | 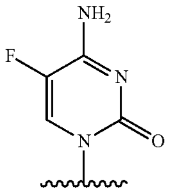 |
| 205 | H | H | H | OH | i-Bu | 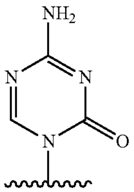 |
| 206 | H | H | H | F | i-Bu | 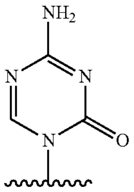 [SMILES: *n1cnc(N)nc1=O] |
| 207 | H | Me | Me | OH | i-Bu | 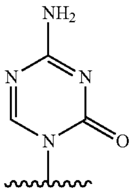 |
TABLE 2-continued
(IV-1)
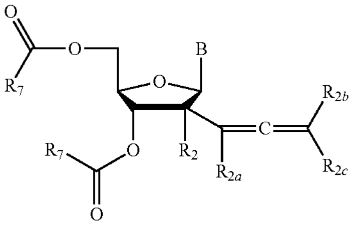
| Example# | $R_{2a}$ | $R_{2b}$ | $R_{2c}$ | $R_2$ | $R_7$ | B |
|---|---|---|---|---|---|---|
| 208 | H | Me | Me | F | i-Bu | 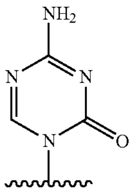 [SMILES: *n1cnc(N)nc1=O] |
| 209 | H | F | F | OH | i-Bu | 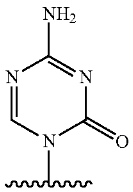 [SMILES: *n1cnc(N)nc1=O] |
| 210 | H | F | F | F | i-Bu | 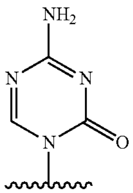 [SMILES: *n1cnc(N)nc1=O] |
| 211 | H | H | H | OH | i-Bu | 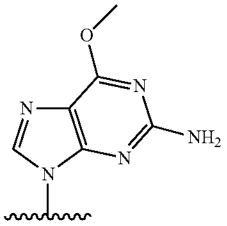 [SMILES: *n1cnc2c(OC)nc(N)nc21] |
| 212 | H | H | H | F | i-Bu | 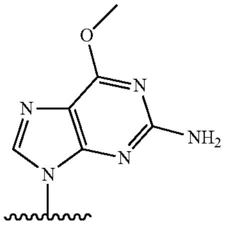 [SMILES: *n1cnc2c(OC)nc(N)nc21] |
| 213 | H | Me | Me | OH | i-Bu | 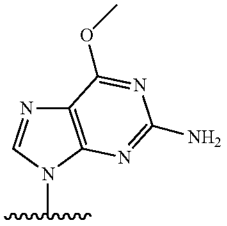 [SMILES: *n1cnc2c(OC)nc(N)nc21] |

TABLE 2-continued
(IV-1)
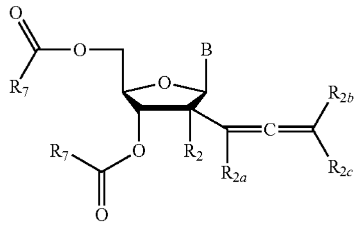
| Example# | $R_{2a}$ | $R_{2b}$ | $R_{2c}$ | $R_2$ | $R_7$ | B |
|---|---|---|---|---|---|---|
| 214 | H | Me | Me | F | i-Bu | 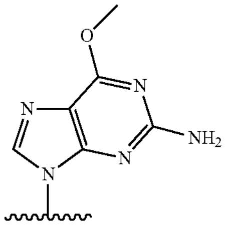 [SMILES: *n1cnc2c(OC)nc(N)nc21] |
| 215 | H | F | F | OH | i-Bu | 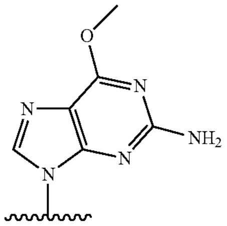 [SMILES: *n1cnc2c(OC)nc(N)nc21] |
| 216 | H | F | F | F | i-Bu | 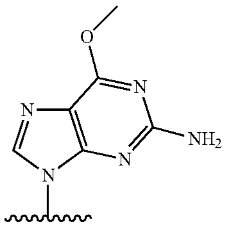 [SMILES: *n1cnc2c(OC)nc(N)nc21] |
| 217 | H | H | H | OH | i-Bu | 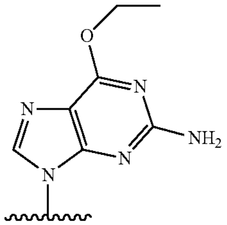 [SMILES: *n1cnc2c(OCC)nc(N)nc21] |
| 218 | H | H | H | F | i-Bu | 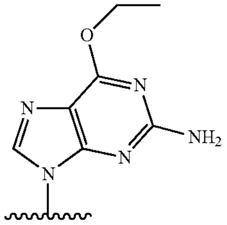 [SMILES: *n1cnc2c(OCC)nc(N)nc21] |
TABLE 2-continued
(IV-1)
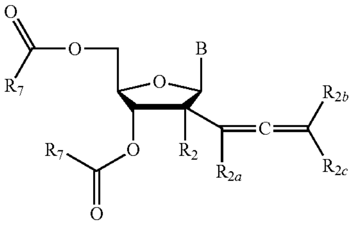
| Example# | $R_{2a}$ | $R_{2b}$ | $R_{2c}$ | $R_2$ | $R_7$ | B |
|---|---|---|---|---|---|---|
| 219 | H | Me | Me | OH | i-Bu | 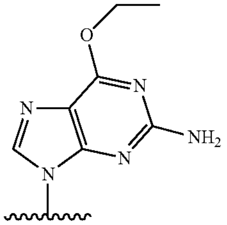 [SMILES: *n1cnc2c(OCC)nc(N)nc21] |
| 220 | H | Me | Me | F | i-Bu | 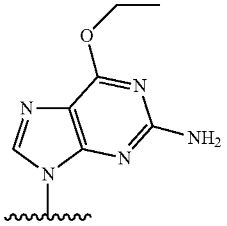 [SMILES: *n1cnc2c(OCC)nc(N)nc21] |
| 221 | H | F | F | OH | i-Bu | 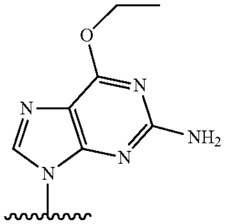 [SMILES: *n1cnc2c(OCC)nc(N)nc21] |
| 222 | H | F | F | F | i-Bu | 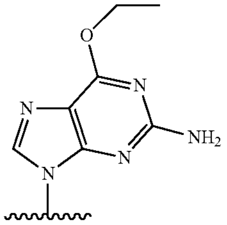 [SMILES: *n1cnc2c(OCC)nc(N)nc21] |
| 223 | H | H | H | OH | i-Bu | 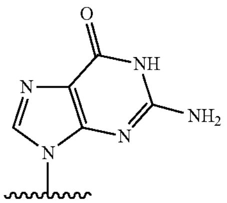 [SMILES: *n1cnc2c(=O)[nH]c(N)nc21] |
| 224 | H | H | H | F | i-Bu | 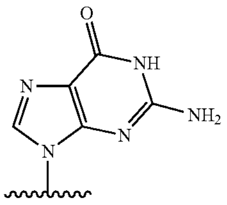 [SMILES: *n1cnc2c(=O)[nH]c(N)nc21] |

TABLE 2-continued
(IV-1)
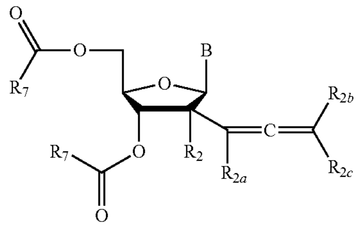
| Example# | $R_{2a}$ | $R_{2b}$ | $R_{2c}$ | $R_2$ | $R_7$ | B |
|---|---|---|---|---|---|---|
| 225 | H | Me | Me | OH | i-Bu | 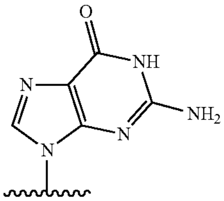 [SMILES: *n1cnc2c(=O)[nH]c(N)nc21] |
| 226 | H | Me | Me | F | i-Bu | 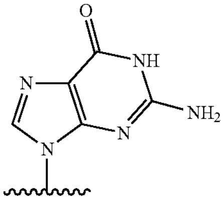 [SMILES: *n1cnc2c(=O)[nH]c(N)nc21] |
| 227 | H | F | F | OH | i-Bu | 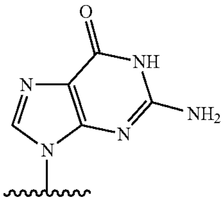 [SMILES: *n1cnc2c(=O)[nH]c(N)nc21] |
| 228 | H | F | F | F | i-Bu | 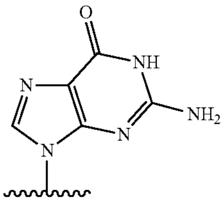 [SMILES: *n1cnc2c(=O)[nH]c(N)nc21] |
| 229 | H | H | H | OH | i-Bu | 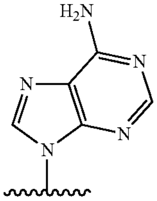 [SMILES: *n1cnc2c(N)ncnc21] |
| 230 | H | H | H | F | i-Bu | 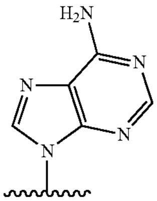 |
TABLE 2-continued
(IV-1)
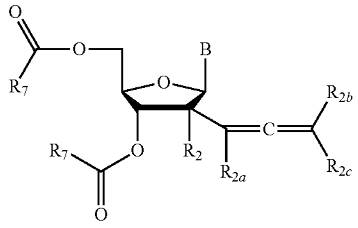
| Example# | $R_{2a}$ | $R_{2b}$ | $R_{2c}$ | $R_2$ | $R_7$ | B |
|---|---|---|---|---|---|---|
| 231 | H | Me | Me | OH | i-Bu | 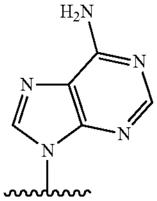 [SMILES: *n1cnc2c(N)ncnc21] |
| 232 | H | Me | Me | F | i-Bu | 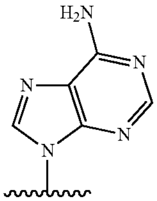 [SMILES: *n1cnc2c(N)ncnc21] |
| 233 | H | F | F | OH | i-Bu | 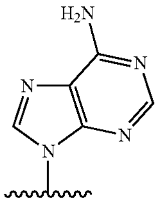 |
| 234 | H | F | F | F | i-Bu | 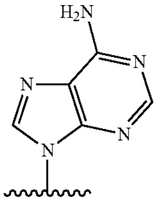 [SMILES: *n1cnc2c(N)ncnc21] |
| 235 | H | H | H | OH | i-Bu | 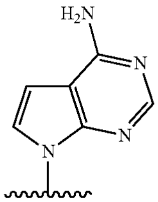 [SMILES: *n1ccc2c(N)ncnc21] |
| 236 | H | H | H | F | i-Bu | 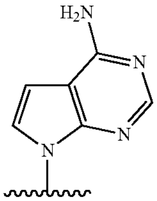 [SMILES: *n1ccc2c(N)ncnc21] |

TABLE 2-continued
(IV-1)
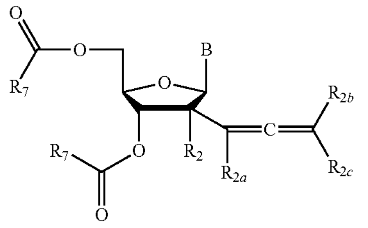
| Example# | $R_{2a}$ | $R_{2b}$ | $R_{2c}$ | $R_2$ | $R_7$ | B |
|---|---|---|---|---|---|---|
| 237 | H | Me | Me | OH | i-Bu | 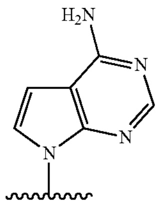 [SMILES: *n1ccc2c(N)ncnc21] |
| 238 | H | Me | Me | F | i-Bu | 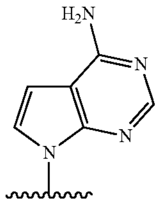 [SMILES: *n1ccc2c(N)ncnc21] |
| 239 | H | F | F | OH | i-Bu | 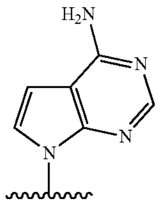 |
| 240 | H | F | F | F | i-Bu | 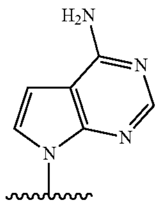 [SMILES: *n1ccc2c(N)ncnc21] |
Compounds in Table 3 are represented by Formula (V-1) wherein $R_2$, $R_9$, $R_{12}$, $R_{13}$, and B are delineated for each example in Table 3.
(V-1)
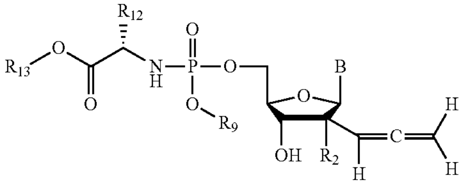
| Example # | $R_2$ | $R_9$ | $R_{12}$ | $R_{13}$ | B |
|---|---|---|---|---|---|
| 241 | OH | Ph | Me | Me | 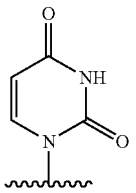 |
| 242 | F | Ph | Me | Me | 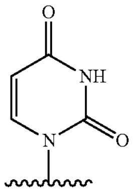 [SMILES: *n1ccc(=O)[nH]c1=O] |
| 243 | OH | Ph | Me | Me | 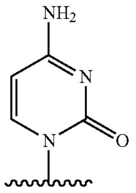 |
| 244 | F | Ph | Me | Me | 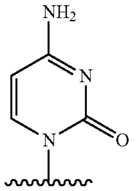 |
| 245 | OH | Ph | Me | Me | 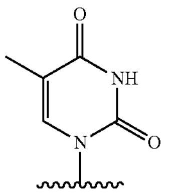 [SMILES: *n1cc(C)c(=O)[nH]c1=O] |
| 246 | F | Ph | Me | Me | 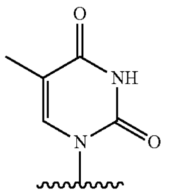 [SMILES: *n1cc(C)c(=O)[nH]c1=O] |

-continued
(V-1)
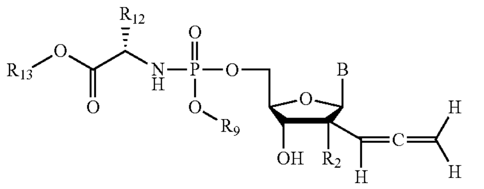
| Example # | $R_2$ | $R_9$ | $R_{12}$ | $R_{13}$ | B |
|---|---|---|---|---|---|
| 247 | OH | Ph | Me | Me | 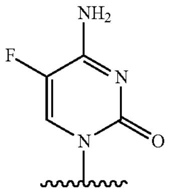 |
| 248 | F | Ph | Me | Me | 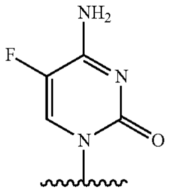 |
| 249 | OH | Ph | Me | Me | 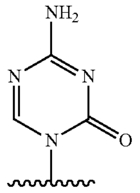 |
| 250 | F | Ph | Me | Me | 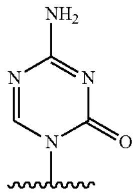 |
| 251 | OH | Ph | Me | Me | 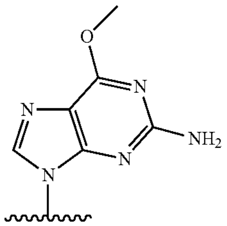 [SMILES: *n1cnc2c(OC)nc(N)nc21] |
| 252 | F | Ph | Me | Me | 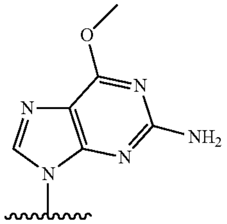 [SMILES: *n1cnc2c(OC)nc(N)nc21] |
-continued
(V-1)
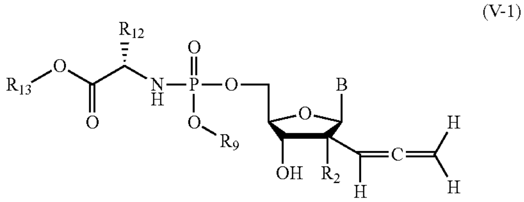
| Example # | $R_2$ | $R_9$ | $R_{12}$ | $R_{13}$ | B |
|---|---|---|---|---|---|
| 253 | OH | Ph | Me | Me | 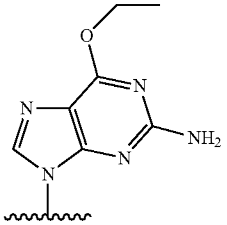 [SMILES: *n1cnc2c(OCC)nc(N)nc21] |
| 254 | F | Ph | Me | Me | 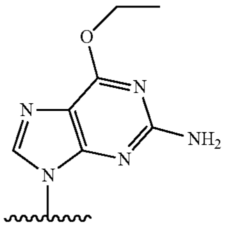 [SMILES: *n1cnc2c(OCC)nc(N)nc21] |
| 255 | OH | Ph | Me | Me | 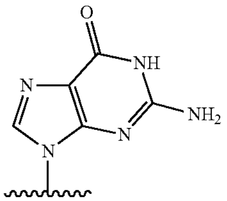 [SMILES: *n1cnc2c(=O)[nH]c(N)nc21] |
| 256 | F | Ph | Me | Me | 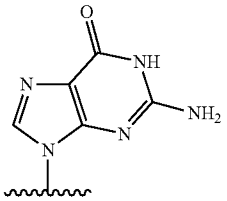 [SMILES: *n1cnc2c(=O)[nH]c(N)nc21] |
| 257 | OH | Ph | Me | Me | 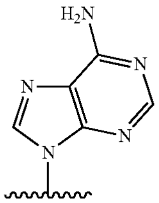 |
| 258 | F | Ph | Me | Me | 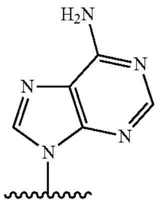 |

-continued
(V-1)
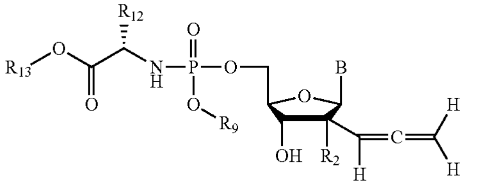
| Example # | $R_2$ | $R_9$ | $R_{12}$ | $R_{13}$ | B |
|---|---|---|---|---|---|
| 259 | OH | Ph | Me | Me | 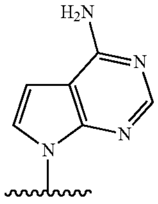 |
| 260 | F | Ph | Me | Me | 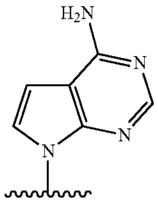 [SMILES: *n1ccc2c(N)ncnc21] |
| 261 | OH | 1-Naphthyl | Me | Me | 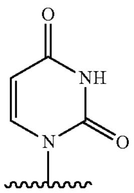 [SMILES: *n1ccc(=O)[nH]c1=O] |
| 262 | F | 1-Naphthyl | Me | Me | 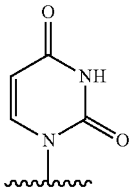 [SMILES: *n1ccc(=O)[nH]c1=O] |
| 263 | OH | 1-Naphthyl | Me | Me | 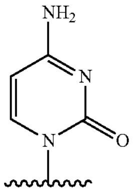 |
| 264 | F | 1-Naphthyl | Me | Me | 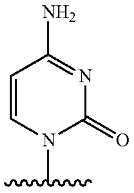 |
-continued
(V-1)
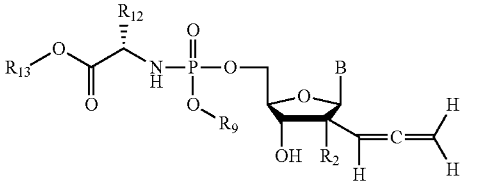
| Example # | $R_2$ | $R_9$ | $R_{12}$ | $R_{13}$ | B |
|---|---|---|---|---|---|
| 265 | OH | 1-Naphthyl | Me | Me | 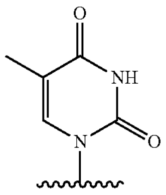 [SMILES: *n1cc(C)c(=O)[nH]c1=O] |
| 266 | F | 1-Naphthyl | Me | Me | 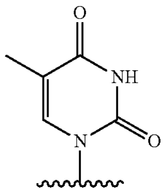 [SMILES: *n1cc(C)c(=O)[nH]c1=O] |
| 267 | OH | 1-Naphthyl | Me | Me | 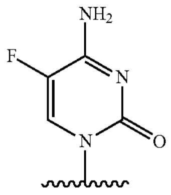 |
| 268 | F | 1-Naphthyl | Me | Me | 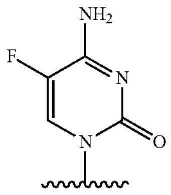 |
| 269 | OH | 1-Naphthyl | Me | Me | 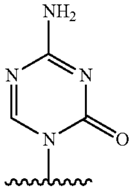 [SMILES: *n1cnc(N)nc1=O] |
| 270 | F | 1-Naphthyl | Me | Me | 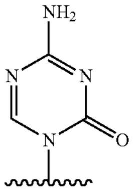 [SMILES: *n1cnc(N)nc1=O] |

-continued
(V-1)
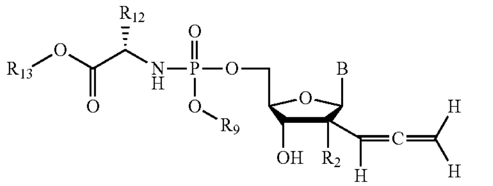
| Example # | $R_2$ | $R_9$ | $R_{12}$ | $R_{13}$ | B |
|---|---|---|---|---|---|
| 271 | OH | 1-Naphthyl | Me | Me | 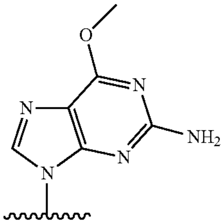 [SMILES: *n1cnc2c(OC)nc(N)nc21] |
| 272 | F | 1-Naphthyl | Me | Me | 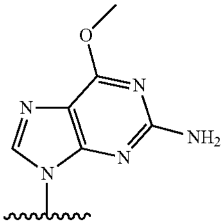 [SMILES: *n1cnc2c(OC)nc(N)nc21] |
| 273 | OH | 1-Naphthyl | Me | Me | 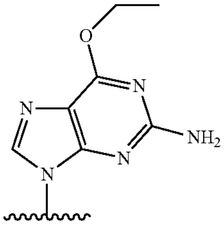 [SMILES: *n1cnc2c(OCC)nc(N)nc21] |
| 274 | F | 1-Naphthyl | Me | Me | 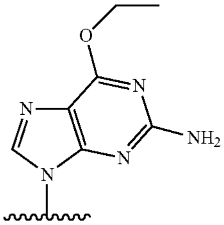 [SMILES: *n1cnc2c(OCC)nc(N)nc21] |
| 275 | OH | 1-Naphthyl | Me | Me | 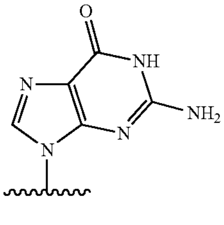 [SMILES: *n1cnc2c(=O)[nH]c(N)nc21] |
-continued
(V-1)
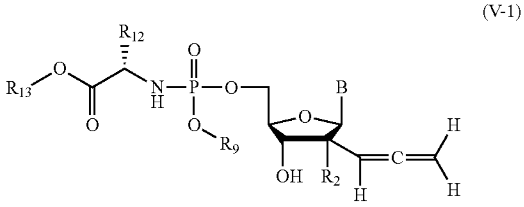
| Example # | $R_2$ | $R_9$ | $R_{12}$ | $R_{13}$ | B |
|---|---|---|---|---|---|
| 276 | F | 1-Naphthyl | Me | Me | 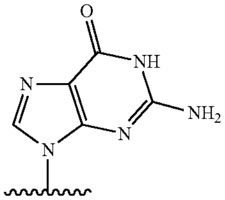 [SMILES: *n1cnc2c(=O)[nH]c(N)nc21] |
| 277 | OH | 1-Naphthyl | Me | Me | 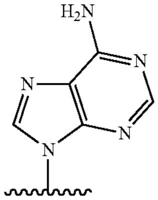 [SMILES: *n1cnc2c(N)ncnc21] |
| 278 | F | 1-Naphthyl | Me | Me | 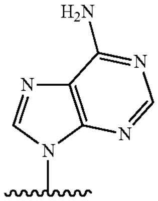 |
| 279 | OH | 1-Naphthyl | Me | Me | 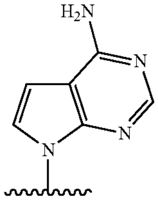 |
| 280 | F | 1-Naphthyl | Me | Me | 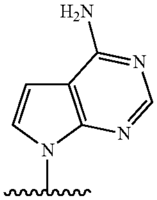 [SMILES: *n1ccc2c(N)ncnc21] |
| 281 | OH | Ph | H | Me | 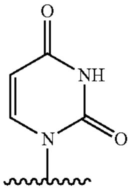 [SMILES: *n1ccc(=O)[nH]c1=O] |

-continued
(V-1)
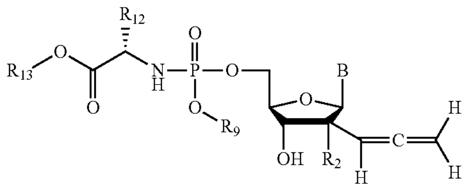
| Example # | $R_2$ | $R_9$ | $R_{12}$ | $R_{13}$ | B |
|---|---|---|---|---|---|
| 282 | F | Ph | H | Me | 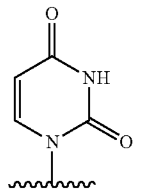 [SMILES: *n1ccc(=O)[nH]c1=O] |
| 283 | OH | Ph | H | Me | 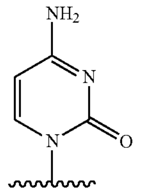 |
| 284 | F | Ph | H | Me | 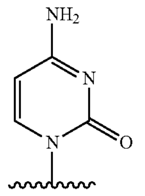 |
| 285 | OH | Ph | H | Me | 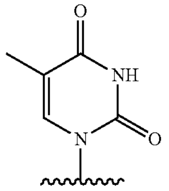 [SMILES: *n1cc(C)c(=O)[nH]c1=O] |
| 286 | F | Ph | H | Me | 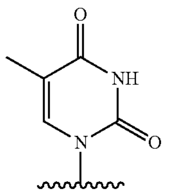 [SMILES: *n1cc(C)c(=O)[nH]c1=O] |
| 287 | OH | Ph | H | Me | 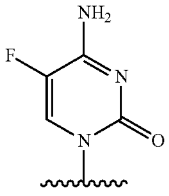 |
-continued
(V-1)
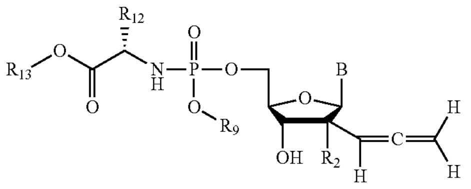
| Example # | $R_2$ | $R_9$ | $R_{12}$ | $R_{13}$ | B |
|---|---|---|---|---|---|
| 288 | F | Ph | H | Me | 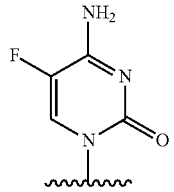 |
| 289 | OH | Ph | H | Me | 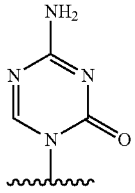 [SMILES: *n1cnc(N)nc1=O] |
| 290 | F | Ph | H | Me | 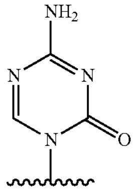 |
| 291 | OH | Ph | H | Me | 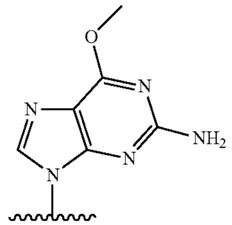 [SMILES: *n1cnc2c(OC)nc(N)nc21] |
| 292 | F | Ph | H | Me | 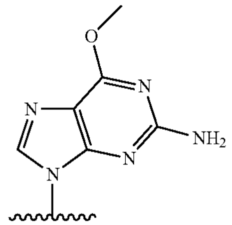 [SMILES: *n1cnc2c(OC)nc(N)nc21] |
| 293 | OH | Ph | H | Me | 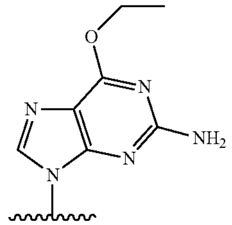 [SMILES: *n1cnc2c(OCC)nc(N)nc21] |

-continued
(V-1)
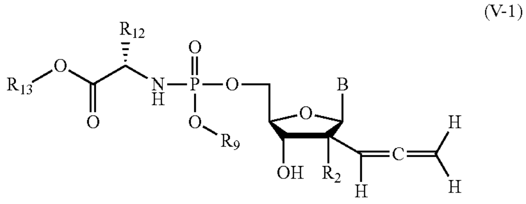
| Example # | $R_2$ | $R_9$ | $R_{12}$ | $R_{13}$ | B |
|---|---|---|---|---|---|
| 294 | F | Ph | H | Me | 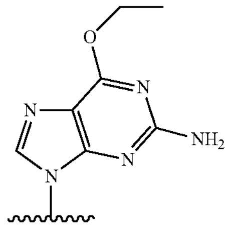 [SMILES: *n1cnc2c(OCC)nc(N)nc21] |
| 295 | OH | Ph | H | Me | 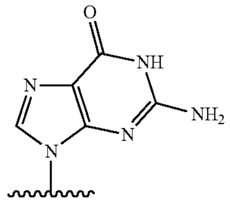 [SMILES: *n1cnc2c(=O)[nH]c(N)nc21] |
| 296 | F | Ph | H | Me | 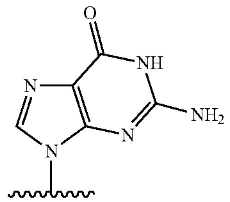 [SMILES: *n1cnc2c(=O)[nH]c(N)nc21] |
| 297 | OH | Ph | H | Me | 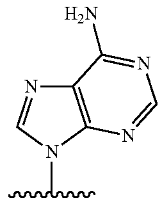 [SMILES: *n1cnc2c(N)ncnc21] |
| 298 | F | Ph | H | Me | 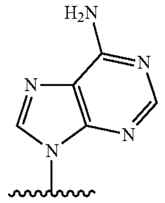 [SMILES: *n1cnc2c(N)ncnc21] |
| 299 | OH | Ph | H | Me | 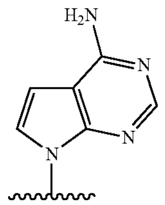 [SMILES: *n1ccc2c(N)ncnc21] |
-continued
(V-1)
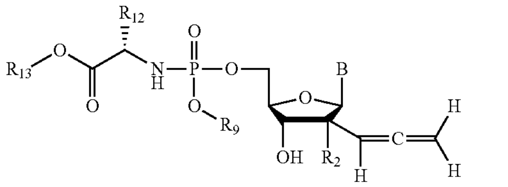
| Example # | $R_2$ | $R_9$ | $R_{12}$ | $R_{13}$ | B |
|---|---|---|---|---|---|
| 300 | F | Ph | H | Me | 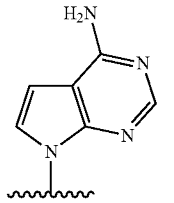 [SMILES: *n1ccc2c(N)ncnc21] |
| 301 | OH | 1-Naphthyl | H | Me | 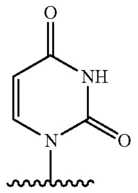 [SMILES: *n1ccc(=O)[nH]c1=O] |
| 302 | F | 1-Naphthyl | H | Me | 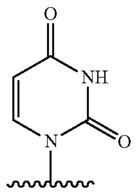 |
| 303 | OH | 1-Naphthyl | H | Me | 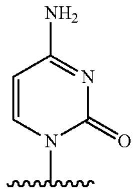 [SMILES: *n1ccc(N)nc1=O] |
| 304 | F | 1-Naphthyl | H | Me | 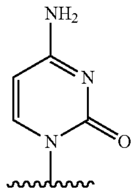 |
| 305 | OH | 1-Naphthyl | H | Me | 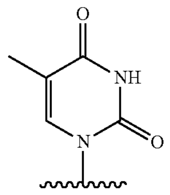 [SMILES: *n1cc(C)c(=O)[nH]c1=O] |

-continued
(V-1)
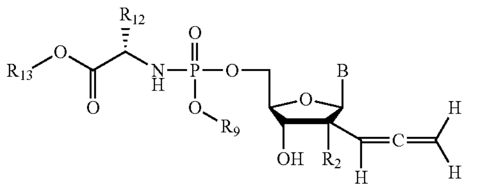
| Example # | $R_2$ | $R_9$ | $R_{12}$ | $R_{13}$ | B |
|---|---|---|---|---|---|
| 306 | F | 1-Naphthyl | H | Me | 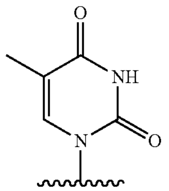 [SMILES: *n1cc(C)c(=O)[nH]c1=O] |
| 307 | OH | 1-Naphthyl | H | Me | 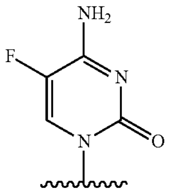 |
| 308 | F | 1-Naphthyl | H | Me | 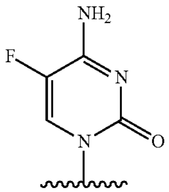 |
| 309 | OH | 1-Naphthyl | H | Me | 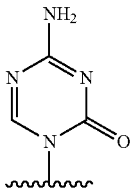 [SMILES: *n1cnc(N)nc1=O] |
| 310 | F | 1-Naphthyl | H | Me | 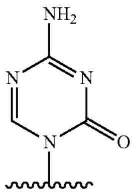 |
| 311 | OH | 1-Naphthyl | H | Me | 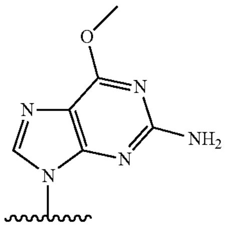 [SMILES: *n1cnc2c(OC)nc(N)nc21] |
-continued
(V-1)
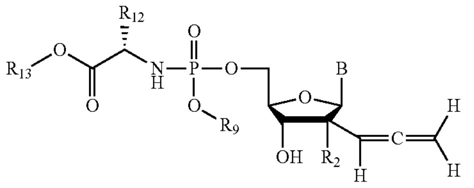
| Example # | $R_2$ | $R_9$ | $R_{12}$ | $R_{13}$ | B |
|---|---|---|---|---|---|
| 312 | F | 1-Naphthyl | H | Me | 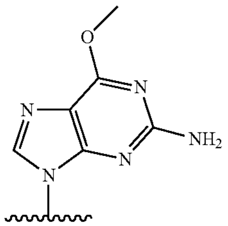 |
| 313 | OH | 1-Naphthyl | H | Me | 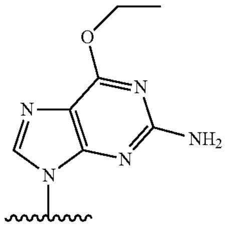 [SMILES: *n1cnc2c(OCC)nc(N)nc21] |
| 314 | F | 1-Naphthyl | H | Me | 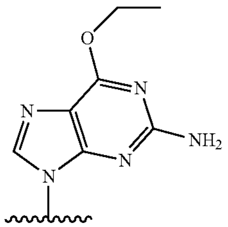 [SMILES: *n1cnc2c(OCC)nc(N)nc21] |
| 315 | OH | 1-Naphthyl | H | Me | 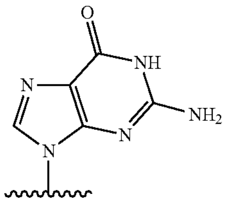 [SMILES: *n1cnc2c(=O)[nH]c(N)nc21] |
| 316 | F | 1-Naphthyl | H | Me | 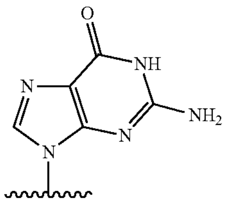 [SMILES: *n1cnc2c(=O)[nH]c(N)nc21] |
| 317 | OH | 1-Naphthyl | H | Me | 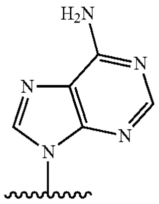 |

-continued
(V-1)
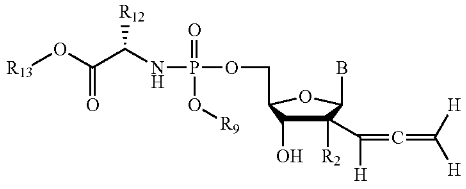
| Example # | $R_2$ | $R_9$ | $R_{12}$ | $R_{13}$ | B |
|---|---|---|---|---|---|
| 318 | F | 1-Naphthyl | H | Me | 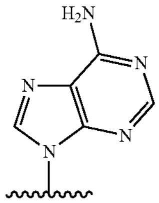 [SMILES: *n1cnc2c(N)ncnc21] |
| 319 | OH | 1-Naphthyl | H | Me | 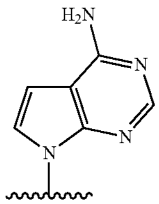 [SMILES: *n1ccc2c(N)ncnc21] |
| 320 | F | 1-Naphthyl | H | Me | 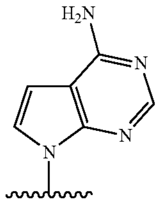 [SMILES: *n1ccc2c(N)ncnc21] |
| 321 | OH | Ph | Me | n-Pentyl | 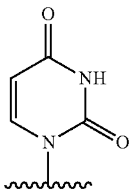 [SMILES: *n1ccc(=O)[nH]c1=O] |
| 322 | F | Ph | Me | n-Pentyl | 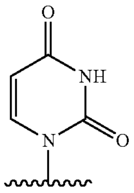 [SMILES: *n1ccc(=O)[nH]c1=O] |
| 323 | OH | Ph | Me | n-Pentyl | 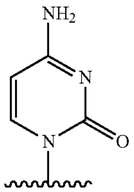 |
-continued
(V-1)
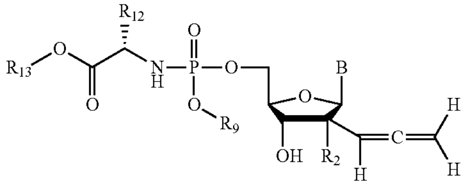
| Example # | $R_2$ | $R_9$ | $R_{12}$ | $R_{13}$ | B |
|---|---|---|---|---|---|
| 324 | F | Ph | Me | n-Pentyl | 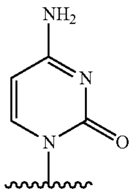 |
| 325 | OH | Ph | Me | n-Pentyl | 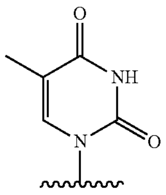 [SMILES: *n1cc(C)c(=O)[nH]c1=O] |
| 326 | F | Ph | Me | n-Pentyl | 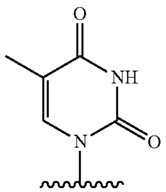 [SMILES: *n1cc(C)c(=O)[nH]c1=O] |
| 327 | OH | Ph | Me | n-Pentyl | 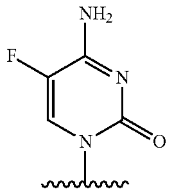 |
| 328 | F | Ph | Me | n-Pentyl | 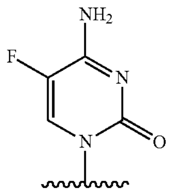 |
| 329 | OH | Ph | Me | n-Pentyl | 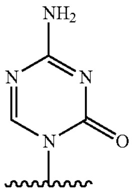 [SMILES: *n1cnc(N)nc1=O] |

-continued
(V-1)
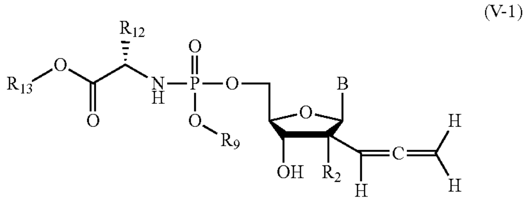
| Example # | $R_2$ | $R_9$ | $R_{12}$ | $R_{13}$ | B |
|---|---|---|---|---|---|
| 330 | F | Ph | Me | n-Pentyl | 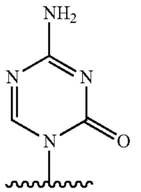 |
| 331 | OH | Ph | Me | n-Pentyl | 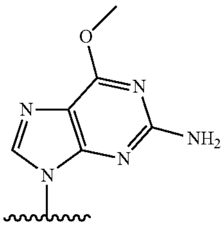 [SMILES: *n1cnc2c(OC)nc(N)nc21] |
| 332 | F | Ph | Me | n-Pentyl | 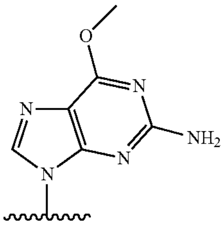 [SMILES: *n1cnc2c(OC)nc(N)nc21] |
| 333 | OH | Ph | Me | n-Pentyl | 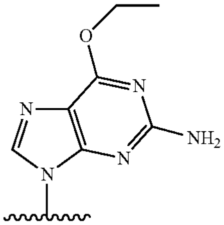 [SMILES: *n1cnc2c(OCC)nc(N)nc21] |
| 334 | F | Ph | Me | n-Pentyl | 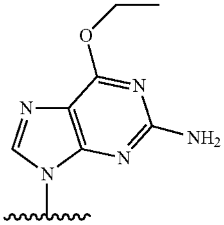 [SMILES: *n1cnc2c(OCC)nc(N)nc21] |
| 335 | OH | Ph | Me | n-Pentyl | 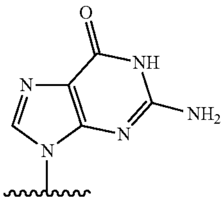 [SMILES: *n1cnc2c(=O)[nH]c(N)nc21] |
-continued
(V-1)
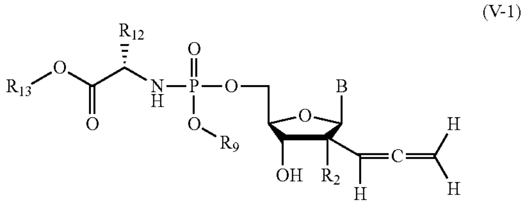
| Example # | $R_2$ | $R_9$ | $R_{12}$ | $R_{13}$ | B |
|---|---|---|---|---|---|
| 336 | F | Ph | Me | n-Pentyl | 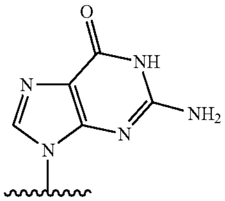 [SMILES: *n1cnc2c(=O)[nH]c(N)nc21] |
| 337 | OH | Ph | Me | n-Pentyl | 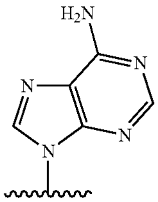 |
| 338 | F | Ph | Me | n-Pentyl | 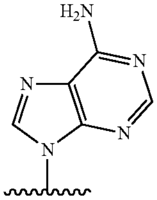 |
| 339 | OH | Ph | Me | n-Pentyl | 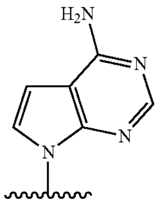 |
| 340 | F | Ph | Me | n-Pentyl | 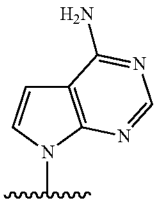 [SMILES: *n1ccc2c(N)ncnc21] |
| 341 | OH | 1-Naphthyl | Me | n-Pentyl | 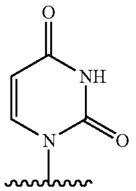 [SMILES: *n1ccc(=O)[nH]c1=O] |

-continued
(V-1)
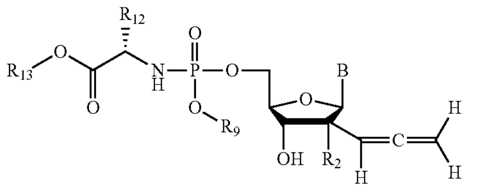
| Example # | $R_2$ | $R_9$ | $R_{12}$ | $R_{13}$ | B |
|---|---|---|---|---|---|
| 342 | F | 1-Naphthyl | Me | n-Pentyl | 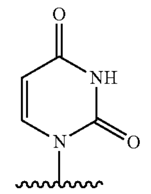 [SMILES: *n1ccc(=O)[nH]c1=O] |
| 343 | OH | 1-Naphthyl | Me | n-Pentyl | 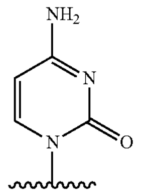 |
| 344 | F | 1-Naphthyl | Me | n-Pentyl | 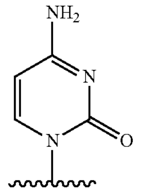 |
| 345 | OH | 1-Naphthyl | Me | n-Pentyl | 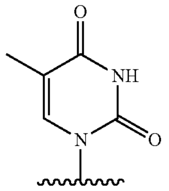 [SMILES: *n1cc(C)c(=O)[nH]c1=O] |
| 346 | F | 1-Naphthyl | Me | n-Pentyl | 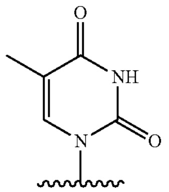 [SMILES: *n1cc(C)c(=O)[nH]c1=O] |
| 347 | OH | 1-Naphthyl | Me | n-Pentyl | 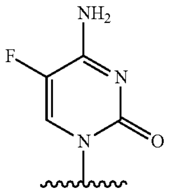 |
-continued
(V-1)
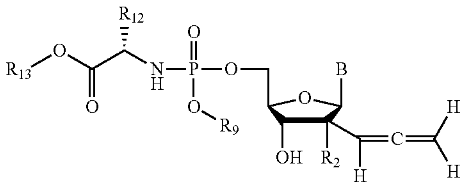
| Example # | $R_2$ | $R_9$ | $R_{12}$ | $R_{13}$ | B |
|---|---|---|---|---|---|
| 348 | F | 1-Naphthyl | Me | n-Pentyl | 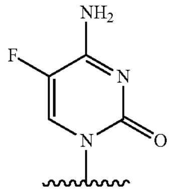 |
| 349 | OH | 1-Naphthyl | Me | n-Pentyl | 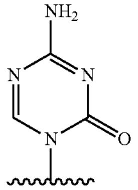 [SMILES: *n1cnc(N)nc1=O] |
| 350 | F | 1-Naphthyl | Me | n-Pentyl | 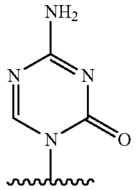 [SMILES: *n1cnc(N)nc1=O] |
| 351 | OH | 1-Naphthyl | Me | n-Pentyl | 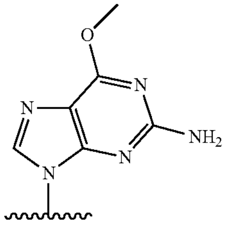 [SMILES: *n1cnc2c(OC)nc(N)nc21] |
| 352 | F | 1-Naphthyl | Me | n-Pentyl | 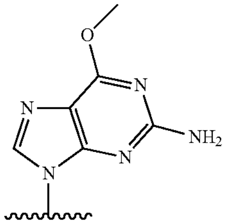 [SMILES: *n1cnc2c(OC)nc(N)nc21] |
| 353 | OH | 1-Naphthyl | Me | n-Pentyl | 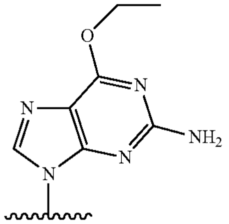 [SMILES: *n1cnc2c(OCC)nc(N)nc21] |

-continued
(V-1)
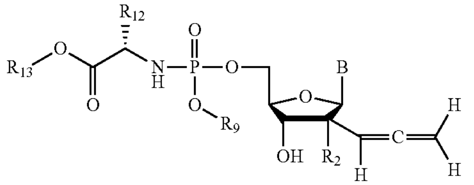
| Example # | $R_2$ | $R_9$ | $R_{12}$ | $R_{13}$ | B |
|---|---|---|---|---|---|
| 354 | F | 1-Naphthyl | Me | n-Pentyl | 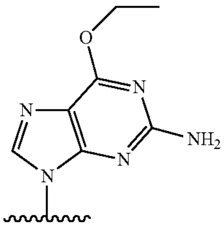 [SMILES: *n1cnc2c(OCC)nc(N)nc21] |
| 355 | OH | 1-Naphthyl | Me | n-Pentyl | 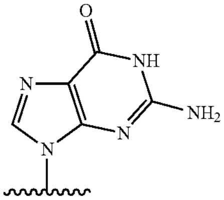 [SMILES: *n1cnc2c(=O)[nH]c(N)nc21] |
| 356 | F | 1-Naphthyl | Me | n-Pentyl | 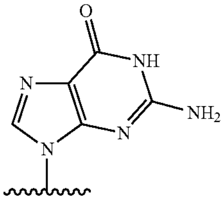 [SMILES: *n1cnc2c(=O)[nH]c(N)nc21] |
| 357 | OH | 1-Naphthyl | Me | n-Pentyl | 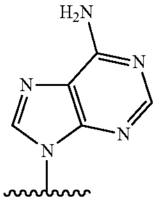 [SMILES: *n1cnc2c(N)ncnc21] |
| 358 | F | 1-Naphthyl | Me | n-Pentyl | 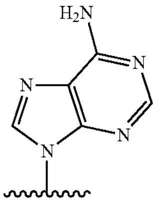 |
| 359 | OH | 1-Naphthyl | Me | n-Pentyl | 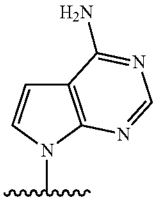 [SMILES: *n1ccc2c(N)ncnc21] |
-continued
(V-1)
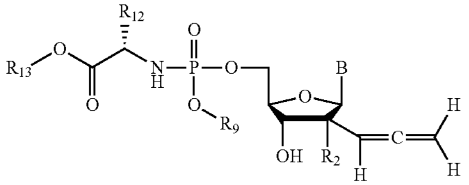
| Example # | $R_2$ | $R_9$ | $R_{12}$ | $R_{13}$ | B |
|---|---|---|---|---|---|
| 360 | F | 1-Naphthyl | Me | n-Pentyl | 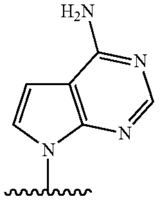 |
| 361 | OH | Ph | H | n-Pentyl | 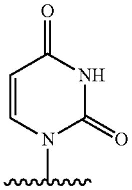 |
| 362 | F | Ph | H | n-Pentyl | 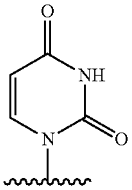 [SMILES: *n1ccc(=O)[nH]c1=O] |
| 363 | OH | Ph | H | n-Pentyl | 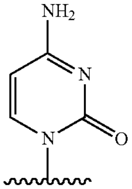 |
| 364 | F | Ph | H | n-Pentyl | 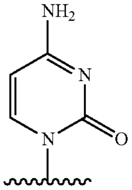 |
| 365 | OH | Ph | H | n-Pentyl | 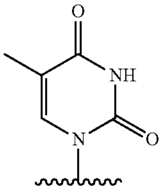 [SMILES: *n1cc(C)c(=O)[nH]c1=O] |

-continued
(V-1)
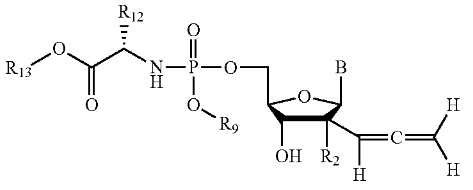
| Example # | $R_2$ | $R_9$ | $R_{12}$ | $R_{13}$ | B |
|---|---|---|---|---|---|
| 366 | F | Ph | H | n-Pentyl | 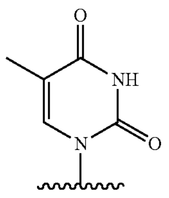 [SMILES: *n1cc(C)c(=O)[nH]c1=O] |
| 367 | OH | Ph | H | n-Pentyl | 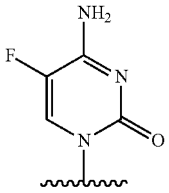 |
| 368 | F | Ph | H | n-Pentyl | 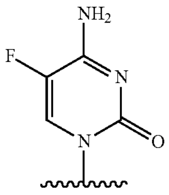 |
| 369 | OH | Ph | H | n-Pentyl | 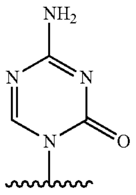 |
| 370 | F | Ph | H | n-Pentyl | 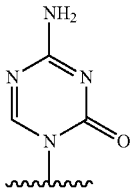 |
| 371 | OH | Ph | H | n-Pentyl | 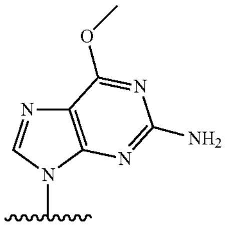 [SMILES: *n1cnc2c(OC)nc(N)nc21] |
-continued
(V-1)
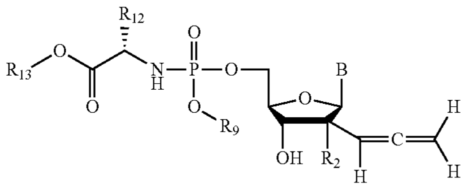
| Example # | $R_2$ | $R_9$ | $R_{12}$ | $R_{13}$ | B |
|---|---|---|---|---|---|
| 372 | F | Ph | H | n-Pentyl | 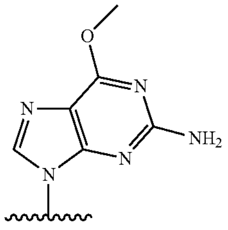 [SMILES: *n1cnc2c(OC)nc(N)nc21] |
| 373 | OH | Ph | H | n-Pentyl | 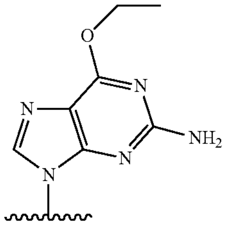 [SMILES: *n1cnc2c(OCC)nc(N)nc21] |
| 374 | F | Ph | H | n-Pentyl | 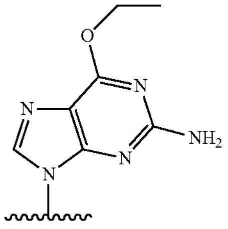 [SMILES: *n1cnc2c(OCC)nc(N)nc21] |
| 375 | OH | Ph | H | n-Pentyl | 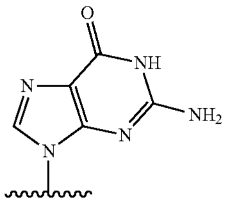 [SMILES: *n1cnc2c(=O)[nH]c(N)nc21] |
| 376 | F | Ph | H | n-Pentyl | 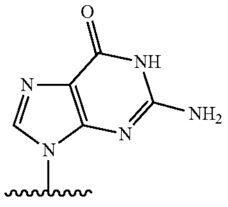 [SMILES: *n1cnc2c(=O)[nH]c(N)nc21] |
| 377 | OH | Ph | H | n-Pentyl | 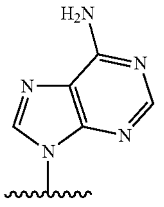 [SMILES: *n1cnc2c(N)ncnc21] |

-continued
(V-1)
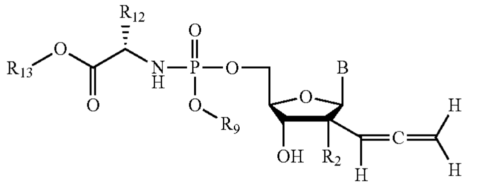
| Example # | $R_2$ | $R_9$ | $R_{12}$ | $R_{13}$ | B |
|---|---|---|---|---|---|
| 378 | F | Ph | H | n-Pentyl | 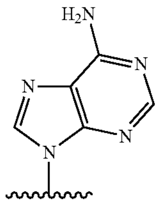 [SMILES: *n1cnc2c(N)ncnc21] |
| 379 | OH | Ph | H | n-Pentyl | 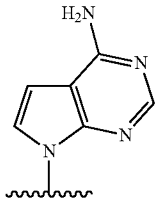 [SMILES: *n1ccc2c(N)ncnc21] |
| 380 | F | Ph | H | n-Pentyl | 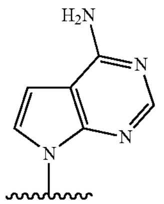 [SMILES: *n1ccc2c(N)ncnc21] |
| 381 | OH | 1-Naphthyl | H | n-Pentyl | 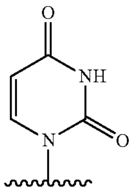 [SMILES: *n1ccc(=O)[nH]c1=O] |
| 382 | F | 1-Naphthyl | H | n-Pentyl | 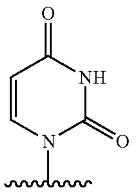 [SMILES: *n1ccc(=O)[nH]c1=O] |
| 383 | OH | 1-Naphthyl | H | n-Pentyl | 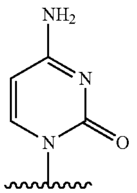 |
-continued
(V-1)
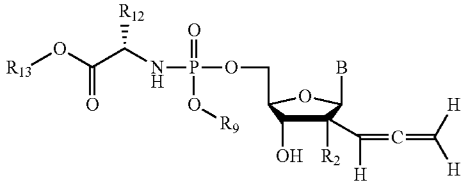
| Example # | $R_2$ | $R_9$ | $R_{12}$ | $R_{13}$ | B |
|---|---|---|---|---|---|
| 384 | F | 1-Naphthyl | H | n-Pentyl | 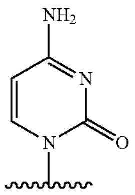 [SMILES: *n1ccc(N)nc1=O] |
| 385 | OH | 1-Naphthyl | H | n-Pentyl | 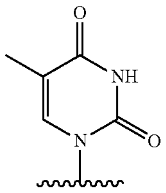 [SMILES: *n1cc(C)c(=O)[nH]c1=O] |
| 386 | F | 1-Naphthyl | H | n-Pentyl | 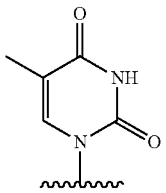 [SMILES: *n1cc(C)c(=O)[nH]c1=O] |
| 387 | OH | 1-Naphthyl | H | n-Pentyl | 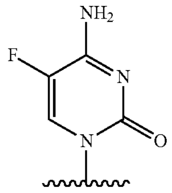 |
| 388 | F | 1-Naphthyl | H | n-Pentyl | 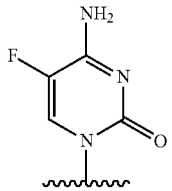 |
| 389 | OH | 1-Naphthyl | H | n-Pentyl | 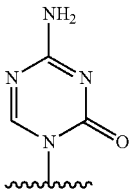 [SMILES: *n1cnc(N)nc1=O] |

-continued
(V-1)
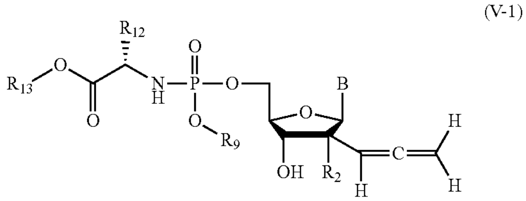
| Example # | $R_2$ | $R_9$ | $R_{12}$ | $R_{13}$ | B |
|---|---|---|---|---|---|
| 390 | F | 1-Naphthyl | H | n-Pentyl | 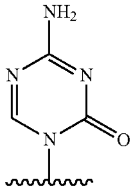 [SMILES: *n1cnc(N)nc1=O] |
| 391 | OH | 1-Naphthyl | H | n-Pentyl | 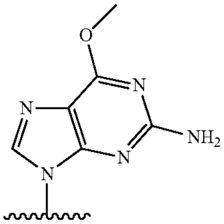 [SMILES: *n1cnc2c(OC)nc(N)nc21] |
| 392 | F | 1-Naphthyl | H | n-Pentyl | 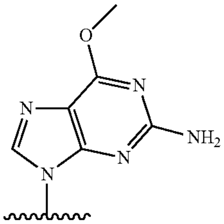 [SMILES: *n1cnc2c(OC)nc(N)nc21] |
| 393 | OH | 1-Naphthyl | H | n-Pentyl | 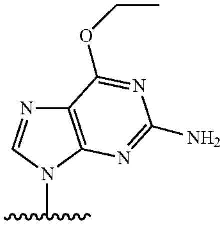 [SMILES: *n1cnc2c(OCC)nc(N)nc21] |
| 394 | F | 1-Naphthyl | H | n-Pentyl | 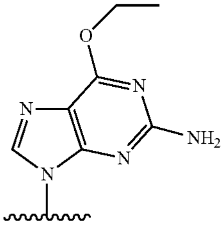 [SMILES: *n1cnc2c(OCC)nc(N)nc21] |
| 395 | OH | 1-Naphthyl | H | n-Pentyl | 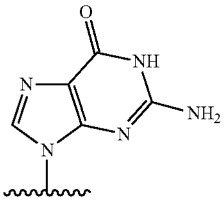 [SMILES: *n1cnc2c(=O)[nH]c(N)nc21] |
-continued
(V-1)
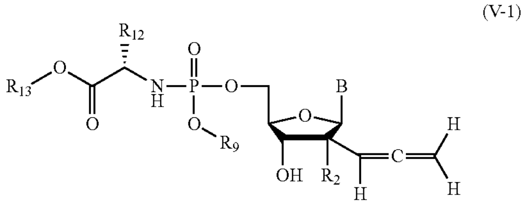
| Example # | $R_2$ | $R_9$ | $R_{12}$ | $R_{13}$ | B |
|---|---|---|---|---|---|
| 396 | F | 1-Naphthyl | H | n-Pentyl | 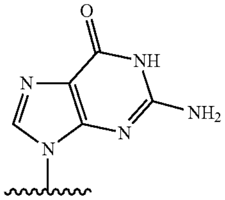 [SMILES: *n1cnc2c(=O)[nH]c(N)nc21] |
| 397 | OH | 1-Naphthyl | H | n-Pentyl | 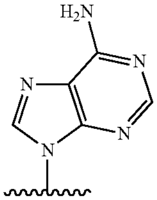 [SMILES: *n1cnc2c(N)ncnc21] |
| 398 | F | 1-Naphthyl | H | n-Pentyl | 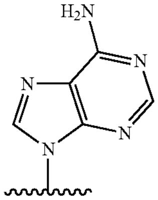 |
| 399 | OH | 1-Naphthyl | H | n-Pentyl | 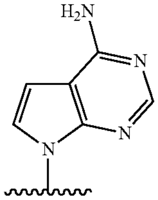 |
| 400 | F | 1-Naphthyl | H | n-Pentyl | 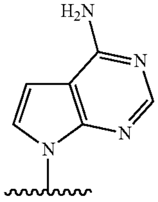 |
| 401 | OH | Ph | Me | i-Pr | 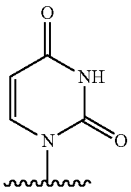 [SMILES: *n1ccc(=O)[nH]c1=O] |

-continued
(V-1)
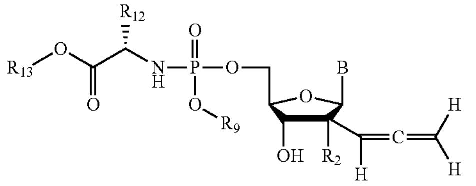
| Example # | $R_2$ | $R_9$ | $R_{12}$ | $R_{13}$ | B |
|---|---|---|---|---|---|
| 402 | F | Ph | Me | i-Pr | 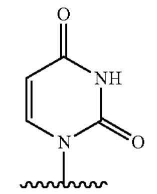 [SMILES: *n1ccc(=O)[nH]c1=O] |
| 403 | OH | Ph | Me | i-Pr | 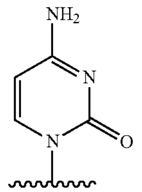 |
| 404 | F | Ph | Me | i-Pr | 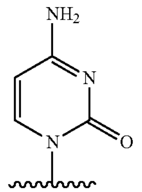 |
| 405 | OH | Ph | Me | i-Pr | 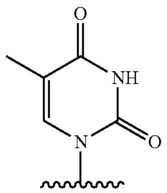 [SMILES: *n1cc(C)c(=O)[nH]c1=O] |
| 406 | F | Ph | Me | i-Pr | 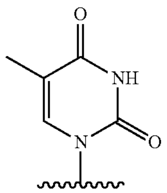 [SMILES: *n1cc(C)c(=O)[nH]c1=O] |
| 407 | OH | Ph | Me | i-Pr | 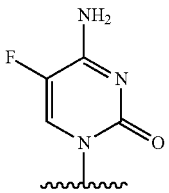 |
-continued
(V-1)
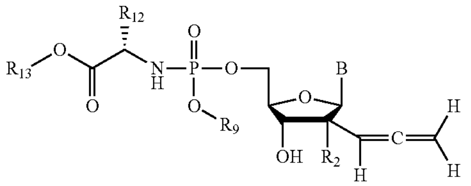
| Example # | $R_2$ | $R_9$ | $R_{12}$ | $R_{13}$ | B |
|---|---|---|---|---|---|
| 408 | F | Ph | Me | i-Pr | 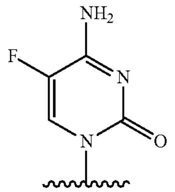 |
| 409 | OH | Ph | Me | i-Pr | 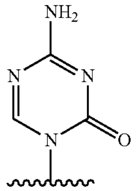 [SMILES: *n1cnc(N)nc1=O] |
| 410 | F | Ph | Me | i-Pr | 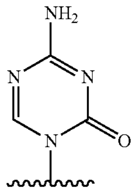 [SMILES: *n1cnc(N)nc1=O] |
| 411 | OH | Ph | Me | i-Pr | 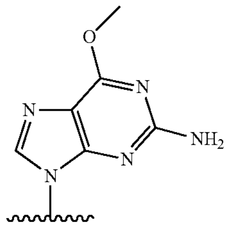 [SMILES: *n1cnc2c(OC)nc(N)nc21] |
| 412 | F | Ph | Me | i-Pr | 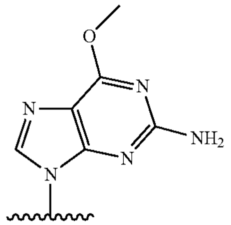 [SMILES: *n1cnc2c(OC)nc(N)nc21] |
| 413 | OH | Ph | Me | i-Pr | 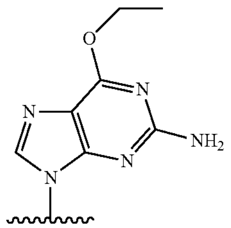 [SMILES: *n1cnc2c(OCC)nc(N)nc21] |

-continued
(V-1)
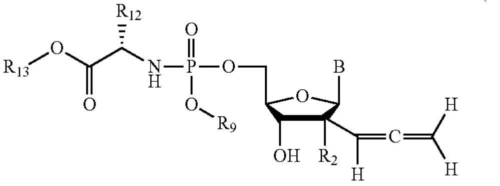
| Example # | $R_2$ | $R_9$ | $R_{12}$ | $R_{13}$ | B |
|---|---|---|---|---|---|
| 414 | F | Ph | Me | i-Pr | 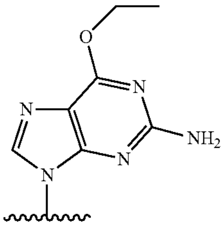 [SMILES: *n1cnc2c(OCC)nc(N)nc21] |
| 415 | OH | Ph | Me | i-Pr | 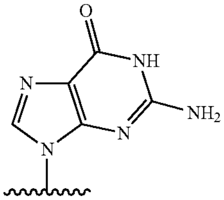 [SMILES: *n1cnc2c(=O)[nH]c(N)nc21] |
| 416 | F | Ph | Me | i-Pr | 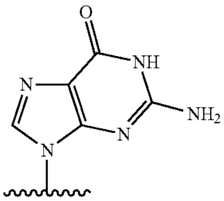 [SMILES: *n1cnc2c(=O)[nH]c(N)nc21] |
| 417 | OH | Ph | Me | i-Pr | 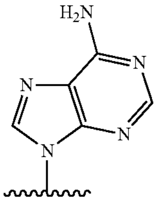 [SMILES: *n1cnc2c(N)ncnc21] |
| 418 | F | Ph | Me | i-Pr | 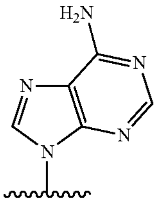 [SMILES: *n1cnc2c(N)ncnc21] |
| 419 | OH | Ph | Me | i-Pr | 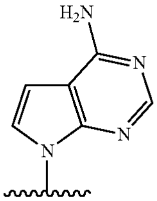 [SMILES: *n1ccc2c(N)ncnc21] |
-continued
(V-1)
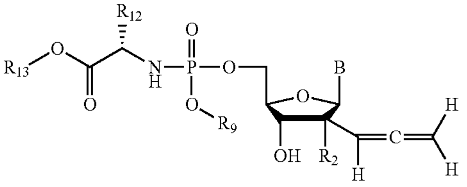
| Example # | $R_2$ | $R_9$ | $R_{12}$ | $R_{13}$ | B |
|---|---|---|---|---|---|
| 420 | F | Ph | Me | i-Pr | 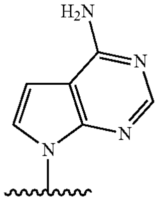 |
| 421 | OH | 1-Naphthyl | Me | i-Pr | 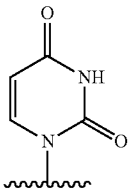 |
| 422 | F | 1-Naphthyl | Me | i-Pr | 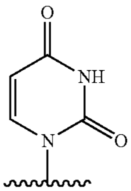 [SMILES: *n1ccc(=O)[nH]c1=O] |
| 423 | OH | 1-Naphthyl | Me | i-Pr | 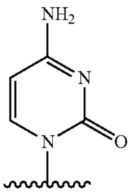 |
| 424 | F | 1-Naphthyl | Me | i-Pr | 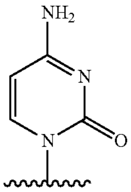 |
| 425 | OH | 1-Naphthyl | Me | i-Pr | 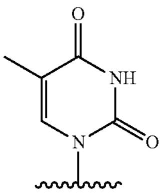 [SMILES: *n1cc(C)c(=O)[nH]c1=O] |

-continued
(V-1)
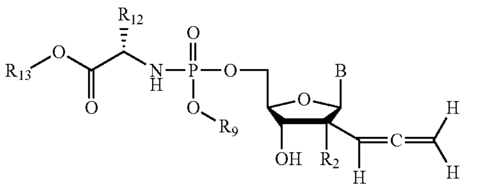
| Example # | $R_2$ | $R_9$ | $R_{12}$ | $R_{13}$ | B |
|---|---|---|---|---|---|
| 426 | F | 1-Naphthyl | Me | i-Pr | 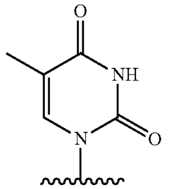 |
| 427 | OH | 1-Naphthyl | Me | i-Pr | 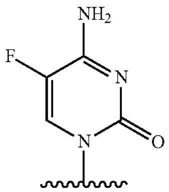 |
| 428 | F | 1-Naphthyl | Me | i-Pr | 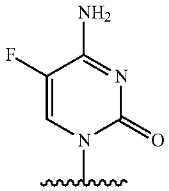 |
| 429 | OH | 1-Naphthyl | Me | i-Pr | 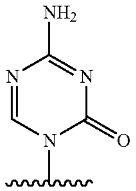 [SMILES: *n1cnc(N)nc1=O] |
| 430 | F | 1-Naphthyl | Me | i-Pr | 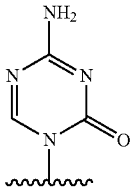 [SMILES: *n1cnc(N)nc1=O] |
| 431 | OH | 1-Naphthyl | Me | i-Pr | 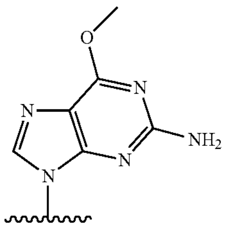 [SMILES: *n1cnc2c(OC)nc(N)nc21] |
-continued
(V-1)
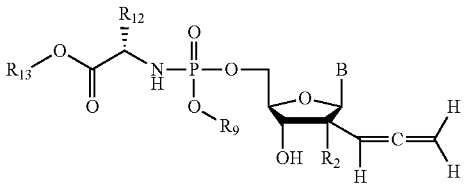
| Example # | $R_2$ | $R_9$ | $R_{12}$ | $R_{13}$ | B |
|---|---|---|---|---|---|
| 432 | F | 1-Naphthyl | Me | i-Pr | 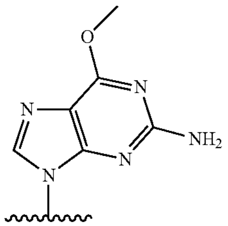 [SMILES: *n1cnc2c(OC)nc(N)nc21] |
| 433 | OH | 1-Naphthyl | Me | i-Pr | 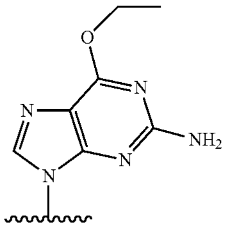 [SMILES: *n1cnc2c(OCC)nc(N)nc21] |
| 434 | F | 1-Naphthyl | Me | i-Pr | 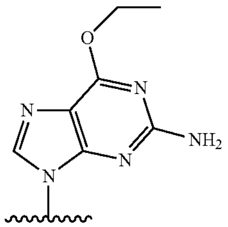 [SMILES: *n1cnc2c(OCC)nc(N)nc21] |
| 435 | OH | 1-Naphthyl | Me | i-Pr | 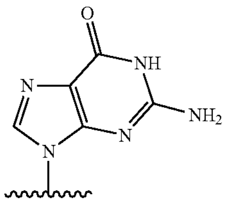 [SMILES: *n1cnc2c(=O)[nH]c(N)nc21] |
| 436 | F | 1-Naphthyl | Me | i-Pr | 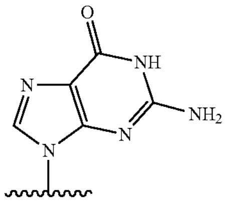 [SMILES: *n1cnc2c(=O)[nH]c(N)nc21] |
| 437 | OH | 1-Naphthyl | Me | i-Pr | 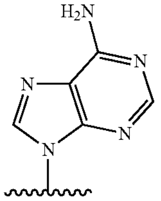 |

-continued
(V-1)
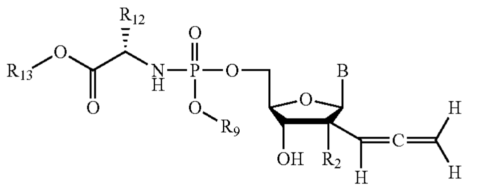
| Example # | $R_2$ | $R_9$ | $R_{12}$ | $R_{13}$ | B |
|---|---|---|---|---|---|
| 438 | F | 1-Naphthyl | Me | i-Pr | 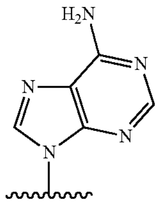 [SMILES: *n1cnc2c(N)ncnc21] |
| 439 | OH | 1-Naphthyl | Me | i-Pr | 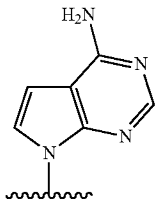 [SMILES: *n1ccc2c(N)ncnc21] |
| 440 | F | 1-Naphthyl | Me | i-Pr | 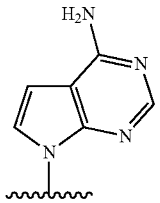 [SMILES: *n1ccc2c(N)ncnc21] |
| 441 | OH | Ph | H | i-Pr | 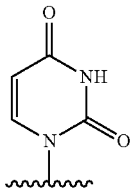 [SMILES: *n1ccc(=O)[nH]c1=O] |
| 442 | F | Ph | H | i-Pr | 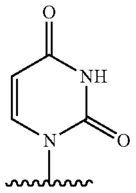 [SMILES: *n1ccc(=O)[nH]c1=O] |
| 443 | OH | Ph | H | i-Pr | 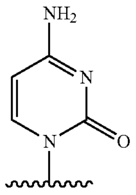 |
-continued
(V-1)
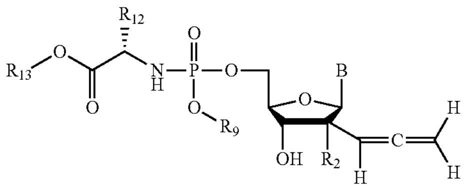
| Example # | $R_2$ | $R_9$ | $R_{12}$ | $R_{13}$ | B |
|---|---|---|---|---|---|
| 444 | F | Ph | H | i-Pr | 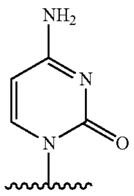 |
| 445 | OH | Ph | H | i-Pr | 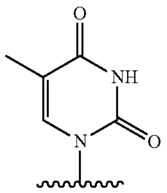 [SMILES: *n1cc(C)c(=O)[nH]c1=O] |
| 446 | F | Ph | H | i-Pr | 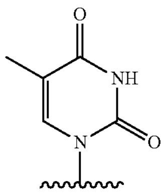 |
| 447 | OH | Ph | H | i-Pr | 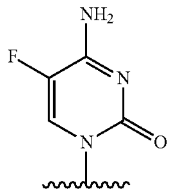 |
| 448 | F | Ph | H | i-Pr | 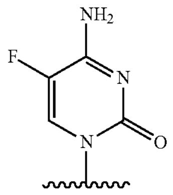 |
| 449 | OH | Ph | H | i-Pr | 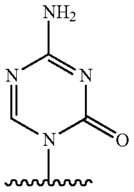 [SMILES: *n1cnc(N)nc1=O] |

-continued
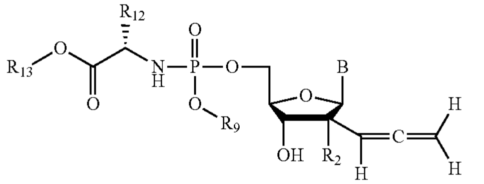
(V-1)
| Example # | $R_2$ | $R_9$ | $R_{12}$ | $R_{13}$ | B |
|---|---|---|---|---|---|
| 450 | F | Ph | H | i-Pr | 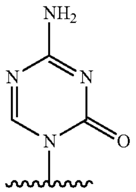 |
| 451 | OH | Ph | H | i-Pr | 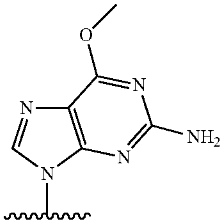 [SMILES: *n1cnc2c(OC)nc(N)nc21] |
| 452 | F | Ph | H | i-Pr | 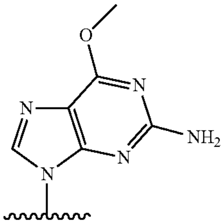 [SMILES: *n1cnc2c(OC)nc(N)nc21] |
| 453 | OH | Ph | H | i-Pr | 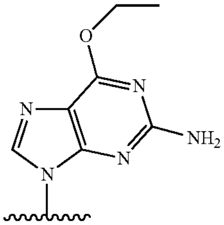 [SMILES: *n1cnc2c(OCC)nc(N)nc21] |
| 454 | F | Ph | H | i-Pr | 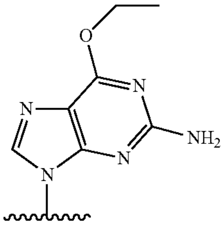 [SMILES: *n1cnc2c(OCC)nc(N)nc21] |
| 455 | OH | Ph | H | i-Pr | 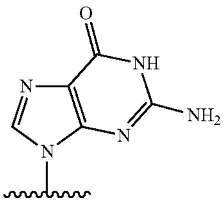 [SMILES: *n1cnc2c(=O)[nH]c(N)nc21] |
-continued
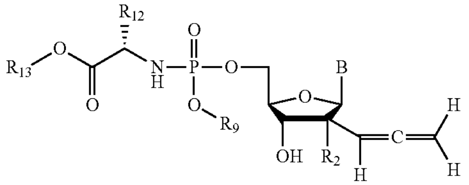
(V-1)
| Example # | $R_2$ | $R_9$ | $R_{12}$ | $R_{13}$ | B |
|---|---|---|---|---|---|
| 456 | F | Ph | H | i-Pr | 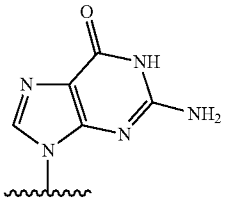 [SMILES: *n1cnc2c(=O)[nH]c(N)nc21] |
| 457 | OH | Ph | H | i-Pr | 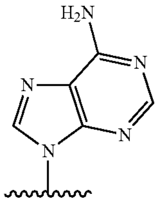 [SMILES: *n1cnc2c(N)ncnc21] |
| 458 | F | Ph | H | i-Pr | 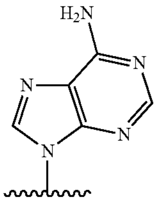 |
| 459 | OH | Ph | H | i-Pr | 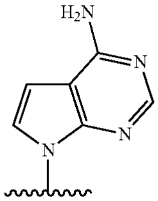 [SMILES: *n1ccc2c(N)ncnc21] |
| 460 | F | Ph | H | i-Pr | 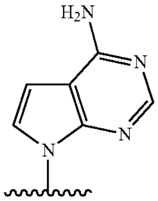 [SMILES: *n1ccc2c(N)ncnc21] |
| 461 | OH | 1-Naphthyl | H | i-Pr | 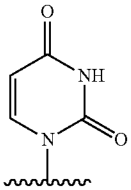 [SMILES: *n1ccc(=O)[nH]c1=O] |

-continued
(V-1)
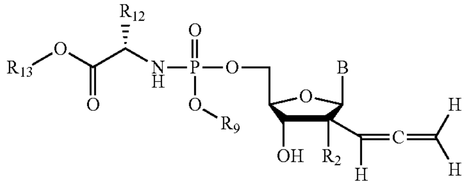
| Example # | $R_2$ | $R_9$ | $R_{12}$ | $R_{13}$ | B |
|---|---|---|---|---|---|
| 462 | F | 1-Naphthyl | H | i-Pr | 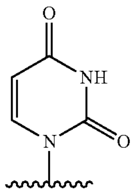 [SMILES: *n1ccc(=O)[nH]c1=O] |
| 463 | OH | 1-Naphthyl | H | i-Pr | 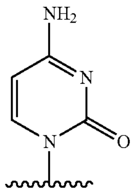 |
| 464 | F | 1-Naphthyl | H | i-Pr | 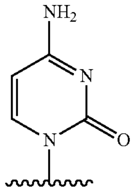 |
| 465 | OH | 1-Naphthyl | H | i-Pr | 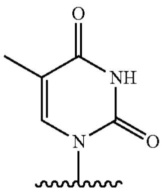 [SMILES: *n1cc(C)c(=O)[nH]c1=O] |
| 466 | F | 1-Naphthyl | H | i-Pr | 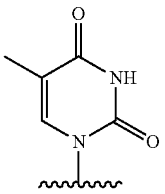 |
| 467 | OH | 1-Naphthyl | H | i-Pr | 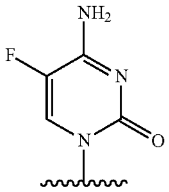 |
-continued
(V-1)
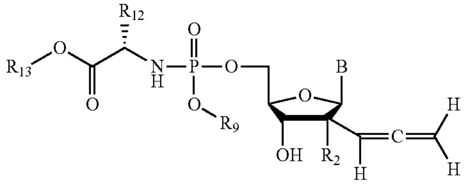
| Example # | $R_2$ | $R_9$ | $R_{12}$ | $R_{13}$ | B |
|---|---|---|---|---|---|
| 468 | F | 1-Naphthyl | H | i-Pr | 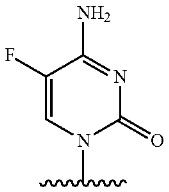 |
| 469 | OH | 1-Naphthyl | H | i-Pr | 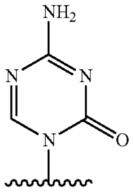 [SMILES: *n1cnc(N)nc1=O] |
| 470 | F | 1-Naphthyl | H | i-Pr | 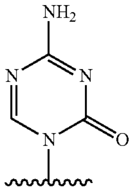 [SMILES: *n1cnc(N)nc1=O] |
| 471 | OH | 1-Naphthyl | H | i-Pr | 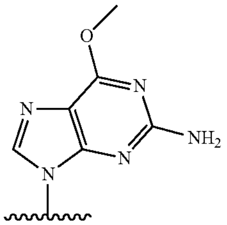 [SMILES: *n1cnc2c(OC)nc(N)nc21] |
| 472 | F | 1-Naphthyl | H | i-Pr | 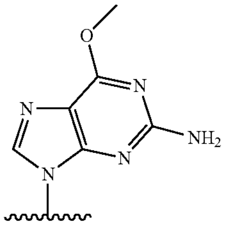 [SMILES: *n1cnc2c(OC)nc(N)nc21] |
| 473 | OH | 1-Naphthyl | H | i-Pr | 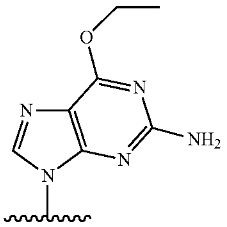 [SMILES: *n1cnc2c(OCC)nc(N)nc21] |

-continued
(V-1)
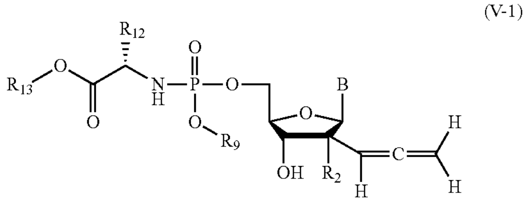
| Example # | $R_2$ | $R_9$ | $R_{12}$ | $R_{13}$ | B |
|---|---|---|---|---|---|
| 474 | F | 1-Naphthyl | H | i-Pr | 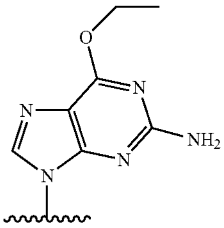 [SMILES: *n1cnc2c(OCC)nc(N)nc21] |
| 475 | OH | 1-Naphthyl | H | i-Pr | 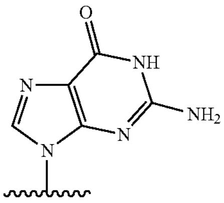 [SMILES: *n1cnc2c(=O)[nH]c(N)nc21] |
| 476 | F | 1-Naphthyl | H | i-Pr | 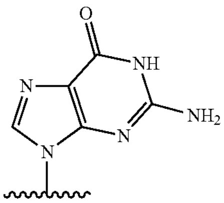 [SMILES: *n1cnc2c(=O)[nH]c(N)nc21] |
| 477 | OH | 1-Naphthyl | H | i-Pr | 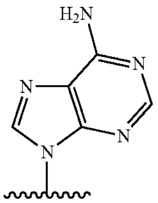 [SMILES: *n1cnc2c(N)ncnc21] |
| 478 | F | 1-Naphthyl | H | i-Pr | 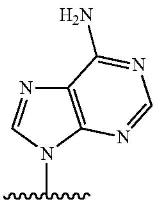 [SMILES: *n1cnc2c(N)ncnc21] |
| 479 | OH | 1-Naphthyl | H | i-Pr | 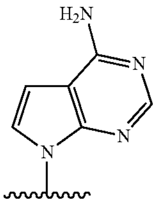 [SMILES: *n1ccc2c(N)ncnc21] |
-continued
(V-1)
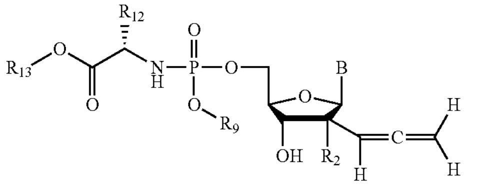
| Example # | $R_2$ | $R_9$ | $R_{12}$ | $R_{13}$ | B |
|---|---|---|---|---|---|
| 480 | F | 1-Naphthyl | H | i-Pr | 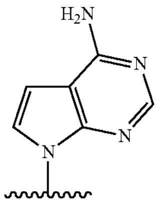 [SMILES: *n1ccc2c(N)ncnc21] |
| 481 | OH | Ph | Me | Benzyl | 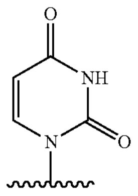 |
| 482 | F | Ph | Me | Benzyl | 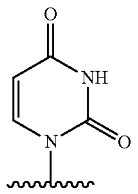 [SMILES: *n1ccc(=O)[nH]c1=O] |
| 483 | OH | Ph | Me | Benzyl | 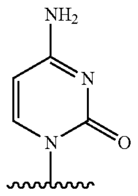 |
| 484 | F | Ph | Me | Benzyl | 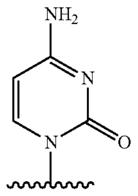 |
| 485 | OH | Ph | Me | Benzyl | 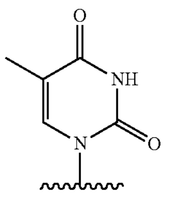 [SMILES: *n1cc(C)c(=O)[nH]c1=O] |

-continued
(V-1)
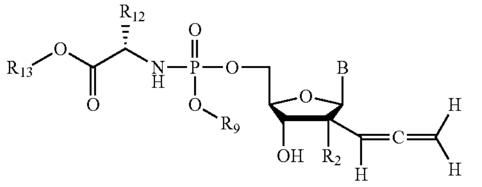
| Example # | $R_2$ | $R_9$ | $R_{12}$ | $R_{13}$ | B |
|---|---|---|---|---|---|
| 486 | F | Ph | Me | Benzyl | 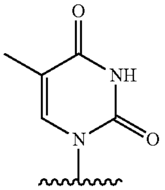 [SMILES: *n1cc(C)c(=O)[nH]c1=O] |
| 487 | OH | Ph | Me | Benzyl | 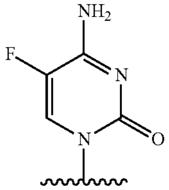 |
| 488 | F | Ph | Me | Benzyl | 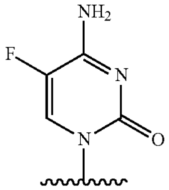 |
| 489 | OH | Ph | Me | Benzyl | 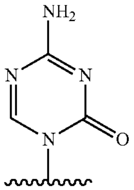 [SMILES: *n1cnc(N)nc1=O] |
| 490 | F | Ph | Me | Benzyl | 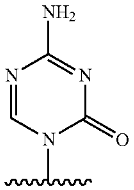 |
| 491 | OH | Ph | Me | Benzyl | 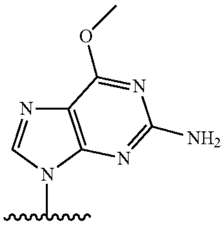 [SMILES: *n1cnc2c(OC)nc(N)nc21] |
-continued
(V-1)
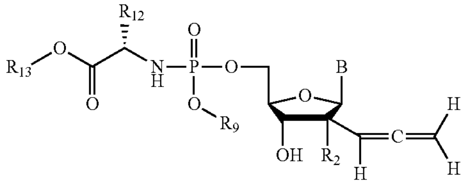
| Example # | $R_2$ | $R_9$ | $R_{12}$ | $R_{13}$ | B |
|---|---|---|---|---|---|
| 492 | F | Ph | Me | Benzyl | 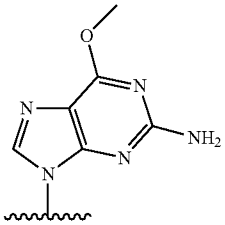 [SMILES: *n1cnc2c(OC)nc(N)nc21] |
| 493 | OH | Ph | Me | Benzyl | 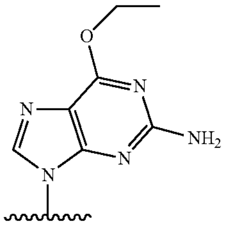 [SMILES: *n1cnc2c(OCC)nc(N)nc21] |
| 494 | F | Ph | Me | Benzyl | 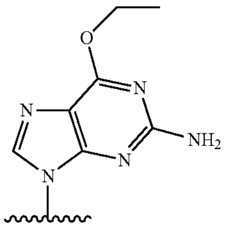 [SMILES: *n1cnc2c(OCC)nc(N)nc21] |
| 495 | OH | Ph | Me | Benzyl | 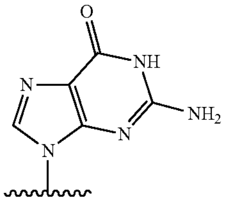 [SMILES: *n1cnc2c(=O)[nH]c(N)nc21] |
| 496 | F | Ph | Me | Benzyl | 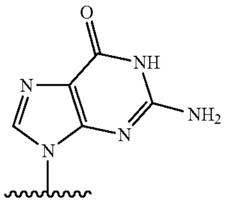 [SMILES: *n1cnc2c(=O)[nH]c(N)nc21] |
| 497 | OH | Ph | Me | Benzyl | 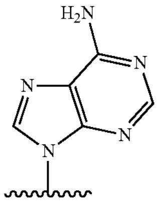 [SMILES: *n1cnc2c(N)ncnc21] |

-continued
(V-1)
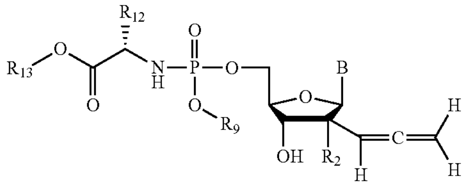
| Example # | $R_2$ | $R_9$ | $R_{12}$ | $R_{13}$ | B |
|---|---|---|---|---|---|
| 498 | F | Ph | Me | Benzyl | 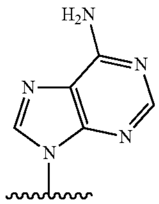 [SMILES: *n1cnc2c(N)ncnc21] |
| 499 | OH | Ph | Me | Benzyl | 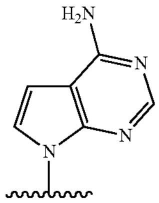 [SMILES: *n1ccc2c(N)ncnc21] |
| 500 | F | Ph | Me | Benzyl | 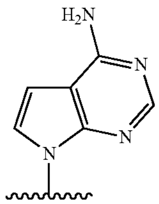 |
| 501 | OH | 1-Naphthyl | Me | Benzyl | 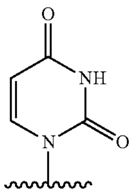 [SMILES: *n1ccc(=O)[nH]c1=O] |
| 502 | F | 1-Naphthyl | Me | Benzyl | 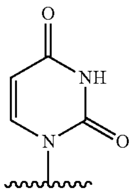 [SMILES: *n1ccc(=O)[nH]c1=O] |
| 503 | OH | 1-Naphthyl | Me | Benzyl | 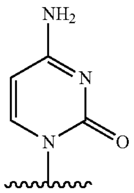 |
-continued
(V-1)
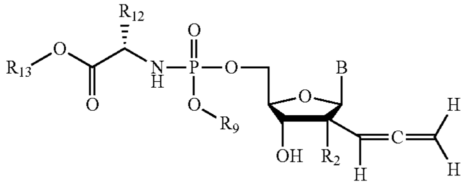
| Example # | $R_2$ | $R_9$ | $R_{12}$ | $R_{13}$ | B |
|---|---|---|---|---|---|
| 504 | F | 1-Naphthyl | Me | Benzyl | 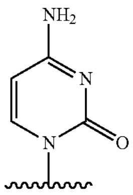 |
| 505 | OH | 1-Naphthyl | Me | Benzyl | 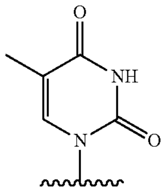 [SMILES: *n1cc(C)c(=O)[nH]c1=O] |
| 506 | F | 1-Naphthyl | Me | Benzyl | 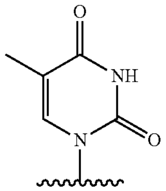 [SMILES: *n1cc(C)c(=O)[nH]c1=O] |
| 507 | OH | 1-Naphthyl | Me | Benzyl | 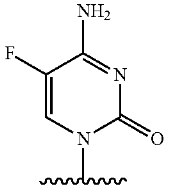 |
| 508 | F | 1-Naphthyl | Me | Benzyl | 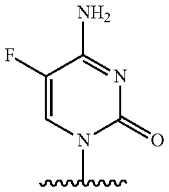 |
| 509 | OH | 1-Naphthyl | Me | Benzyl | 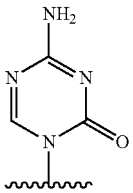 [SMILES: *n1cnc(N)nc1=O] |

-continued
(V-1)
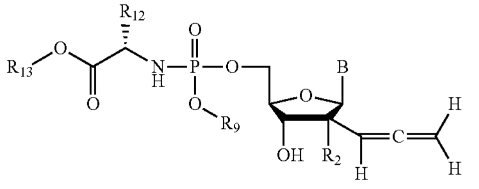
| Example # | $R_2$ | $R_9$ | $R_{12}$ | $R_{13}$ | B |
|---|---|---|---|---|---|
| 510 | F | 1-Naphthyl | Me | Benzyl | 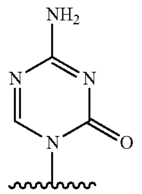 |
| 511 | OH | 1-Naphthyl | Me | Benzyl | 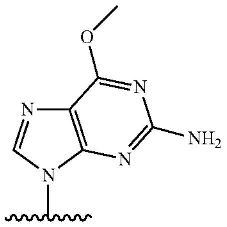 [SMILES: *n1cnc2c(OC)nc(N)nc21] |
| 512 | F | 1-Naphthyl | Me | Benzyl | 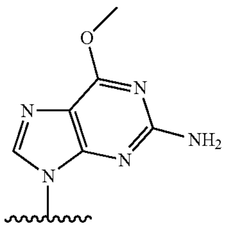 [SMILES: *n1cnc2c(OC)nc(N)nc21] |
| 513 | OH | 1-Naphthyl | Me | Benzyl | 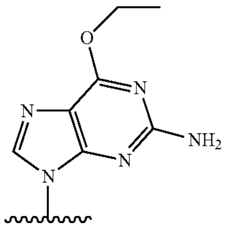 [SMILES: *n1cnc2c(OCC)nc(N)nc21] |
| 514 | F | 1-Naphthyl | Me | Benzyl | 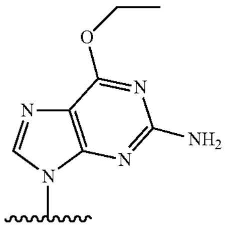 [SMILES: *n1cnc2c(OCC)nc(N)nc21] |
| 515 | OH | 1-Naphthyl | Me | Benzyl | 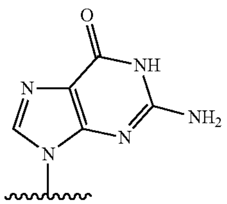 [SMILES: *n1cnc2c(=O)[nH]c(N)nc21] |
-continued
(V-1)
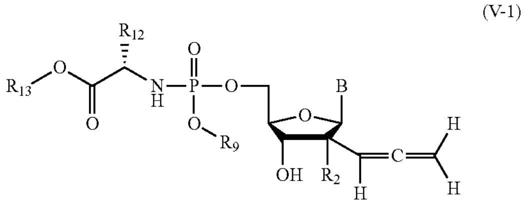
| Example # | $R_2$ | $R_9$ | $R_{12}$ | $R_{13}$ | B |
|---|---|---|---|---|---|
| 516 | F | 1-Naphthyl | Me | Benzyl | 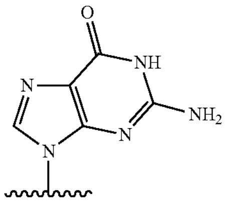 [SMILES: *n1cnc2c(=O)[nH]c(N)nc21] |
| 517 | OH | 1-Naphthyl | Me | Benzyl | 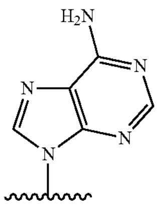 [SMILES: *n1cnc2c(N)ncnc21] |
| 518 | F | 1-Naphthyl | Me | Benzyl | 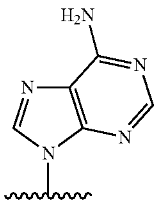 [SMILES: *n1cnc2c(N)ncnc21] |
| 519 | OH | 1-Naphthyl | Me | Benzyl | 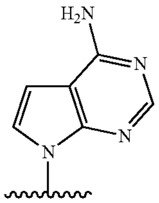 [SMILES: *n1ccc2c(N)ncnc21] |
| 520 | F | 1-Naphthyl | Me | Benzyl | 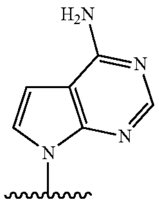 |
| 521 | OH | Ph | H | Benzyl | 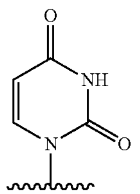 [SMILES: *n1ccc(=O)[nH]c1=O] |

-continued
(V-1)
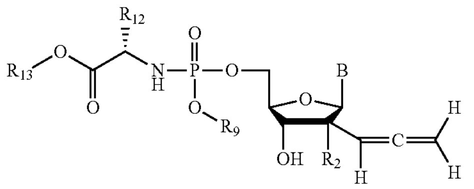
| Example # | $R_2$ | $R_9$ | $R_{12}$ | $R_{13}$ | B |
|---|---|---|---|---|---|
| 522 | F | Ph | H | Benzyl | 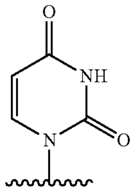 [SMILES: *n1ccc(=O)[nH]c1=O] |
| 523 | OH | Ph | H | Benzyl | 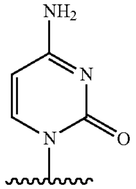 |
| 524 | F | Ph | H | Benzyl | 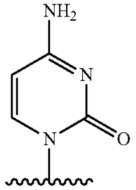 |
| 525 | OH | Ph | H | Benzyl | 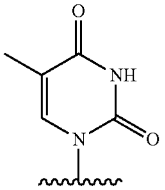 |
| 526 | F | Ph | H | Benzyl | 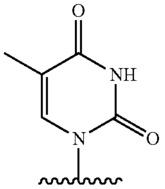 [SMILES: *n1cc(C)c(=O)[nH]c1=O] |
| 527 | OH | Ph | H | Benzyl | 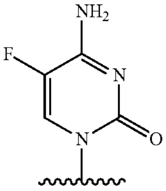 |
-continued
(V-1)
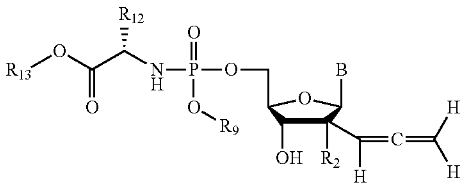
| Example # | $R_2$ | $R_9$ | $R_{12}$ | $R_{13}$ | B |
|---|---|---|---|---|---|
| 528 | F | Ph | H | Benzyl | 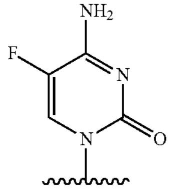 |
| 529 | OH | Ph | H | Benzyl | 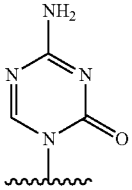 [SMILES: *n1cnc(N)nc1=O] |
| 530 | F | Ph | H | Benzyl | 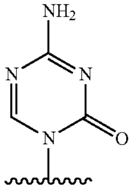 [SMILES: *n1cnc(N)nc1=O] |
| 531 | OH | Ph | H | Benzyl | 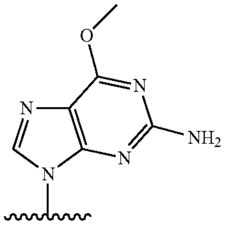 [SMILES: *n1cnc2c(OC)nc(N)nc21] |
| 532 | F | Ph | H | Benzyl | 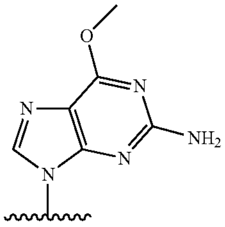 [SMILES: *n1cnc2c(OC)nc(N)nc21] |
| 533 | OH | Ph | H | Benzyl | 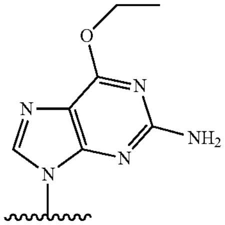 [SMILES: *n1cnc2c(OCC)nc(N)nc21] |

-continued
(V-1)
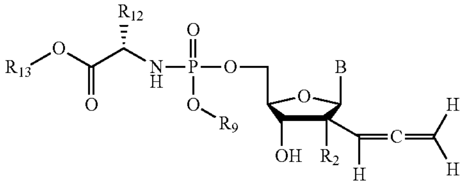
| Example # | $R_2$ | $R_9$ | $R_{12}$ | $R_{13}$ | B |
|---|---|---|---|---|---|
| 534 | F | Ph | H | Benzyl | 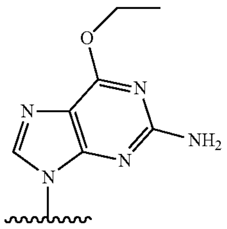 [SMILES: *n1cnc2c(OCC)nc(N)nc21] |
| 535 | OH | Ph | H | Benzyl | 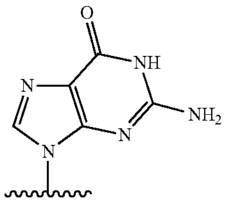 [SMILES: *n1cnc2c(=O)[nH]c(N)nc21] |
| 536 | F | Ph | H | Benzyl | 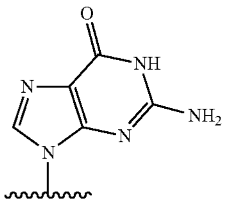 [SMILES: *n1cnc2c(=O)[nH]c(N)nc21] |
| 537 | OH | Ph | H | Benzyl | 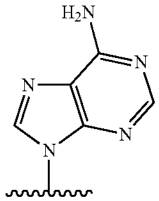 |
| 538 | F | Ph | H | Benzyl | 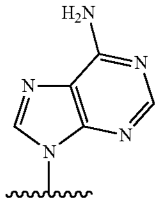 [SMILES: *n1cnc2c(N)ncnc21] |
| 539 | OH | Ph | H | Benzyl | 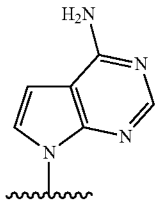 [SMILES: *n1ccc2c(N)ncnc21] |
-continued
(V-1)
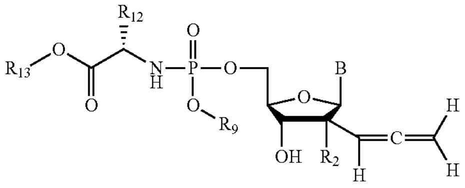
| Example # | $R_2$ | $R_9$ | $R_{12}$ | $R_{13}$ | B |
|---|---|---|---|---|---|
| 540 | F | Ph | H | Benzyl | 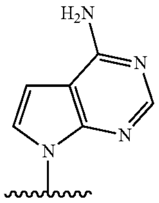 [SMILES: *n1ccc2c(N)ncnc21] |
| 541 | OH | 1-Naphthyl | H | Benzyl | 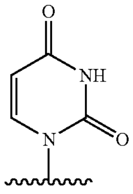 [SMILES: *n1ccc(=O)[nH]c1=O] |
| 542 | F | 1-Naphthyl | H | Benzyl | 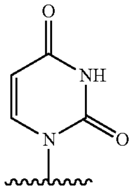 |
| 543 | OH | 1-Naphthyl | H | Benzyl | 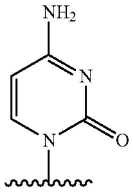 |
| 544 | F | 1-Naphthyl | H | Benzyl | 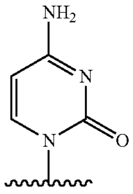 [SMILES: *n1ccc(N)nc1=O] |
| 545 | OH | 1-Naphthyl | H | Benzyl | 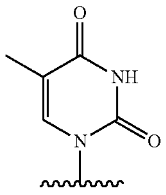 [SMILES: *n1cc(C)c(=O)[nH]c1=O] |

-continued
(V-1)
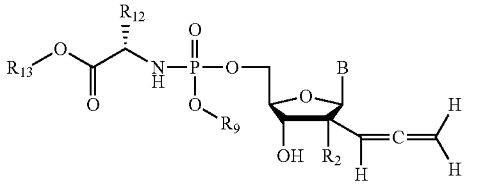
| Example # | $R_2$ | $R_9$ | $R_{12}$ | $R_{13}$ | B |
|---|---|---|---|---|---|
| 546 | F | 1-Naphthyl | H | Benzyl | 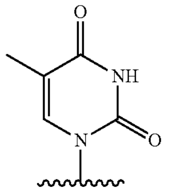 [SMILES: *n1cc(C)c(=O)[nH]c1=O] |
| 547 | OH | 1-Naphthyl | H | Benzyl | 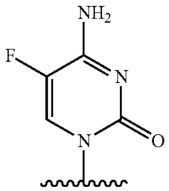 |
| 548 | F | 1-Naphthyl | H | Benzyl | 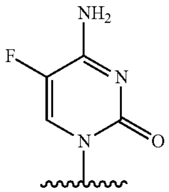 |
| 549 | OH | 1-Naphthyl | H | Benzyl | 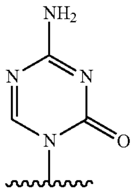 |
| 550 | F | 1-Naphthyl | H | Benzyl | 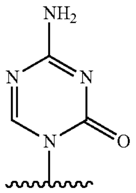 |
| 551 | OH | 1-Naphthyl | H | Benzyl | 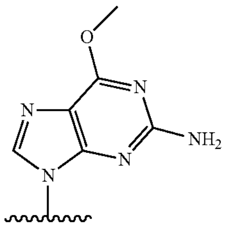 [SMILES: *n1cnc2c(OC)nc(N)nc21] |
-continued
(V-1)
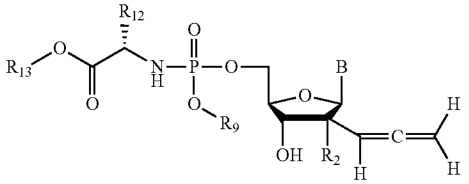
| Example # | $R_2$ | $R_9$ | $R_{12}$ | $R_{13}$ | B |
|---|---|---|---|---|---|
| 552 | F | 1-Naphthyl | H | Benzyl | 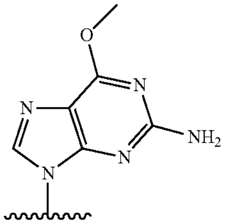 [SMILES: *n1cnc2c(OC)nc(N)nc21] |
| 553 | OH | 1-Naphthyl | H | Benzyl | 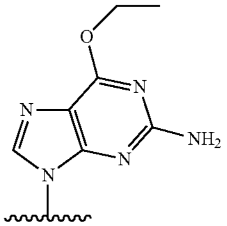 [SMILES: *n1cnc2c(OCC)nc(N)nc21] |
| 554 | F | 1-Naphthyl | H | Benzyl | 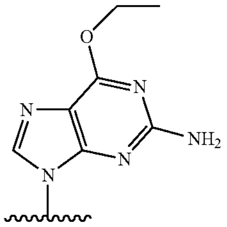 [SMILES: *n1cnc2c(OCC)nc(N)nc21] |
| 555 | OH | 1-Naphthyl | H | Benzyl | 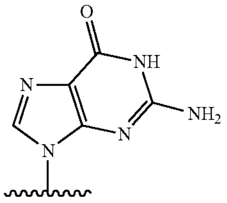 [SMILES: *n1cnc2c(=O)[nH]c(N)nc21] |
| 556 | F | 1-Naphthyl | H | Benzyl | 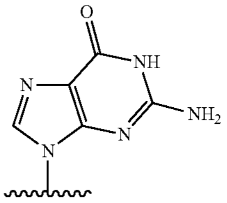 [SMILES: *n1cnc2c(=O)[nH]c(N)nc21] |
| 557 | OH | 1-Naphthyl | H | Benzyl | 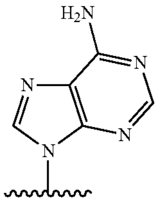 |

-continued
(V-1)
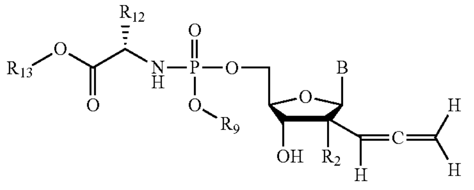
| Example # | $R_2$ | $R_9$ | $R_{12}$ | $R_{13}$ | B |
|---|---|---|---|---|---|
| 558 | F | 1-Naphthyl | H | Benzyl | 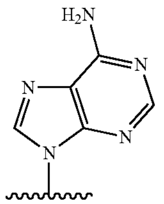 [SMILES: *n1cnc2c(N)ncnc21] |
| 559 | OH | 1-Naphthyl | H | Benzyl | 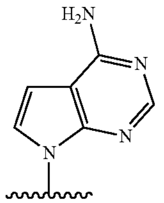 [SMILES: *n1ccc2c(N)ncnc21] |
| 560 | F | 1-Naphthyl | H | Benzyl | 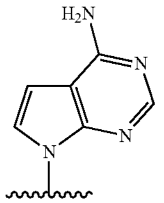 [SMILES: *n1ccc2c(N)ncnc21] |
| 561 | OH | Ph | Me | t-BuCH$_2$— | 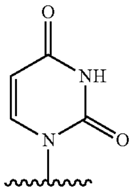 [SMILES: *n1ccc(=O)[nH]c1=O] |
| 562 | F | Ph | Me | t-BuCH$_2$— | 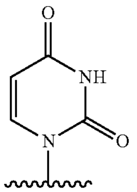 [SMILES: *n1ccc(=O)[nH]c1=O] |
| 563 | OH | Ph | Me | t-BuCH$_2$— | 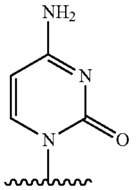 |
-continued
(V-1)
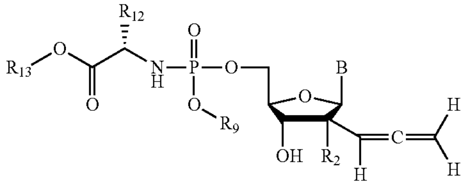
| Example # | $R_2$ | $R_9$ | $R_{12}$ | $R_{13}$ | B |
|---|---|---|---|---|---|
| 564 | F | Ph | Me | t-BuCH$_2$— | 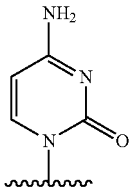 [SMILES: *n1ccc(N)nc1=O] |
| 565 | OH | Ph | Me | t-BuCH$_2$— | 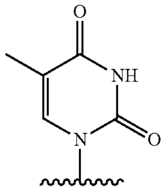 [SMILES: *n1cc(C)c(=O)[nH]c1=O] |
| 566 | F | Ph | Me | t-BuCH$_2$— | 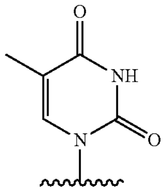 [SMILES: *n1cc(C)c(=O)[nH]c1=O] |
| 567 | OH | Ph | Me | t-BuCH$_2$— | 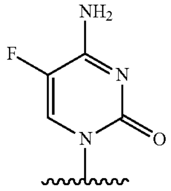 |
| 568 | F | Ph | Me | t-BuCH$_2$— | 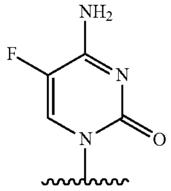 |
| 569 | OH | Ph | Me | t-BuCH$_2$— | 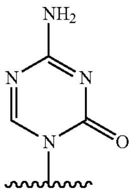 [SMILES: *n1cnc(N)nc1=O] |

-continued
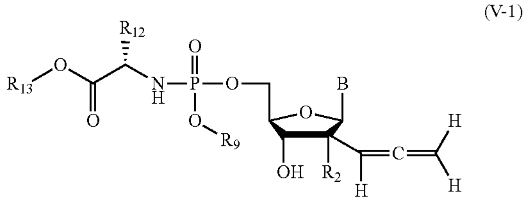
(V-1)
| Example # | $R_2$ | $R_9$ | $R_{12}$ | $R_{13}$ | B |
|---|---|---|---|---|---|
| 570 | F | Ph | Me | t-BuCH$_2$— | 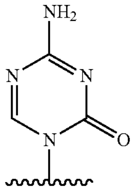 |
| 571 | OH | Ph | Me | t-BuCH$_2$— | 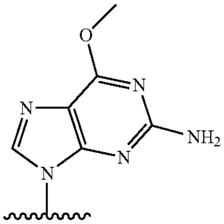 [SMILES: *n1cnc2c(OC)nc(N)nc21] |
| 572 | F | Ph | Me | t-BuCH$_2$— | 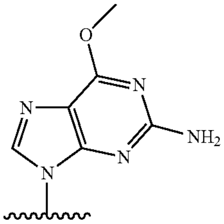 [SMILES: *n1cnc2c(OC)nc(N)nc21] |
| 573 | OH | Ph | Me | t-BuCH$_2$— | 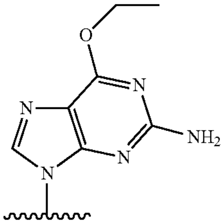 [SMILES: *n1cnc2c(OCC)nc(N)nc21] |
| 574 | F | Ph | Me | t-BuCH$_2$— | 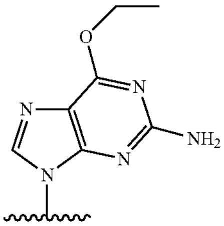 [SMILES: *n1cnc2c(OCC)nc(N)nc21] |
| 575 | OH | Ph | Me | t-BuCH$_2$— | 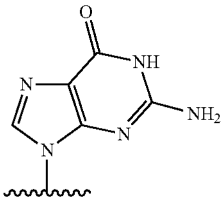 [SMILES: *n1cnc2c(=O)[nH]c(N)nc21] |
-continued
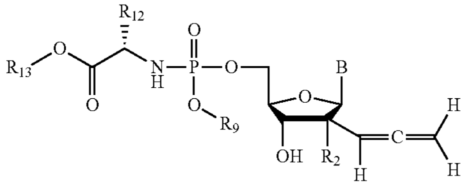
(V-1)
| Example # | $R_2$ | $R_9$ | $R_{12}$ | $R_{13}$ | B |
|---|---|---|---|---|---|
| 576 | F | Ph | Me | t-BuCH$_2$— | 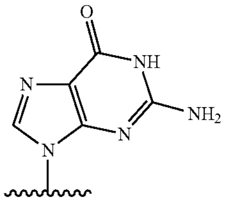 [SMILES: *n1cnc2c(=O)[nH]c(N)nc21] |
| 577 | OH | Ph | Me | t-BuCH$_2$— | 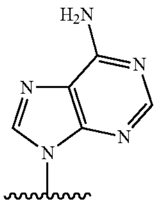 [SMILES: *n1cnc2c(N)ncnc21] |
| 578 | F | Ph | Me | t-BuCH$_2$— | 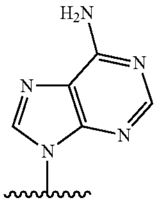 [SMILES: *n1cnc2c(N)ncnc21] |
| 579 | OH | Ph | Me | t-BuCH$_2$— | 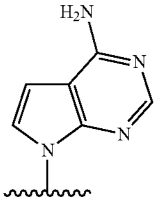 [SMILES: *n1ccc2c(N)ncnc21] |
| 580 | F | Ph | Me | t-BuCH$_2$— | 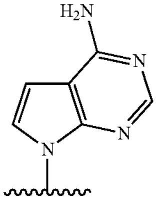 [SMILES: *n1ccc2c(N)ncnc21] |
| 581 | OH | 1-Naphthyl | Me | t-BuCH$_2$— | 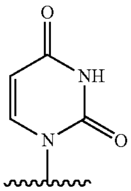 [SMILES: *n1ccc(=O)[nH]c1=O] |

-continued
(V-1)
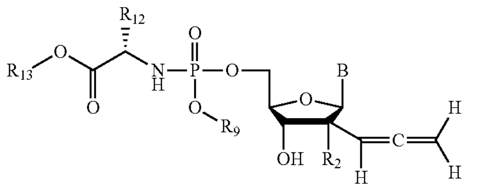
-continued
(V-1)
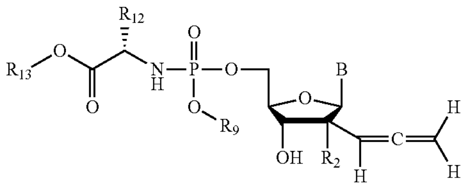
| Example # | $R_2$ | $R_9$ | $R_{12}$ | $R_{13}$ | B |
|---|---|---|---|---|---|
| 582 | F | 1-Naphthyl | Me | t-$BuCH_2$— | 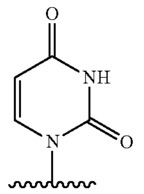 [SMILES: *n1ccc(=O)[nH]c1=O] |
| 583 | OH | 1-Naphthyl | Me | t-$BuCH_2$— | 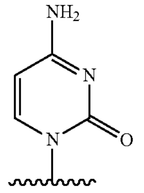 |
| 584 | F | 1-Naphthyl | Me | t-$BuCH_2$— | 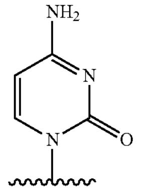 |
| 585 | OH | 1-Naphthyl | Me | t-$BuCH_2$— | 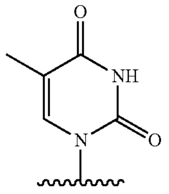 [SMILES: *n1cc(C)c(=O)[nH]c1=O] |
| 586 | F | 1-Naphthyl | Me | t-$BuCH_2$— | 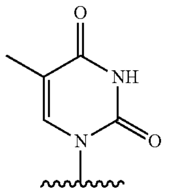 [SMILES: *n1cc(C)c(=O)[nH]c1=O] |
| 587 | OH | 1-Naphthyl | Me | t-$BuCH_2$— | 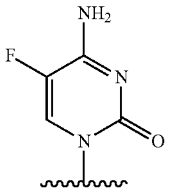 |
| 588 | F | 1-Naphthyl | Me | t-$BuCH_2$— | 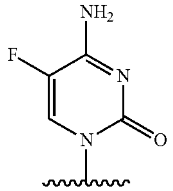 |
| 589 | OH | 1-Naphthyl | Me | t-$BuCH_2$— | 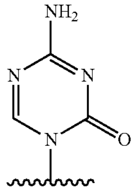 [SMILES: *n1cnc(N)nc1=O] |
| 590 | F | 1-Naphthyl | Me | t-$BuCH_2$— | 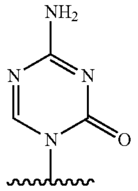 [SMILES: *n1cnc(N)nc1=O] |
| 591 | OH | 1-Naphthyl | Me | t-$BuCH_2$— | 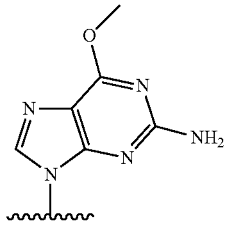 [SMILES: *n1cnc2c(OC)nc(N)nc21] |
| 592 | F | 1-Naphthyl | Me | t-$BuCH_2$— | 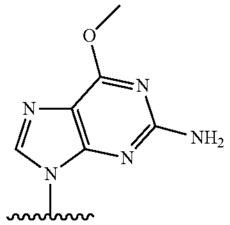 [SMILES: *n1cnc2c(OC)nc(N)nc21] |
| 593 | OH | 1-Naphthyl | Me | t-$BuCH_2$— | 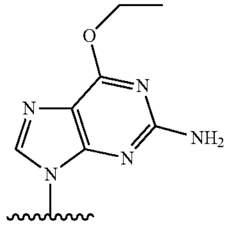 [SMILES: *n1cnc2c(OCC)nc(N)nc21] |

-continued
(V-1)
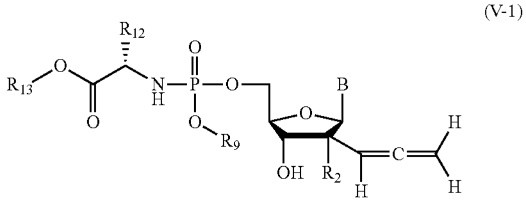
| Example # | $R_2$ | $R_9$ | $R_{12}$ | $R_{13}$ | B |
|---|---|---|---|---|---|
| 594 | F | 1-Naphthyl | Me | t-BuCH$_2$— | 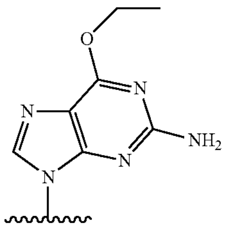 [SMILES: *n1cnc2c(OCC)nc(N)nc21] |
| 595 | OH | 1-Naphthyl | Me | t-BuCH$_2$— | 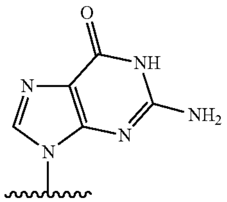 [SMILES: *n1cnc2c(=O)[nH]c(N)nc21] |
| 596 | F | 1-Naphthyl | Me | t-BuCH$_2$— | 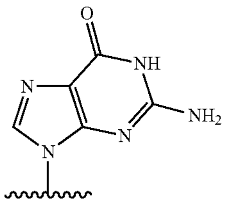 [SMILES: *n1cnc2c(=O)[nH]c(N)nc21] |
| 597 | OH | 1-Naphthyl | Me | t-BuCH$_2$— | 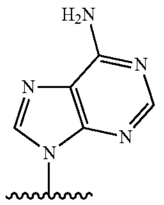 [SMILES: *n1cnc2c(N)ncnc21] |
| 598 | F | 1-Naphthyl | Me | t-BuCH$_2$— | 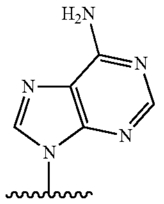 [SMILES: *n1cnc2c(N)ncnc21] |
| 599 | OH | 1-Naphthyl | Me | t-BuCH$_2$— | 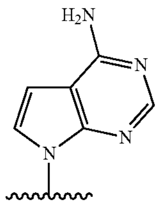 [SMILES: *n1ccc2c(N)ncnc21] |
-continued
(V-1)
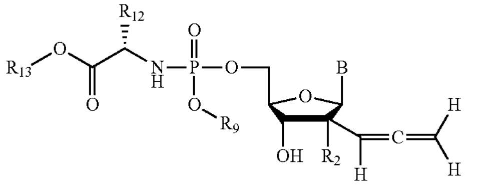
| Example # | $R_2$ | $R_9$ | $R_{12}$ | $R_{13}$ | B |
|---|---|---|---|---|---|
| 600 | F | 1-Naphthyl | Me | t-BuCH$_2$— | 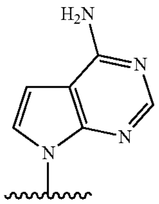 [SMILES: *n1ccc2c(N)ncnc21] |
| 601 | OH | Ph | H | t-BuCH$_2$— | 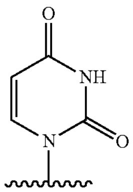 [SMILES: *n1ccc(=O)[nH]c1=O] |
| 602 | F | Ph | H | t-BuCH$_2$— | 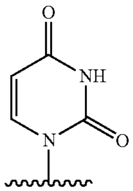 [SMILES: *n1ccc(=O)[nH]c1=O] |
| 603 | OH | Ph | H | t-BuCH$_2$— | 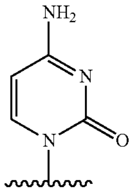 |
| 604 | F | Ph | H | t-BuCH$_2$— | 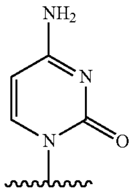 |
| 605 | OH | Ph | H | t-BuCH$_2$— | 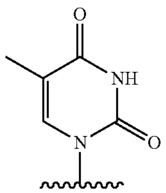 [SMILES: *n1cc(C)c(=O)[nH]c1=O] |

-continued
(V-1)
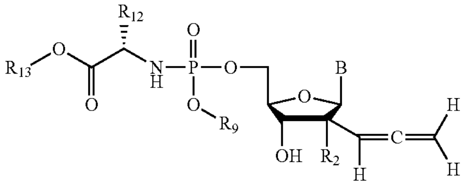
| Example # | $R_2$ | $R_9$ | $R_{12}$ | $R_{13}$ | B |
|---|---|---|---|---|---|
| 606 | F | Ph | H | t-BuCH₂— | 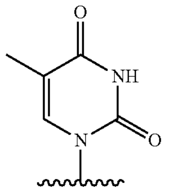 |
| 607 | OH | Ph | H | t-BuCH₂— | 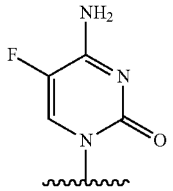 |
| 608 | F | Ph | H | t-BuCH₂— | 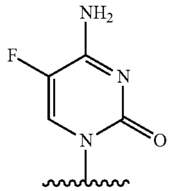 |
| 609 | OH | Ph | H | t-BuCH₂— | 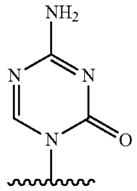 |
| 610 | F | Ph | H | t-BuCH₂— | 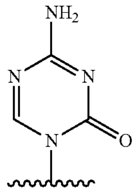 |
| 611 | OH | Ph | H | t-BuCH₂— | 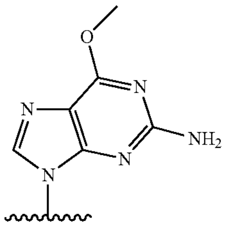 [SMILES: *n1cnc2c(OC)nc(N)nc21] |
-continued
(V-1)
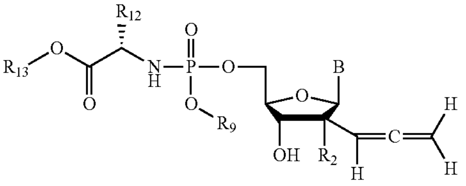
| Example # | $R_2$ | $R_9$ | $R_{12}$ | $R_{13}$ | B |
|---|---|---|---|---|---|
| 612 | F | Ph | H | t-BuCH₂— | 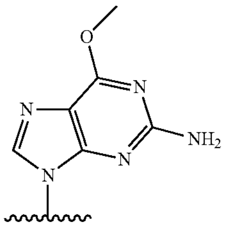 [SMILES: *n1cnc2c(OC)nc(N)nc21] |
| 613 | OH | Ph | H | t-BuCH₂— | 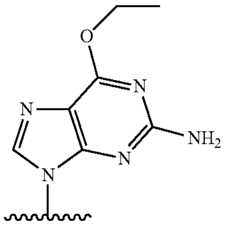 [SMILES: *n1cnc2c(OCC)nc(N)nc21] |
| 614 | F | Ph | H | t-BuCH₂— | 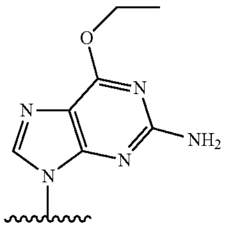 [SMILES: *n1cnc2c(OCC)nc(N)nc21] |
| 615 | OH | Ph | H | t-BuCH₂— | 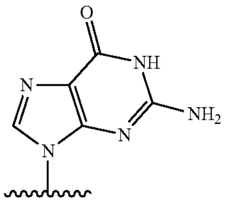 [SMILES: *n1cnc2c(=O)[nH]c(N)nc21] |
| 616 | F | Ph | H | t-BuCH₂— | 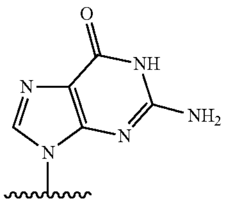 [SMILES: *n1cnc2c(=O)[nH]c(N)nc21] |
| 617 | OH | Ph | H | t-BuCH₂— | 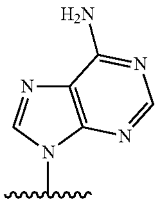 |

-continued
(V-1)
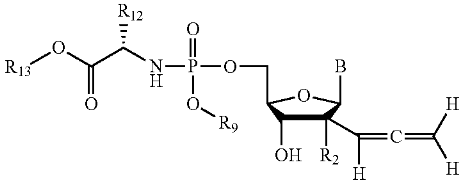
| Example # | $R_2$ | $R_9$ | $R_{12}$ | $R_{13}$ | B |
|---|---|---|---|---|---|
| 618 | F | Ph | H | t-BuCH$_2$— | 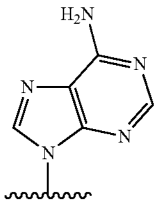 [SMILES: *n1cnc2c(N)ncnc21] |
| 619 | OH | Ph | H | t-BuCH$_2$— | 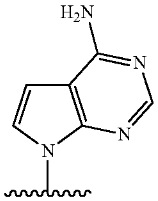 |
| 620 | F | Ph | H | t-BuCH$_2$— | 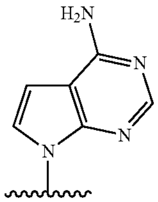 [SMILES: *n1ccc2c(N)ncnc21] |
| 621 | OH | 1-Naphthyl | H | t-BuCH$_2$— | 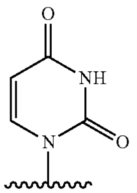 [SMILES: *n1ccc(=O)[nH]c1=O] |
| 622 | F | 1-Naphthyl | H | t-BuCH$_2$— | 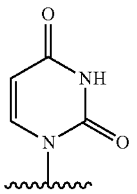 [SMILES: *n1ccc(=O)[nH]c1=O] |
| 623 | OH | 1-Naphthyl | H | t-BuCH$_2$— | 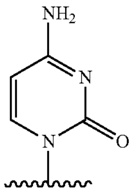 |
-continued
(V-1)
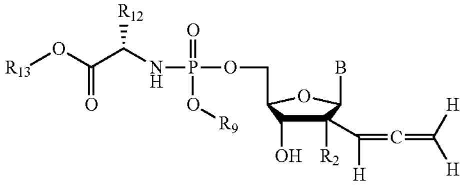
| Example # | $R_2$ | $R_9$ | $R_{12}$ | $R_{13}$ | B |
|---|---|---|---|---|---|
| 624 | F | 1-Naphthyl | H | t-BuCH$_2$— | 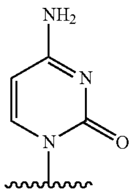 |
| 625 | OH | 1-Naphthyl | H | t-BuCH$_2$— | 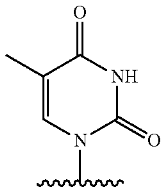 [SMILES: *n1cc(C)c(=O)[nH]c1=O] |
| 626 | F | 1-Naphthyl | H | t-BuCH$_2$— | 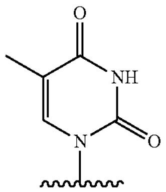 [SMILES: *n1cc(C)c(=O)[nH]c1=O] |
| 627 | OH | 1-Naphthyl | H | t-BuCH$_2$— | 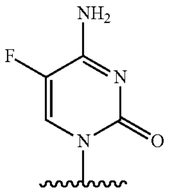 |
| 628 | F | 1-Naphthyl | H | t-BuCH$_2$— | 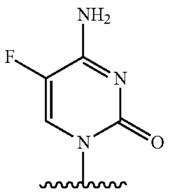 |
| 629 | OH | 1-Naphthyl | H | t-BuCH$_2$— | 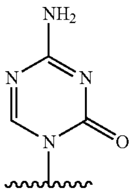 [SMILES: *n1cnc(N)nc1=O] |

-continued (V-1)

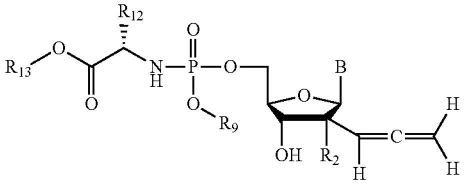

| Example # | $R_2$ | $R_9$ | $R_{12}$ | $R_{13}$ | B |
|---|---|---|---|---|---|
| 630 | F | 1-Naphthyl | H | t-$BuCH_2$— | 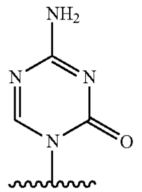 |
| 631 | OH | 1-Naphthyl | H | t-$BuCH_2$— | 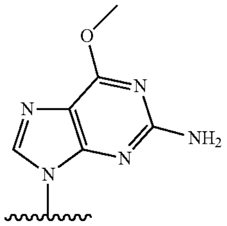 [SMILES: *n1cnc2c(OC)nc(N)nc21] |
| 632 | F | 1-Naphthyl | H | t-$BuCH_2$— | 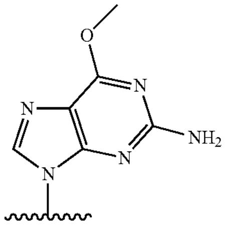 [SMILES: *n1cnc2c(OC)nc(N)nc21] |
| 633 | OH | 1-Naphthyl | H | t-$BuCH_2$— | 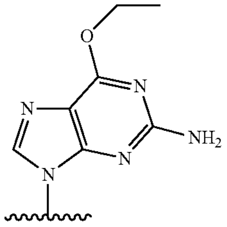 [SMILES: *n1cnc2c(OCC)nc(N)nc21] |
| 634 | F | 1-Naphthyl | H | t-$BuCH_2$— | 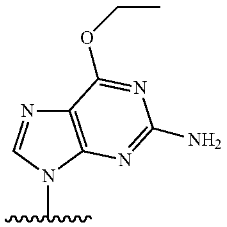 [SMILES: *n1cnc2c(OCC)nc(N)nc21] |
| 635 | OH | 1-Naphthyl | H | t-$BuCH_2$— | 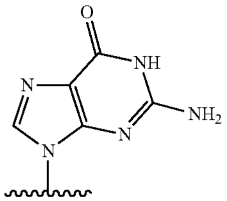 [SMILES: *n1cnc2c(=O)[nH]c(N)nc21] |

-continued (V-1)

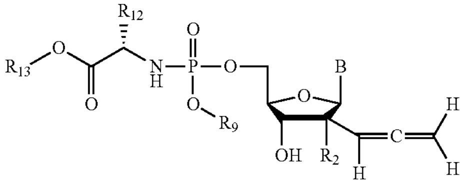

| Example # | $R_2$ | $R_9$ | $R_{12}$ | $R_{13}$ | B |
|---|---|---|---|---|---|
| 636 | F | 1-Naphthyl | H | t-$BuCH_2$— | 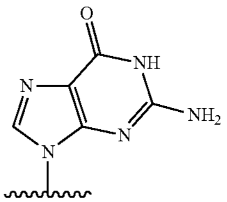 [SMILES: *n1cnc2c(=O)[nH]c(N)nc21] |
| 637 | OH | 1-Naphthyl | H | t-$BuCH_2$— | 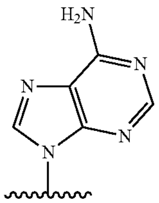 [SMILES: *n1cnc2c(N)ncnc21] |
| 638 | F | 1-Naphthyl | H | t-$BuCH_2$— | 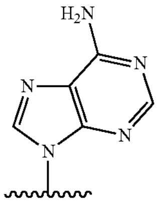 [SMILES: *n1cnc2c(N)ncnc21] |
| 639 | OH | 1-Naphthyl | H | t-$BuCH_2$— | 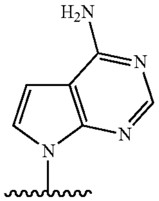 [SMILES: *n1ccc2c(N)ncnc21] |
| 640 | F | 1-Naphthyl | H | t-$BuCH_2$— | 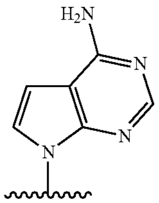 |

Compounds in Table 4 are represented by Formula (VI-1) wherein $R_2$, $R_{8a}$, $R_{8b}$, $R_{14}$, and B are delineated for each example in Table 4.

(VI-1)
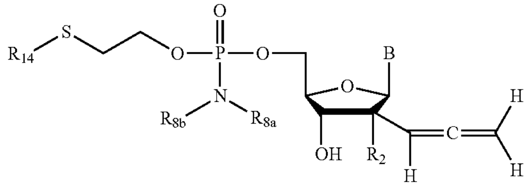
| Example # | $R_2$ | $R_{14}$ | $NR_{8a}R_{8b}$ | B |
|---|---|---|---|---|
| 641 | OH | 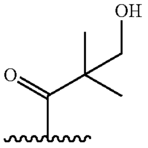 [SMILES: *C(=O)C(C)(C)CO] | 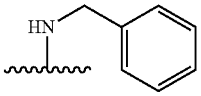 [SMILES: *NCc1ccccc1] | 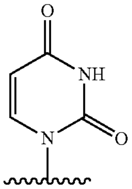 [SMILES: *n1ccc(=O)[nH]c1=O] |
| 642 | F | 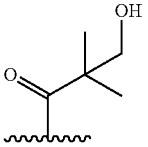 [SMILES: *C(=O)C(C)(C)CO] | 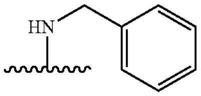 [SMILES: *NCc1ccccc1] | 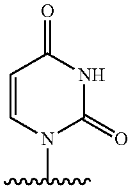 [SMILES: *n1ccc(=O)[nH]c1=O] |
| 643 | OH | 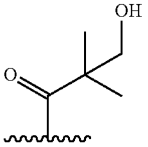 [SMILES: *C(=O)C(C)(C)CO] | 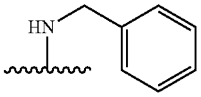 [SMILES: *NCc1ccccc1] | 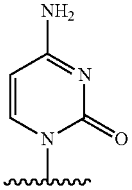 |
| 644 | F | 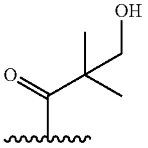 [SMILES: *C(=O)C(C)(C)CO] | 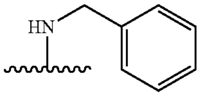 | 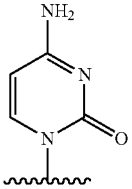 |
| 645 | OH | 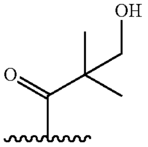 [SMILES: *C(=O)C(C)(C)CO] | 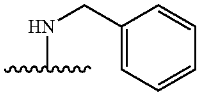 [SMILES: *NCc1ccccc1] | 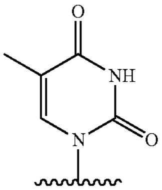 [SMILES: *n1cc(C)c(=O)[nH]c1=O] |
| 646 | F | 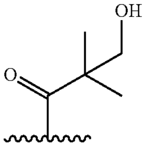 [SMILES: *C(=O)C(C)(C)CO] | 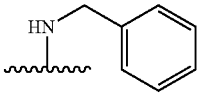 [SMILES: *NCc1ccccc1] | 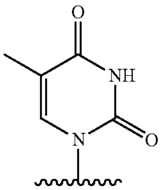 [SMILES: *n1cc(C)c(=O)[nH]c1=O] |
| 647 | OH | 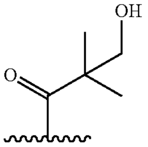 [SMILES: *C(=O)C(C)(C)CO] | 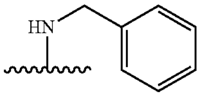 [SMILES: *NCc1ccccc1] | 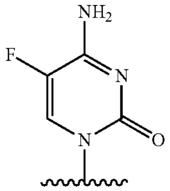 [SMILES: *n1cc(F)c(N)nc1=O] |

-continued
(VI-1)
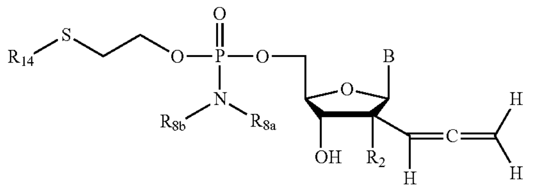
| Example # | $R_2$ | $R_{14}$ | $NR_{8a}R_{8b}$ | B |
|---|---|---|---|---|
| 648 | F | 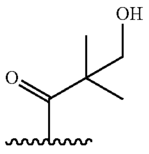 [SMILES: *C(=O)C(C)(C)CO] | 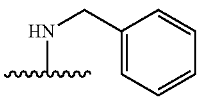 [SMILES: *NCc1ccccc1] | 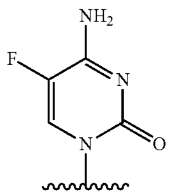 [SMILES: *n1cc(F)c(N)nc1=O] |
| 649 | OH | 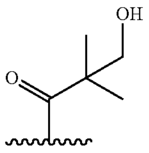 [SMILES: *C(=O)C(C)(C)CO] | 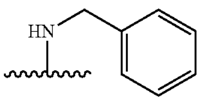 | 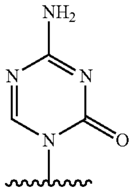 [SMILES: *n1cnc(N)nc1=O] |
| 650 | F | 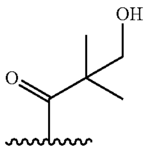 [SMILES: *C(=O)C(C)(C)CO] | 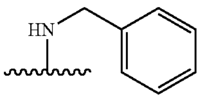 | 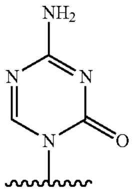 [SMILES: *n1cnc(N)nc1=O] |
| 651 | OH | 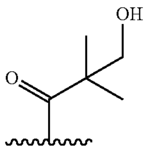 [SMILES: *C(=O)C(C)(C)CO] | 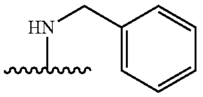 [SMILES: *NCc1ccccc1] | 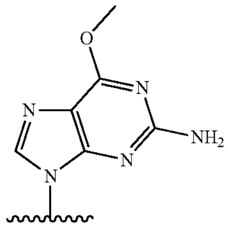 [SMILES: *n1cnc2c(OC)nc(N)nc21] |
| 652 | F | 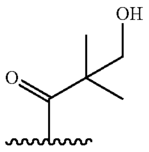 [SMILES: *C(=O)C(C)(C)CO] | 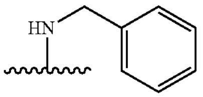 [SMILES: *NCc1ccccc1] | 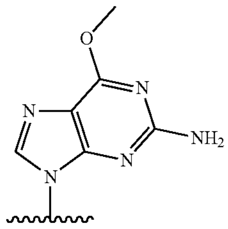 [SMILES: *n1cnc2c(OC)nc(N)nc21] |
| 653 | OH | 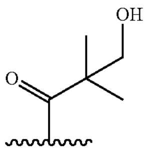 [SMILES: *C(=O)C(C)(C)CO] | 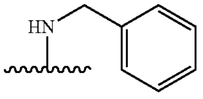 | 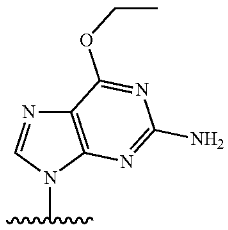 [SMILES: *n1cnc2c(OCC)nc(N)nc21] |

-continued
(VI-1)
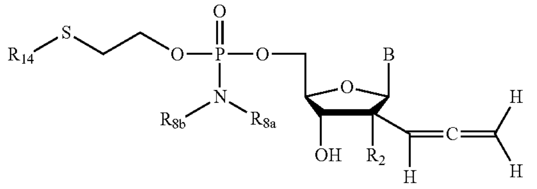
| Example # | $R_2$ | $R_{14}$ | $NR_{8a}R_{8b}$ | B |
|---|---|---|---|---|
| 654 | F | 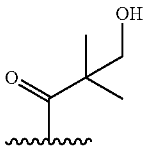 [SMILES: *C(=O)C(C)(C)CO] | 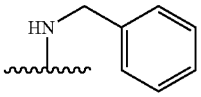 | 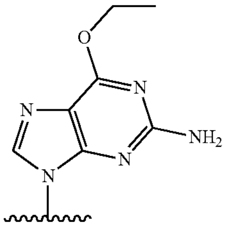 [SMILES: *n1cnc2c(OCC)nc(N)nc21] |
| 655 | OH | 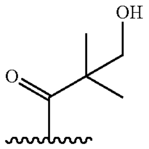 [SMILES: *C(=O)C(C)(C)CO] | 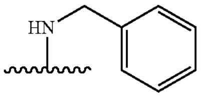 [SMILES: *NCc1ccccc1] | 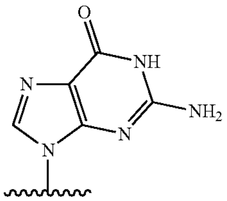 [SMILES: *n1cnc2c(=O)[nH]c(N)nc21] |
| 656 | F | 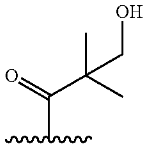 [SMILES: *C(=O)C(C)(C)CO] | 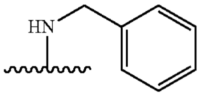 [SMILES: *NCc1ccccc1] | 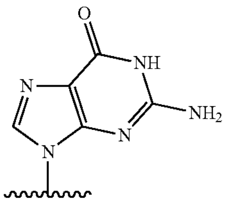 [SMILES: *n1cnc2c(=O)[nH]c(N)nc21] |
| 657 | OH | 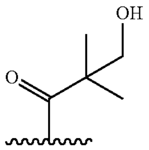 [SMILES: *C(=O)C(C)(C)CO] | 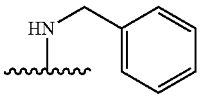 [SMILES: *NCc1ccccc1] | 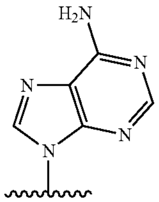 |
| 658 | F | 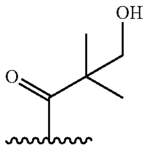 [SMILES: *C(=O)C(C)(C)CO] | 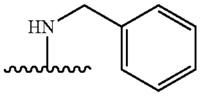 | 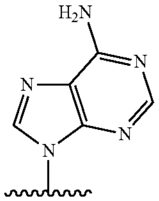 |
| 659 | OH | 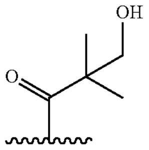 [SMILES: *C(=O)C(C)(C)CO] | 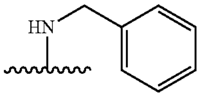 | 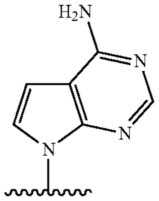 |

-continued
(VI-1)
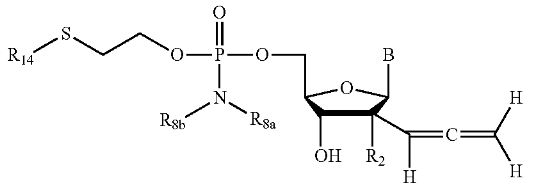
| Example # | $R_2$ | $R_{14}$ | $NR_{8a}R_{8b}$ | B |
|---|---|---|---|---|
| 660 | F | 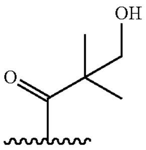 [SMILES: *C(=O)C(C)(C)CO] | 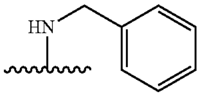 [SMILES: *NCc1ccccc1] | 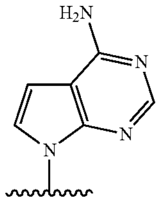 |
| 661 | OH | 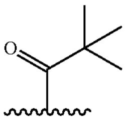 [SMILES: *C(=O)C(C)(C)C] | 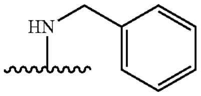 [SMILES: *NCc1ccccc1] | 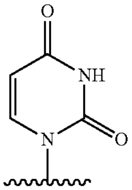 [SMILES: *n1ccc(=O)[nH]c1=O] |
| 662 | F | 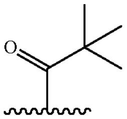 [SMILES: *C(=O)C(C)(C)C] | 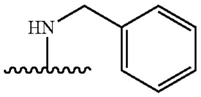 | 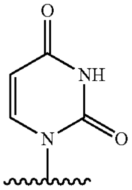 [SMILES: *n1ccc(=O)[nH]c1=O] |
| 663 | OH | 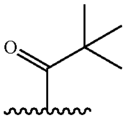 [SMILES: *C(=O)C(C)(C)C] | 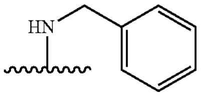 | 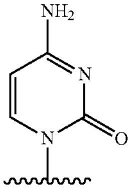 |
| 664 | F | 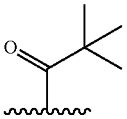 [SMILES: *C(=O)C(C)(C)C] | 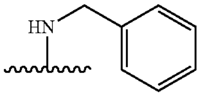 [SMILES: *NCc1ccccc1] | 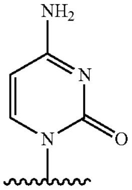 |
| 665 | OH | 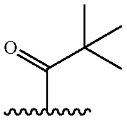 [SMILES: *C(=O)C(C)(C)C] | 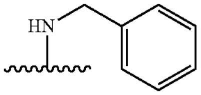 [SMILES: *NCc1ccccc1] | 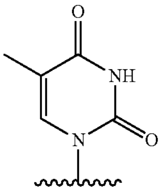 [SMILES: *n1cc(C)c(=O)[nH]c1=O] |

-continued
(VI-1)
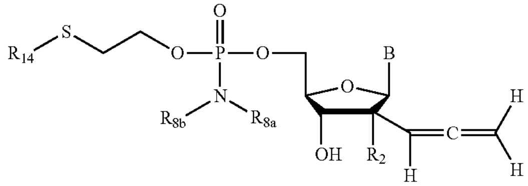
| Example # | $R_2$ | $R_{14}$ | $NR_{8a}R_{8b}$ | B |
|---|---|---|---|---|
| 666 | F | 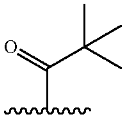 [SMILES: *C(=O)C(C)(C)C] | 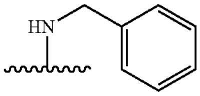 | 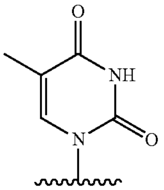 [SMILES: *n1cc(C)c(=O)[nH]c1=O] |
| 667 | OH | 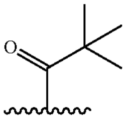 | 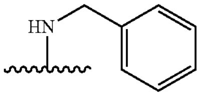 [SMILES: *NCc1ccccc1] | 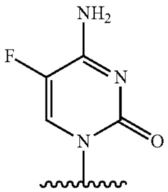 [SMILES: *n1cc(F)c(N)nc1=O] |
| 668 | F | 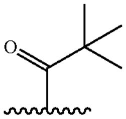 [SMILES: *C(=O)C(C)(C)C] | 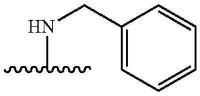 [SMILES: *NCc1ccccc1] | 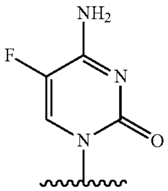 [SMILES: *n1cc(F)c(N)nc1=O] |
| 669 | OH | 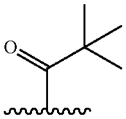 [SMILES: *C(=O)C(C)(C)C] | 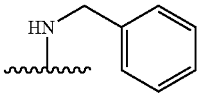 | 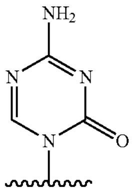 [SMILES: *n1cnc(N)nc1=O] |
| 670 | F | 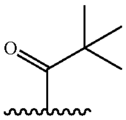 | 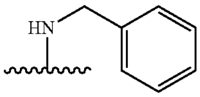 [SMILES: *NCc1ccccc1] | 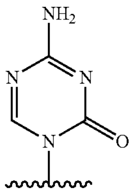 [SMILES: *n1cnc(N)nc1=O] |
| 671 | OH | 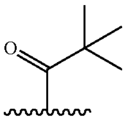 [SMILES: *C(=O)C(C)(C)C] | 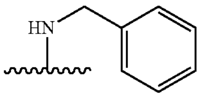 [SMILES: *NCc1ccccc1] | 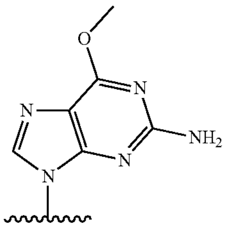 |

-continued
(VI-1)
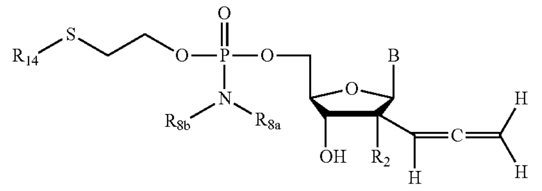
| Example # | $R_2$ | $R_{14}$ | $NR_{8a}R_{8b}$ | B |
|---|---|---|---|---|
| 672 | F | 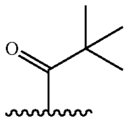 [SMILES: *C(=O)C(C)(C)C] | 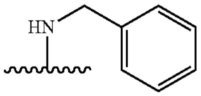 [SMILES: *NCc1ccccc1] | 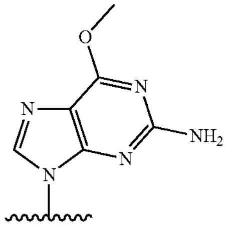 [SMILES: *n1cnc2c(OC)nc(N)nc21] |
| 673 | OH | 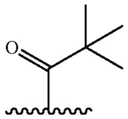 [SMILES: *C(=O)C(C)(C)C] | 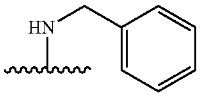 | 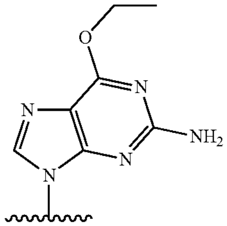 [SMILES: *n1cnc2c(OCC)nc(N)nc21] |
| 674 | F | 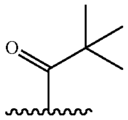 [SMILES: *C(=O)C(C)(C)C] | 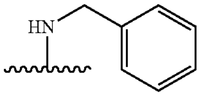 | 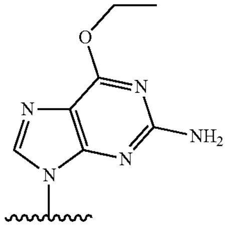 [SMILES: *n1cnc2c(OCC)nc(N)nc21] |
| 675 | OH | 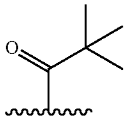 [SMILES: *C(=O)C(C)(C)C] | 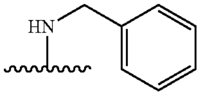 [SMILES: *NCc1ccccc1] | 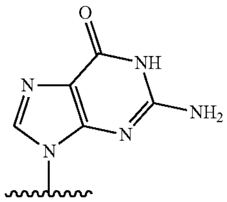 [SMILES: *n1cnc2c(=O)[nH]c(N)nc21] |
| 676 | F | 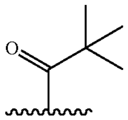 [SMILES: *C(=O)C(C)(C)C] | 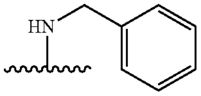 [SMILES: *NCc1ccccc1] | 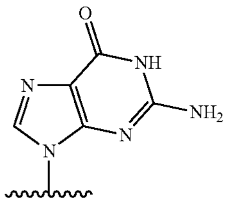 [SMILES: *n1cnc2c(=O)[nH]c(N)nc21] |
| 677 | OH | 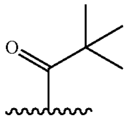 [SMILES: *C(=O)C(C)(C)C] | 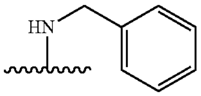 [SMILES: *NCc1ccccc1] | 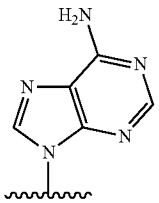 |

-continued
(VI-1)
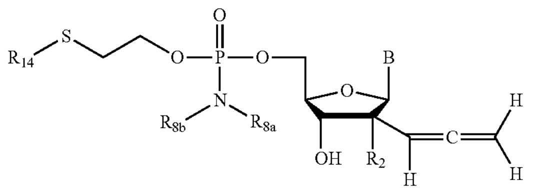
| Example # | $R_2$ | $R_{14}$ | $NR_{8a}R_{8b}$ | B |
|---|---|---|---|---|
| 678 | F | 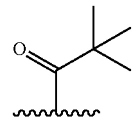 [SMILES: *C(=O)C(C)(C)C] | 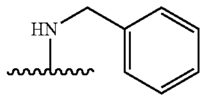 [SMILES: *NCc1ccccc1] | 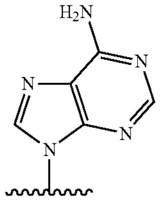 |
| 679 | OH | 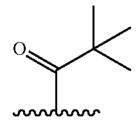 [SMILES: *C(=O)C(C)(C)C] | 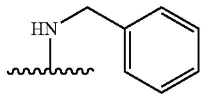 | 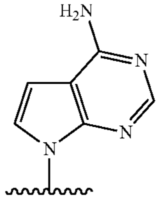 |
| 680 | F | 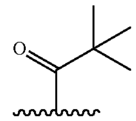 [SMILES: *C(=O)C(C)(C)C] | 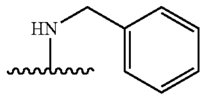 | 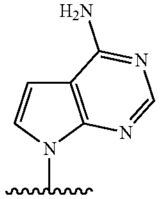 |
| 681 | OH | 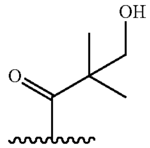 [SMILES: *C(=O)C(C)(C)CO] | 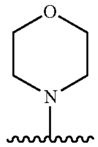 [SMILES: *N1CCOCC1] | 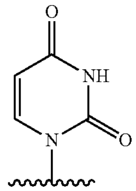 [SMILES: *n1ccc(=O)[nH]c1=O] |
| 682 | F | 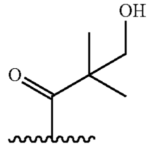 [SMILES: *C(=O)C(C)(C)CO] | 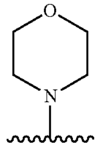 [SMILES: *N1CCOCC1] | 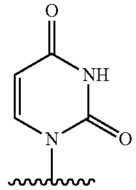 [SMILES: *n1ccc(=O)[nH]c1=O] |
| 683 | OH | 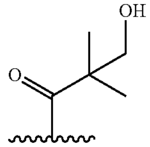 [SMILES: *C(=O)C(C)(C)CO] | 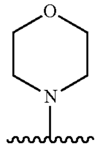 [SMILES: *N1CCOCC1] | 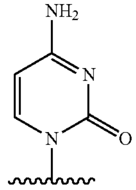 |

-continued
(VI-1)
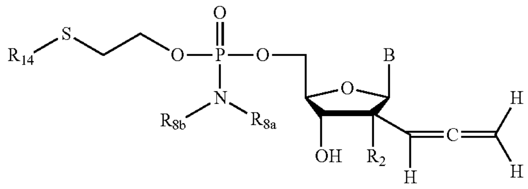
| Example # | $R_2$ | $R_{14}$ | $NR_{8a}R_{8b}$ | B |
|---|---|---|---|---|
| 684 | F | 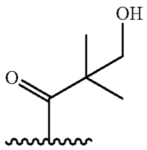 [SMILES: *C(=O)C(C)(C)CO] | 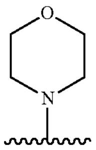 [SMILES: *N1CCOCC1] | 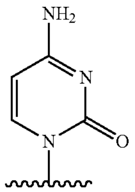 |
| 685 | OH | 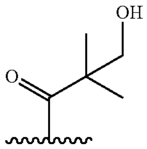 [SMILES: *C(=O)C(C)(C)CO] | 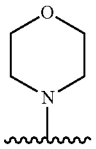 [SMILES: *N1CCOCC1] | 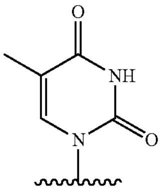 [SMILES: *n1cc(C)c(=O)[nH]c1=O] |
| 686 | F | 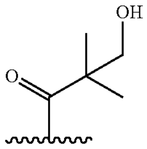 [SMILES: *C(=O)C(C)(C)CO] | 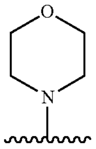 [SMILES: *N1CCOCC1] | 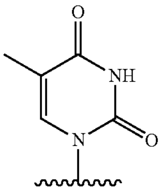 [SMILES: *n1cc(C)c(=O)[nH]c1=O] |
| 687 | OH | 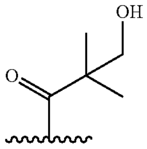 [SMILES: *C(=O)C(C)(C)CO] | 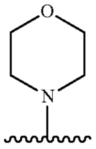 [SMILES: *N1CCOCC1] | 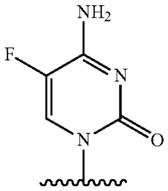 [SMILES: *n1cc(F)c(N)nc1=O] |
| 688 | F | 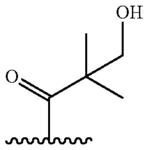 [SMILES: *C(=O)C(C)(C)CO] | 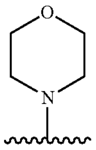 [SMILES: *N1CCOCC1] | 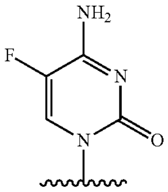 [SMILES: *n1cc(F)c(N)nc1=O] |
| 689 | OH | 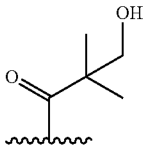 [SMILES: *C(=O)C(C)(C)CO] | 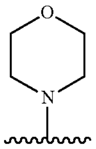 [SMILES: *N1CCOCC1] | 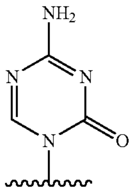 [SMILES: *n1cnc(N)nc1=O] |

-continued
(VI-1)
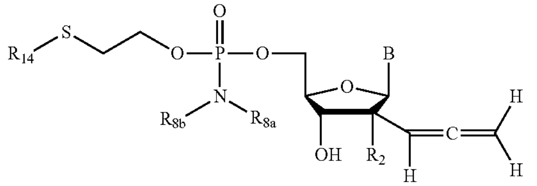
| Example # | $R_2$ | $R_{14}$ | $NR_{8a}R_{8b}$ | B |
|---|---|---|---|---|
| 690 | F | 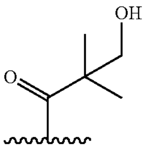 [SMILES: *C(=O)C(C)(C)CO] | 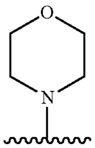 [SMILES: *N1CCOCC1] | 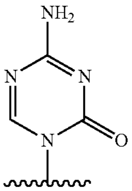 [SMILES: *n1cnc(N)nc1=O] |
| 691 | OH | 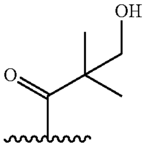 [SMILES: *C(=O)C(C)(C)CO] | 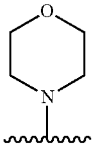 [SMILES: *N1CCOCC1] | 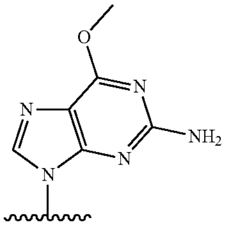 [SMILES: *n1cnc2c(OC)nc(N)nc21] |
| 692 | F | 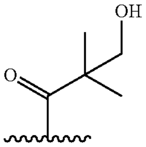 | 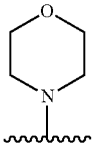 [SMILES: *N1CCOCC1] | 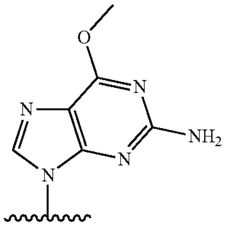 [SMILES: *n1cnc2c(OC)nc(N)nc21] |
| 693 | OH | 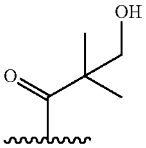 [SMILES: *C(=O)C(C)(C)CO] | 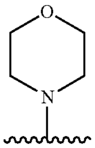 [SMILES: *N1CCOCC1] | 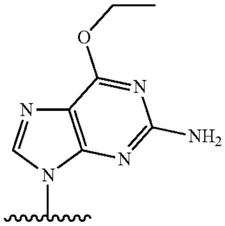 [SMILES: *n1cnc2c(OCC)nc(N)nc21] |
| 694 | F | 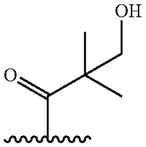 [SMILES: *C(=O)C(C)(C)CO] | 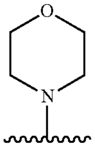 [SMILES: *N1CCOCC1] | 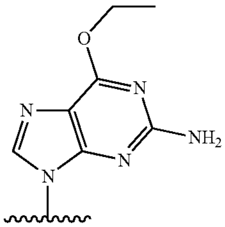 [SMILES: *n1cnc2c(OCC)nc(N)nc21] |
| 695 | OH | 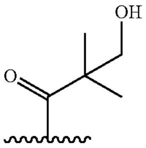 [SMILES: *C(=O)C(C)(C)CO] | 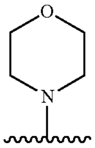 [SMILES: *N1CCOCC1] | 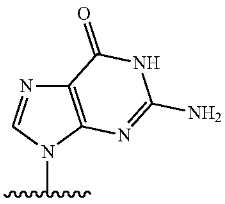 [SMILES: *n1cnc2c(=O)[nH]c(N)nc21] |

-continued
(VI-1)
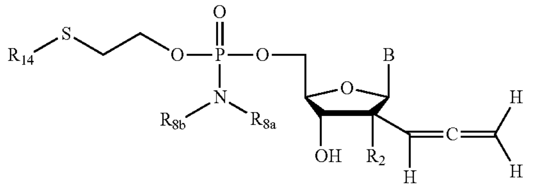
| Example # | $R_2$ | $R_{14}$ | $NR_{8a}R_{8b}$ | B |
|---|---|---|---|---|
| 696 | F | 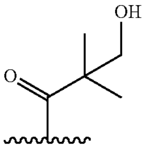 [SMILES: *C(=O)C(C)(C)CO] | 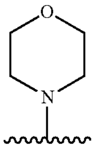 [SMILES: *N1CCOCC1] | 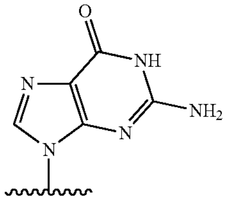 [SMILES: *n1cnc2c(=O)[nH]c(N)nc21] |
| 697 | OH | 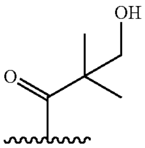 [SMILES: *C(=O)C(C)(C)CO] | 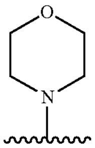 [SMILES: *N1CCOCC1] | 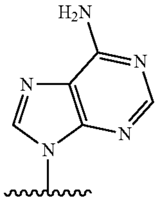 |
| 698 | F | 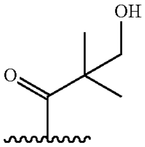 [SMILES: *C(=O)C(C)(C)CO] | 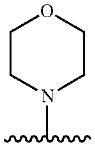 [SMILES: *N1CCOCC1] | 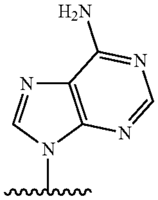 |
| 699 | OH | 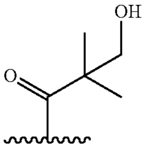 [SMILES: *C(=O)C(C)(C)CO] | 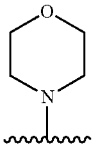 [SMILES: *N1CCOCC1] | 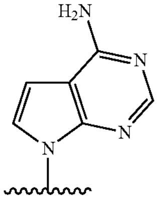 |
| 700 | F | 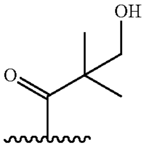 [SMILES: *C(=O)C(C)(C)CO] | 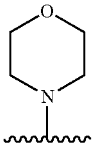 [SMILES: *N1CCOCC1] | 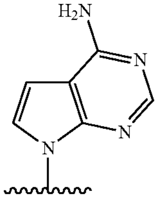 |
| 701 | OH | 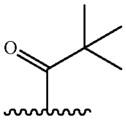 [SMILES: *C(=O)C(C)(C)C] | 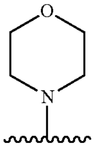 [SMILES: *N1CCOCC1] | 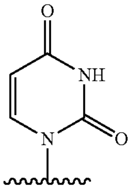 [SMILES: *n1ccc(=O)[nH]c1=O] |

-continued
(VI-1)
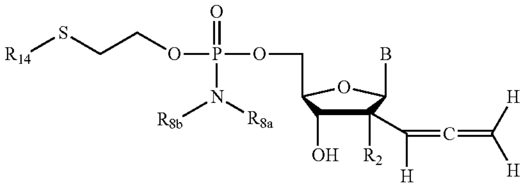
| Example # | $R_2$ | $R_{14}$ | $NR_{8a}R_{8b}$ | B |
|---|---|---|---|---|
| 702 | F | 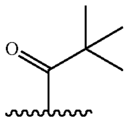 [SMILES: *C(=O)C(C)(C)C] | 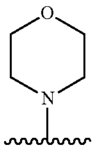 [SMILES: *N1CCOCC1] | 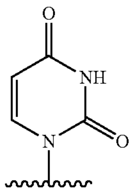 [SMILES: *n1ccc(=O)[nH]c1=O] |
| 703 | OH | 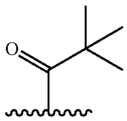 | 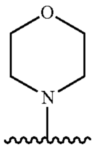 [SMILES: *N1CCOCC1] | 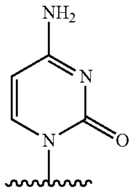 |
| 704 | F | 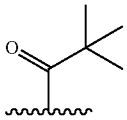 [SMILES: *C(=O)C(C)(C)C] | 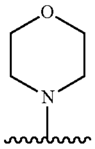 [SMILES: *N1CCOCC1] | 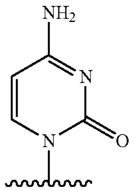 |
| 705 | OH | 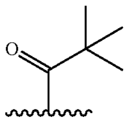 [SMILES: *C(=O)C(C)(C)C] | 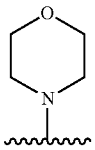 [SMILES: *N1CCOCC1] | 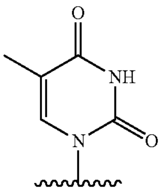 [SMILES: *n1cc(C)c(=O)[nH]c1=O] |
| 706 | F | 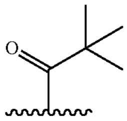 [SMILES: *C(=O)C(C)(C)C] | 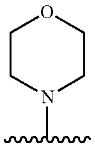 [SMILES: *N1CCOCC1] | 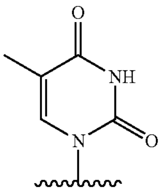 [SMILES: *n1cc(C)c(=O)[nH]c1=O] |
| 707 | OH | 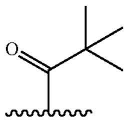 [SMILES: *C(=O)C(C)(C)C] | 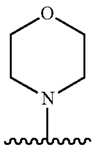 [SMILES: *N1CCOCC1] | 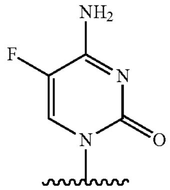 [SMILES: *n1cc(F)c(N)nc1=O] |

-continued
(VI-1)
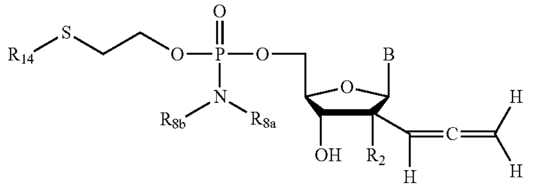
| Example # | $R_2$ | $R_{14}$ | $NR_{8a}R_{8b}$ | B |
| --- | --- | --- | --- | --- |
| 708 | F | 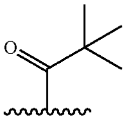 [SMILES: *C(=O)C(C)(C)C] | 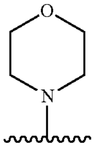 [SMILES: *N1CCOCC1] | 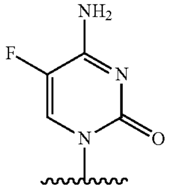 [SMILES: *n1cc(F)c(N)nc1=O] |
| 709 | OH | 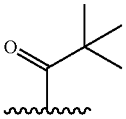 | 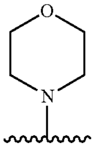 [SMILES: *N1CCOCC1] | 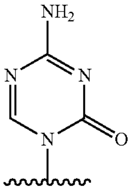 [SMILES: *n1cnc(N)nc1=O] |
| 710 | F | 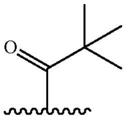 [SMILES: *C(=O)C(C)(C)C] | 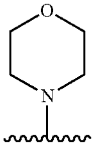 [SMILES: *N1CCOCC1] | 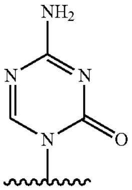 [SMILES: *n1cnc(N)nc1=O] |
| 711 | OH | 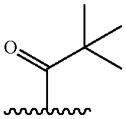 [SMILES: *C(=O)C(C)(C)C] | 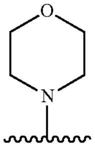 [SMILES: *N1CCOCC1] | 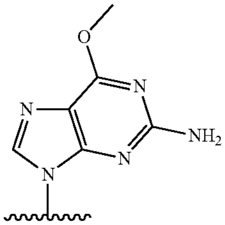 [SMILES: *n1cnc2c(OC)nc(N)nc21] |
| 712 | F | 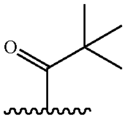 [SMILES: *C(=O)C(C)(C)C] | 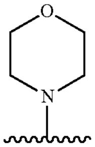 [SMILES: *N1CCOCC1] | 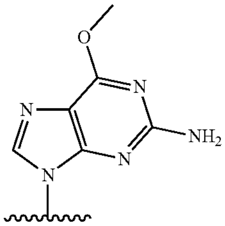 |
| 713 | OH | 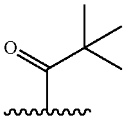 [SMILES: *C(=O)C(C)(C)C] | 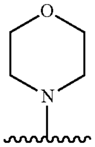 [SMILES: *N1CCOCC1] | 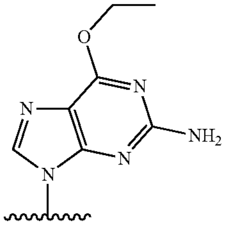 [SMILES: *n1cnc2c(OCC)nc(N)nc21] |

-continued
(VI-1)
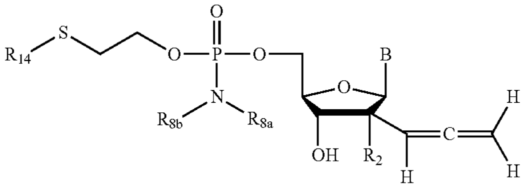
| Example # | $R_2$ | $R_{14}$ | $NR_{8a}R_{8b}$ | B |
|---|---|---|---|---|
| 714 | F | 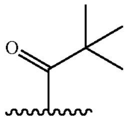 [SMILES: *C(=O)C(C)(C)C] | 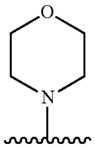 [SMILES: *N1CCOCC1] | 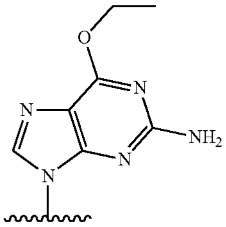 [SMILES: *n1cnc2c(OCC)nc(N)nc21] |
| 715 | OH | 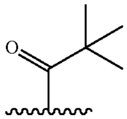 [SMILES: *C(=O)C(C)(C)C] | 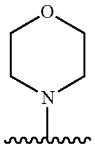 [SMILES: *N1CCOCC1] | 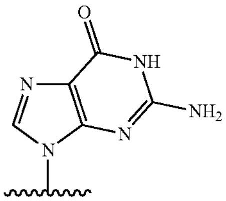 [SMILES: *n1cnc2c(=O)[nH]c(N)nc21] |
| 716 | F | 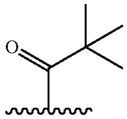 [SMILES: *C(=O)C(C)(C)C] | 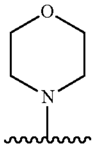 [SMILES: *N1CCOCC1] | 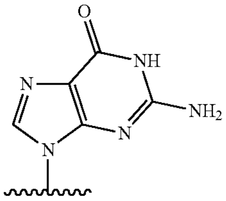 [SMILES: *n1cnc2c(=O)[nH]c(N)nc21] |
| 717 | OH | 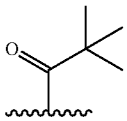 [SMILES: *C(=O)C(C)(C)C] | 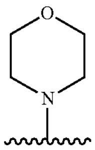 [SMILES: *N1CCOCC1] | 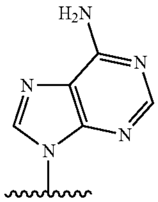 |
| 718 | F | 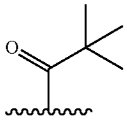 [SMILES: *C(=O)C(C)(C)C] | 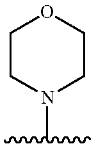 [SMILES: *N1CCOCC1] | 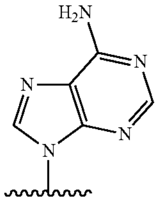 |
| 719 | OH | 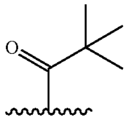 [SMILES: *C(=O)C(C)(C)C] | 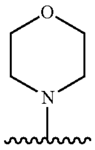 [SMILES: *N1CCOCC1] | 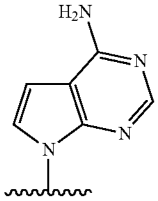 |

-continued
(VI-1)
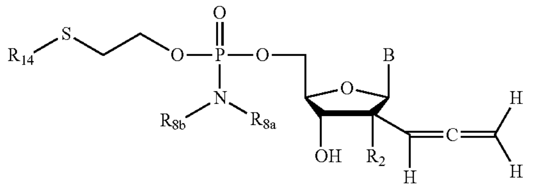
| Example # | $R_2$ | $R_{14}$ | $NR_{8a}R_{8b}$ | B |
|---|---|---|---|---|
| 720 | F | 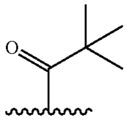 [SMILES: *C(=O)C(C)(C)C] | 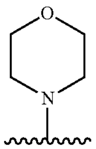 [SMILES: *N1CCOCC1] | 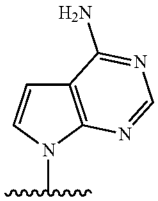 |
| 721 | OH | 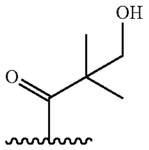 [SMILES: *C(=O)C(C)(C)CO] | 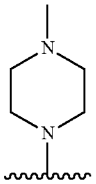 [SMILES: *N1CCN(C)CC1] | 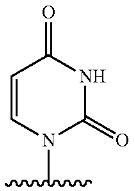 [SMILES: *n1ccc(=O)[nH]c1=O] |
| 722 | F | 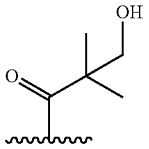 [SMILES: *C(=O)C(C)(C)CO] | 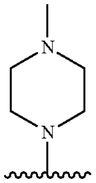 [SMILES: *N1CCN(C)CC1] | 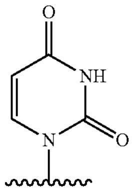 [SMILES: *n1ccc(=O)[nH]c1=O] |
| 723 | OH | 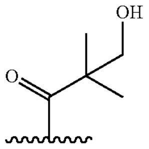 [SMILES: *C(=O)C(C)(C)CO] | 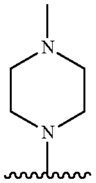 [SMILES: *N1CCN(C)CC1] | 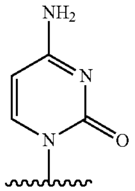 |
| 724 | F | 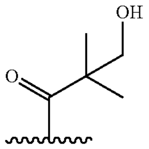 [SMILES: *C(=O)C(C)(C)CO] | 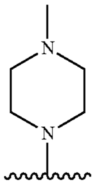 [SMILES: *N1CCN(C)CC1] | 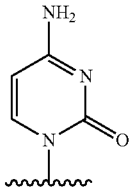 |
| 725 | OH | 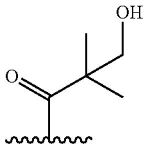 [SMILES: *C(=O)C(C)(C)CO] | 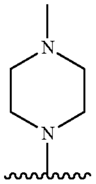 [SMILES: *N1CCN(C)CC1] | 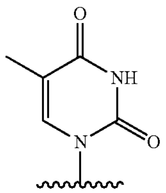 [SMILES: *n1cc(C)c(=O)[nH]c1=O] |

-continued
(VI-1)
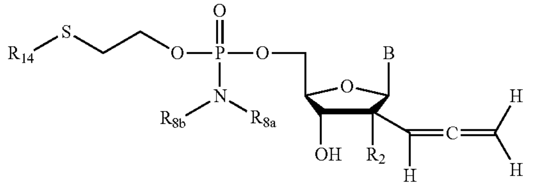
| Example # | $R_2$ | $R_{14}$ | $NR_{8a}R_{8b}$ | B |
|---|---|---|---|---|
| 726 | F | 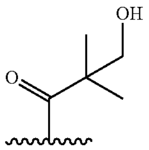 [SMILES: *C(=O)C(C)(C)CO] | 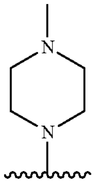 [SMILES: *N1CCN(C)CC1] | 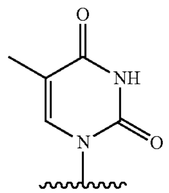 [SMILES: *n1cc(C)c(=O)[nH]c1=O] |
| 727 | OH | 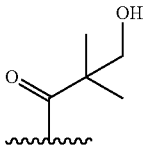 [SMILES: *C(=O)C(C)(C)CO] | 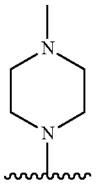 [SMILES: *N1CCN(C)CC1] | 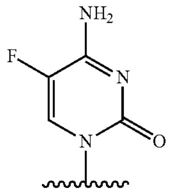 [SMILES: *n1cc(F)c(N)nc1=O] |
| 728 | F | 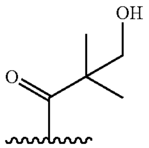 [SMILES: *C(=O)C(C)(C)CO] | 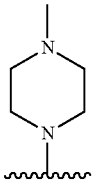 [SMILES: *N1CCN(C)CC1] | 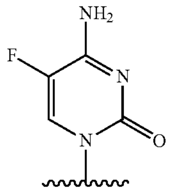 [SMILES: *n1cc(F)c(N)nc1=O] |
| 729 | OH | 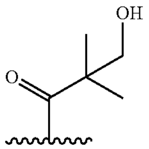 [SMILES: *C(=O)C(C)(C)CO] | 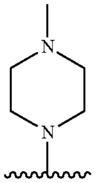 [SMILES: *N1CCN(C)CC1] | 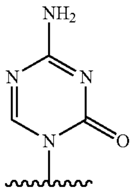 [SMILES: *n1cnc(N)nc1=O] |
| 730 | F | 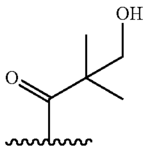 [SMILES: *C(=O)C(C)(C)CO] | 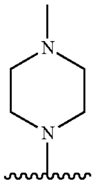 [SMILES: *N1CCN(C)CC1] | 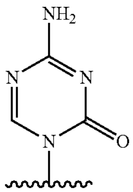 [SMILES: *n1cnc(N)nc1=O] |
| 731 | OH | 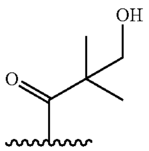 [SMILES: *C(=O)C(C)(C)CO] | 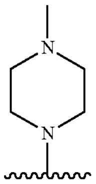 [SMILES: *N1CCN(C)CC1] | 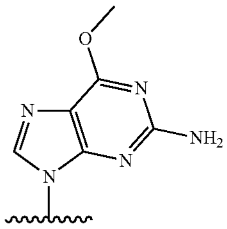 |

-continued
(VI-1)
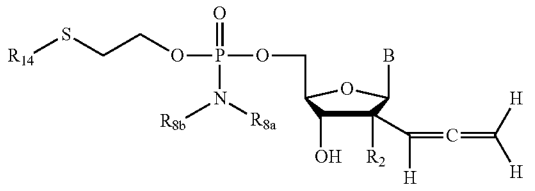
| Example # | $R_2$ | $R_{14}$ | $NR_{8a}R_{8b}$ | B |
|---|---|---|---|---|
| 732 | F | 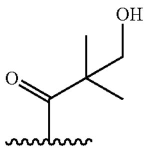 [SMILES: *C(=O)C(C)(C)CO] | 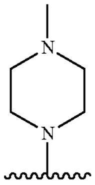 [SMILES: *N1CCN(C)CC1] | 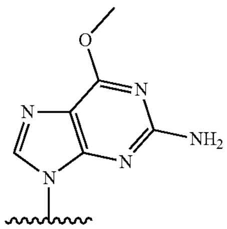 [SMILES: *n1cnc2c(OC)nc(N)nc21] |
| 733 | OH | 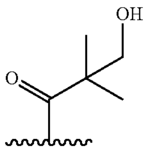 [SMILES: *C(=O)C(C)(C)CO] | 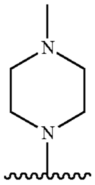 [SMILES: *N1CCN(C)CC1] | 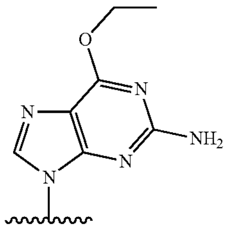 [SMILES: *n1cnc2c(OCC)nc(N)nc21] |
| 734 | F | 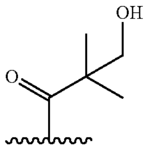 [SMILES: *C(=O)C(C)(C)CO] | 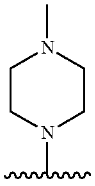 [SMILES: *N1CCN(C)CC1] | 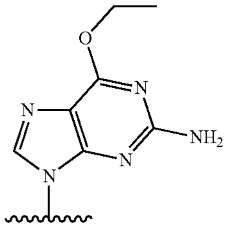 [SMILES: *n1cnc2c(OCC)nc(N)nc21] |
| 735 | OH | 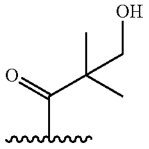 [SMILES: *C(=O)C(C)(C)CO] | 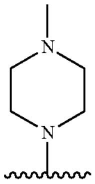 [SMILES: *N1CCN(C)CC1] | 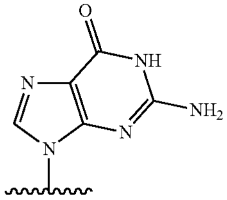 [SMILES: *n1cnc2c(=O)[nH]c(N)nc21] |
| 736 | F | 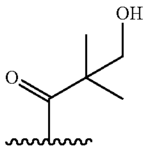 [SMILES: *C(=O)C(C)(C)CO] | 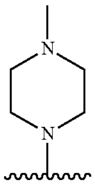 [SMILES: *N1CCN(C)CC1] | 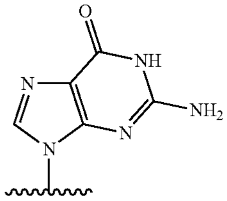 [SMILES: *n1cnc2c(=O)[nH]c(N)nc21] |
| 737 | OH | 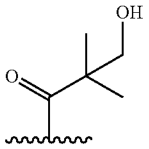 [SMILES: *C(=O)C(C)(C)CO] | 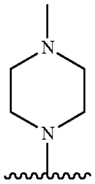 [SMILES: *N1CCN(C)CC1] | 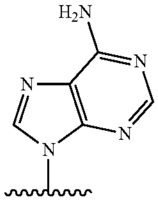 |

-continued
(VI-1)
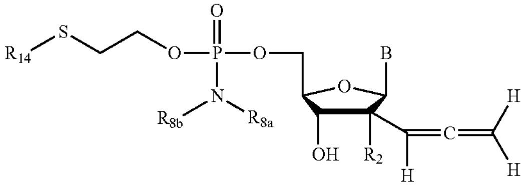
| Example # | $R_2$ | $R_{14}$ | $NR_{8a}R_{8b}$ | B |
|---|---|---|---|---|
| 738 | F | 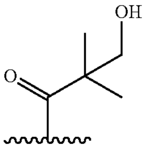 [SMILES: *C(=O)C(C)(C)CO] | 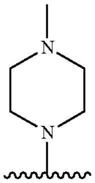 [SMILES: *N1CCN(C)CC1] | 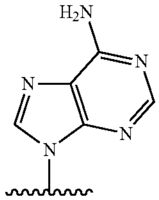 |
| 739 | OH | 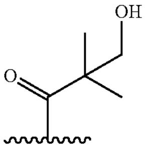 [SMILES: *C(=O)C(C)(C)CO] | 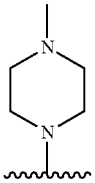 [SMILES: *N1CCN(C)CC1] | 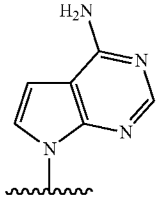 |
| 740 | F | 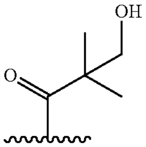 [SMILES: *C(=O)C(C)(C)CO] | 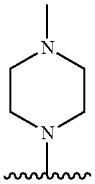 [SMILES: *N1CCN(C)CC1] | 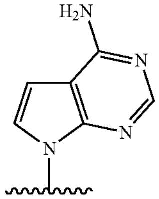 |
| 741 | OH | 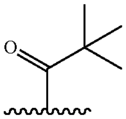 [SMILES: *C(=O)C(C)(C)C] | 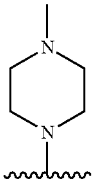 [SMILES: *N1CCN(C)CC1] | 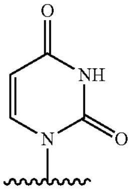 [SMILES: *n1ccc(=O)[nH]c1=O] |
| 742 | F | 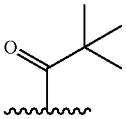 [SMILES: *C(=O)C(C)(C)C] | 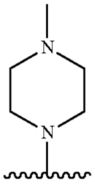 [SMILES: *N1CCN(C)CC1] | 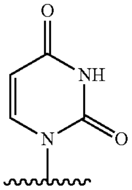 [SMILES: *n1ccc(=O)[nH]c1=O] |
| 743 | OH | 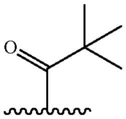 [SMILES: *C(=O)C(C)(C)C] | 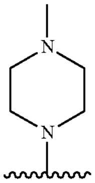 [SMILES: *N1CCN(C)CC1] | 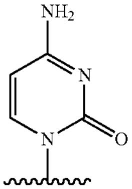 |

-continued
(VI-1)
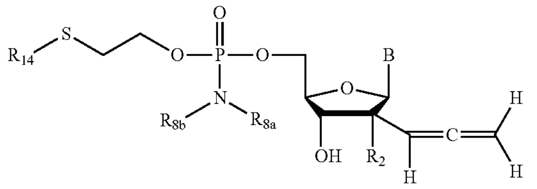
| Example # | $R_2$ | $R_{14}$ | $NR_{8a}R_{8b}$ | B |
|---|---|---|---|---|
| 744 | F | 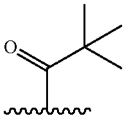 [SMILES: *C(=O)C(C)(C)C] | 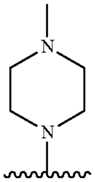 [SMILES: *N1CCN(C)CC1] | 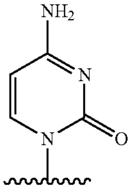 |
| 745 | OH | 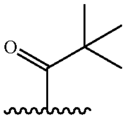 | 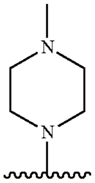 [SMILES: *N1CCN(C)CC1] | 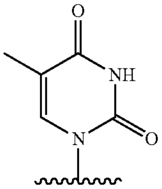 [SMILES: *n1cc(C)c(=O)[nH]c1=O] |
| 746 | F | 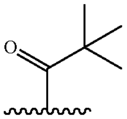 [SMILES: *C(=O)C(C)(C)C] | 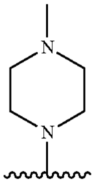 [SMILES: *N1CCN(C)CC1] | 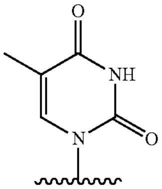 [SMILES: *n1cc(C)c(=O)[nH]c1=O] |
| 747 | OH | 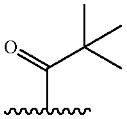 [SMILES: *C(=O)C(C)(C)C] | 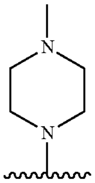 [SMILES: *N1CCN(C)CC1] | 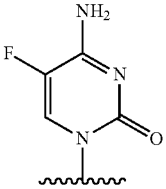 [SMILES: *n1cc(F)c(N)nc1=O] |
| 748 | F | 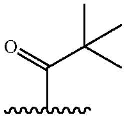 [SMILES: *C(=O)C(C)(C)C] | 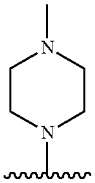 [SMILES: *N1CCN(C)CC1] | 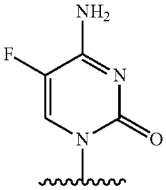 [SMILES: *n1cc(F)c(N)nc1=O] |
| 749 | OH | 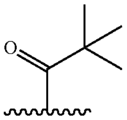 [SMILES: *C(=O)C(C)(C)C] | 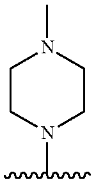 [SMILES: *N1CCN(C)CC1] | 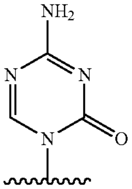 [SMILES: *n1cnc(N)nc1=O] |

-continued
(VI-1)
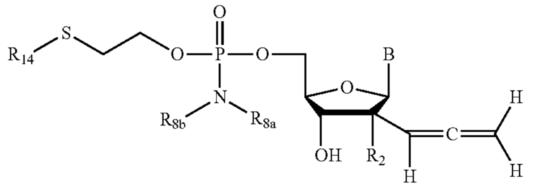
| Example # | $R_2$ | $R_{14}$ | $NR_{8a}R_{8b}$ | B |
|---|---|---|---|---|
| 750 | F | 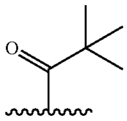 | 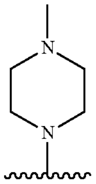 [SMILES: *N1CCN(C)CC1] | 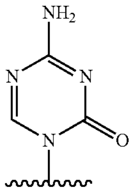 [SMILES: *n1cnc(N)nc1=O] |
| 751 | OH | 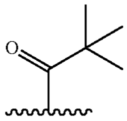 [SMILES: *C(=O)C(C)(C)C] | 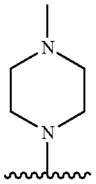 [SMILES: *N1CCN(C)CC1] | 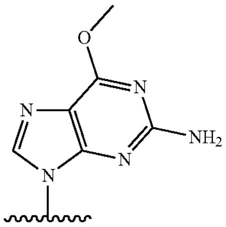 [SMILES: *n1cnc2c(OC)nc(N)nc21] |
| 752 | F | 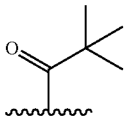 [SMILES: *C(=O)C(C)(C)C] | 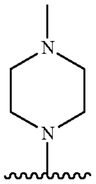 [SMILES: *N1CCN(C)CC1] | 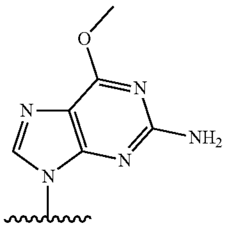 [SMILES: *n1cnc2c(OC)nc(N)nc21] |
| 753 | OH | 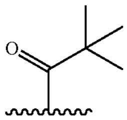 [SMILES: *C(=O)C(C)(C)C] | 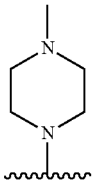 [SMILES: *N1CCN(C)CC1] | 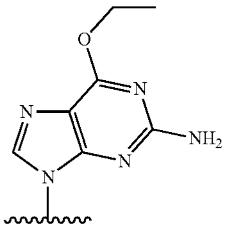 [SMILES: *n1cnc2c(OCC)nc(N)nc21] |
| 754 | F | 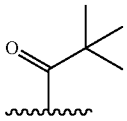 [SMILES: *C(=O)C(C)(C)C] | 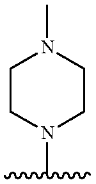 [SMILES: *N1CCN(C)CC1] | 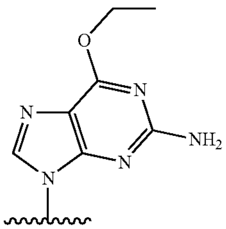 [SMILES: *n1cnc2c(OCC)nc(N)nc21] |
| 755 | OH | 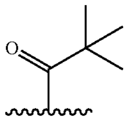 [SMILES: *C(=O)C(C)(C)C] | 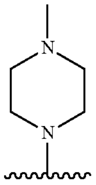 [SMILES: *N1CCN(C)CC1] | 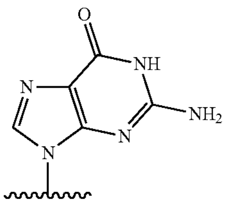 [SMILES: *n1cnc2c(=O)[nH]c(N)nc21] |

-continued
(VI-1)
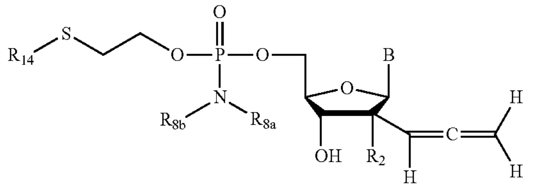
| Example # | $R_2$ | $R_{14}$ | $NR_{8a}R_{8b}$ | B |
|---|---|---|---|---|
| 756 | F | 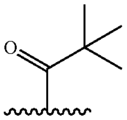 [SMILES: *C(=O)C(C)(C)C] | 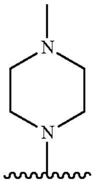 [SMILES: *N1CCN(C)CC1] | 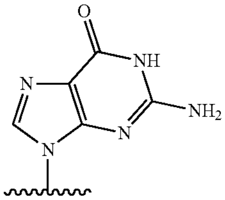 [SMILES: *n1cnc2c(=O)[nH]c(N)nc21] |
| 757 | OH | 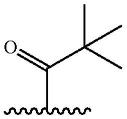 [SMILES: *C(=O)C(C)(C)C] | 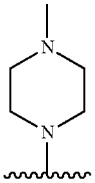 [SMILES: *N1CCN(C)CC1] | 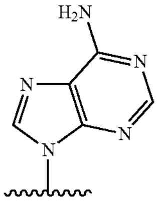 |
| 758 | F | 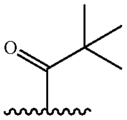 [SMILES: *C(=O)C(C)(C)C] | 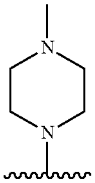 [SMILES: *N1CCN(C)CC1] | 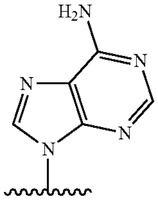 |
| 759 | OH | 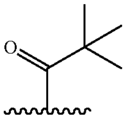 [SMILES: *C(=O)C(C)(C)C] | 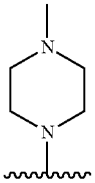 [SMILES: *N1CCN(C)CC1] | 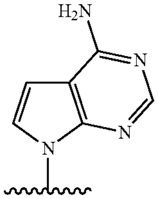 |
| 760 | F | 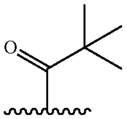 [SMILES: *C(=O)C(C)(C)C] | 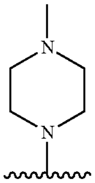 [SMILES: *N1CCN(C)CC1] | 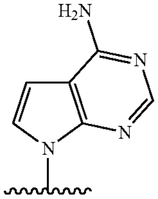 |
| 761 | OH | 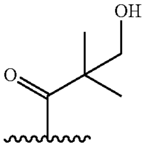 [SMILES: *C(=O)C(C)(C)CO] | 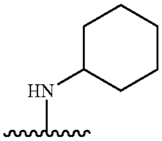 [SMILES: *NC1CCCCC1] | 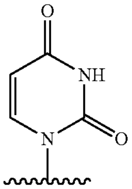 [SMILES: *n1ccc(=O)[nH]c1=O] |

-continued
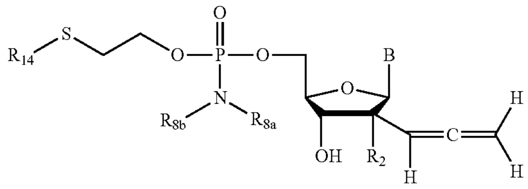
(VI-1)
| Example # | $R_2$ | $R_{14}$ | $NR_{8a}R_{8b}$ | B |
|---|---|---|---|---|
| 762 | F | 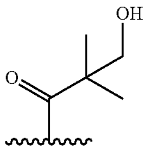 [SMILES: *C(=O)C(C)(C)CO] | 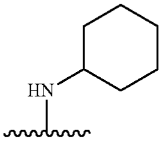 [SMILES: *NC1CCCCC1] | 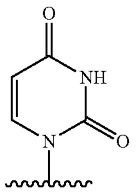 [SMILES: *n1ccc(=O)[nH]c1=O] |
| 763 | OH | 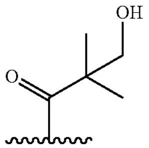 [SMILES: *C(=O)C(C)(C)CO] | 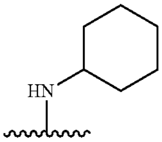 [SMILES: *NC1CCCCC1] | 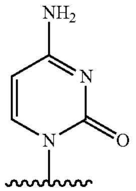 |
| 764 | F | 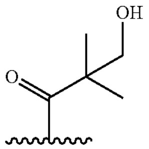 [SMILES: *C(=O)C(C)(C)CO] | 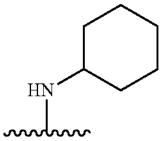 [SMILES: *NC1CCCCC1] | 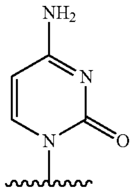 |
| 765 | OH | 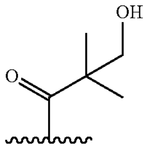 [SMILES: *C(=O)C(C)(C)CO] | 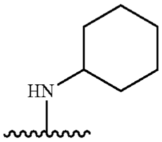 [SMILES: *NC1CCCCC1] | 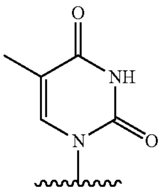 [SMILES: *n1cc(C)c(=O)[nH]c1=O] |
| 766 | F | 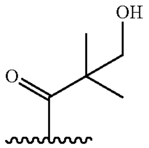 [SMILES: *C(=O)C(C)(C)CO] | 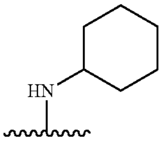 [SMILES: *NC1CCCCC1] | 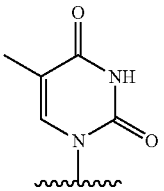 [SMILES: *n1cc(C)c(=O)[nH]c1=O] |
| 767 | OH | 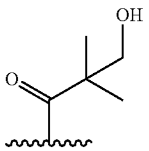 [SMILES: *C(=O)C(C)(C)CO] | 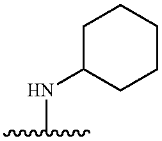 [SMILES: *NC1CCCCC1] | 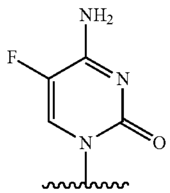 [SMILES: *n1cc(F)c(N)nc1=O] |

-continued
(VI-1)
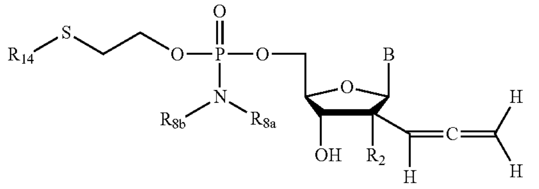
| Example # | $R_2$ | $R_{14}$ | $NR_{8a}R_{8b}$ | B |
|---|---|---|---|---|
| 768 | F | 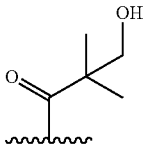 [SMILES: *C(=O)C(C)(C)CO] | 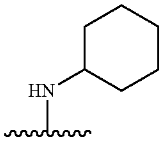 [SMILES: *NC1CCCCC1] | 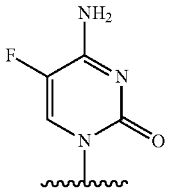 [SMILES: *n1cc(F)c(N)nc1=O] |
| 769 | OH | 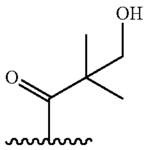 [SMILES: *C(=O)C(C)(C)CO] | 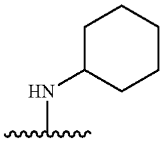 [SMILES: *NC1CCCCC1] | 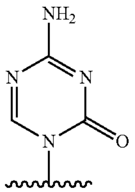 [SMILES: *n1cnc(N)nc1=O] |
| 770 | F | 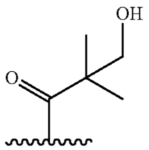 [SMILES: *C(=O)C(C)(C)CO] | 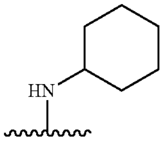 [SMILES: *NC1CCCCC1] | 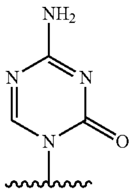 [SMILES: *n1cnc(N)nc1=O] |
| 771 | OH | 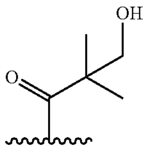 [SMILES: *C(=O)C(C)(C)CO] | 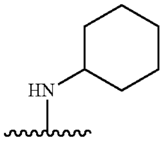 [SMILES: *NC1CCCCC1] | 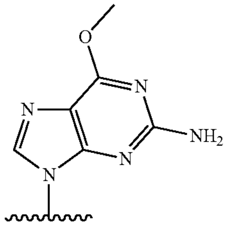 [SMILES: *n1cnc2c(OC)nc(N)nc21] |
| 772 | F | 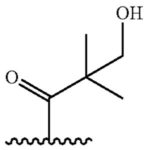 [SMILES: *C(=O)C(C)(C)CO] | 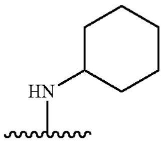 [SMILES: *NC1CCCCC1] | 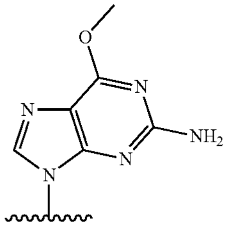 |
| 773 | OH | 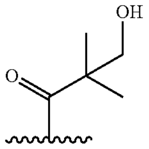 [SMILES: *C(=O)C(C)(C)CO] | 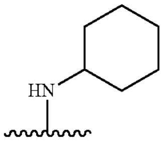 [SMILES: *NC1CCCCC1] | 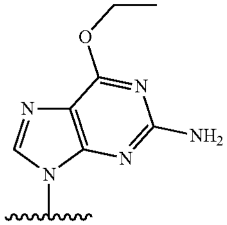 [SMILES: *n1cnc2c(OCC)nc(N)nc21] |

-continued
(VI-1)
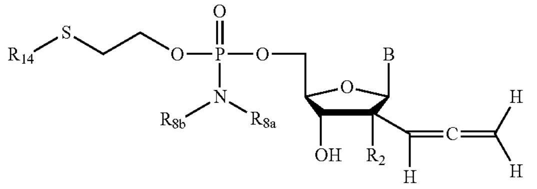
| Example # | $R_2$ | $R_{14}$ | $NR_{8a}R_{8b}$ | B |
|---|---|---|---|---|
| 774 | F | 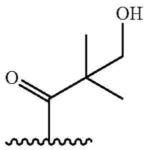 [SMILES: *C(=O)C(C)(C)CO] | 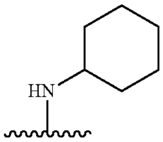 [SMILES: *NC1CCCCC1] | 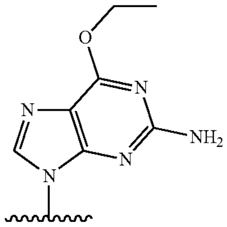 [SMILES: *n1cnc2c(OCC)nc(N)nc21] |
| 775 | OH | 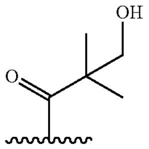 [SMILES: *C(=O)C(C)(C)CO] | 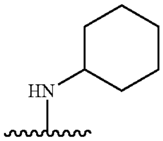 [SMILES: *NC1CCCCC1] | 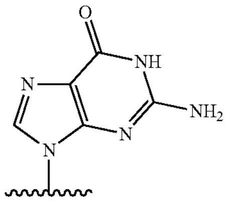 [SMILES: *n1cnc2c(=O)[nH]c(N)nc21] |
| 776 | F | 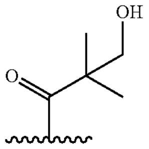 [SMILES: *C(=O)C(C)(C)CO] | 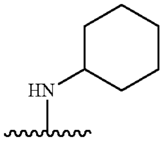 [SMILES: *NC1CCCCC1] | 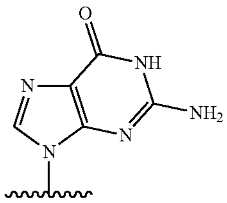 [SMILES: *n1cnc2c(=O)[nH]c(N)nc21] |
| 777 | OH | 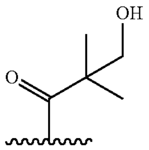 [SMILES: *C(=O)C(C)(C)CO] | 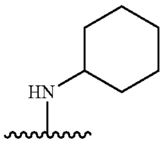 [SMILES: *NC1CCCCC1] | 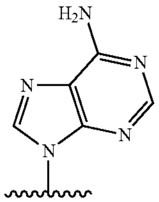 |
| 778 | F | 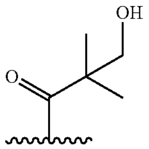 [SMILES: *C(=O)C(C)(C)CO] | 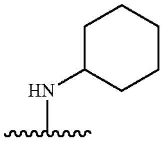 [SMILES: *NC1CCCCC1] | 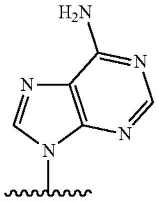 |
| 779 | OH | 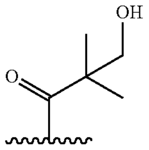 [SMILES: *C(=O)C(C)(C)CO] | 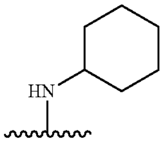 [SMILES: *NC1CCCCC1] | 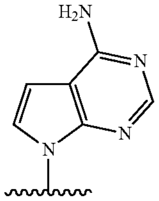 |

-continued
(VI-1)
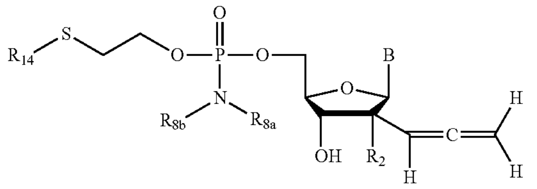
| Example # | $R_2$ | $R_{14}$ | $NR_{8a}R_{8b}$ | B |
|---|---|---|---|---|
| 780 | F | 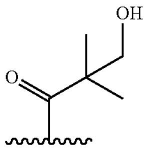 [SMILES: *C(=O)C(C)(C)CO] | 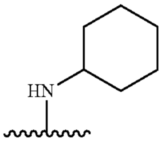 [SMILES: *NC1CCCCC1] | 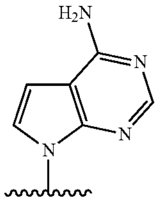 |
| 781 | OH | 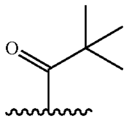 [SMILES: *C(=O)C(C)(C)C] | 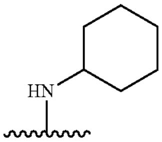 [SMILES: *NC1CCCCC1] | 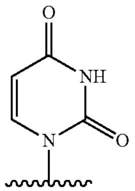 [SMILES: *n1ccc(=O)[nH]c1=O] |
| 782 | F | 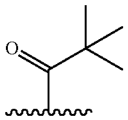 [SMILES: *C(=O)C(C)(C)C] | 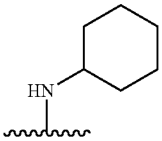 [SMILES: *NC1CCCCC1] | 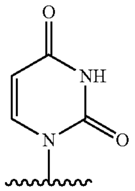 [SMILES: *n1ccc(=O)[nH]c1=O] |
| 783 | OH | 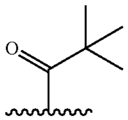 [SMILES: *C(=O)C(C)(C)C] | 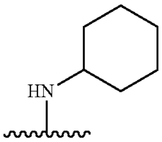 [SMILES: *NC1CCCCC1] | 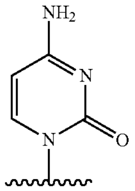 |
| 784 | F | 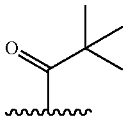 [SMILES: *C(=O)C(C)(C)C] | 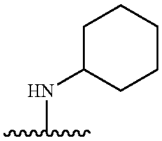 [SMILES: *NC1CCCCC1] | 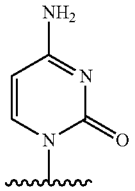 |
| 785 | OH | 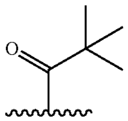 [SMILES: *C(=O)C(C)(C)C] | 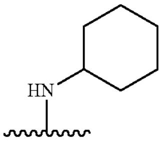 [SMILES: *NC1CCCCC1] | 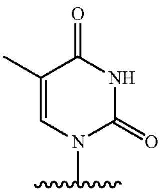 [SMILES: *n1cc(C)c(=O)[nH]c1=O] |

-continued
(VI-1)
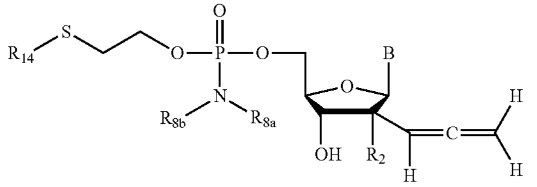
| Example # | $R_2$ | $R_{14}$ | $NR_{8a}R_{8b}$ | B |
|---|---|---|---|---|
| 786 | F | 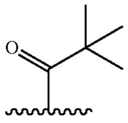 [SMILES: *C(=O)C(C)(C)C] | 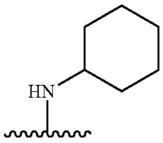 [SMILES: *NC1CCCCC1] | 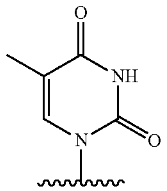 [SMILES: *n1cc(C)c(=O)[nH]c1=O] |
| 787 | OH | 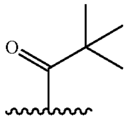 | 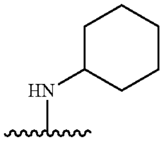 [SMILES: *NC1CCCCC1] | 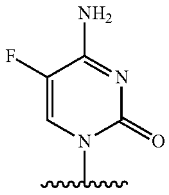 [SMILES: *n1cc(F)c(N)nc1=O] |
| 788 | F | 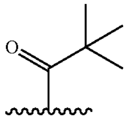 [SMILES: *C(=O)C(C)(C)C] | 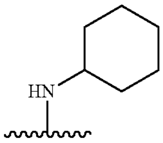 [SMILES: *NC1CCCCC1] | 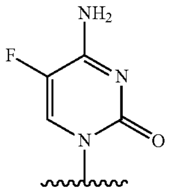 [SMILES: *n1cc(F)c(N)nc1=O] |
| 789 | OH | 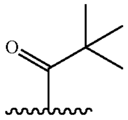 [SMILES: *C(=O)C(C)(C)C] | 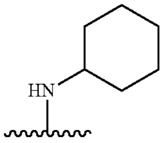 [SMILES: *NC1CCCCC1] | 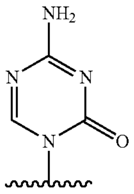 [SMILES: *n1cnc(N)nc1=O] |
| 790 | F | 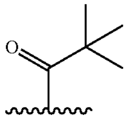 | 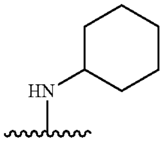 [SMILES: *NC1CCCCC1] | 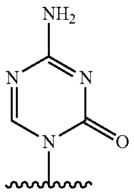 [SMILES: *n1cnc(N)nc1=O] |
| 791 | OH | 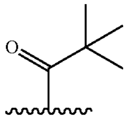 [SMILES: *C(=O)C(C)(C)C] | 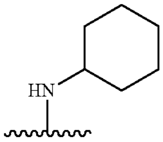 [SMILES: *NC1CCCCC1] | 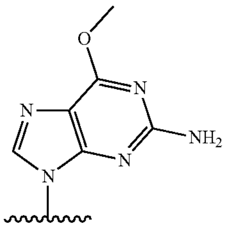 |

-continued
(VI-1)
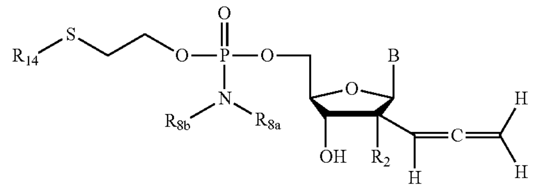
| Example # | $R_2$ | $R_{14}$ | $NR_{8a}R_{8b}$ | B |
|---|---|---|---|---|
| 792 | F | 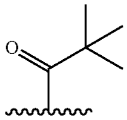 [SMILES: *C(=O)C(C)(C)C] | 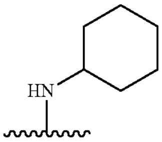 [SMILES: *NC1CCCCC1] | 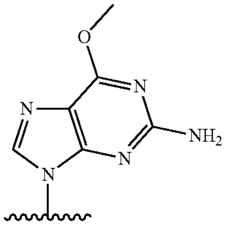 [SMILES: *n1cnc2c(OC)nc(N)nc21] |
| 793 | OH | 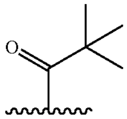 [SMILES: *C(=O)C(C)(C)C] | 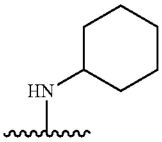 [SMILES: *NC1CCCCC1] | 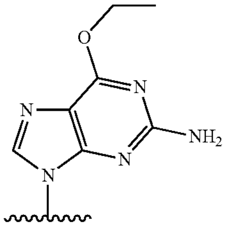 [SMILES: *n1cnc2c(OCC)nc(N)nc21] |
| 794 | F | 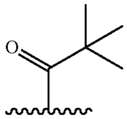 [SMILES: *C(=O)C(C)(C)C] | 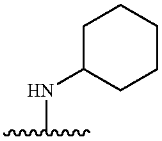 [SMILES: *NC1CCCCC1] | 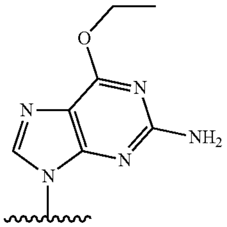 [SMILES: *n1cnc2c(OCC)nc(N)nc21] |
| 795 | OH | 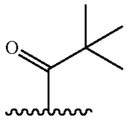 [SMILES: *C(=O)C(C)(C)C] | 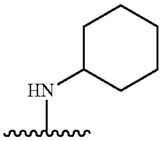 [SMILES: *NC1CCCCC1] | 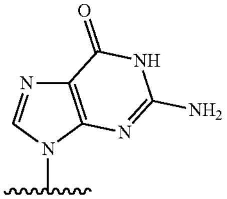 [SMILES: *n1cnc2c(=O)[nH]c(N)nc21] |
| 796 | F | 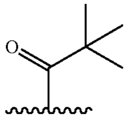 [SMILES: *C(=O)C(C)(C)C] | 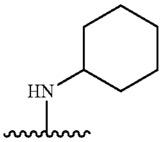 [SMILES: *NC1CCCCC1] | 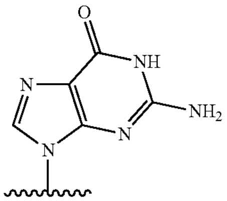 [SMILES: *n1cnc2c(=O)[nH]c(N)nc21] |
| 797 | OH | 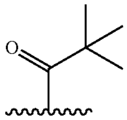 [SMILES: *C(=O)C(C)(C)C] | 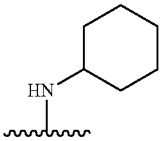 [SMILES: *NC1CCCCC1] | 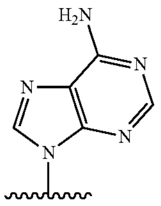 |

-continued
(VI-1)
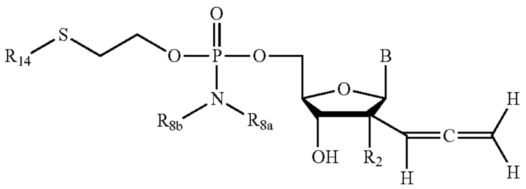
| Example # | $R_2$ | $R_{14}$ | $NR_{8a}R_{8b}$ | B |
|---|---|---|---|---|
| 798 | F | 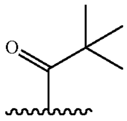 [SMILES: *C(=O)C(C)(C)C] | 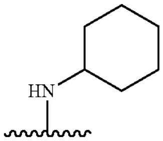 [SMILES: *NC1CCCCC1] | 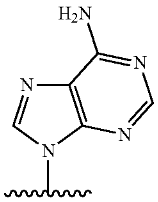 |
| 799 | OH | 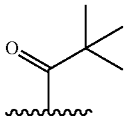 [SMILES: *C(=O)C(C)(C)C] | 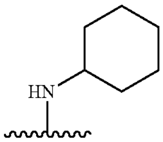 [SMILES: *NC1CCCCC1] | 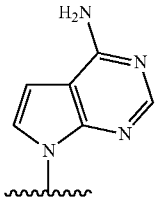 |
| 800 | F | 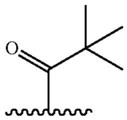 [SMILES: *C(=O)C(C)(C)C] | 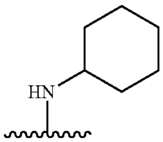 [SMILES: *NC1CCCCC1] | 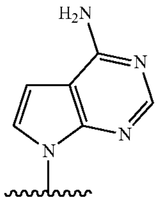 |
Compounds in Table 5 are represented by Formula (VII-1) wherein $R_2$, $R_{2b}$, $R_{2c}$, $R_6$, and B are delineated for each example in Table 5.
(VII-1)
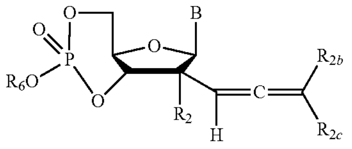
| Example# | $R_6$ | $R_{2b}$ | $R_{2c}$ | $R_2$ | B |
|---|---|---|---|---|---|
| 801 | i-Pr | H | H | OH | 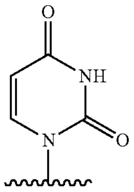 [SMILES: *n1ccc(=O)[nH]c1=O] |
-continued
(VII-1)
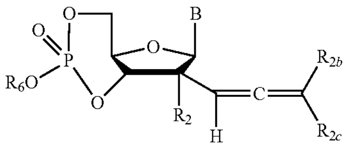
| Example# | $R_6$ | $R_{2b}$ | $R_{2c}$ | $R_2$ | B |
|---|---|---|---|---|---|
| 802 | i-Pr | H | H | F | 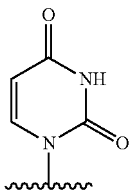 [SMILES: *n1ccc(=O)[nH]c1=O] |
| 803 | i-Pr | Me | Me | OH | 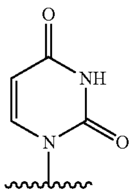 [SMILES: *n1ccc(=O)[nH]c1=O] |

-continued
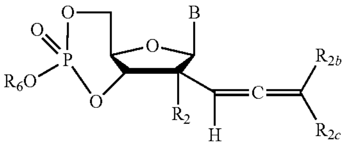
(VII-1)
| Example# | $R_6$ | $R_{2b}$ | $R_{2c}$ | $R_2$ | B |
|---|---|---|---|---|---|
| 804 | i-Pr | Me | Me | F | 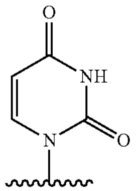 [SMILES: *n1ccc(=O)[nH]c1=O] |
| 805 | i-Pr | F | F | OH | 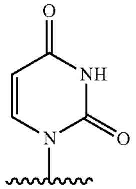 [SMILES: *n1ccc(=O)[nH]c1=O] |
| 806 | i-Pr | F | F | F | 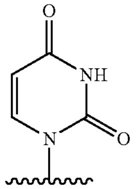 [SMILES: *n1ccc(=O)[nH]c1=O] |
| 807 | i-Pr | H | H | OH | 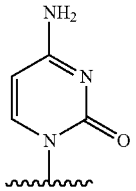 |
| 808 | i-Pr | H | H | F | 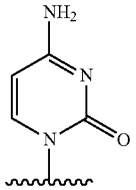 |
| 809 | i-Pr | Me | Me | OH | 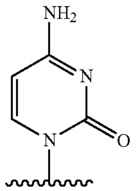 |
| 810 | i-Pr | Me | Me | F | 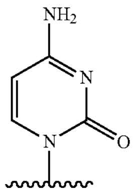 |
-continued
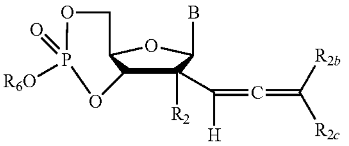
(VII-1)
| Example# | $R_6$ | $R_{2b}$ | $R_{2c}$ | $R_2$ | B |
|---|---|---|---|---|---|
| 811 | i-Pr | F | F | OH | 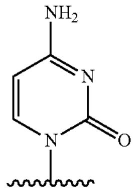 |
| 812 | i-Pr | F | F | F | 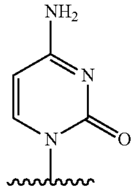 |
| 813 | i-Pr | H | H | OH | 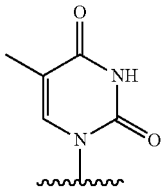 [SMILES: *n1cc(C)c(=O)[nH]c1=O] |
| 814 | i-Pr | H | H | F | 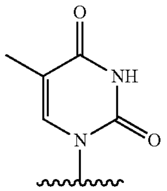 [SMILES: *n1cc(C)c(=O)[nH]c1=O] |
| 815 | i-Pr | Me | Me | OH | 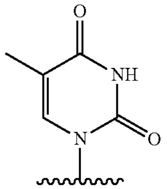 [SMILES: *n1cc(C)c(=O)[nH]c1=O] |
| 816 | i-Pr | Me | Me | F | 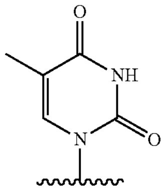 [SMILES: *n1cc(C)c(=O)[nH]c1=O] |
| 817 | i-Pr | F | F | OH | 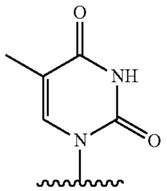 [SMILES: *n1cc(C)c(=O)[nH]c1=O] |

-continued
(VII-1)
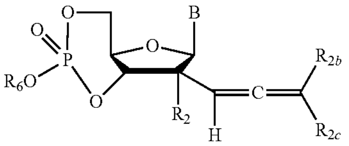
| Example# | $R_6$ | $R_{2b}$ | $R_{2c}$ | $R_2$ | B |
|---|---|---|---|---|---|
| 818 | i-Pr | F | F | F | 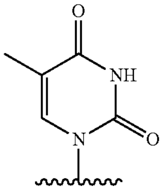 |
| 819 | i-Pr | H | H | OH | 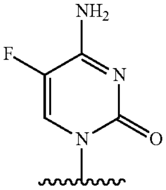 |
| 820 | i-Pr | H | H | F | 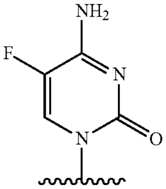 |
| 821 | i-Pr | Me | Me | OH | 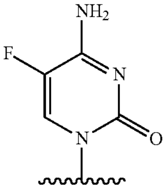 |
| 822 | i-Pr | Me | Me | F | 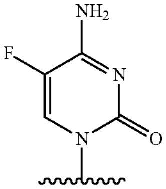 |
| 823 | i-Pr | F | F | OH | 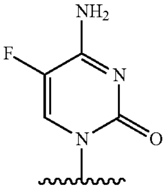 |
| 824 | i-Pr | F | F | F | 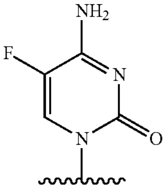 |
-continued
(VII-1)
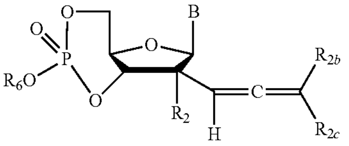
| Example# | $R_6$ | $R_{2b}$ | $R_{2c}$ | $R_2$ | B |
|---|---|---|---|---|---|
| 825 | i-Pr | H | H | OH | 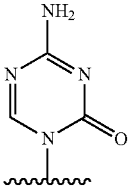 [SMILES: *n1cnc(N)nc1=O] |
| 826 | i-Pr | H | H | F | 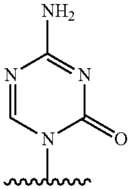 [SMILES: *n1cnc(N)nc1=O] |
| 827 | i-Pr | Me | Me | OH | 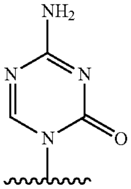 [SMILES: *n1cnc(N)nc1=O] |
| 828 | i-Pr | Me | Me | F | 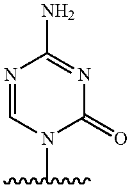 [SMILES: *n1cnc(N)nc1=O] |
| 829 | i-Pr | F | F | OH | 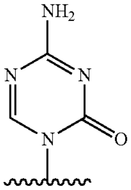 [SMILES: *n1cnc(N)nc1=O] |
| 830 | i-Pr | F | F | F | 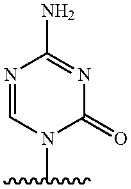 [SMILES: *n1cnc(N)nc1=O] |

-continued
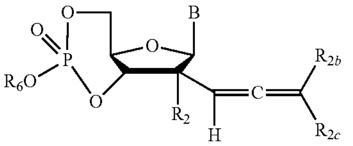
(VII-1)
| Example# | $R_6$ | $R_{2b}$ | $R_{2c}$ | $R_2$ | B |
|---|---|---|---|---|---|
| 831 | i-Pr | H | H | OH | 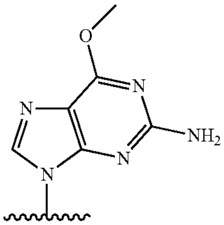 [SMILES: *n1cnc2c(OC)nc(N)nc21] |
| 832 | i-Pr | H | H | F | 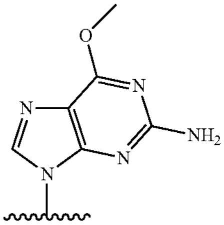 [SMILES: *n1cnc2c(OC)nc(N)nc21] |
| 833 | i-Pr | Me | Me | OH | 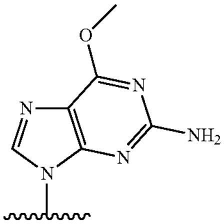 [SMILES: *n1cnc2c(OC)nc(N)nc21] |
| 834 | i-Pr | Me | Me | F | 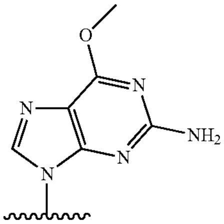 [SMILES: *n1cnc2c(OC)nc(N)nc21] |
| 835 | i-Pr | F | F | OH | 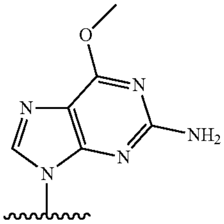 [SMILES: *n1cnc2c(OC)nc(N)nc21] |
| 836 | i-Pr | F | F | F | 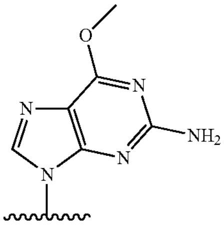 [SMILES: *n1cnc2c(OC)nc(N)nc21] |
-continued
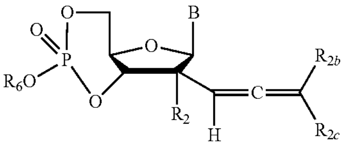
(VII-1)
| Example# | $R_6$ | $R_{2b}$ | $R_{2c}$ | $R_2$ | B |
|---|---|---|---|---|---|
| 837 | i-Pr | H | H | OH | 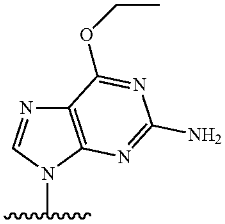 [SMILES: *n1cnc2c(OCC)nc(N)nc21] |
| 838 | i-Pr | H | H | F | 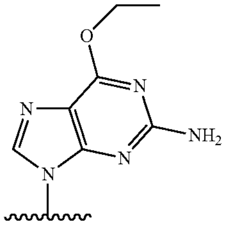 [SMILES: *n1cnc2c(OCC)nc(N)nc21] |
| 839 | i-Pr | Me | Me | OH | 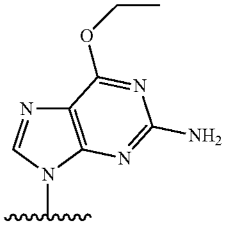 [SMILES: *n1cnc2c(OCC)nc(N)nc21] |
| 840 | i-Pr | Me | Me | F | 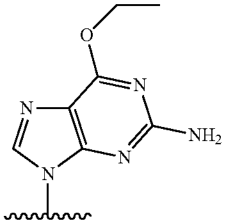 [SMILES: *n1cnc2c(OCC)nc(N)nc21] |
| 841 | i-Pr | F | F | OH | 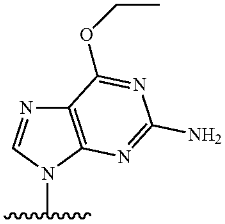 [SMILES: *n1cnc2c(OCC)nc(N)nc21] |
| 842 | i-Pr | F | F | F | 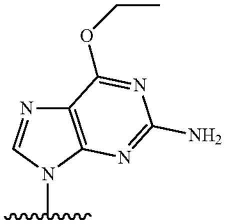 [SMILES: *n1cnc2c(OCC)nc(N)nc21] |

-continued
(VII-1)
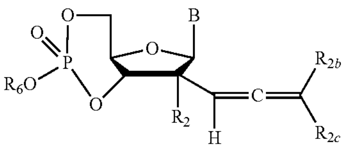
| Example# | $R_6$ | $R_{2b}$ | $R_{2c}$ | $R_2$ | B |
|---|---|---|---|---|---|
| 843 | i-Pr | H | H | OH | 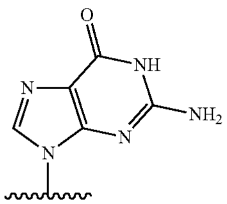 [SMILES: *n1cnc2c(=O)[nH]c(N)nc21] |
| 844 | i-Pr | H | H | F | 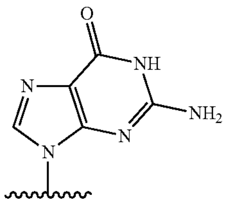 [SMILES: *n1cnc2c(=O)[nH]c(N)nc21] |
| 845 | i-Pr | Me | Me | OH | 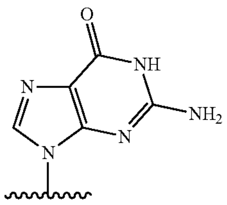 [SMILES: *n1cnc2c(=O)[nH]c(N)nc21] |
| 846 | i-Pr | Me | Me | F | 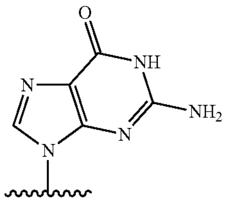 [SMILES: *n1cnc2c(=O)[nH]c(N)nc21] |
| 847 | i-Pr | F | F | OH | 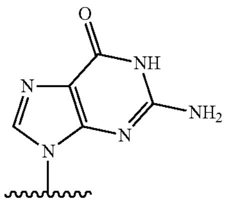 [SMILES: *n1cnc2c(=O)[nH]c(N)nc21] |
| 848 | i-Pr | F | F | F | 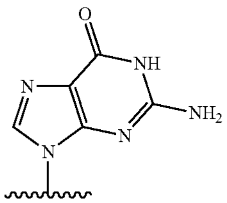 [SMILES: *n1cnc2c(=O)[nH]c(N)nc21] |
-continued
(VII-1)
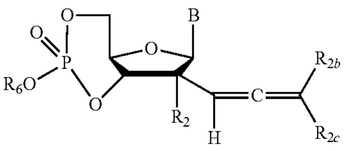
| Example# | $R_6$ | $R_{2b}$ | $R_{2c}$ | $R_2$ | B |
|---|---|---|---|---|---|
| 849 | i-Pr | H | H | OH | 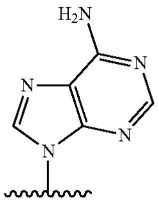 |
| 850 | i-Pr | H | H | F | 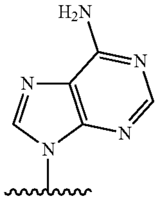 [SMILES: *n1cnc2c(N)ncnc21] |
| 851 | i-Pr | Me | Me | OH | 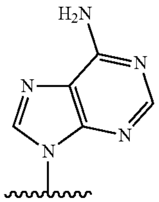 [SMILES: *n1cnc2c(N)ncnc21] |
| 852 | i-Pr | Me | Me | F | 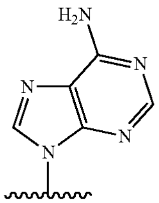 |
| 853 | i-Pr | F | F | OH | 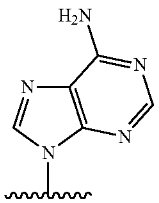 [SMILES: *n1cnc2c(N)ncnc21] |
| 854 | i-Pr | F | F | F | 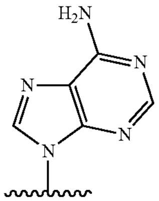 [SMILES: *n1cnc2c(N)ncnc21] |

-continued
(VII-1)
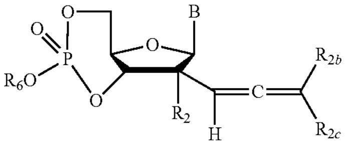
| Example# | $R_6$ | $R_{2b}$ | $R_{2c}$ | $R_2$ | B |
|---|---|---|---|---|---|
| 855 | i-Pr | H | H | OH | 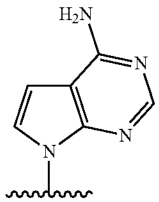 [SMILES: *n1ccc2c(N)ncnc21] |
| 856 | i-Pr | H | H | F | 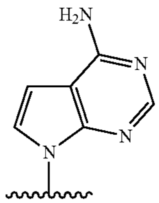 [SMILES: *n1ccc2c(N)ncnc21] |
| 857 | i-Pr | Me | Me | OH | 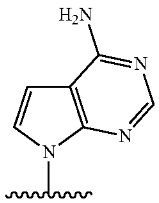 [SMILES: *n1ccc2c(N)ncnc21] |
| 858 | i-Pr | Me | Me | F | 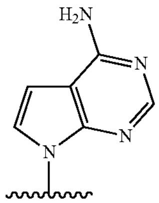 [SMILES: *n1ccc2c(N)ncnc21] |
| 859 | i-Pr | F | F | OH | 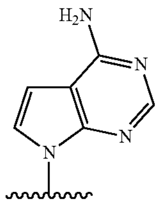 [SMILES: *n1ccc2c(N)ncnc21] |
| 860 | i-Pr | F | F | F | 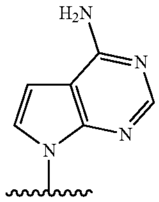 [SMILES: *n1ccc2c(N)ncnc21] |
-continued
(VII-1)
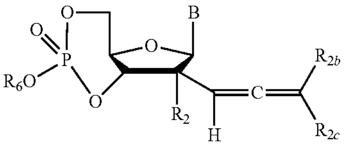
| Example# | $R_6$ | $R_{2b}$ | $R_{2c}$ | $R_2$ | B |
|---|---|---|---|---|---|
| 861 | Et | H | H | OH | 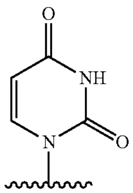 [SMILES: *n1ccc(=O)[nH]c1=O] |
| 862 | Et | H | H | F | 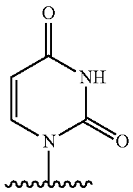 [SMILES: *n1ccc(=O)[nH]c1=O] |
| 863 | Et | Me | Me | OH | 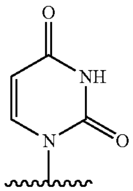 [SMILES: *n1ccc(=O)[nH]c1=O] |
| 864 | Et | Me | Me | F | 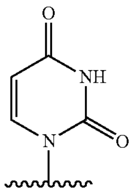 |
| 865 | Et | F | F | OH | 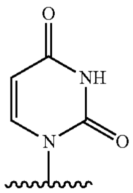 [SMILES: *n1ccc(=O)[nH]c1=O] |
| 866 | Et | F | F | F | 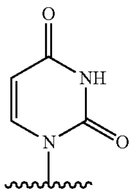 [SMILES: *n1ccc(=O)[nH]c1=O] |
| 867 | Et | H | H | OH | 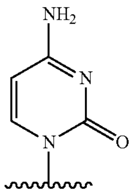 |

(VII-1)
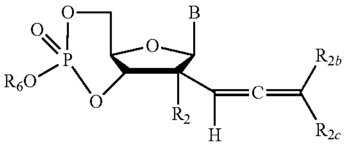
| Example# | $R_6$ | $R_{2b}$ | $R_{2c}$ | $R_2$ | B |
|---|---|---|---|---|---|
| 868 | Et | H | H | F | 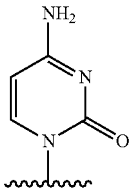 |
| 869 | Et | Me | Me | OH | 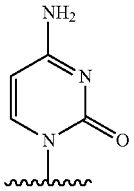 |
| 870 | Et | Me | Me | F | 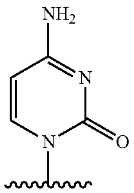 |
| 871 | Et | F | F | OH | 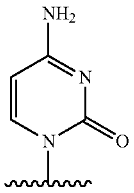 |
| 872 | Et | F | F | F | 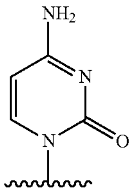 |
| 873 | Et | H | H | OH | 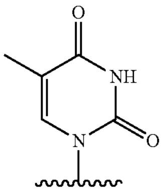 [SMILES: *n1cc(C)c(=O)[nH]c1=O] |
| 874 | Et | H | H | F | 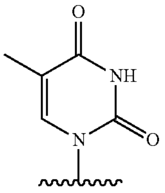 |
(VII-1)
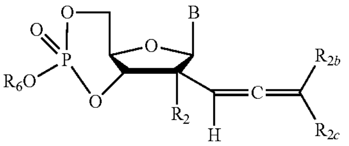
| Example# | $R_6$ | $R_{2b}$ | $R_{2c}$ | $R_2$ | B |
|---|---|---|---|---|---|
| 875 | Et | Me | Me | OH | 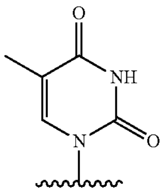 [SMILES: *n1cc(C)c(=O)[nH]c1=O] |
| 876 | Et | Me | Me | F | 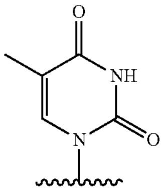 [SMILES: *n1cc(C)c(=O)[nH]c1=O] |
| 877 | Et | F | F | OH | 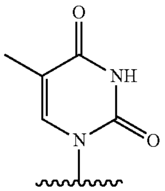 [SMILES: *n1cc(C)c(=O)[nH]c1=O] |
| 878 | Et | F | F | F | 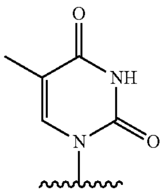 [SMILES: *n1cc(C)c(=O)[nH]c1=O] |
| 879 | Et | H | H | OH | 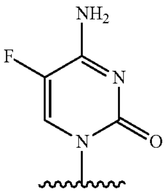 |
| 880 | Et | H | H | F | 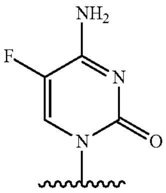 |
| 881 | Et | Me | Me | OH | 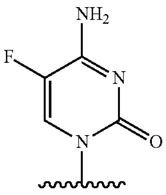 |

-continued
(VII-1)
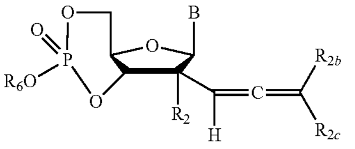
| Example# | $R_6$ | $R_{2b}$ | $R_{2c}$ | $R_2$ | B |
|---|---|---|---|---|---|
| 882 | Et | Me | Me | F | 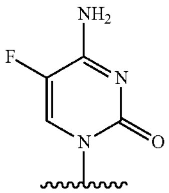 |
| 883 | Et | F | F | OH | 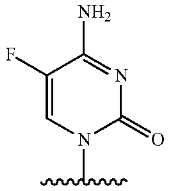 |
| 884 | Et | F | F | F | 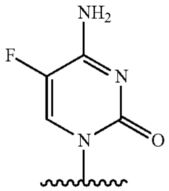 |
| 885 | Et | H | H | OH | 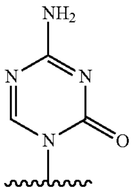 |
| 886 | Et | H | H | F | 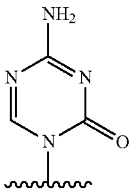 [SMILES: *n1cnc(N)nc1=O] |
| 887 | Et | Me | Me | OH | 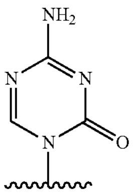 |
| 888 | Et | Me | Me | F | 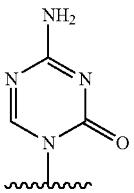 [SMILES: *n1cnc(N)nc1=O] |
-continued
(VII-1)
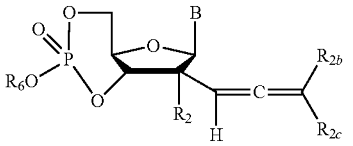
| Example# | $R_6$ | $R_{2b}$ | $R_{2c}$ | $R_2$ | B |
|---|---|---|---|---|---|
| 889 | Et | F | F | OH | 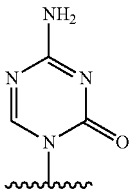 [SMILES: *n1cnc(N)nc1=O] |
| 890 | Et | F | F | F | 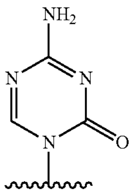 [SMILES: *n1cnc(N)nc1=O] |
| 891 | Et | H | H | OH | 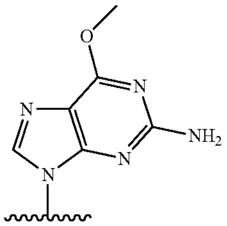 [SMILES: *n1cnc2c(OC)nc(N)nc21] |
| 892 | Et | H | H | F | 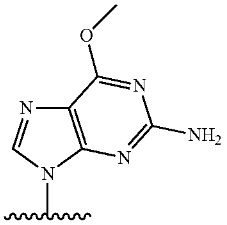 [SMILES: *n1cnc2c(OC)nc(N)nc21] |
| 893 | Et | Me | Me | OH | 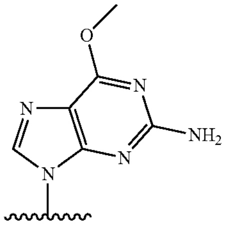 [SMILES: *n1cnc2c(OC)nc(N)nc21] |
| 894 | Et | Me | Me | F | 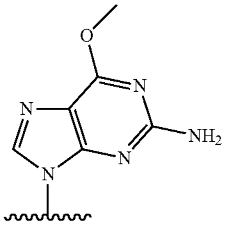 [SMILES: *n1cnc2c(OC)nc(N)nc21] |

-continued
(VII-1)
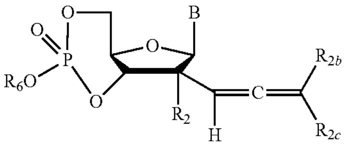
| Example# | $R_6$ | $R_{2b}$ | $R_{2c}$ | $R_2$ | B |
|---|---|---|---|---|---|
| 895 | Et | F | F | OH | 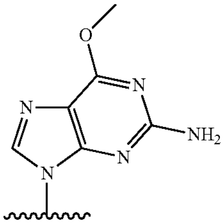 [SMILES: *n1cnc2c(OC)nc(N)nc21] |
| 896 | Et | F | F | F | 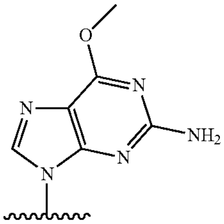 [SMILES: *n1cnc2c(OC)nc(N)nc21] |
| 897 | Et | H | H | OH | 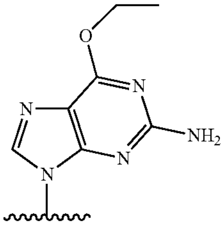 [SMILES: *n1cnc2c(OCC)nc(N)nc21] |
| 898 | Et | H | H | F | 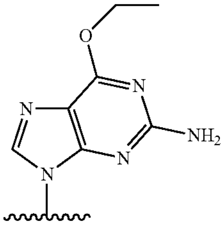 [SMILES: *n1cnc2c(OCC)nc(N)nc21] |
| 899 | Et | Me | Me | OH | 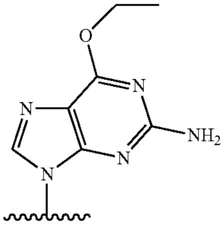 [SMILES: *n1cnc2c(OCC)nc(N)nc21] |
| 900 | Et | Me | Me | F | 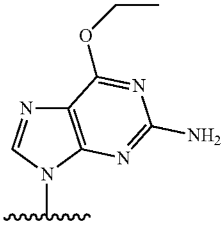 [SMILES: *n1cnc2c(OCC)nc(N)nc21] |
-continued
(VII-1)
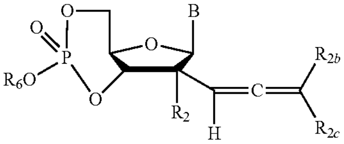
| Example# | $R_6$ | $R_{2b}$ | $R_{2c}$ | $R_2$ | B |
|---|---|---|---|---|---|
| 901 | Et | F | F | OH | 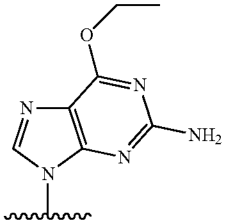 [SMILES: *n1cnc2c(OCC)nc(N)nc21] |
| 902 | Et | F | F | F | 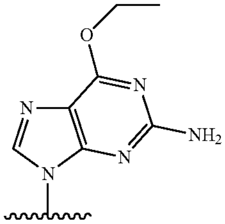 [SMILES: *n1cnc2c(OCC)nc(N)nc21] |
| 903 | Et | H | H | OH | 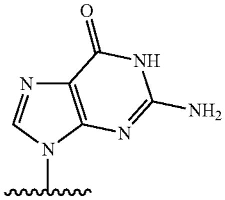 [SMILES: *n1cnc2c(=O)[nH]c(N)nc21] |
| 904 | Et | H | H | F | 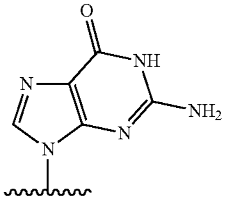 [SMILES: *n1cnc2c(=O)[nH]c(N)nc21] |
| 905 | Et | Me | Me | OH | 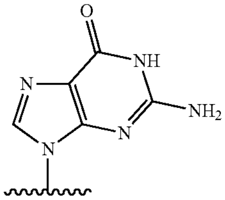 [SMILES: *n1cnc2c(=O)[nH]c(N)nc21] |
| 906 | Et | Me | Me | F | 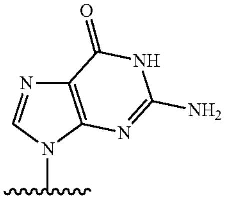 [SMILES: *n1cnc2c(=O)[nH]c(N)nc21] |

-continued
(VII-1)
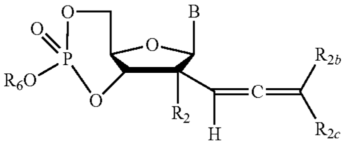
| Example# | $R_6$ | $R_{2b}$ | $R_{2c}$ | $R_2$ | B |
|---|---|---|---|---|---|
| 907 | Et | F | F | OH | 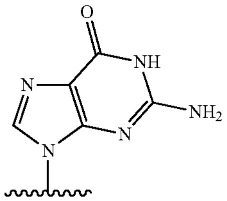 [SMILES: *n1cnc2c(=O)[nH]c(N)nc21] |
| 908 | Et | F | F | F | 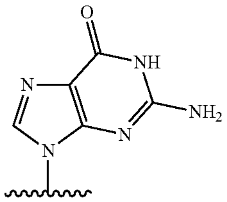 [SMILES: *n1cnc2c(=O)[nH]c(N)nc21] |
| 909 | Et | H | H | OH | 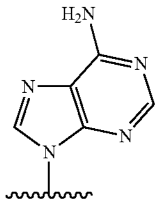 [SMILES: *n1cnc2c(N)ncnc21] |
| 910 | Et | H | H | F | 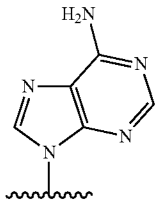 [SMILES: *n1cnc2c(N)ncnc21] |
| 911 | Et | Me | Me | OH | 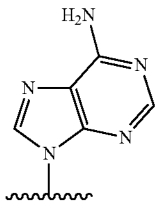 [SMILES: *n1cnc2c(N)ncnc21] |
| 912 | Et | Me | Me | F | 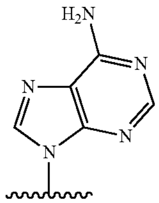 [SMILES: *n1cnc2c(N)ncnc21] |
-continued
(VII-1)
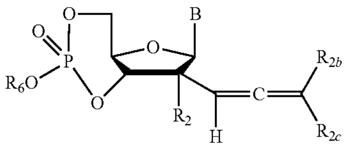
| Example# | $R_6$ | $R_{2b}$ | $R_{2c}$ | $R_2$ | B |
|---|---|---|---|---|---|
| 913 | Et | F | F | OH | 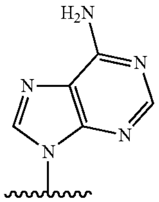 [SMILES: *n1cnc2c(N)ncnc21] |
| 914 | Et | F | F | F | 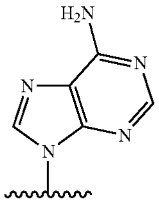 [SMILES: *n1cnc2c(N)ncnc21] |
| 915 | Et | H | H | OH | 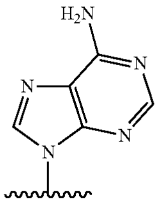 [SMILES: *n1cnc2c(N)ncnc21] |
| 916 | Et | H | H | F | 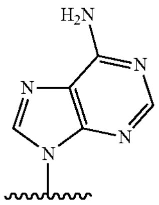 [SMILES: *n1cnc2c(N)ncnc21] |
| 917 | Et | Me | Me | OH | 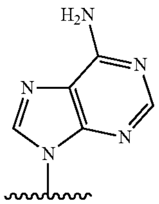 |
| 918 | Et | Me | Me | F | 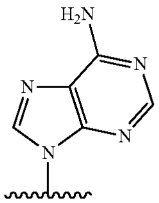 [SMILES: *n1cnc2c(N)ncnc21] |

-continued (VII-1)

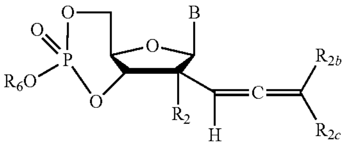

| Example# | $R_6$ | $R_{2b}$ | $R_{2c}$ | $R_2$ | B |
|---|---|---|---|---|---|
| 919 | Et | F | F | OH | 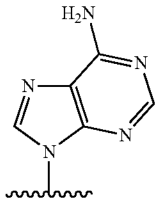 [SMILES: *n1cnc2c(N)ncnc21] |
| 920 | Et | F | F | F | 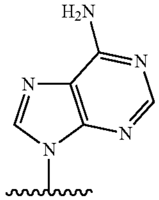 [SMILES: *n1cnc2c(N)ncnc21] |

In one embodiment of the invention, the 2'-allene-substituted nucleoside derivatives of the invention are the isolated β-D or β-L isomer. In another embodiment of the invention, the nucleoside derivative is in an enantiomeric mixture in which the desired enantiomer is at least 95%, 98% or 99% free of its enantiomer. In a preferred embodiment, the nucleoside derivatives are enantiomerically enriched.

In one embodiment of the present invention, the compounds of the formula (I) are in the β-D configuration. In an alternate embodiment of the present invention, the compounds of formula (I) are in the β-L configuration.

The nucleoside derivatives depicted above are in the β-D configuration, however, it should be understood that the nucleoside derivatives can be either in the β-L or β-D configuration.

The nucleoside derivatives of the present invention are biologically active molecules that are useful in the treatment or prophylaxis of viral infections, and in particular human immunodeficiency virus (HIV) and/or hepatitis B virus (HBV) infection. The compounds are also useful for the treatment of abnormal cellular proliferation, including tumors and cancer. In another embodiment of the present invention, any of the active compounds are useful in the treatment of HCV. One can easily determine the spectrum of activity by evaluating the compound in the assays described herein or with another confirmatory assay.

For instance, in one embodiment the efficacy of the antiviral compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or preferably, less than 10 micromolar in vitro.

In another embodiment, for the treatment or prophylaxis of a viral infection, and in particular an HIV, HCV or HBV infection, in a host, the active compound or its derivative or salt can be administered in combination or alternation with another antiviral agent, such as an anti-HIV agent or anti-hepatitis agent, including those of the formula above. Alternatively, for the treatment of abnormal cellular proliferation, such as tumors and cancer, in a host, the active compound or its derivative or salt can be administered in combination or alternation with another antiproliferative agent, such as an anti-neoplastic agent, including those of the formula above. In general, in combination therapy, effective dosages of two or more agents are administered together, whereas during alternation therapy, an effective dosage of each agent is administered serially. The dosages will depend on absorption, inactivation and excretion rates of the drug as well as other factors known to those skilled in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The compounds of the present invention can also be used to treat equine infectious anemia virus (EIAV), feline immunodeficiency virus, and simian immunodeficiency virus. (Wang, S., et al, "Activity of nucleoside and non-nucleoside reverse transcriptase inhibitors (NNRTI) against equine infectious anemia virus (*EIAV*). "*First National Conference on Human Retroviruses and Related Infections*, Washington, D.C., Dec. 12-16, 1993; Sellon D. C., "Equine Infectious Anemia" *Vet. Clin. North Am. Equine Pract. United States,* 9: 321-336, 1993; Philpott, M. S., et al "Evaluation of 9-(2-phosphonylmethoxyethyl)adenine therapy for feline immunodeficiency virus using a quantitative polymerase chain reaction" *Vet. Immunol. Immunopathol.* 35:155166, 1992.

The present invention also provides a pharmaceutical composition for the treatment and/or prophylaxis of a viral infection, and in particular a HBV, HCV or HIV infection, in a host, preferably a human, comprising a therapeutically effective amount of an active compound of the present invention, optionally in a pharmaceutically acceptable carrier.

The present invention also provides a pharmaceutical composition for the treatment and/or prophylaxis of an abnormal cellular proliferation, such as tumors and cancer, in a host, preferably a human, comprising a therapeutically effective amount of an active compound of the present invention, optionally in a pharmaceutically acceptable carrier.

The present invention also provides a pharmaceutical composition for the treatment and/or prophylaxis of a viral infection, and in particular a HBV, HCV or HIV infection, in a host, preferably a human, comprising a therapeutically effective amount of an active compound of the present invention, in combination with one or more other effective antiviral agent, and in particular an anti-HBV, anti-HCV or anti-HIV agent, optionally in a pharmaceutically acceptable carrier.

The present invention also provides a pharmaceutical composition for the treatment and/or prophylaxis of an abnormal cellular proliferation, such as tumors and cancer, in a host, preferably a human, comprising a therapeutically effective amount of an active compound of the present invention, in combination with one or more other effective antinrolifera-tive agent, such as an antineoplastic agent, optionally in a pharmaceutically acceptable carrier.

The present invention also provides a method for the treatment and/or prophylaxis of a viral infection, and in particular a HBV, HCV or HIV infection, in a host, preferably a human, comprising administering to the host a therapeutically effective amount of an active compound of the present invention, optionally in a pharmaceutically acceptable carrier.

The present invention also provides a method for the treatment and/or prophylaxis of an abnormal cellular proliferation, such as tumors and cancer, in a host, preferably a human, comprising administering to the host a therapeutically effective amount of an active compound of the present invention, optionally in a pharmaceutically acceptable carrier.

The present invention also provides a method for the treatment and/or prophylaxis of a viral infection, and in particular a HBV, HCV or HIV infection, in a host, preferably a human, comprising administering to the host a therapeutically effective amount of an active compound of the present invention, in combination and/or alternation with one or more other effective antiviral agent, and in particular an anti-HBV, anti-HCV or anti-HIV agent, optionally in a pharmaceutically acceptable carrier.

The present invention also provides a method for the treatment and/or prophylaxis of an abnormal cellular proliferation, such as tumors and cancer, in a host, preferably a human, comprising administering to the host a therapeutically effective amount of an active compound of the present invention, in combination and/or alternation with one or more other effective antiproliferative agent, such as an antineoplastic agent, optionally in a pharmaceutically acceptable carrier.

The present invention also provides a use of an active compound of the present invention, optionally in a pharmaceutically acceptable carrier, for the treatment and/or prophylaxis of a viral infection, and in particular a HBV, HCV or HIV infection, in a host, preferably a human.

The present invention also provides a use of an active compound of the present invention, optionally in a pharmaceutically acceptable carrier, for the treatment and/or prophylaxis of an abnormal cellular proliferation, such as tumors and cancer, in a host, preferably a human.

The present invention also provides a use of an active compound of the present invention, in combination and/or alternation with one or more other effective antiviral agent, and in particular an anti-HBV, anti-HCV or anti-HIV agent, optionally in a pharmaceutically acceptable carrier, for the treatment and/or prophylaxis of a viral infection, and in particular a HBV, HCV or HIV infection, in a host, preferably a human.

The present invention also provides a use of an active compound of the present invention, in combination and/or alternation with one or more other effective antiproliferative agent, such as an antineoplastic agent, optionally in a pharmaceutically acceptable carrier, for the treatment and/or prophylaxis of an abnormal cellular proliferation, such as tumors and cancer, in a host, preferably a human.

The present invention also provides a use of an active compound of the present invention, optionally in a pharmaceutically acceptable carrier, in the manufacture of a medicament for the treatment and/or prophylaxis of a viral infection, and in particular a HBV, HCV or HIV infection, in a host, preferably a human.

The present invention also provides a use of an active compound of the present invention, optionally in a pharmaceutically acceptable carrier, in the manufacture of a medicament for the treatment and/or prophylaxis of an abnormal cellular proliferation, such as tumors and cancer, in a host, preferably a human.

The present invention also provides a use of an active compound of the present invention, in combination and/or alternation with one or more other effective antiviral agent, and in particular an anti-HBV, anti-HCV or anti-HIV agent, optionally in a pharmaceutically acceptable carrier, in the manufacture of a medicament for the treatment and/or prophylaxis of a viral infection, and in particular a HBV, HCV or HIV infection, in a host, preferably a human.

The present invention also provides an use of an active compound of the present invention, in combination and/or alternation with one or more other effective antiproliferative agent, such as an antineoplastic agent, optionally in a pharmaceutically acceptable carrier, in the manufacture of a medicament for the treatment and/or prophylaxis of an abnormal cellular proliferation, such as tumors and cancer, in a host, preferably a human.

The invention also provides synthetic methods useful for preparing the compounds of the invention, as well as intermediates disclosed herein that are useful in the preparation of the compounds of the present invention.

The invention as disclosed herein is method and composition for the treatment of HIV, hepatitis B or C, or abnormal cellular proliferation, in humans or other host animals, that includes administering a therapeutically effective amount of a β-D- or β-L-nucleoside derivatives, a pharmaceutically acceptable derivative, including a compound which has been alkylated or acylated on sugar or phosphonate moiety, or on the purine or pyrimidine, or a pharmaceutically acceptable salt thereof, optionally in a pharmaceutically acceptable carrier. The compounds of this invention either possess antiviral (i.e., anti-HIV-1, anti-HIV-2, anti-hepatitis B/C virus) activity or antiproliferative activity, or are metabolized to a compound that exhibits such activity. The invention as disclosed herein also includes the process for the preparation of such β-D- or β-L-nucleoside derivatives.

Stereoisomerism and Polymorphism

The compounds of the present invention may have asymmetric centers and occur as racemates, racemic mixtures, individual diastereomers or enantiomers, with all isomeric forms being included in the present invention. Compounds of the present invention having a chiral center may exist in and be isolated in optically active and racemic forms. Some compounds may exhibit polymorphism. The present invention encompasses racemic, optically-active, polymorphic, or stereoisomeric form, or mixtures thereof, of a compound of the invention, which possess the useful properties described herein. Optically active forms of the compounds can be prepared using any method known in the art, including but not limited to by resolution of the racemic form by recrystallization techniques, by synthesis from optically-active starting materials; by chiral synthesis, or by chromatographic separation using a chiral stationary phase or by enzymatic resolution.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbons, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The terms "$C_1$-$C_8$ alkyl," or "$C_1$-$C_{12}$ alkyl," as used herein, refer to saturated, straight- or branched-chain hydrocarbon radicals containing between one and eight, or one and twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals.

The term "$C_2$-$C_8$ alkenyl," or "$C_2$-$C_{20}$ alkenyl," as used herein, refer to straight- or branched-chain hydrocarbon radicals containing from two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The term "$C_2$-$C_8$ alkynyl," or "$C_2$-$C_{20}$ alkynyl," as used herein, refer to straight- or branched-chain hydrocarbon radicals containing from two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_3$-$C_{12}$-cycloalkyl," as used herein, refers to a monocyclic or polycyclic saturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The terms "$C_2$-$C_8$ alkylene," or "$C_2$-$C_8$ alkenylene," as used herein, refer to saturated or unsaturated respectively, straight- or branched-chain hydrocarbon di-radicals containing between two and eight carbon atoms, while the diradical may reside at the same or different carbon atoms.

The term "$C_3$-$C_8$ cycloalkenyl", or "$C_3$-$C_{12}$ cycloalkenyl" as used herein, refers to monocyclic or polycyclic carbocyclic ring compound having at least one carbon-carbon double bond. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (iv) any of the above rings may be fused to an aromatic ring, and (v) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$- cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reactions. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group" or "thiol protecting group," as used herein, refers to a labile chemical moiety which is known in the art to protect a hydroxyl group or thiol against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl) ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —$C(O)CH_3$), benzoyl (Bz or —C(O) $C_6H_5$), and trimethylsilyl (TMS or —$Si(CH_3)_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent" as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "hydrogen" includes deuterium. In general, the identification of an element embraces the isotopes of the element, as suitable for the preparation a pharmaceutical.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers, or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews,* 8:1-38 (1992); Bundgaard, *J. of Pharmaceutical Sciences,* 77:285 et seq. (1988); Higuchi and Stella (eds.) Prodrugs as Novel Drug Delivery Systems, American Chemical Society (1975); Bernard Testa & Joachim Mayer, “Hydrolysis In Drug And Prodrug Metabolism: Chemistry, Biochemistry And Enzymology,” John Wiley and Sons, Ltd. (2002); and J. Rautio et al, “Prodrugs: design and clinical applications”, *Nature Review—Drug Discovery,* 7, 255-270 (2008).

The present invention also relates to solvates of the compounds of Formula (I), for example hydrates.

It is to be understood that when a variable appears two or more times in a formula set forth herein, each occurrence of the variable is independently selected from the identities set forth for that variable.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term “pharmaceutically acceptable carrier or excipient” means a non-toxic, inert solid, semi-solid or liquid filler, diluent, excipient, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer’s solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer’s solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof and j) coloring agents. In the case of capsules, tablets and pills, the dosage form may also comprise buffering agents.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active or dispersing agent. Molded tablets, may be, made by molding in a suitable machine a mixture of the powdered compound moistened with an inert liquid diluent.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another anti-HCV agent), or they may achieve different effects (e.g., control of any adverse effects).

The compounds of the invention may be administered intravenously, intramuscularly, intraperitoneally, subcutaneously, topically, orally, or by other acceptable means. The compounds may be used to treat mammals (i.e., humans, livestock, and domestic animals), birds, lizards, and any other organism, which can tolerate the compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Antiviral Activity

According to the methods of treatment of the present invention, viral infections, and conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the invention described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of a therapeutically effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Pharmaceutically Acceptable Derivatives

The compound of the present invention can be administered as any derivative that upon administration to the recipient, is capable of providing directly or indirectly, the parent compound. Further, the modifications can affect the biological activity of the compound, in some cases increasing the activity over the parent compound. This can easily be assessed by preparing the derivative and testing its antiviral and anti-proliferative activity according to the methods described herein, or other method known to those skilled in the art.

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administrated as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research,* 27 (1995) 1-17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S. et al 1990. "Novel membrane interactive ether lipid analogs that inhibit infectious HIV-1 production and induce defective virus formation."*AIDS Res. Hum. Retro Viruses.* 6:491-501; Piantadosi, C., J. et al 1991. "Synthesis and evaluation of novel ether lipid nucleoside conjugates for anti-HIV activity." *J. Med. Chem.* 34:1408.1414; Hosteller, K. Y. et al 1992. "Greatly enhanced inhibition of human immunodeficiency virus type 1 replication in CEM and HT4-6C cells by 3'-deoxythymidine diphosphate dimyristoylglycerol, a lipid prodrug of 3'-deoxythymidine." *Antimicrob. Agents Chemother.* 36:2025.2029; Hosetler, K. Y., et al 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent publications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, and WO 91/19721.

Nonlimiting examples of nucleotide prodrugs are described in the following references: J. K. Dickson, Jr. et al, "Orally active squalene synthetase inhibitors: bis((acyloxy) alkyl) prodrugs of the α-phosphonosylfonic acid moiety" *J. Med. Chem.* 1996, 39, 661-664; T. Kurz, et al, "Synthesis and antimalarial activity of chain substituted pivaloyloxymethyl ester analogues of Fosmidomycin and FR900098" *Bioorg. Med. Chem.* 2006, 14, 5121-5135; J. E. Starrett, Jr. et al, "Synthesis, oral bioavailability determination, and in vitro evaluation of prodrugs of the antiviral agent 9-[2-(phosphonomethoxy)ethyl]adenine (PMEA)" *J. Med. Chem.* 1994, 37, 1857-1864; H. T. Serafinowska, et al, "Synthesis and in vivo evaluation of prodrugs of 9-[2-(phosphonomethoxy)ethoxy] adenine" *J. Med. Chem.* 1995, 38, 1372-1379; S. Benzaria, et al, "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability" *J. Med. Chem.* 1996, 39, 4958-4965; M. S. Louie and H. Chapman, "An efficient process for the synthesis of cyclic HPMPC" *Nucleosides, Nucleotides Nucleic acid* 2001, 20, 1099-1102; J.-R. Choi et al, "A novel class of phosphonate nucleosides. 9-[(1-phosphonomethoxy)-cyclopropyl)methyl]guanine as a potent and selective anti-HBV agent" *J. Med. Chem.* 2004, 47, 2864-2869; M. Wu, et al, "Synthesis of 9-[1-(substituted)-3-(phosphonomethoxy)propyl]adenine derivatives as possible antiviral agents" *Nucleosides, Nucleotides Nucleic acid.* 2005, 24, 1543-1568; X. Fu, et al, "Design and synthesis of novel bis(L-amino acid) ester prodrugs of 9-[2-(phosphonomethoxy)ethyl]adenine (PMEA) with improved anti-HBV activity" *Bioorg. Med. Chem. Lett.* 2007, 17, 465-470.

Similarly, the 5'-phosphonate can also be provided as various phosphonate prodrug to increase the activity, bioavailability, stability or otherwise alter the properties of the phosphonate. A number of phosphonate prodrug ligands are known. In general, alkylation, acylation or other lipophilic modification of one or more hydroxy on the phosphonate moiety can be used to achieve a desired effect.

Combination and Alternation Therapy for HIV, HBV or HCV

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HIV, in one embodiment, can be a reverse transcriptase inhibitor (a "RTI"), which can be either a synthetic nucleoside (a "NRTI") or a non-nucleoside compound (a "NNRTI"). In an alternative embodiment, in the case of HIV, the second (or third) antiviral agent can be a protease inhibitor. In other embodiments, the second (or third) compound can be a pyrophosphate analog, or a fusion binding inhibitor. A list compiling resistance data collected in vitro and in vivo for a number of antiviral compounds is found in Schinazi, et al, Mutations in retroviral genes associated with drug resistance, *International Antiviral News,* 1997.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC),β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Preferred examples of antiviral agents that can be used in combination or alternation with the compounds disclosed herein for HIV therapy include cis-2-hydroxymethyl-5-(5-fluorocytosin-1-yl)-1,3-oxathiolane (FTC); the (−)-enantiomer of 2-hydroxymethyl-5-(cytosin-1-yl)-1,3-oxathiolane (3TC); ziagen (abacavir), emtriva, viread (tenofovir DF), carbovir, acyclovir, foscarnet, interferon, AZT, DD1, D4T, CS-87 (3'-azido-2',3'-dideoxyuridine), and β-D-dioxolane nucleosides such as β-D-dioxolanyl-guanine (DXG), β-D-dioxolanyl-2,6-diaminopurine (DAPD), and β-D-dioxolanyl-6-chloropurine (ACP), and integrase inhibitors such as MK-0518.

Preferred protease inhibitors (PIs) include crixivan (indinavir), viracept (nelfinavir), norvir (ritonavir), invirase (saquinavir), aptivus (tipranavir), kaletra, lexiva (fosamprenavir), reyataz (atazanavir) and TMC-114.

Preferred Non-Nucleoside Reverse Transcriptase Inhibitors (NNRTIs) include rescripton (delavirdine), sustiva (efavirenz), viramune (nevirapine) and TMC-125.

Preferred Entry inhibitors include fuzeon (T-20), PRO-542, TNX-355, vicriviroc, aplaviroc and maraviroc.

A more comprehensive list of compounds that can be administered in combination or alternation with any of the disclosed nucleosides include (1S,4R)-4-[2-amino-6-cyclopropylamino)-9H-purin-9-yl]-2-cyclopentene-1-methanol succinate ("1592", a carbovir analog; GlaxoWellcome); 3TC: (+β-L-2',3'-dideoxy-3'-thiacytidine (GlaxoWellcome); a-APA R18893: a-nitro-anilino-phenylacetamide; A-77003; C2 symmetry-based protease inhibitor (Abbott); A-75925: C2 symmetry-based protease inhibitor (Abbott); AAP-BHAP: bishetero-arylpiperazine analog (Upjohn); ABT-538: C2-symmetry-based protease inhibitor (Abbott); AzddU: 3'-azido-2',3'-dideoxyuridine; AZT: 3'-azido-3'-deoxythymidine (GlaxoWellcome); AZT-p-ddI: 3'-azido-3'-deoxythymidilyl-(5',5)-2',3'-dideoxyinosinic acid (Ivax); BHAP: bisheteroaryl-piperazine; BILA 1906: N-{1S-[[[3-[2S-{(1,1-dimethylethyl)amino]carbonyl}-4R]-3-pyridinylmethyl) thio]-1-piperidinyl]-2R-hydroxy-1S-(phenylmethyl)-propyl]amino]-carbonyl]-2-methylpropyl}-2-quinolinecarboxamide (Bio Mega/Boehringer-Ingelheim); BILA 2185: N-(1,1-dimethylethyl)-1-[2S-[[2-2,6-dimethyphenoxy)-1-xoethyl]amino]-2R-hydroxy-4-phenylbutyl]-4R-pyridinylthio)-2-piperidinecarboxamide (BioMega/Boehringer-Ingelheim); BMS 186,318: aminodiol derivative HIV-1 protease inhibitor (Bristol-Myers-Squibb); d4API: 9-[2,5-d]hydro-5-(phosphonomethoxy)-2-furanyladenine (Gilead); d4C: 2',3'-didehydro-2',3'-dideoxycytidined; d4T: 2',3'-didehydro-3'-deoxythymidine (Bristol-Myers-Squibb); ddC; 2',3'-dideoxycytidine (Roche); ddI: 2',3'-dideoxyinosine (Bristol-Myers-Squibb); DMP-266: a 1,4-dihydro-2H-3,1-benzoxazin-2-one; DMP-450: {[4R-(4-a,5-a,6-b,7-b)]-hexahydro-5,6-bis(hydroxy)-1,3-bis(3-amino)phenyl]-methyl)-4,7-bis-(phenylmethyl)-2H-1,3-diazepin-2-one}-bismesylate (Gilead); DXG: (−)-β-D-dioxolane-guanosine (Gilead); EBU-dM: 5-ethyl-1-ethoxymethyl-6-(3,5-dimethylbenzyl)-uracil; E-EBU: 5-ethyl-1-ethoxymethyl-6-benzyluracil; DS: dextran sulfate; E-EPSeU: 1-(ethoxymethyl)-(6-phenylselenyl)-5-ethyluracil; E-EPU: 1-(ethoxymethyl)-(6-phenylthio)-5-ethyluracil; FTC: β-2',3'-dideoxy-5-fluoro-3'-thiacytidine (Gilead); HBY097: S-4-isopropoxycarbonyl-6-methoxy-3-(methylthio-methyl)-3,4-dihydroquinoxalin-2 (1H)-thione; HEPT: 1-[(2-hydroxyethoxy)methyl]-6-(phenylthio)thymine; HIV-1: human immunodeficiency virus type 1; JM2763: 1,1'-(1,3-propanediyl)-bis-1,4,8,11-tetraaza-cyclotetradecane (Johnson Matthey); JM3100:1,1'-[1,4-phenylenebis-(methylene)]-bis-1,4,8,11-tetraazacyclotetradecane (Johnson Matthey); KNI-272: (2S,3S)-3-amino-2-hydroxy-4-phenylbutyric acid-containing tripeptide; L-697,593; 5-ethyl-6-methyl-3-(2-phthalimido-ethyl)pyridin-2(1H)-one; L-735,524: hydroxy-amino-pentane amide HIV-1 protease inhibitor (Merck); L-697,661: 3-{[(4,7-dichloro-1,3-benzoxazol-2-yl)methyl]amino}-5-ethyl-6-methylpyridin-2(1H)-one; L-FDDC: (−)-β-L-5-fluoro-2',3'-dideoxycytidine; L-FDOC: (−)-β-L-5-fluoro-dioxolane cytosine; MKC442: 6-benzyl-1-ethoxymethyl-5-isopropyluracil (1-EBU; Mitsubishi); Nevirapine: 11-cyclopropyl-5,11-dihydro-4-methyl-6H-dipyridol-[3,2-b:2',3'-e]-diazepin-6-one (Boehringer-Ingelheim); NSC648400: 1-benzyloxymethyl-5-ethyl-6-(alpha-pyridylthio)uracil (E-BPTU); P9941: [2-pyridylacetyl-Il-ePheAla-y(CHOH)]$_2$ (Dupont Merck); PFA: phosphonoformate (foscarnet; Astra); PMEA: 9-(2-phosphonylmethoxyethyl)adenine (Gilead); PMPA: (R)-9-(2-phosphonylmethoxypropyl)adenine (Gilead); Ro 31-8959: hydroxyethylamine derivative HIV-1 protease inhibitor (Roche); RPI-312: peptidyl protease inhibitor, 1-[(3S)-3-(n-alpha-benzyloxycarbonyl)-1-asparginyl)-amino-2-hydroxy-4-phenylbutyryl]-n-tert-1-proline amide; 2720: 6-chloro-3,3-dimethyl-4-(isopropenyloxycarbonyl)-3,4-dihydro-quinoxalin-2-(1H)-thione; SC-52151: hydroxyethylurea isostere protease inhibitor (Searle); SC-55389A: hydroxyethyl-urea isostere protease inhibitor (Searle); TIBO R82150: (+)-(5S)-4,5,6,7-tetrahydro-5-methyl-6-(3-methyl-2-butenyl)-imidazo[4,5,1-jk]-[1,4]benzodiazepin-2(1H)-thione (Janssen); TIBO 82913: (+)-(5s)-4,5,6,7,-tetrahydro-9-chloro-5-methyl-6-(3-methyl-2-butenyl)imidazo[4,5,1jk]-[1,4]benzo-diazepin-2(1H)-thione (Janssen); TSAO-m3T: [2',5'-bis-O-(tert-butyl-dimethylsilyl)-3'-spiro-5'-(4'-amino-1',2'-oxathiole-2',2'-dioxide)]-β-D-pento-furanosyl-N3-methylthymine; U90152: 1-[3-[(1-methylethyl)-amino]-2-pyridinyl]-4-[[5-[(methylsulphonyl)-amino]-1H-indol-2-yl] carbonyl]piperazine; UC: thiocarboxanilide derivatives (Uniroyal); UC-781: N-[4-chloro-3-(3-methyl-2-butenyloxy)phenyl]-2-methyl-3-furancarbothioamide; UC-82: N-[4-chloro-3-(3-methyl-2-butenyloxy)phenyl]-2-methyl-3-thiophenecarbothioamide; VB 11,328: hydroxyethyl-sulphonamide protease inhibitor (Vertex); VX-478: hydroxyethylsulphonamide protease inhibitor (Vertex); XM 323: cyclic urea protease inhibitor (Dupont Merck).

The active compound can also be administered in combination or alternation with ribavarin, interferon, interleukin or a stabilized prodrug of any of them. More broadly described, the compound can be administered in combination or alternation with any of the anti-HCV drugs listed below in Table 6.

TABLE 6

Table of anti-Hepatitis C Compounds in Current Clinical Development

| Drug name | Drug category | Pharmaceutical Company |
|---|---|---|
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-la | Interferon | Ares-Serono |
| Omega Interferon | Interferon | BioMedicine |
| Oral Interferon alpha | Oral Interferon | Amarillo Biosciences |
| Interferon gamma-lb | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HepX ™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| R7227 (ITMN-191) | protease inhibitor | InterMune |
| Narlaprevir (SCH 900518) | Protease inhibitor | Schering/Merck |
| Alinia (nitazoxanide) | To be determined | Romark |
| ABT-072 | Polymerase Inhibitor | Abbott |
| ABT-333 | Polymerase Inhibitor | Abbott |
| Filibuvir (PF-00868554) | Polymerase Inhibitor | Pfizer |
| VCH-916 | Polymerase Inhibitor | Vertex |
| R7128 (PSI6130) | Polymerase Inhibitor | Roche/Pharmasset |
| IDX184 | Polymerase Inhibitor | Idenix |
| R1626 | Polymerase inhibitor | Roche |
| MK-3281 | Polymerase inhibitor | Merck |
| PSI-7851 | Polymerase inhibitor | Pharmasset |
| ANA598 | Polymerase inhibitor | Anadys Pharmaceuticals |
| BI-207127 | Polymerase inhibitor | Boehringer-Ingelheim |
| GS-9190 | Polymerase inhibitor | Gilead |
| VCH-759 | Polymerase Inhibitor | Vertex |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| ITX5061 | Entry inhibitor | iTherx |
| GS-9450 | Caspase inhibitor | Gilead |
| ANA773 | TLR agonist | Anadys |
| CYT107 | Immunomodulator | Cytheris |

TABLE 6-continued

| Table of anti-Hepatitis C Compounds in Current Clinical Development | | |
|---|---|---|
| Drug name | Drug category | Pharmaceutical Company |
| SPC3649 (LNA-antimiR ™-122) | microRNA | Santaris Pharma |
| Debio 025 | Cyclophilin inhibitor | Debiopharm |
| SCY-635 | Cyclophilin inhibitor | Scynexis |

Combination Therapy for the Treatment of Proliferative Conditions

In another embodiment, the compounds, when used as an antiproliferative, can be administered in combination with another compound that increases the effectiveness of the therapy, including but not limited to an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifosfamide, mechlorethamine, melphalan, and thiotepa), nonclassical alkylating agents, platinum containing compounds, bleomycin, an anti-tumor antibiotic, an anthracycline such as doxorubicin and daunomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. The compounds of the present invention can also be used in combination with enzyme therapy agents and immune system modulators such as an interferon, interleukin, tumor necrosis factor, macrophage colony-stimulating factor and colony stimulating factor.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Although the invention has been described with respect to various preferred embodiments, it is not intended to be limited thereto, but rather those skilled in the art will recognize that variations and modifications may be made therein which are within the spirit of the invention and the scope of the appended claims.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; $Boc_2O$ for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; $Bu_3SnH$ for tributyltin hydride; BOP for (benzotriazol-1-yloxy)tris(dimethylamino)phosphonium Hexafluorophosphate; Brine for sodium chloride solution in water; CDI for carbonyldiimidazole; $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; dppb for diphenylphosphino butane; DBU for 1,8-diazabicyclo[5.4.0]undec-7-ene; DCC for N,N'-dicyclohexylcarbodiimide; DEAD for diethylazodicarboxylate; DIAD for diisopropyl azodicarboxylate; DIPEA or $(i\text{-}Pr)_2EtN$ for N,N,-diisopropylethyl amine; Dess-Martin periodinane for 1,1,1-tris(acetyloxy)-1,1-dihydro-1,2-benziodoxol-3-(1H)-one; DMAP for 4-dimethylaminopyridine; DME for 1,2-dimethoxyethane; DMF for N,N-dimethylformamide; DMSO for dimethyl sulfoxide; DMT for di(p-methoxyphenyl)phenylmethyl or dimethoxytrityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; $Et_2O$ for diethyl ether; HATU for O-(7-azabenzotriazol-1-yl)-N,N,N',N',-tetramethyluronium Hexafluorophosphate; HCl for hydrogen chloride; HOBT for 1-hydroxybenzotriazole; $K_2CO_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethylpiperidinate; MeOH for methanol; Mg for magnesium; MOM for methoxymethyl; Ms for mesyl or $—SO_2—CH_3$; $Ms_2O$ for methanesulfonic anhydride or mesyl-anhydride; $NaN(TMS)_2$ for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4Cl$ for ammonium chloride; NMMO for N-methylmorpholine N-oxide; $NaIO_4$ for sodium periodate; Ni for nickel; OH for hydroxyl; $OsO_4$ for osmium tetroxide; TBAF for tetrabutylammonium fluoride; TEA or $Et_3N$ for triethylamine; TFA for trifluoroacetic acid; THF for tetrahydrofuran; TMEDA for N,N,N',N'-tetramethylethylenediamine; TPP or $PPh_3$ for triphenyl-phosphine; Troc for 2,2,2-trichloroethyl carbonyl; Ts for tosyl or $—SO_2—C_6H_4—CH_3$; $Ts_2O$ for tolylsulfonic anhydride or tosyl-anhydride; TsOH for p-tolylsulfonic acid; Pd for palladium; Ph for phenyl; POPd for dihydrogen dichlorobis(di-tert-butylphosphinito-κP)palladate(II); $Pd_2(dba)_3$ for tris(dibenzylideneacetone) dipalladium (0); $Pd(PPh_3)_4$ for tetrakis(triphenylphosphine)palladium (0); $PdCl_2(PPh_3)_2$ for trans-dichlorobis-(triphenylphosphine)palladium (II); Pt for platinum; Rh for rhodium; Ru for ruthenium; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

The syntheses of various nucleoside analogs have been well documented in the literature, the following reviews are incorporated hereinwith by references: D. M. Huryn and M. Okabe, *Chem. Rev.* 1992, 92, 1745; K. W. Pankiewicz, *Carbohydrate Research,* 2000, 327, 87-105; G. Gumina et al, *Antiviral Nucleosides: Chiral Synthesis and Chemotherapy*, C. K. Chu (Ed.), Elsevier, 2003, pages 1-76 and 77-189; nucleoside analogs used as antimetabolites have been summarized: M. M. Mader and J. R. Henry, *Comprehensive Medicinal Chemistry II*, Elsevier, 2007, Vol 7, pages 55-79; nucleoside analogs used as antiviral agents have been summarized: *Comprehensive Medicinal Chemistry II*, Elsevier, 2007, Vol 7, pages 295-327 by E. Littler and X-X Zhou; and pages 338-343 by T. A. Lyle; and pages 398-400 by U. Schmitz et al. The synthesis of each of these individual analog can be found in the literatures cited therein. Nonlimiting examples of process are also incorporated hereinwith by reference: Clark et al, *J. Med. Chem.* 2005, 48, 5504; Clark et al, *Bioorg. Med. Chem. Lett.* 2006, 16, 1712; Clark et al, *J. Carbohydr. Chem.* 2006, 25, 461; Seela et al, *Org. Biomol. Chem.* 2008, 6, 596; Pan et al, *J. Org. Chem.* 1999, 94, 4; Shi et al, *Bioorg. Med. Chem.* 2005, 13, 1641; He et al, *J. Org. Chem.* 2003, 68, 5519; Gudmundsson et al, *J. Med. Chem.* 2000, 43, 2473; Jean-Baptiste et al, *Synlett* 2008, 817; Wilson et al, *Synthesis* 1995, 1465; Lin et al, *J. Med. Chem.* 1991, 34, 2607; Matsuda et al, *J. Med. Chem.* 1991, 34, 812; Robins et al, *J. Med. Chem.* 1992, 35, 2283; Serafinowski et al, *Tetrahedron* 1996, 52, 7929; Serafinowski et al, *Tetrahedron* 2000, 56, 333; Houlton et al, *Tetrahedron* 1993, 49, 8087; Serafinowski et al, *Synthesis* 1997, 225; McCarthy et al, *Tetrahedron* 1996, 52, 45; Schmit, *Synlett* 1994, 241; Hirota et al, *ChemComm* 1999, 1827; Babu et al, *Org. Biomol. Chem.* 2003, 1, 3514; Samano et al, *J. Am. Chem. Soc.* 1992, 114, 4007; Beard et al, *Carbohydrate Res.* 1990, 87; Wigerinck et al, *J. Med. Chem.* 1991, 34, 2383; Ye et al, *J. Org. Chem.* 2005, 70, 7902; Eldrup et al, *J. Med. Chem.* 2004, 47, 2283 and 5284; Tang et al, *J. Org. Chem.* 1999, 64, 747; Jeannot et al, *Org. Biomol. Chem.* 2003, 1, 2096; Li et al, *Org. Lett.* 2001, 3, 1025; Marcotte et al, *Synthesis* 2001, 929; Dai et al, *Org. Lett.* 2001, 3, 807; Yoshimura et al, *Bioorg. Med. Chem. Lett.* 1994, 4, 721; Ohtawa et al, *J. Med. Chem.* 2007, 50, 2007; McGee et al, *J. Org. Chem.* 1996, 61, 781; Ogamino et al, *J. Org. Chem.* 2005, 70, 1684; Ichikawa et al, *Org. Biomol. Chem.* 2006, 4, 1284; Pan et al, *J. Org. Chem.* 1999, 64, 4; Huang et al, *J. Med. Chem.* 1991, 34, 1640; Kodama et al, *Tetrahedron* 2006, 62, 10011; He et al, *J. Org. Chem.* 2003, 68, 5519; Kumamoto et al, *J. Med. Chem.* 2006, 49, 7861; and Haraguchi et al, *Org. Lett.* 2004, 6, 2645.

One of the general procedures to synthesize the 2'-allenic nucleosides (III) of the present invention is shown in Scheme 1, in which 2'-substituents containing an alkyne group or a carbonyl group can be transformed and/or isomerized to an allenic moiety under a variety of conditions, wherein unless otherwise defined, $R_1$, $R_2$, $R_3$, $R_{2a}$, $R_{2b}$, $R_{2c}$, and B are as previously defined; P is a hydroxy protecting group; and L is a leaving group such as halide, OAc, OMe, OTMS, OTHP, the like.

The alkyne moiety of compound (1-1) can be transformed to an allenic moiety via a hydroxyl directed aluminum hydride reduction while $R_2$ is OH. The reaction conditions and the choice of leaving group L are well documented in the literature, see references cited in accounts by Cowie, J. S.; Landor, P. D.; Landor, S. R. *J. Chem. Soc., Perkin Trans.* 1, 1973, 720. Claesson, A; Olsson, L.-I. *J. Am. Chem. Soc.* 1979, 101, 7302. Kumareswaran, R.; Shin, S.; Gallou, I.; Rajan-Babu, T. V. *J. Org. Chem.* 2004, 69, 7157. Yoshida, M.; Komatsuzaki, Y.; Nemoto, H.; Ihara, M. *Org. Biomol. Chem.* 2004, 2, 3099. VanBrunt, M. P.; Standaert, R. F. *Org. Lett.* 2000, 2, 705. Cao, H.; Flippen-Anderson, J.; Cook, J. *J. Am. Chem. Soc.* 2003, 125, 3230. Bungard, C. J.; Morris, J. *J. Org. chem.* 2002, 67, 2361.

Horner-Wadsworth-Emmons (HWE) reaction of compound (1-2) with methylenebisphosphonate (1-2a), followed by another HWE reaction with aldehyde or ketone (1-2b) to give a 2'-allenic nucleosides (III). The bases used in this reaction can be, but not limited to, such as alkyl lithium (MeLi or n-BuLi or the like), LDA, NaH, t-BuOK, KOH, the like. The solvent can be, but not limited to, such as THF, DMF.

Scheme 1

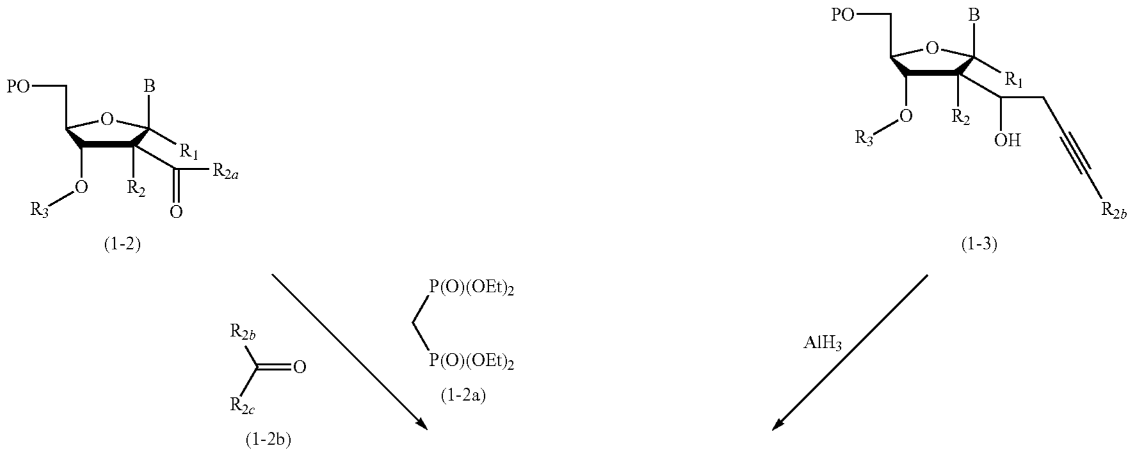

(1-2) (1-3) (1-2a) (1-2b)

-continued

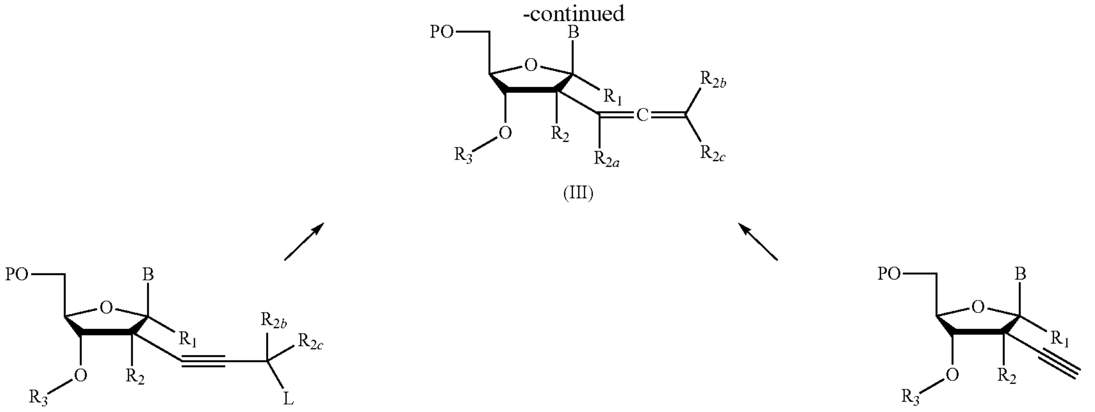

(III)

(1-1)

(1-4)

The propargyl alcohol of compound (1-3) can be converted into allenic compound (III) with $AlH_3$. The terminal acetylene of compound (1-4) can be transformed to allene by Crabbe homologation reaction. These transformations are well documented in the literature, see references cited in accounts by Hung, S.-C.; Wen, Y.-F.; Chang, J.-W.; Liao, C.-C.; Uang, B.-J. *J. Org. Chem.* 2002, 67, 1308. Crabbe, P.; Andre, D.; Fillion, H. *Tetrahedron Lett.* 1979, 20, 893. Crabbe, P.; Fillion, H; Andre, D.; Luche, J.-L. *J Chem. Soc., Chem. Commun.,* 1979, 859. Crabbe, P.; Nassim, B.; Robert-Lopes, M.-T. *Org. Synth.* 1985, 63, 203.

Another general procedure to prepare 2'-allenyl nucleoside of present invention is depicted in scheme 2. The ketone compound (2-1), herein $P_1$, $P_2$ and $P_3$ are hydroxyl protecting group, such as but not limited to, benzoyl, acetyl, TMS, TIPS, was treated with propargyl bromide in the presence of combination metal halides such as, but not limited to, $SnCl_2$, LiI in aprotic solvent such as THF, DME, DMF, toluene to give the allenyl compound (2-2) in good yield. The reaction temperature was from room temperature ~150° C.

Scheme 2

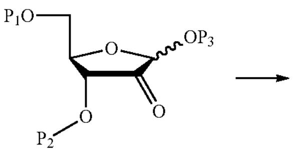

(2-1)

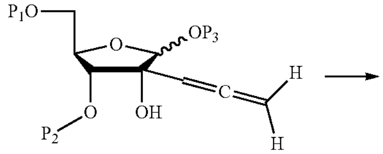

(2-2)

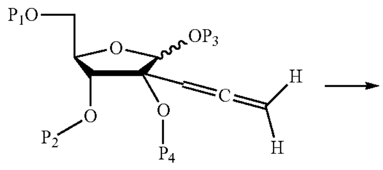

(2-3)

-continued

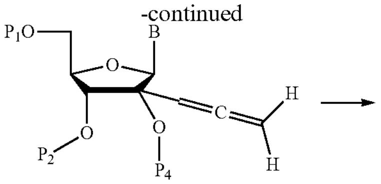

(2-4)

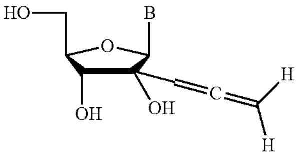

(2-5)

The 2'-hydroxyl group was protected with hydroxyl protecting group $P_4$, such as but not limited to, benzoyl, acetyl, TMS, TIPS to give the compound (2-3). A more thorough discussion of the procedures, reagents and conditions for protecting hydroxyl group is described in literature, for example, by T. W. Greene and P. G. M. Wuts in "*Protective Groups in Organic Synthesis*" $3^{rd}$ed., John Wiley & Son, Inc., 1999.

Further glycosylation of the nucleobase with compound (2-3) was accomplished by treatment of the compound (2-3) with the appropriate persilylated nucleobase in the presence of a Lewis acid such as, but not limited to, $SnCl_4$, $TiCl_4$, TMSOTf, HgO or $HgBr_2$ in an aprotic solvent such as, but not limited to, toluene, acetonitrile, benzene, THF, DME, or a mixture of any or all of these solvents. The reaction temperature was from room temperature to 150° C. The optional protecting groups in the protected nucleosides or the compound formula (2-4) can be cleaved following established deprotection methodologies. A more thorough discussion of the procedures, reagents and conditions for deprotection is described in literature, for example, by T. W. Greene and P. G. M. Wuts in "*Protective Groups in Organic Synthesis*" $3^{rd}$ed., John Wiley & Son, Inc., 1999. The synthesis of nucleoside 5'-monophosphate prodrugs have also been well documented in the literature, see references cited in accounts by Cahard et al, *Mini-Reviews Med. Chem.* 2004, 4, 371; Meier et al, *Mini-Reviews Med. Chem.* 2004, 4, 383; Peyrottes et al, *Mini-Reviews Med. Chem.* 2004, 4, 395; Drontle et al, *Mini-Reviews Med. Chem.* 2004, 4, 409; and nonlimiting examples of recent process: Gisch et al, *J. Med. Chem.* 2007, 50, 1658;

Boyer et al, *J. Med. Chem.* 2006, 49, 7711; Khamnei et al, *J. Med. Chem.* 1996, 39, 4109; Li et al, Synlett 2004, 2600; Perrone et al, *J. Med. Chem.* 2007, 50, 5463; Gisch et al, *J. Med. Chem.* 2007, 50, 1658 and 1840; Hecker et al, *J. Med. Chem.* 2007, 50, 3891; Prakash et al, *J. Med. Chem.* 2005, 48, 1199; and Gunic et al, *Bioorg. Med. Chem. Lett.* 2007, 17, 2452 (for 3',5'-cyclic monophosphate prodrug).

The synthesis of nucleoside phosphonates and/or their prodrugs have also been well documented in the literature, see references cited in accounts by Hecker et al, *J. Med. Chem.* 2008, 51, 2328; Krise et al, *Adv. Drug Deliv. Rev.* 1996, 19, 287; Berkowitz et al, *J. Fluorine Chem.* 2001, 112, 13; Romanenko et al, *Chem. Rev.* 2006, 106, 3868; De Clercq, *Antiviral Res.* 2007, 75, 1; De Clercq et al, *Nat. Rev.-Drug Disc.* 2005, 4, 928; and nonlimiting examples of recent process: Mackman et al, *Bioorg. Med. Chem.* 2007, 15, 5519; Dang et al, *Bioorg. Med. Chem. Lett.* 2007, 17, 3412; Meier et al, *J. Med. Chem.* 2005, 48, 8079; Wu et al, *Nucleosides Nucleotides Nucleic Acids* 2005, 24, 1543; Choi et al, *J. Med. Chem.* 2004, 47, 2864; Sekiya et al, *J. Med. Chem.* 2002, 45, 3138; Louie et al, *Nucleosides Nucleotides Nucleic Acids* 2001, 20, 1099; Serafinowska et al, *J. Med. Chem.* 1995, 38, 1372; Koh et al, *J. Med. Chem.* 2005, 48, 2867; Mackman et al, *Bioorg. Med. Chem.* 2007, 15, 5519; Wang et al, *Nucleosides Nucleotides Nucleic Acids* 2004, 23, 317; Dyatkina et al, *Tetrahedron* 1995, 51, 761; Reddy et al, *J. Med. Chem.* 2008, 51, 666; Krecmerova et al, *J. Med. Chem.* 2007, 50, 5765.

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula (I), wherein $R_1 = R_3 = R_5 = R_{2a} = R_{2b} = R_{2c} = H$, $R_2 = OH$,

B =

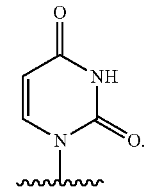

Step 1a:

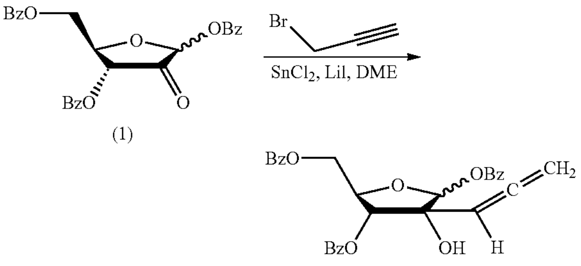

(1)

(2)

To a mixture of ketone (1) (830 mg, 1.802 mmol), $SnCl_2.2H_2O$ (611 mg, 2.708 mmol), and $LiI.3H_2O$ (678 mg, 3.605 mmol) in dimethoxyethane (18 mL) was added propargyl bromide and the resulted yellow suspension was heated up in 85° C. oil bath for 60 mins. The solvent was removed under vacuo and the residue was purified by CombiFlash (eluted with hexane to 25% ethyl acetate in Hexane) to afford the alleneyl compound (2) (650 mg, 72%). $^1$HNMR (500 MHz, $CDCl_3$) δ 8.03-8.17 (m, 6H), 7.53-7.68 (m, 3H), 7.35-7.53 (m, 6H), 6.53 (s, 1H), 5.64 (t, J=6.7 Hz, 1H), 5.47 (d, J=3.2 Hz, 1H), 5.16 (d, J=6.6 Hz, 2H), 4.8-4.83 (m, 1H), 4.65 (dd, J=12, 6.5 Hz, 1H), 4.63 (dd, J=11.8, 6.4 Hz, 1H).

Step 1b:

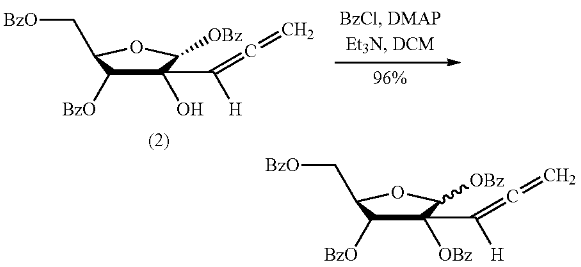

(2)

(3)

To the allenyl compound (2) (650 mg, 1.299 mmol), which was from step 1a in DCM (15 mL) was added BzCl (0.30 mL, 2.598 mmol) and DMAP (159 mg, 1.299 mmol) and $Et_3N$ (1.5 mL) and the resulted solution was stirred at RT for 4 h. The solvent was removed under vacuo and the residue was dissolved in ethyl acetate. The organic layer was washed with 1N HCl, water, $NaHCO_3$ solution, water, brine, dried ($Na_2SO_4$) and concentrated. The residue was purified by CombiFlash (eluted with hexane to 30% ethyl acetate in Hexane) to afford the full protected allenyl compound (3) (750 mg, 96%). $^1$H NMR (500 MHz, $CDCl_3$) δ 8.10 (d, J=8.5 Hz, 2H), 8.03 (d, J=8.5 Hz, 2H), 7.99 (d, J=8.0 Hz, 2H), 7.85 (d, J=8.5 Hz, 2H). 7.52-7.60 (m, 3H), 7.34-7.47 (m, 7H), 7.10 (d, J=8.0 Hz, 2H), 7.05 (s, 1H), 6.16 (d, J=7.5 Hz, 1H), 5.94 (dt, J=7.0, 1.0 Hz, 1H), 4.66-4.8 (m, 4H), 4.46 (dd, J=13.5, 6.5 Hz, 1H).

Step 1c

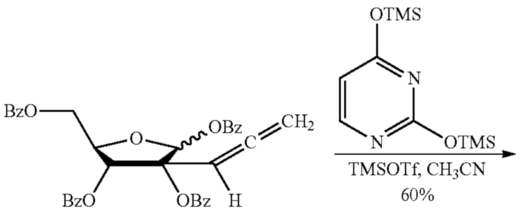

(3)

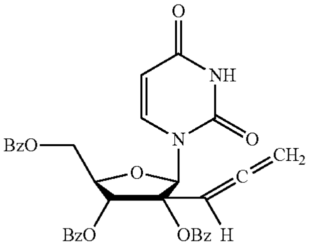

(4)

To a solution of the allenyl compound (3) (41 mg, 0.0678 mmol), which was from step 1b, in acetonitrile (1 mL) was added 2,4-bis(trimethylsilyloxy)-pyrimidine (52 mg, 0.203 mmol) and TMSOTf (50 uL, 0.271) at 0° C. The resulted solution was warmed up to RT and stirred for 14 h, then heated up to 85° C. for 6 h. The mixture was diluted with ethyl acetate, washed with $NaHCO_3$ solution, water, brine, dried ($Na_2SO_4$) and concentrated. The residue was purified by CombiFlash (eluted with hexane to 80% ethyl acetate in Hexane) to afford the compound (4) (24 mg, 60%). MS-ESI m/z 617.17 $(M+Na)^+$. $^1H$ NMR (500 MHz, $CDCl_3$) δ 8.91 (s, 1H), 8.05-8.12 (m, 4H), 7.86 (d, J=8.0 Hz, 2H), 7.6 (t, J=7.5 Hz, 2H), 7.55 (d, J=8.5 Hz, 1H), 7.44-7.52 (m, 5H), 7.27 (t, J=8.5 Hz, 2H), 6.7 (s, 1H), 6.01 (d, J=3.8 Hz, 1H), 5.51 (t, J=6.5 Hz, 1H), 5.05-5.14 (m, 2H), 4.81-4.91 (m, 2H), 4.60-4.65 (m, 1H).

Step 1d:

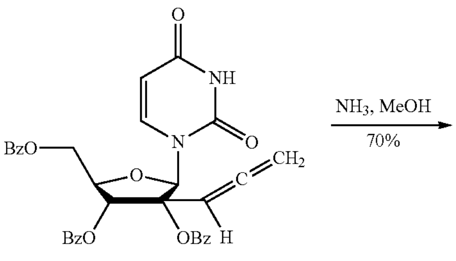

(4)

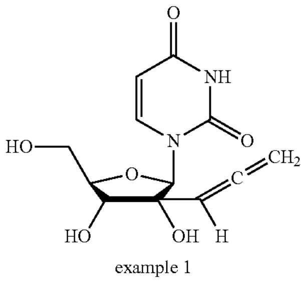

example 1

To the compound (4)(24 mg, 0.0404 mmol), which was from step 1c, was added $NH_3$ (7N in MeOH) and the resulted mixture was stirred at RT for 40 h. The solvent was removed under vacuo and the residue was purified by CombiFlash (eluted with hexane to 20% MeOH in DCM) to afford the compound of example 1 (8 mg, 70%). MS-ESI m/z 305.12 $(M+Na)^+$. $^1H$ NMR (500 MHz, $CD_3OD$) δ 8.13 (d, J=8 Hz, 1H), 5.97 (s, 1H), 5.66 (d, J=8 Hz, 1H), 5.15 (t, J=7 Hz, 1H), 4.94 (dd, J=11.5, 7 Hz, 1H), 4.78 (dd, J=11.5, 7 Hz, 1H), 4.23 (d, J=10 Hz, 1H), 3.99 (m, 2H), 3.80 (d, J=12 Hz, 1H).

Example 2

Compound of Formula (I), wherein $R_1=R_3=R_{2a}=R_{2b}=R_{2c}=H$, $R_2=OH$

B = 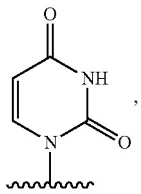, $R_5$ = 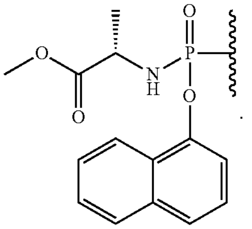.

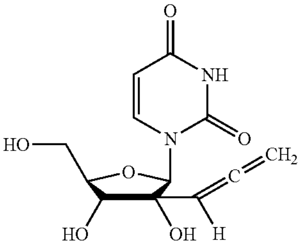

example 1

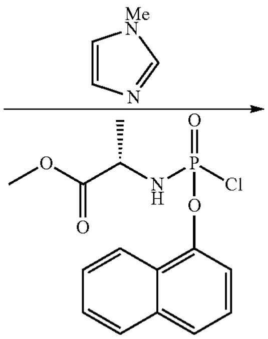

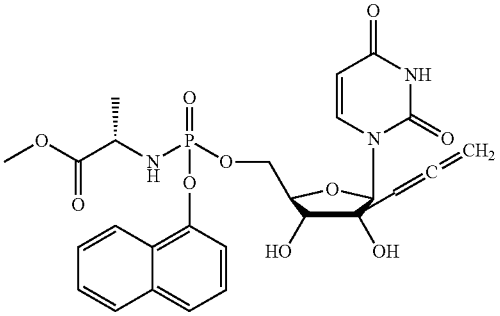

example 2

To the compound of example 1 (27 mg, 0.0956 mmol) in THF (2 mL) was added (2S)-methyl 2-(chloro(naphthalen-1-yloxy)phosphorylamino)propanoate (125.4 mg, 0.383 mmol) and N-methyl imidazole (38 uL, 1.478 mmol). The resulted suspension was stirred at RT for 14 h and then diluted with ethyl acetate. The organic layer was washed with 1N HCl, water, $NaHCO_3$ solution, water, brine, dried ($Na_2SO_4$) and concentrated. The residue was purified by CombiFlash (eluted with DCM to 20% MeOH in DCM) to afford the product which was further purified by HPLC to give the compound of example 2 as white solid (24 mg, 44%, ~1:1 diastereomers on Phosphorous atom). MS-ESI m/z 574.15 $(M+H)^+$.

Example 3

Compound of Formula (I), wherein $R_1{=}R_3{=}R_5{=}R_{2a}{=}R_{2b}{=}R_{2c}{=}H$, $R_2{=}$ F, B = 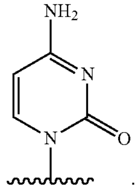 .

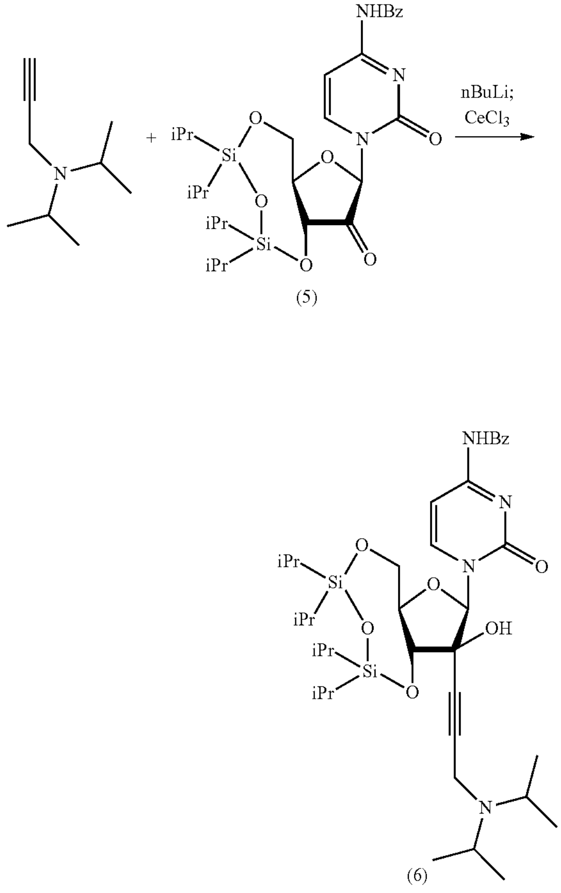

(5)

(6)

Step 3a

To the N,N-diisopropylprop-2-yn-1-amine (1.04 g, 7.48 mmol) in THF (20 mL) at −78° C. was added nBuLi (2.9 mL, 7.31 mmol, 2.5 M in Hexane) and the resulted solution was transferred via cannula at −78° C. into a suspension of $CeCl_3$ (freshly dried from 2.85 g $CeCl_3.7H_2O$) in THF (10 mL). After stirring at −78° C. for 1 h, the compound (5), which was prepared from Cytidine, (1.0 g, 1.7 mmol) in THF (10 mL) at −78° C. was transferred to this suspension via cannula. The resulted mixture was stirred at −78° C. for 2 h then slowly warmed up to 0° C. and quenched with saturated $NH_4Cl$ solution and diluted with EtOAc. The suspension was filtered through celite, and the aqueous layer was extracted with EtOAc after separation. The organic layer was combined, washed with water, brine, dried ($Na_2SO_4$) and concentrated under vacuo. The residue was purified by CombiFlash (eluted with DCM to 10% MeOH in DCM) to afford the compound (6) (758 mg) as yellow foam. MS-ESI m/z 727.20 $(M+H)^+$.

Step 3b

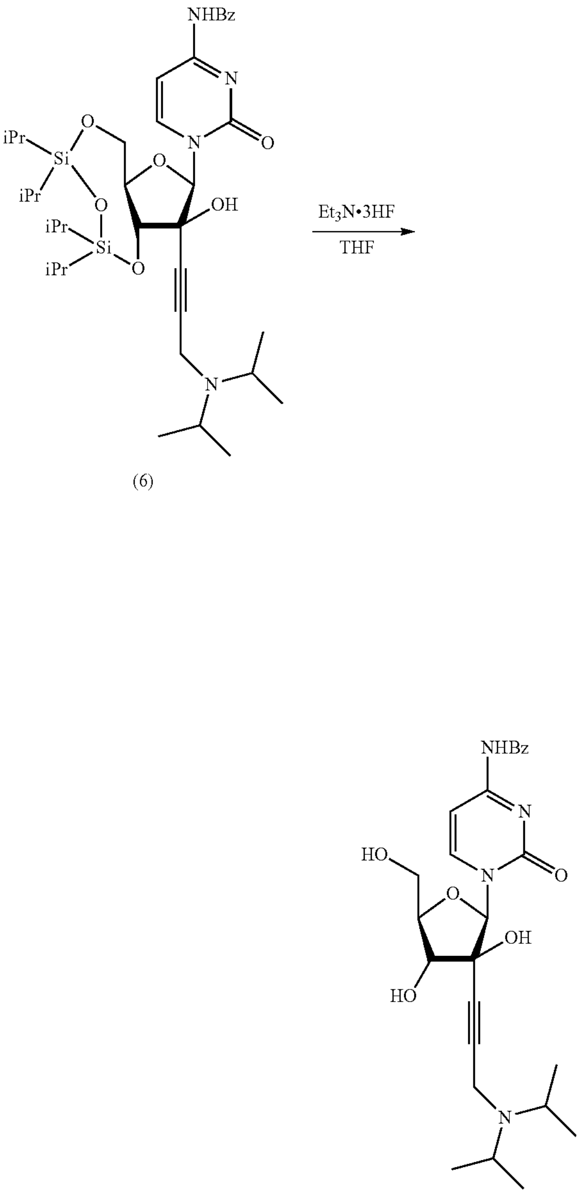

(6)

(7)

To the solution of the compound (6) (520 mg, 0.716 mmol), which was from step 3a, in THF (15 mL) was added $Et_3N$ (0.8 mL) and $Et_3N.HF$ sequentially. The mixture was stirred for 14 hr and solvent was removed under vacuo. The residue was purified by CombiFlash (eluted with DCM to 15% MeOH in DCM) to afford the compound (7) (340 mg) as yellow foam. MS-ESI m/z 485.16 $(M+H)^+$.

Step 3c

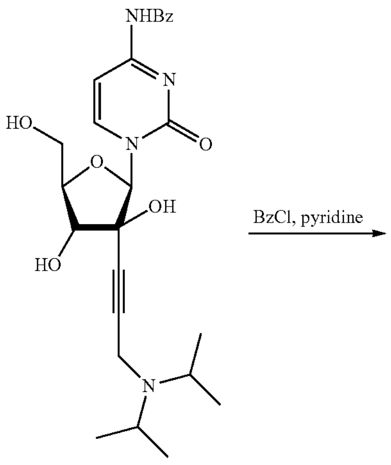

(7)

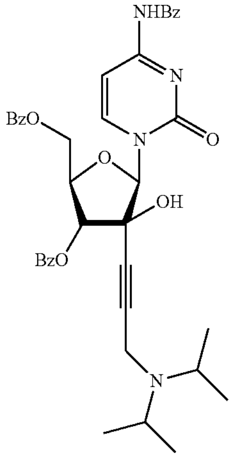

(8)

To the solution of the compound (7) (340 mg, 0.702 mmol), which was from step 3b, in pyridine (10 mL) was added Benzoyl chloride (0.25 mL, 2.148 mmol) and the resulted solution was stirred for 1.5 hr. The mixture was quenched with MeOH and solvent was removed under vacuo. The residue was purified by CombiFlash (eluted with DCM to 15% MeOH in DCM) to afford the compound (8) (350 mg) as yellow foam. MS-ESI m/z 693.26 $(M+H)^+$.

Step 3d

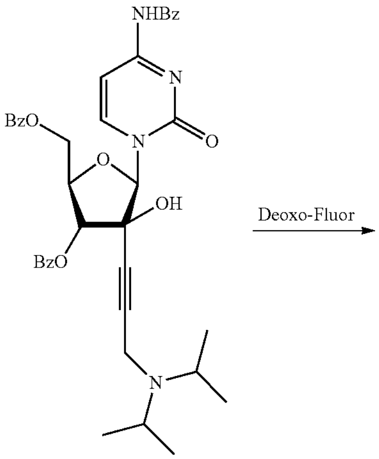

(8)

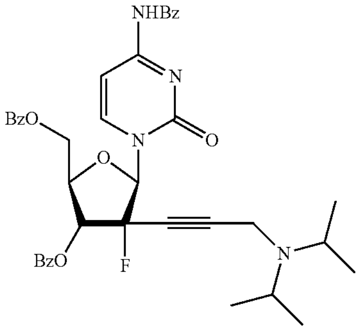

(9)

To the suspension of the compound (8)(70 mg), which was from step 3c, in toluene (4.5 mL) was added Deoxo-Fluor (67.1 mg, 0.303 mmol) and the resulted mixture was stirred for 1.5 hr. The mixture was poured into $EtOAc/NaHCO_3$, and after separation the organic layer was washed with water, brine, dried ($Na_2SO_4$) and concentrated under vacuo. The residue was purified by CombiFlash (eluted with DCM to 10% MeOH in DCM) to afford the compound (9). MS-ESI m/z 695.31 $(M+H)^+$.

Step 3e

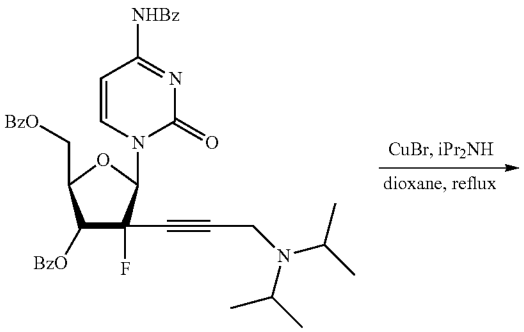

(9)

-continued

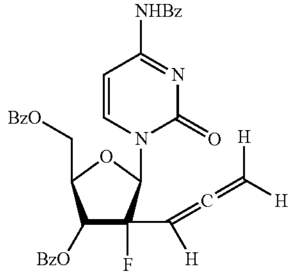

(10)

To the compound (9)(6 mg), which was from step 3d, in dioxane in sealed tube was added CuBr (1.5 mg) and i-$Pr_2NH$ (2.8 uL) and the resulted mixture was heated up to reflux for 16 hr. The mixture was diluted with EtOAc, washed with $NH_4Cl$ (3×), water and brine, dried ($Na_2SO_4$) and concentrated under vacuo. The residue was purified by preparative TLC to afford the compound (10). MS-ESI m/z 596.18 $(M+H)^+$.

Step 3f

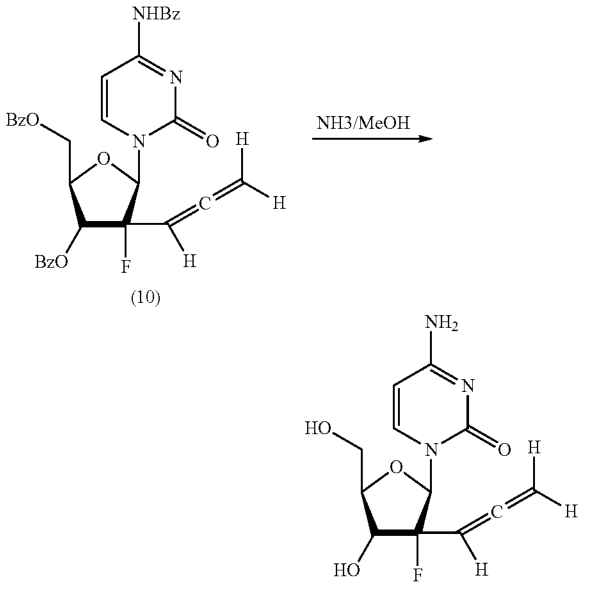

(10)

example 3

Example 4

Compound of Formula (I), wherein $R_1{=}R_3{=}R_{2a}{=}R_{2b}{=}R_{2c}{=}H$, $R_2{=}OH$ B = 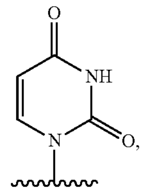

-continued $R_5$ = 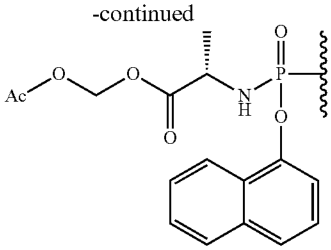

The compound of example 4 was prepared by using similar procedure in the preparation of compound of example 2; MS-ESI m/z 632.18 $(M+H)^+$.

To the compound (10) which was from step 3e, is added $NH_3$ (7N in MeOH) and the resulted mixture is stirred at RT for 40 h. The solvent is removed under vacuo and the residue is purified by CombiFlash to afford the compound of example 3.

While this invention has been particularly shown and described with references to preferred embodiments thereof, it will be understood by those skilled in the art that various changes in form and details may be made therein without departing from the scope of the invention encompassed by the appended claims.

Biological Activity

1. HCV Replicon Cell Lines

HCV replicon cell lines (kindly provided by R. Bartenschlager) isolated from colonies as described by Lohman et al. (Lohman et al. (1999) Science 285: 110-113, expressly incorporated by reference in its entirety) and used for all experiments. One of the HCV replicon cell lines (strain Con1, genotype 1b) has the nucleic acid sequence set forth in EMBL Accession No.: AJ242651, the coding sequence of which is from nucleotides 1801 to 8406. Another replicon cell line (strain H77, genotype 1a) was constructed as described by Yi et. al. (Yi et. al. (2004) Journal of Virology 78(15):7904-15). The coding sequences of the published HCV replicons were synthesized and subsequently assembled in plasmids using standard molecular biology techniques.

One replicon cell line ("SGR 11-7") stably expresses HCV replicon RNA, genotype 1b, which consists of (i) the HCV 5'UTR fused to the first 12 amino acids of the capsid protein, (ii) the neomycin phosphotransferase gene (neo), (iii) the IRES from encephalomyocarditis virus (EMCV) and (iv) HCV NS2 to NS5B genes and the HCV 3'UTR. Another replicon cell line ("Huh-1a7") described by Yi et. al. (Yi et. al. (2004) Journal of Virology 78(15):7904-15, expressly incorporated by reference in its entirety) stably expresses HCV replicon RNA, genotype 1a, which consists of (i) the HCV 5'UTR fused to the first 12 amino acids of the capsid protein, (ii) the HIV tat protein, (iii) the neomycin phosphotransferase gene (neo), (iv) the IRES from encephalomyocarditis virus (EMCV) and (vi) HCV NS3 to NS5B genes that harbor cell culture adaptive mutations (Q1067R, K1691R, S2204I) and the HCV 3'UTR.

These cell lines are maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 100X penicillin/streptomycin (Cat#15140-122, Invitrogen) and Geneticin (Cat#10131-027, Invitrogen) at 0.75 mg/ml or 0.25 mg/ml for 11-7 and Huh-1a7 cells, respectively.

2. HCV Replicon Assay—qRT-PCR $EC_{50}$ values of single agent compounds were determined by HCV RNA detection using quantitative RT-PCR, according to the manufacturer's instructions, with a TAQMAN® One-Step RT-PCR Master Mix Reagents Kit (Cat#AB 4309169, Applied Biosystems) on an ABI Model 7500 thermocycler. $EC_{50}$ values of combinations are similarly determined by HCV RNA detection using quantitative RT-PCR. The TAQMAN primers to use for detecting and quantifying HCV RNA obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat#AM1812). Chemical agent cytotoxicity is evaluated using an MTS assay according to the manufacturer's directions (Promega).

The compounds of the present invention can be effective against the HCV 1a and 1b genotypes. It should also be understood that the compounds of the present invention can inhibit multiple genotypes of HCV. In one embodiment, compounds of the present invention are active against the 1a, 1b, 2a, 2b, 3a, 4a, and 5a genotypes. Table 7 shows the $EC_{50}$ values of representative compounds of the present invention against the HCV 1a and 1b genotypes from the above described qRT-PCR. $EC_{50}$ ranges against HCV 1a or 1b are as follows: A>10 μM; B 1-10 μM; C<1 μM.

TABLE 7

| Genotype-1a or 1b replicon $EC_{50}$ | | |
|---|---|---|
| Example | 1a $EC_{50}$ | 1b $EC_{50}$ |
| 1 | A | A |
| 2 | B | B |
| 3 | A | A |
| 4 | C | C |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula (I):

(I)

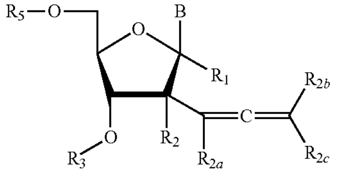

or the β-L enantiomer thereof, or a pharmaceutically acceptable salt, ester, stereoisomer, tautomer, solvate, or combination thereof, wherein:

$R_1$ is selected from the group consisting of:
1) hydrogen;
2) —CN;
3) halogen;
4) —$N_3$; and
5) Substituted or unsubstituted —$C_1$-$C_8$ alkyl;

$R_{2a}$, $R_{2b}$ and $R_2$ are each independently selected from the group consisting of: hydrogen, halogen, and substituted or unsubstituted —$C_1$-$C_8$ alkyl;

$R_2$ is selected from the group consisting of:
1) halogen;
2) —CN;
3) —$N_3$; and
4) $OR_6$; where $R_6$ at each occurrence is independently selected from the group consisting of: hydrogen, hydroxy protecting group, —C(O)$R_7$, —C(O)O$R_7$, and —C(O)N$R_{8a}R_{8b}$; wherein $R_7$ at each occurrence is independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic; $R_{8a}$; and $R_{8b}$ at each occurrence is independently selected from the group consisting of: hydrogen and $R_7$; or alternatively $R_{8a}$ and $R_{8b}$ taken together with the nitrogen atom to which they are attached form a heterocyclic ring;

$R_3$ is $R_6$; or alternatively $R_2$ is —$OR_6$ and $R_3$ and $R_6$ taken together form a group selected from: —C(Me)$_2$-, —C(CH$_2$)$_4$—, —CH(Ph)-, —CH(OMe)- and —P(O)(OH)—;

B is selected from the group consisting of: substituted or unsubstituted aryl, substituted or unsubstituted heteroaryl, and substituted or unsubstituted heterocyclic; and $R_5$ is selected from the group consisting of:
1) hydrogen;
2) $R_6$;
3) —P(O)(O$R_{7a}$)(O$R_{7b}$); wherein $R_{7a}$ and $R_{7b}$ are each independently selected from the group consisting of a) hydrogen; and b) unsubstituted or substituted —$C_1$-$C_8$ alkyl;
4) —P(O)(O$R_{7a}$)—O—P(O)(O$R_{7b}$)(O$R_{7c}$); wherein $R_{7a}$ and $R_{7b}$ are previously defined; $R_7$ is selected from the group consisting of a) hydrogen; and b) unsubstituted or substituted —$C_1$-$C_8$ alkyl; and
5) —P(O)(O$R_{7a}$)—O—P(O)(O$R_{7b}$)—O—P(O)(O$R_{7c}$)(O$R_{7d}$); wherein $R_{7a}$, $R_{7b}$ and $R_{7c}$ are previously defined; $R_{7d}$ is selected from the group consisting of a) hydrogen; and b) unsubstituted or substituted —$C_1$-$C_8$ alkyl;
6)

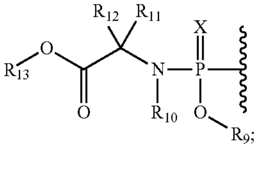

where X is O or S; $R_9$ is $R_7$ wherein $R_7$ is previously defined; $R_{10}$, $R_{11}$ and $R_{12}$ are each independently selected from the group consisting of: a) hydrogen; and b) unsubstituted or substituted —$C_1$-$C_8$ alkyl; or $R_{11}$ is hydrogen, and $R_{12}$ and $R_{10}$ are taken together with the nitrogen atom to which $R_{10}$ is attached to form a heterocyclic ring; or $R_{11}$ and $R_{12}$ are taken together with the carbon to which they are attached form a ring; and $R_{13}$ is hydrogen or $R_7$, wherein $R_7$ is previously defined; and

7)

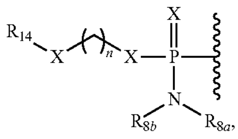

where X is O or S; n is 1-4; $R_{8a}$ and $R_{8b}$ are as previously defined; $R_{14}$ is hydrogen or —(CO)—$R_7$, wherein $R_7$ is as previously defined; or $R_5$ and $R_3$ are taken together to form

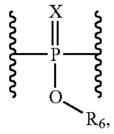

where X is O or S; and $R_6$ is as previously defined.

2. The compound of claim 1 represented by Formula (III):

(III)

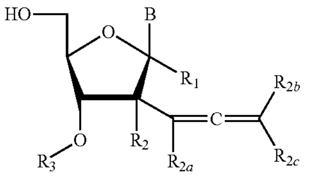

or its β-L enantiomer, or a pharmaceutically acceptable salt, ester, stereoisomer, tautomer, solvate, or combination thereof.

3. The compound of claim 1 represented by Formula (IV):

(IV)

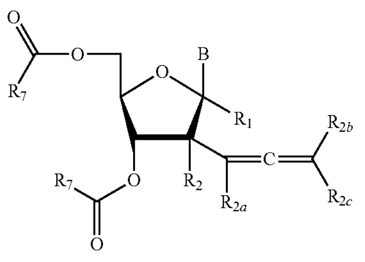

or its β-L enantiomer, or a pharmaceutically acceptable salt, ester, stereoisomer, tautomer, solvate, or combination thereof.

4. The compound of claim 1 represented by Formula (V):

(V)

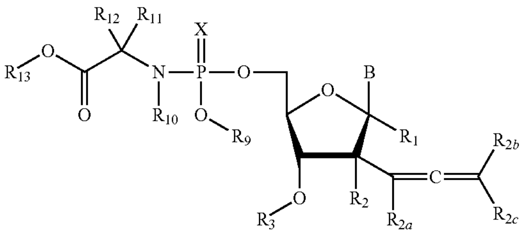

or its β-L enantiomer, or a pharmaceutically acceptable salt, ester, stereoisomer, tautomer, solvate, or combination thereof.

5. The compound of claim 1 represented by Formula (VI):

(VI)

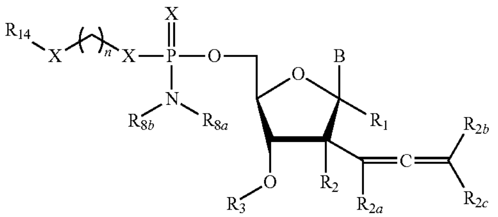

or its β-L enantiomer, or a pharmaceutically acceptable salt, ester, stereoisomer, tautomer, solvate, or combination thereof.

6. The compound of claim 1 represented by Formula (VII):

(VII)

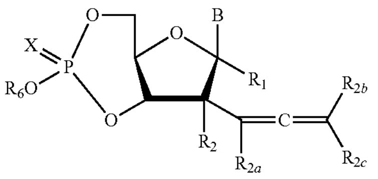

or its β-L enantiomer, or a pharmaceutically acceptable salt, ester, stereoisomer, tautomer, solvate, or combination thereof.

7. The compound of claim 1, wherein B is represented by Formula B1 or Formula B2, (B1)

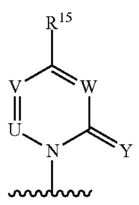

-continued (B2)

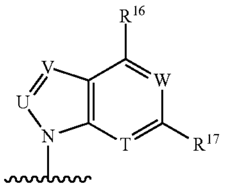

wherein:

Y at each occurrence is independently selected from a group consisting of: O, S, $NR_{8a}$, $NC(O)R_7$, $NC(O)OR_7$ and $NC(O)NR_{8a}R_{8b}$;

T, U, V and W are each independently N or $CR_{18}$; wherein $R_{18}$ is selected from the group consisting of: hydrogen, halogen, —CN, —$C(O)R_7$, —$C(O)NR_{8a}R_{8b}$, —$NO_2$, —$N_3$, —$OR_7$, —$SR_7$, —$NR_{8a}R_{8b}$, —$OC(O)R_7$, —$OC(O)OR_7$, —$NHC(O)R_7$, —$NHC(O)OR_7$ and —$NHC(O)NR_{8a}R_{8b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl; and $R_{15}$, $R_{16}$ and $R_{17}$ are each independently selected from the group consisting of: hydrogen, halogen, —CN, —$C(O)R_D$, —$C(O)NR_{8a}R_{8b}$, —$NO_2$, —$N_3$, —$OR_7$, —$SR_7$, —$NR_{8a}R_{8b}$, —$OC(O)R_7$, —$OC(O)OR_7$, —$NHC(O)R_7$, —$NHC(O)OR_7$ and —$NHC(O)NR_{8a}R_{8b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl.

8. The compound according to claim 1 selected from:

(a) compounds represented by Formula (III-1) wherein $R_2$, $R_{2a}$, $R_{2b}$, $R_{2c}$, and B are delineated for each compound in Table 1;

TABLE 1

(III-1)

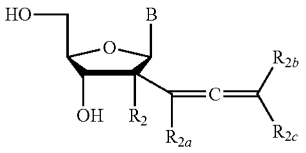

| Example # | $R_{2a}$ | $R_{2b}$ | $R_{2c}$ | $R_2$ | B |
|---|---|---|---|---|---|
| 1 | H | H | H | OH | 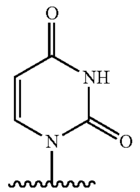 |

TABLE 1-continued (III-1)

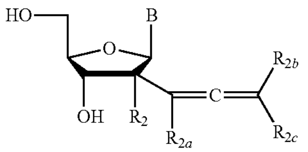

| Example # | $R_{2a}$ | $R_{2b}$ | $R_{2c}$ | $R_2$ | B |
|---|---|---|---|---|---|
| 2 | H | H | H | F | 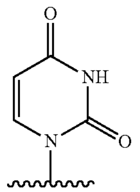 [SMILES: *n1ccc(=O)[nH]c1=O] |
| 3 | H | Me | Me | OH | 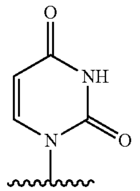 [SMILES: *n1ccc(=O)[nH]c1=O] |
| 4 | H | Me | Me | F | 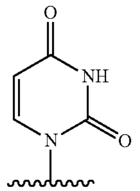 [SMILES: *n1ccc(=O)[nH]c1=O] |
| 5 | H | F | F | OH | 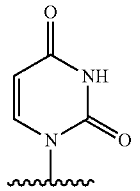 [SMILES: *n1ccc(=O)[nH]c1=O] |
| 6 | H | F | F | F | 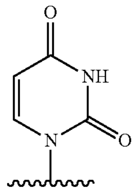 [SMILES: *n1ccc(=O)[nH]c1=O] |
| 7 | H | H | H | OH | 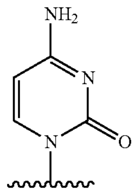 [SMILES: *n1ccc(N)nc1=O] |
| 8 | H | H | H | F | 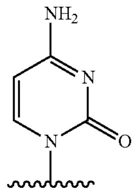 [SMILES: *n1ccc(N)nc1=O] |

TABLE 1-continued
(III-1)
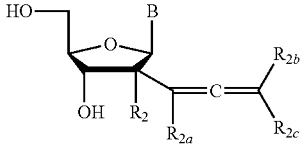
| Example # | $R_{2a}$ | $R_{2b}$ | $R_{2c}$ | $R_2$ | B |
|---|---|---|---|---|---|
| 9 | H | Me | Me | OH | 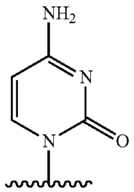 |
| 10 | H | Me | Me | F | 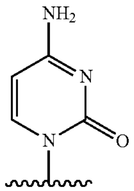 |
| 11 | H | F | F | OH | 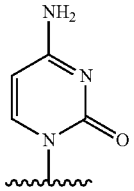 |
| 12 | H | F | F | F | 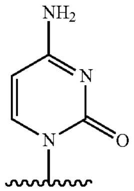 |
| 13 | H | H | H | OH | 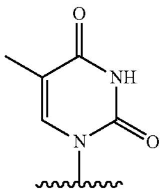 [SMILES: *n1cc(C)c(=O)[nH]c1=O] |
| 14 | H | H | H | F | 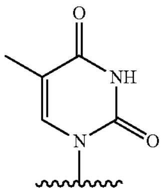 [SMILES: *n1cc(C)c(=O)[nH]c1=O] |
| 15 | H | Me | Me | OH | 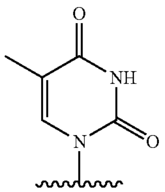 [SMILES: *n1cc(C)c(=O)[nH]c1=O] |
TABLE 1-continued
(III-1)
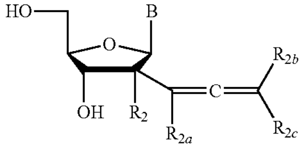
| Example # | $R_{2a}$ | $R_{2b}$ | $R_{2c}$ | $R_2$ | B |
|---|---|---|---|---|---|
| 16 | H | Me | Me | F | 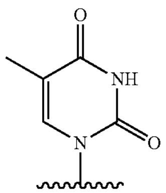 [SMILES: *n1cc(C)c(=O)[nH]c1=O] |
| 17 | H | F | F | OH | 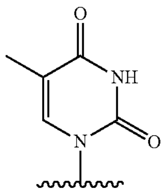 [SMILES: *n1cc(C)c(=O)[nH]c1=O] |
| 18 | H | F | F | F | 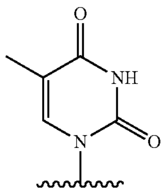 [SMILES: *n1cc(C)c(=O)[nH]c1=O] |
| 19 | H | H | H | OH | 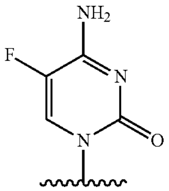 |
| 20 | H | H | H | F | 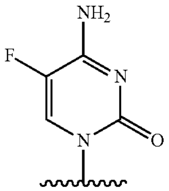 |
| 21 | H | Me | Me | OH | 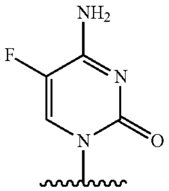 |
| 22 | H | Me | Me | F | 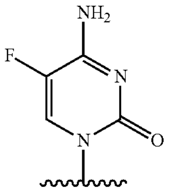 |

TABLE 1-continued
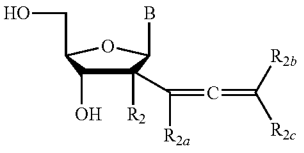
(III-1)
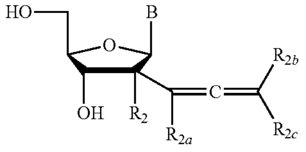
(III-1)
| Example # | $R_{2a}$ | $R_{2b}$ | $R_{2c}$ | $R_2$ | B |
|---|---|---|---|---|---|
| 23 | H | F | F | OH | 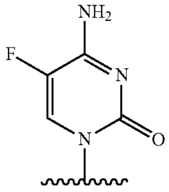 [SMILES: *n1cc(F)c(N)nc1=O] |
| 24 | H | F | F | F | 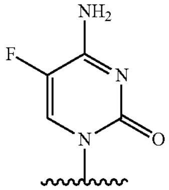 [SMILES: *n1cc(F)c(N)nc1=O] |
| 25 | H | H | H | OH | 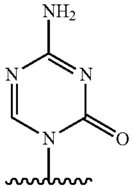 |
| 26 | H | H | H | F | 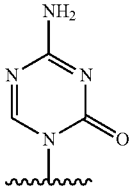 |
| 27 | H | Me | Me | OH | 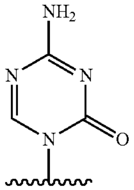 [SMILES: *n1cnc(N)nc1=O] |
| 28 | H | Me | Me | F | 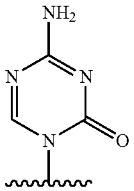 [SMILES: *n1cnc(N)nc1=O] |
| 29 | H | F | F | OH | 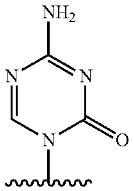 [SMILES: *n1cnc(N)nc1=O] |
| 30 | H | F | F | F | 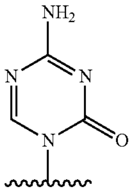 [SMILES: *n1cnc(N)nc1=O] |
| 31 | H | H | H | OH | 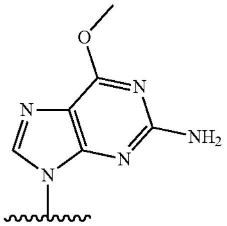 [SMILES: *n1cnc2c(OC)nc(N)nc21] |
| 32 | H | H | H | F | 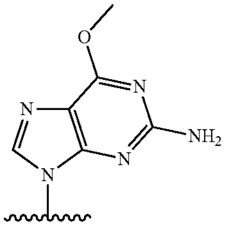 [SMILES: *n1cnc2c(OC)nc(N)nc21] |
| 33 | H | Me | Me | OH | 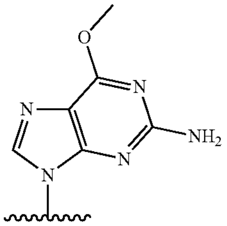 [SMILES: *n1cnc2c(OC)nc(N)nc21] |
| 34 | H | Me | Me | F | 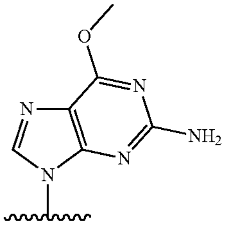 [SMILES: *n1cnc2c(OC)nc(N)nc21] |
| 35 | H | F | F | OH | 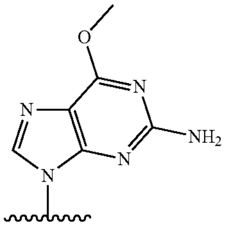 [SMILES: *n1cnc2c(OC)nc(N)nc21] |

TABLE 1-continued
(III-1)
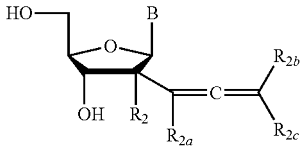
| Example # | $R_{2a}$ | $R_{2b}$ | $R_{2c}$ | $R_2$ | B |
|---|---|---|---|---|---|
| 36 | H | F | F | F | 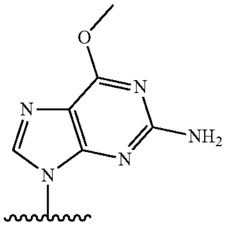 [SMILES: *n1cnc2c(OC)nc(N)nc21] |
| 37 | H | H | H | OH | 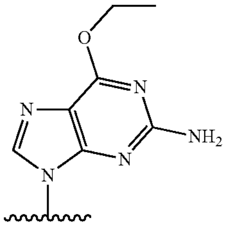 [SMILES: *n1cnc2c(OCC)nc(N)nc21] |
| 38 | H | H | H | F | 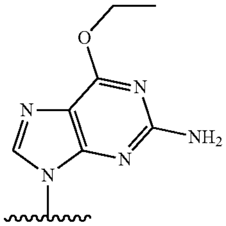 [SMILES: *n1cnc2c(OCC)nc(N)nc21] |
| 39 | H | Me | Me | OH | 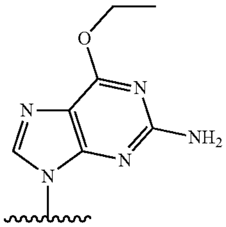 [SMILES: *n1cnc2c(OCC)nc(N)nc21] |
| 40 | H | Me | Me | F | 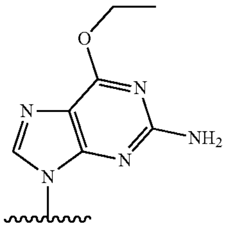 [SMILES: *n1cnc2c(OCC)nc(N)nc21] |
| 41 | H | F | F | OH | 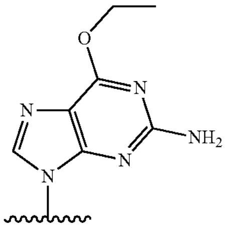 [SMILES: *n1cnc2c(OCC)nc(N)nc21] |
TABLE 1-continued
(III-1)
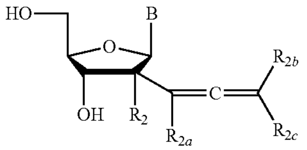
| Example # | $R_{2a}$ | $R_{2b}$ | $R_{2c}$ | $R_2$ | B |
|---|---|---|---|---|---|
| 42 | H | F | F | F | 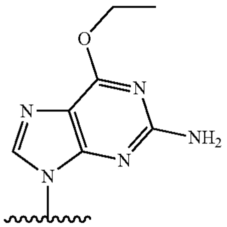 [SMILES: *n1cnc2c(OCC)nc(N)nc21] |
| 43 | H | H | H | OH | 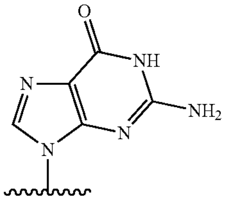 [SMILES: *n1cnc2c(=O)[nH]c(N)nc21] |
| 44 | H | H | H | F | 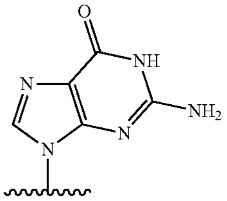 [SMILES: *n1cnc2c(=O)[nH]c(N)nc21] |
| 45 | H | Me | Me | OH | 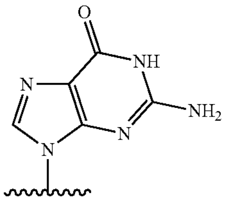 [SMILES: *n1cnc2c(=O)[nH]c(N)nc21] |
| 46 | H | Me | Me | F | 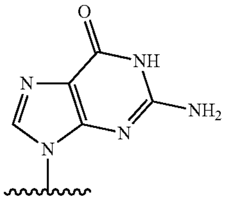 [SMILES: *n1cnc2c(=O)[nH]c(N)nc21] |
| 47 | H | F | F | OH | 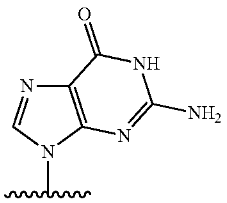 [SMILES: *n1cnc2c(=O)[nH]c(N)nc21] |

TABLE 1-continued
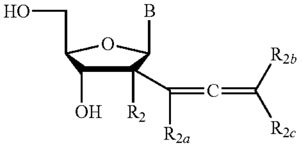
(III-1)
| Example # | $R_{2a}$ | $R_{2b}$ | $R_{2c}$ | $R_2$ | B |
|---|---|---|---|---|---|
| 48 | H | F | F | F | 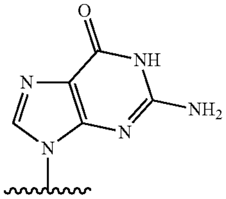 [SMILES: *n1cnc2c(=O)[nH]c(N)nc21] |
| 49 | H | H | H | OH | 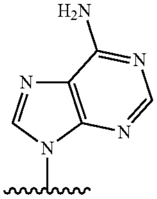 |
| 50 | H | H | H | F | 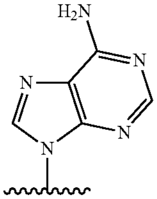 |
| 51 | H | Me | Me | OH | 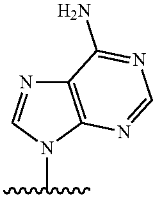 |
| 52 | H | Me | Me | F | 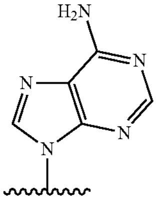 |
| 53 | H | F | F | OH | 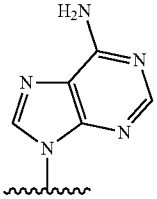 |
TABLE 1-continued
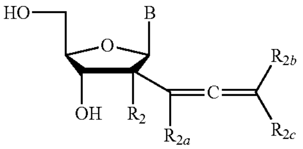
(III-1)
| Example # | $R_{2a}$ | $R_{2b}$ | $R_{2c}$ | $R_2$ | B |
|---|---|---|---|---|---|
| 54 | H | F | F | F | 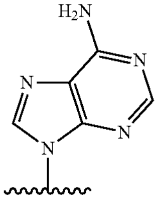 |
| 55 | H | H | H | OH | 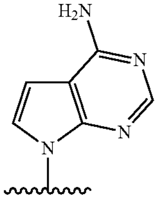 [SMILES: *n1ccc2c(N)ncnc21] |
| 56 | H | H | H | F | 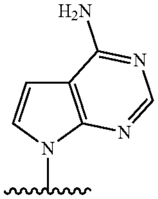 |
| 57 | H | Me | Me | OH | 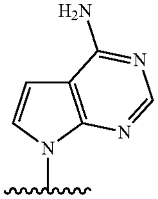 [SMILES: *n1ccc2c(N)ncnc21] |
| 58 | H | Me | Me | F | 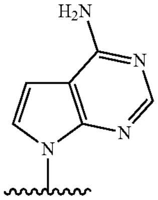 [SMILES: *n1ccc2c(N)ncnc21] |
| 59 | H | F | F | OH | 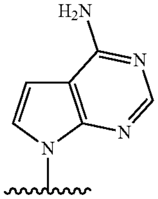 |

TABLE 1-continued
(III-1)
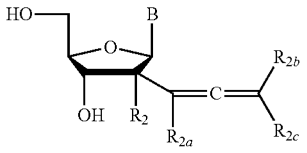
| Example # | $R_{2a}$ | $R_{2b}$ | $R_{2c}$ | $R_2$ | B |
|---|---|---|---|---|---|
| 60 | H | F | F | F | 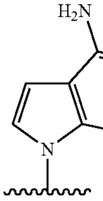 |
(b) compounds represented by Formula (IV-1) wherein $R_2$, $R_7$, $R_{2a}$, $R_{2b}$, $R_{2c}$, and B are delineated for each compound in Table 2
TABLE 2
(IV-1)
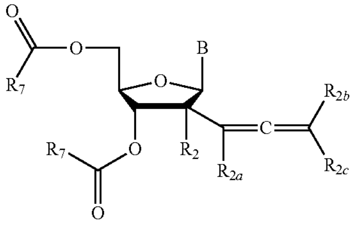
| Compound # | $R_{2a}$ | $R_{2b}$ | $R_{2c}$ | $R_2$ | $R_7$ | B |
|---|---|---|---|---|---|---|
| 61 | H | H | H | OH | i-Pr | 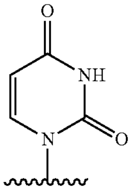 [SMILES: *n1ccc(=O)[nH]c1=O] |
| 62 | H | H | H | F | i-Pr | 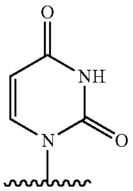 [SMILES: *n1ccc(=O)[nH]c1=O] |
| 63 | H | Me | Me | OH | i-Pr | 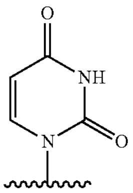 [SMILES: *n1ccc(=O)[nH]c1=O] |
TABLE 2-continued
(IV-1)
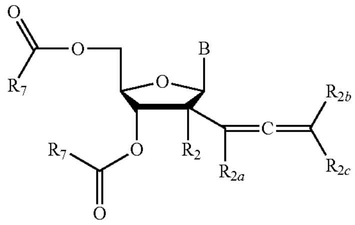
| Compound # | $R_{2a}$ | $R_{2b}$ | $R_{2c}$ | $R_2$ | $R_7$ | B |
|---|---|---|---|---|---|---|
| 64 | H | Me | Me | F | i-Pr | 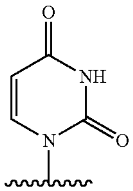 [SMILES: *n1ccc(=O)[nH]c1=O] |
| 65 | H | F | F | OH | i-Pr | 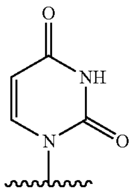 [SMILES: *n1ccc(=O)[nH]c1=O] |
| 66 | H | F | F | F | i-Pr | 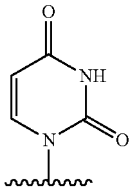 [SMILES: *n1ccc(=O)[nH]c1=O] |
| 67 | H | H | H | OH | i-Pr | 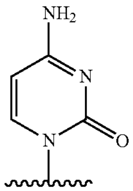 |
| 68 | H | H | H | F | i-Pr | 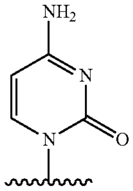 |
| 69 | H | Me | Me | OH | i-Pr | 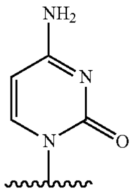 |

TABLE 2-continued
(IV-1)
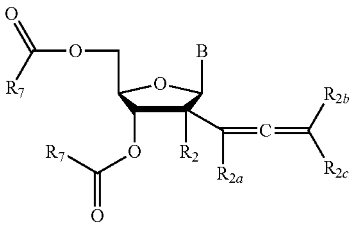
| Compound # | $R_{2a}$ | $R_{2b}$ | $R_{2c}$ | $R_2$ | $R_7$ | B |
|---|---|---|---|---|---|---|
| 70 | H | Me | Me | F | i-Pr | 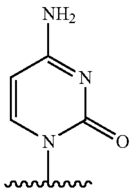 |
| 71 | H | F | F | OH | i-Pr | 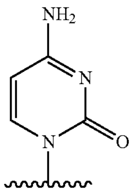 |
| 72 | H | F | F | F | i-Pr | 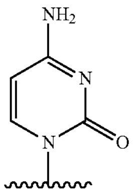 |
| 73 | H | H | H | OH | i-Pr | 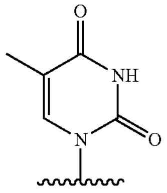 [SMILES: *n1cc(C)c(=O)[nH]c1=O] |
| 74 | H | H | H | F | i-Pr | 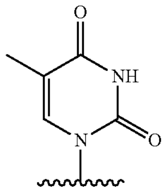 |
| 75 | H | Me | Me | OH | i-Pr | 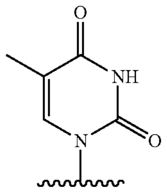 [SMILES: *n1cc(C)c(=O)[nH]c1=O] |
TABLE 2-continued
(IV-1)
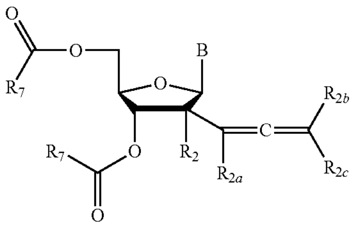
| Compound # | $R_{2a}$ | $R_{2b}$ | $R_{2c}$ | $R_2$ | $R_7$ | B |
|---|---|---|---|---|---|---|
| 76 | H | Me | Me | F | i-Pr | 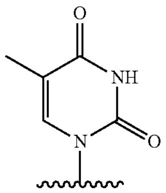 [SMILES: *n1cc(C)c(=O)[nH]c1=O] |
| 77 | H | F | F | OH | i-Pr | 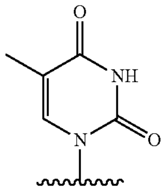 [SMILES: *n1cc(C)c(=O)[nH]c1=O] |
| 78 | H | F | F | F | i-Pr | 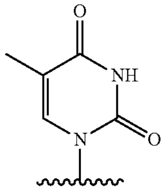 [SMILES: *n1cc(C)c(=O)[nH]c1=O] |
| 79 | H | H | H | OH | i-Pr | 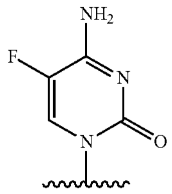 |
| 80 | H | H | H | F | i-Pr | 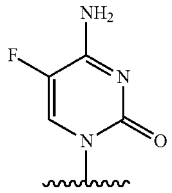 |
| 81 | H | Me | Me | OH | i-Pr | 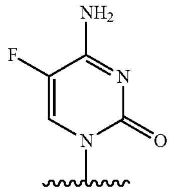 |

TABLE 2-continued
(IV-1)
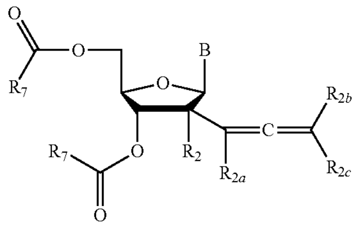
| Compound # | $R_{2a}$ | $R_{2b}$ | $R_{2c}$ | $R_2$ | $R_7$ | B |
|---|---|---|---|---|---|---|
| 82 | H | Me | Me | F | i-Pr | 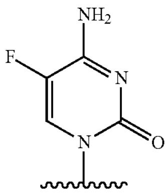 |
| 83 | H | F | F | OH | i-Pr | 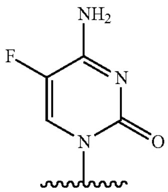 |
| 84 | H | F | F | F | i-Pr | 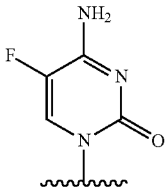 |
| 85 | H | H | H | OH | i-Pr | 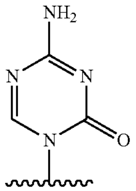 [SMILES: *n1cnc(N)nc1=O] |
| 86 | H | H | H | F | i-Pr | 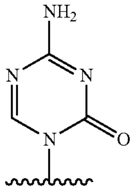 |
| 87 | H | Me | Me | OH | i-Pr | 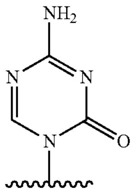 |
TABLE 2-continued
(IV-1)
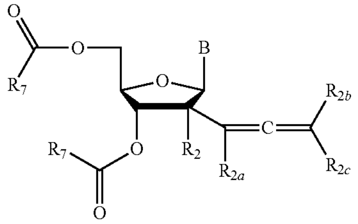
| Compound # | $R_{2a}$ | $R_{2b}$ | $R_{2c}$ | $R_2$ | $R_7$ | B |
|---|---|---|---|---|---|---|
| 88 | H | Me | Me | F | i-Pr | 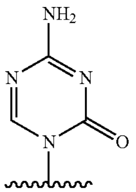 [SMILES: *n1cnc(N)nc1=O] |
| 89 | H | F | F | OH | i-Pr | 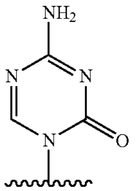 [SMILES: *n1cnc(N)nc1=O] |
| 90 | H | F | F | F | i-Pr | 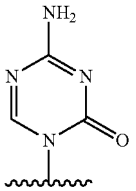 [SMILES: *n1cnc(N)nc1=O] |
| 91 | H | H | H | OH | i-Pr | 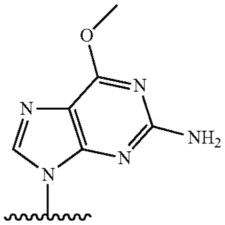 [SMILES: *n1cnc2c(OC)nc(N)nc21] |
| 92 | H | H | H | F | i-Pr | 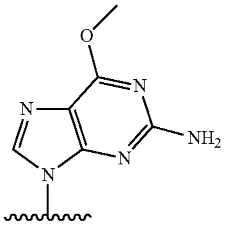 [SMILES: *n1cnc2c(OC)nc(N)nc21] |
| 93 | H | Me | Me | OH | i-Pr | 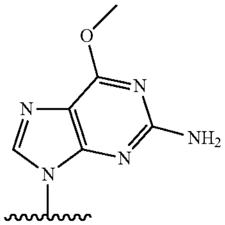 [SMILES: *n1cnc2c(OC)nc(N)nc21] |

TABLE 2-continued
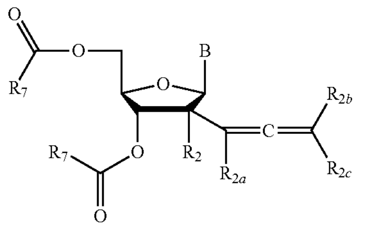
(IV-1)
| Compound # | $R_{2a}$ | $R_{2b}$ | $R_{2c}$ | $R_2$ | $R_7$ | B |
|---|---|---|---|---|---|---|
| 94 | H | Me | Me | F | i-Pr | 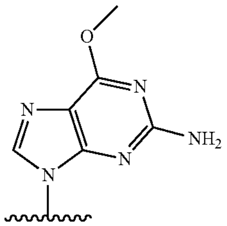 [SMILES: *n1cnc2c(OC)nc(N)nc21] |
| 95 | H | F | F | OH | i-Pr | 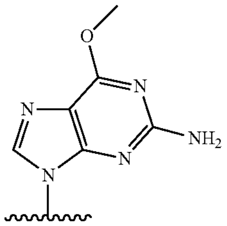 [SMILES: *n1cnc2c(OC)nc(N)nc21] |
| 96 | H | F | F | F | i-Pr | 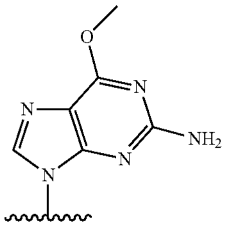 [SMILES: *n1cnc2c(OC)nc(N)nc21] |
| 97 | H | H | H | OH | i-Pr | 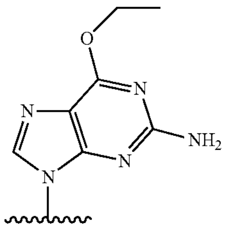 [SMILES: *n1cnc2c(OCC)nc(N)nc21] |
| 98 | H | H | H | F | i-Pr | 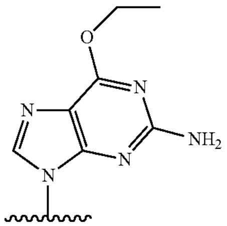 [SMILES: *n1cnc2c(OCC)nc(N)nc21] |
TABLE 2-continued
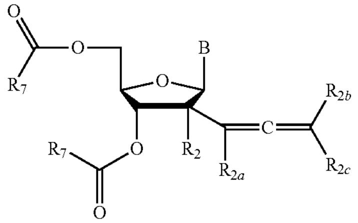
(IV-1)
| Compound # | $R_{2a}$ | $R_{2b}$ | $R_{2c}$ | $R_2$ | $R_7$ | B |
|---|---|---|---|---|---|---|
| 99 | H | Me | Me | OH | i-Pr | 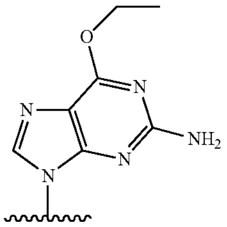 [SMILES: *n1cnc2c(OCC)nc(N)nc21] |
| 100 | H | Me | Me | F | i-Pr | 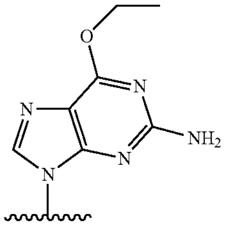 [SMILES: *n1cnc2c(OCC)nc(N)nc21] |
| 101 | H | F | F | OH | i-Pr | 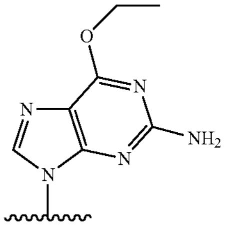 [SMILES: *n1cnc2c(OCC)nc(N)nc21] |
| 102 | H | F | F | F | i-Pr | 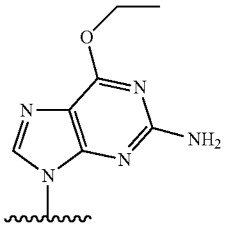 [SMILES: *n1cnc2c(OCC)nc(N)nc21] |
| 103 | H | H | H | OH | i-Pr | 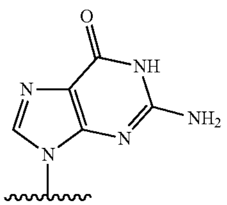 [SMILES: *n1cnc2c(=O)[nH]c(N)nc21] |
| 104 | H | H | H | F | i-Pr | 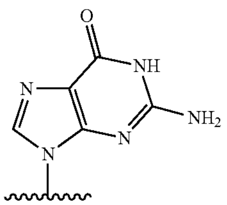 [SMILES: *n1cnc2c(=O)[nH]c(N)nc21] |

TABLE 2-continued
(IV-1)
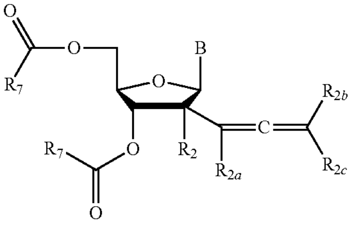
| Compound # | $R_{2a}$ | $R_{2b}$ | $R_{2c}$ | $R_2$ | $R_7$ | B |
|---|---|---|---|---|---|---|
| 105 | H | Me | Me | OH | i-Pr | 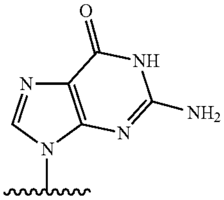 [SMILES: *n1cnc2c(=O)[nH]c(N)nc21] |
| 106 | H | Me | Me | F | i-Pr | 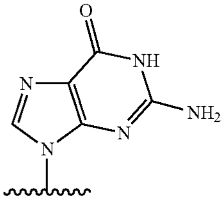 [SMILES: *n1cnc2c(=O)[nH]c(N)nc21] |
| 107 | H | F | F | OH | i-Pr | 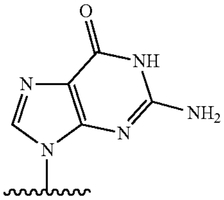 [SMILES: *n1cnc2c(=O)[nH]c(N)nc21] |
| 108 | H | F | F | F | i-Pr | 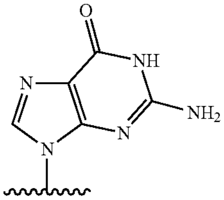 [SMILES: *n1cnc2c(=O)[nH]c(N)nc21] |
| 109 | H | H | H | OH | i-Pr | 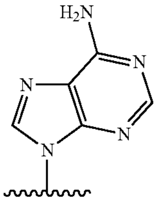 [SMILES: *n1cnc2c(N)ncnc21] |
| 110 | H | H | H | F | i-Pr | 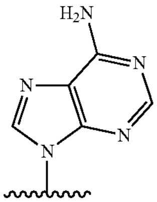 [SMILES: *n1cnc2c(N)ncnc21] |
TABLE 2-continued
(IV-1)
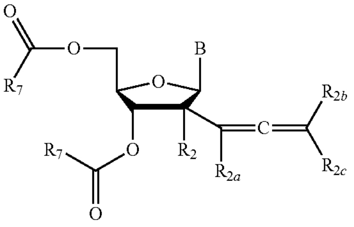
| Compound # | $R_{2a}$ | $R_{2b}$ | $R_{2c}$ | $R_2$ | $R_7$ | B |
|---|---|---|---|---|---|---|
| 111 | H | Me | Me | OH | i-Pr | 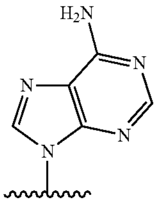 [SMILES: *n1cnc2c(N)ncnc21] |
| 112 | H | Me | Me | F | i-Pr | 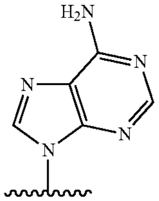 [SMILES: *n1cnc2c(N)ncnc21] |
| 113 | H | F | F | OH | i-Pr | 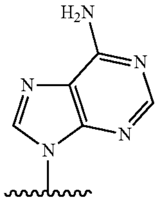 [SMILES: *n1cnc2c(N)ncnc21] |
| 114 | H | F | F | F | i-Pr | 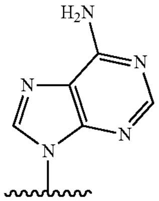 |
| 115 | H | H | H | OH | i-Pr | 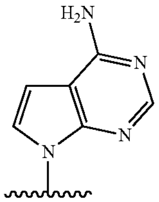 [SMILES: *n1ccc2c(N)ncnc21] |
| 116 | H | H | H | F | i-Pr | 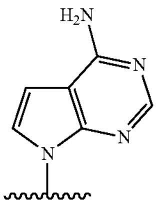 [SMILES: *n1ccc2c(N)ncnc21] |

TABLE 2-continued
(IV-1)
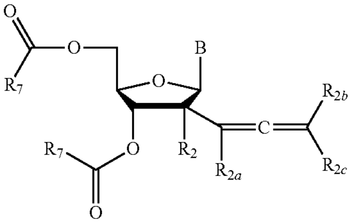
| Compound # | $R_{2a}$ | $R_{2b}$ | $R_{2c}$ | $R_2$ | $R_7$ | B |
|---|---|---|---|---|---|---|
| 117 | H | Me | Me | OH | i-Pr | 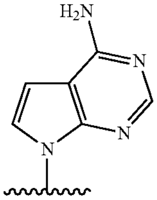 [SMILES: *n1ccc2c(N)ncnc21] |
| 118 | H | Me | Me | F | i-Pr | 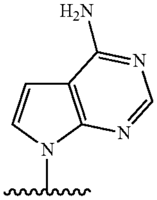 [SMILES: *n1ccc2c(N)ncnc21] |
| 119 | H | F | F | OH | i-Pr | 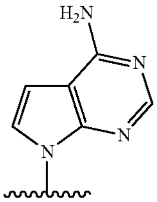 [SMILES: *n1ccc2c(N)ncnc21] |
| 120 | H | F | F | F | i-Pr | 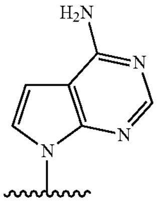 [SMILES: *n1ccc2c(N)ncnc21] |
| 121 | H | H | H | OH | Et | 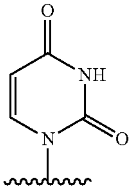 [SMILES: *n1ccc(=O)[nH]c1=O] |
| 122 | H | H | H | F | Et | 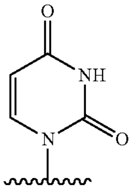 [SMILES: *n1ccc(=O)[nH]c1=O] |
TABLE 2-continued
(IV-1)
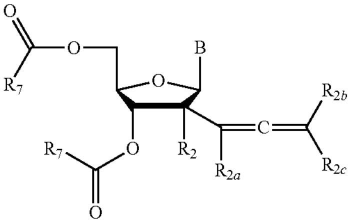
| Compound # | $R_{2a}$ | $R_{2b}$ | $R_{2c}$ | $R_2$ | $R_7$ | B |
|---|---|---|---|---|---|---|
| 123 | H | Me | Me | OH | Et | 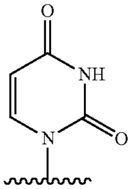 [SMILES: *n1ccc(=O)[nH]c1=O] |
| 124 | H | Me | Me | F | Et | 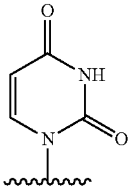 [SMILES: *n1ccc(=O)[nH]c1=O] |
| 125 | H | F | F | OH | Et | 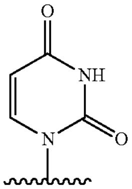 |
| 126 | H | F | F | F | Et | 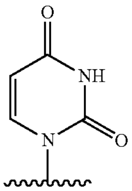 [SMILES: *n1ccc(=O)[nH]c1=O] |
| 127 | H | H | H | OH | Et | 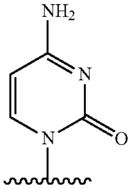 |
| 128 | H | H | H | F | Et | 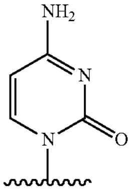 |

TABLE 2-continued
(IV-1)
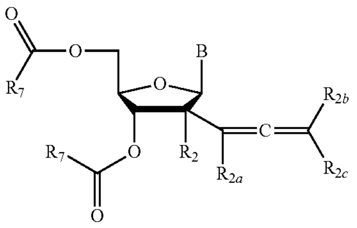
| Compound # | $R_{2a}$ | $R_{2b}$ | $R_{2c}$ | $R_2$ | $R_7$ | B |
|---|---|---|---|---|---|---|
| 129 | H | Me | Me | OH | Et | 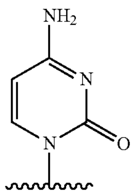 |
| 130 | H | Me | Me | F | Et | 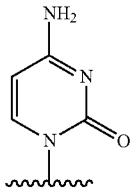 |
| 131 | H | F | F | OH | Et | 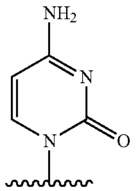 |
| 132 | H | F | F | F | Et | 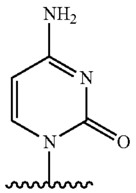 |
| 133 | H | H | H | OH | Et | 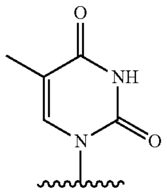 |
| 134 | H | H | H | F | Et | 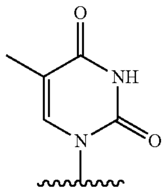 [SMILES: *n1cc(C)c(=O)[nH]c1=O] |
TABLE 2-continued
(IV-1)
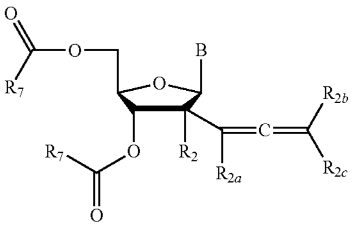
| Compound # | $R_{2a}$ | $R_{2b}$ | $R_{2c}$ | $R_2$ | $R_7$ | B |
|---|---|---|---|---|---|---|
| 135 | H | Me | Me | OH | Et | 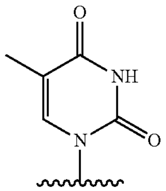 [SMILES: *n1cc(C)c(=O)[nH]c1=O] |
| 136 | H | Me | Me | F | Et | 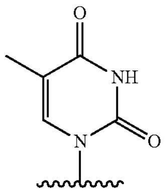 [SMILES: *n1cc(C)c(=O)[nH]c1=O] |
| 137 | H | F | F | OH | Et | 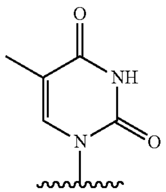 [SMILES: *n1cc(C)c(=O)[nH]c1=O] |
| 138 | H | F | F | F | Et | 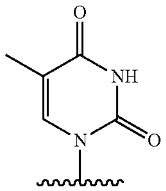 [SMILES: *n1cc(C)c(=O)[nH]c1=O] |
| 139 | H | H | H | OH | Et | 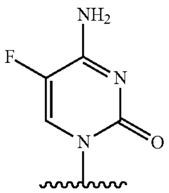 |
| 140 | H | H | H | F | Et | 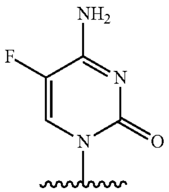 |

TABLE 2-continued
(IV-1)
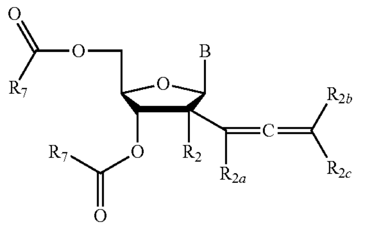
| Compound # | $R_{2a}$ | $R_{2b}$ | $R_{2c}$ | $R_2$ | $R_7$ | B |
|---|---|---|---|---|---|---|
| 141 | H | Me | Me | OH | Et | 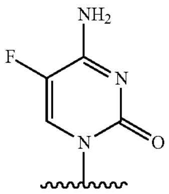 |
| 142 | H | Me | Me | F | Et | 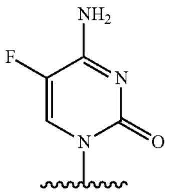 |
| 143 | H | F | F | OH | Et | 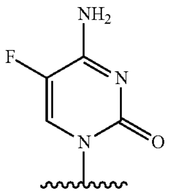 |
| 144 | H | F | F | F | Et | 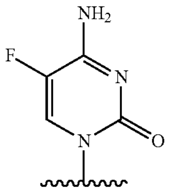 |
| 145 | H | H | H | OH | Et | 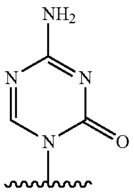 |
| 146 | H | H | H | F | Et | 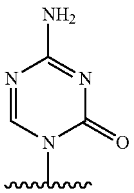 [SMILES: *n1cnc(N)nc1=O] |
TABLE 2-continued
(IV-1)
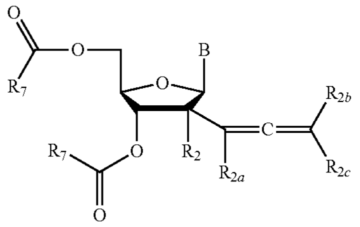
| Compound # | $R_{2a}$ | $R_{2b}$ | $R_{2c}$ | $R_2$ | $R_7$ | B |
|---|---|---|---|---|---|---|
| 147 | H | Me | Me | OH | Et | 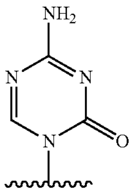 [SMILES: *n1cnc(N)nc1=O] |
| 148 | H | Me | Me | F | Et | 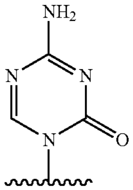 [SMILES: *n1cnc(N)nc1=O] |
| 149 | H | F | F | OH | Et | 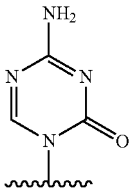 [SMILES: *n1cnc(N)nc1=O] |
| 150 | H | F | F | F | Et | 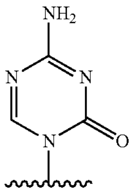 [SMILES: *n1cnc(N)nc1=O] |
| 151 | H | H | H | OH | Et | 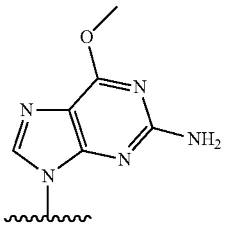 |
| 152 | H | H | H | F | Et | 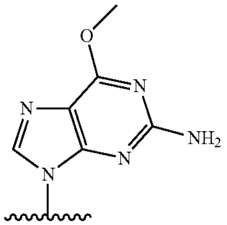 [SMILES: *n1cnc2c(OC)nc(N)nc21] |

TABLE 2-continued
(IV-1)
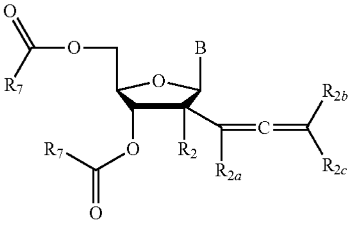
| Compound # | $R_{2a}$ | $R_{2b}$ | $R_{2c}$ | $R_2$ | $R_7$ | B |
|---|---|---|---|---|---|---|
| 153 | H | Me | Me | OH | Et | 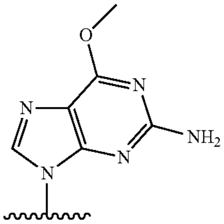 [SMILES: *n1cnc2c(OC)nc(N)nc21] |
| 154 | H | Me | Me | F | Et | 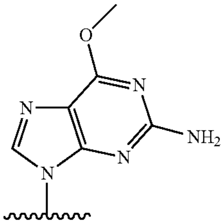 [SMILES: *n1cnc2c(OC)nc(N)nc21] |
| 155 | H | F | F | OH | Et | 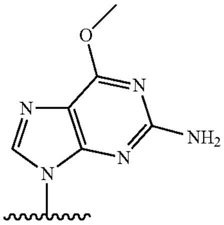 [SMILES: *n1cnc2c(OC)nc(N)nc21] |
| 156 | H | F | F | F | Et | 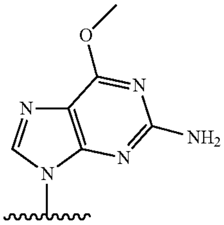 [SMILES: *n1cnc2c(OC)nc(N)nc21] |
| 157 | H | H | H | OH | Et | 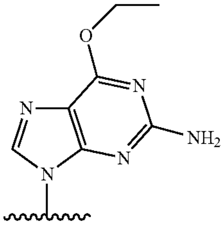 [SMILES: *n1cnc2c(OCC)nc(N)nc21] |
TABLE 2-continued
(IV-1)
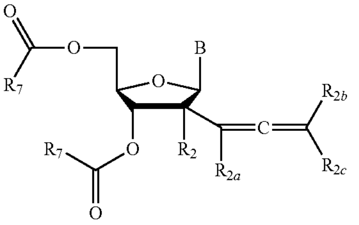
| Compound # | $R_{2a}$ | $R_{2b}$ | $R_{2c}$ | $R_2$ | $R_7$ | B |
|---|---|---|---|---|---|---|
| 158 | H | H | H | F | Et | 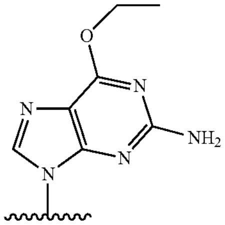 [SMILES: *n1cnc2c(OCC)nc(N)nc21] |
| 159 | H | Me | Me | OH | Et | 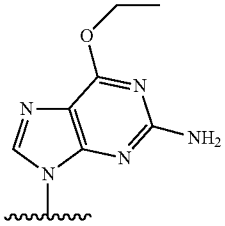 [SMILES: *n1cnc2c(OCC)nc(N)nc21] |
| 160 | H | Me | Me | F | Et | 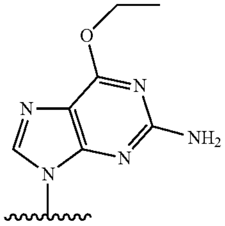 [SMILES: *n1cnc2c(OCC)nc(N)nc21] |
| 161 | H | F | F | OH | Et | 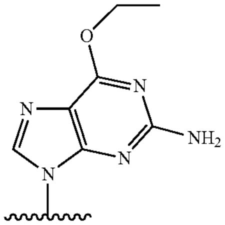 [SMILES: *n1cnc2c(OCC)nc(N)nc21] |
| 162 | H | F | F | F | Et | 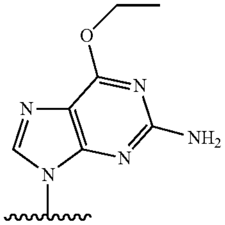 [SMILES: *n1cnc2c(OCC)nc(N)nc21] |

TABLE 2-continued
(IV-1)
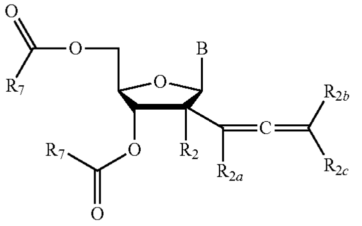
| Compound # | $R_{2a}$ | $R_{2b}$ | $R_{2c}$ | $R_2$ | $R_7$ | B |
|---|---|---|---|---|---|---|
| 163 | H | H | H | OH | Et | 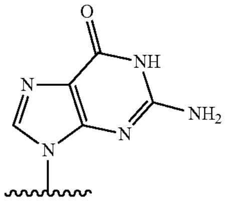 [SMILES: *n1cnc2c(=O)[nH]c(N)nc21] |
| 164 | H | H | H | F | Et | 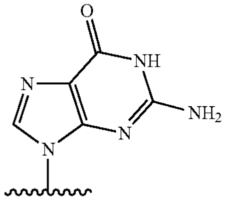 [SMILES: *n1cnc2c(=O)[nH]c(N)nc21] |
| 165 | H | Me | Me | OH | Et | 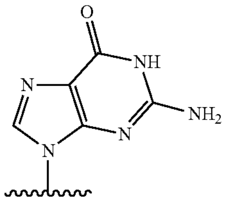 [SMILES: *n1cnc2c(=O)[nH]c(N)nc21] |
| 166 | H | Me | Me | F | Et | 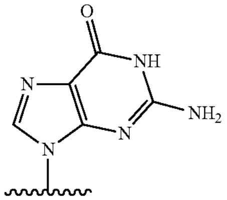 [SMILES: *n1cnc2c(=O)[nH]c(N)nc21] |
| 167 | H | F | F | OH | Et | 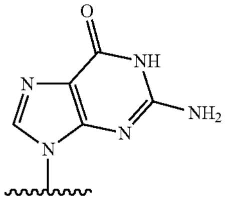 [SMILES: *n1cnc2c(=O)[nH]c(N)nc21] |
| 168 | H | F | F | F | Et | 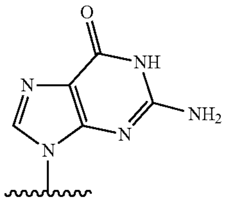 [SMILES: *n1cnc2c(=O)[nH]c(N)nc21] |
TABLE 2-continued
(IV-1)
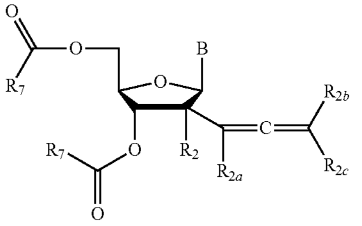
| Compound # | $R_{2a}$ | $R_{2b}$ | $R_{2c}$ | $R_2$ | $R_7$ | B |
|---|---|---|---|---|---|---|
| 169 | H | H | H | OH | Et | 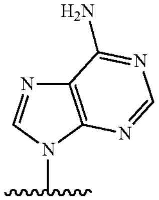 [SMILES: *n1cnc2c(N)ncnc21] |
| 170 | H | H | H | F | Et | 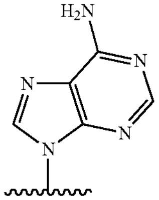 |
| 171 | H | Me | Me | OH | Et | 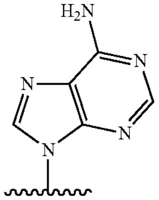 |
| 152 | H | Me | Me | F | Et | 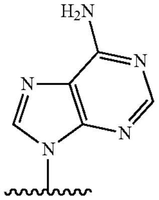 [SMILES: *n1cnc2c(N)ncnc21] |
| 173 | H | F | F | OH | Et | 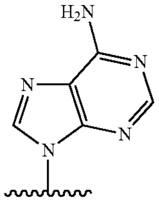 [SMILES: *n1cnc2c(N)ncnc21] |
| 174 | H | F | F | F | Et | 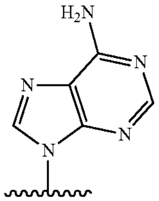 |

TABLE 2-continued
(IV-1)
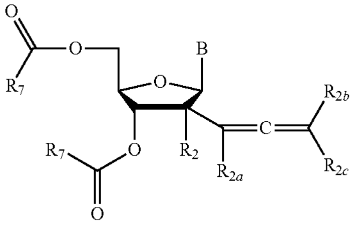
| Compound # | $R_{2a}$ | $R_{2b}$ | $R_{2c}$ | $R_2$ | $R_7$ | B |
|---|---|---|---|---|---|---|
| 175 | H | H | H | OH | Et | 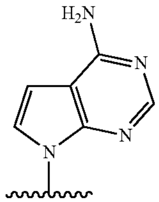 [SMILES: *n1ccc2c(N)ncnc21] |
| 176 | H | H | H | F | Et | 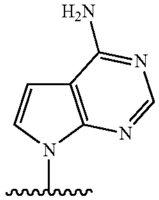 [SMILES: *n1ccc2c(N)ncnc21] |
| 177 | H | Me | Me | OH | Et | 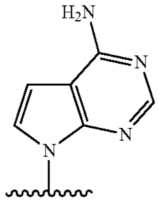 |
| 178 | H | Me | Me | F | Et | 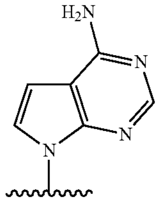 [SMILES: *n1ccc2c(N)ncnc21] |
| 179 | H | F | F | OH | Et | 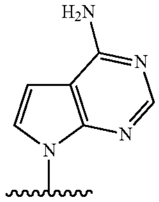 [SMILES: *n1ccc2c(N)ncnc21] |
| 180 | H | F | F | F | Et | 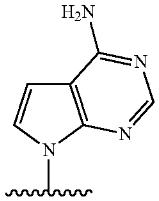 [SMILES: *n1ccc2c(N)ncnc21] |
TABLE 2-continued
(IV-1)
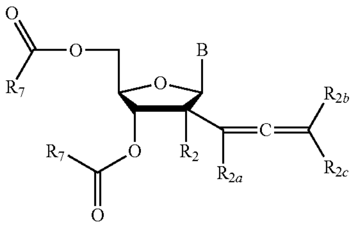
| Compound # | $R_{2a}$ | $R_{2b}$ | $R_{2c}$ | $R_2$ | $R_7$ | B |
|---|---|---|---|---|---|---|
| 181 | H | H | H | OH | i-Bu | 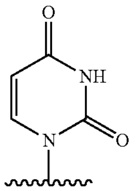 [SMILES: *n1ccc(=O)[nH]c1=O] |
| 182 | H | H | H | F | i-Bu | 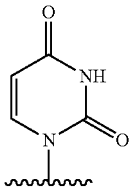 |
| 183 | H | Me | Me | OH | i-Bu | 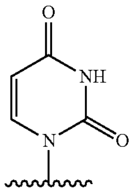 [SMILES: *n1ccc(=O)[nH]c1=O] |
| 184 | H | Me | Me | F | i-Bu | 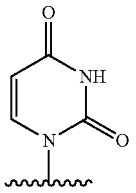 [SMILES: *n1ccc(=O)[nH]c1=O] |
| 185 | H | F | F | OH | i-Bu | 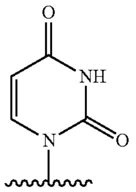 |
| 186 | H | F | F | F | i-Bu | 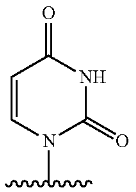 [SMILES: *n1ccc(=O)[nH]c1=O] |

TABLE 2-continued
(IV-1)
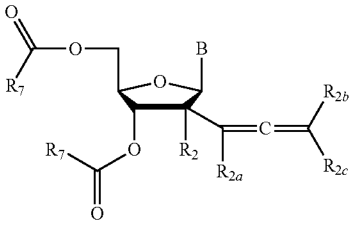
| Compound # | $R_{2a}$ | $R_{2b}$ | $R_{2c}$ | $R_2$ | $R_7$ | B |
|---|---|---|---|---|---|---|
| 187 | H | H | H | OH | i-Bu | 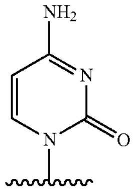 |
| 188 | H | H | H | F | i-Bu | 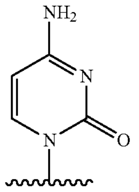 |
| 189 | H | Me | Me | OH | i-Bu | 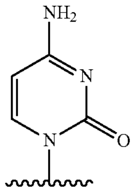 |
| 190 | H | Me | Me | F | i-Bu | 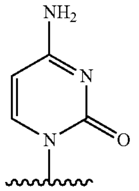 |
| 191 | H | F | F | OH | i-Bu | 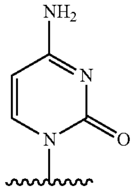 |
| 192 | H | F | F | F | i-Bu | 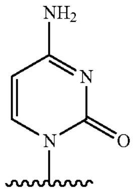 |
TABLE 2-continued
(IV-1)
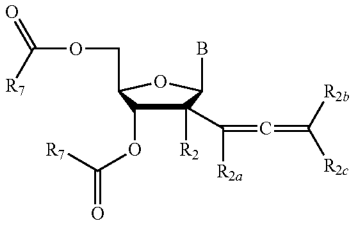
| Compound # | $R_{2a}$ | $R_{2b}$ | $R_{2c}$ | $R_2$ | $R_7$ | B |
|---|---|---|---|---|---|---|
| 193 | H | H | H | OH | i-Bu | 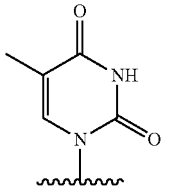 [SMILES: *n1cc(C)c(=O)[nH]c1=O] |
| 194 | H | H | H | F | i-Bu | 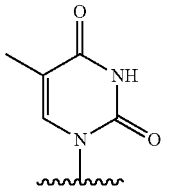 [SMILES: *n1cc(C)c(=O)[nH]c1=O] |
| 195 | H | Me | Me | OH | i-Bu | 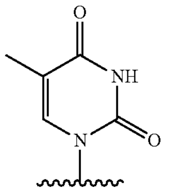 [SMILES: *n1cc(C)c(=O)[nH]c1=O] |
| 196 | H | Me | Me | F | i-Bu | 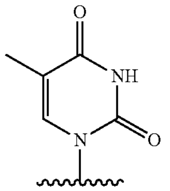 [SMILES: *n1cc(C)c(=O)[nH]c1=O] |
| 197 | H | F | F | OH | i-Bu | 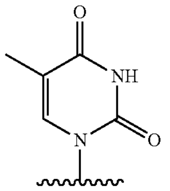 [SMILES: *n1cc(C)c(=O)[nH]c1=O] |
| 198 | H | F | F | F | i-Bu | 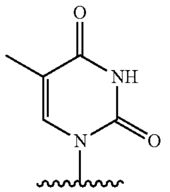 [SMILES: *n1cc(C)c(=O)[nH]c1=O] |

TABLE 2-continued
(IV-1)
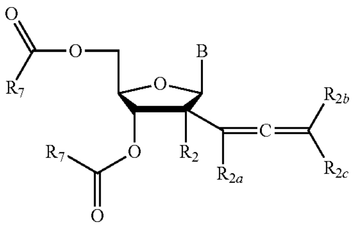
| Compound # | $R_{2a}$ | $R_{2b}$ | $R_{2c}$ | $R_2$ | $R_7$ | B |
|---|---|---|---|---|---|---|
| 199 | H | H | H | OH | i-Bu | 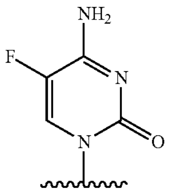 |
| 200 | H | H | H | F | i-Bu | 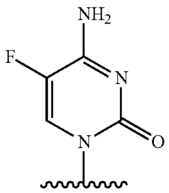 |
| 201 | H | Me | Me | OH | i-Bu | 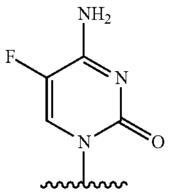 |
| 202 | H | Me | Me | F | i-Bu | 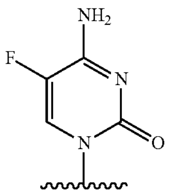 |
| 203 | H | F | F | OH | i-Bu | 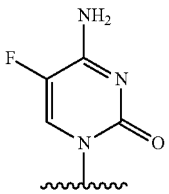 |
| 204 | H | F | F | F | i-Bu | 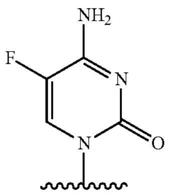 |
TABLE 2-continued
(IV-1)
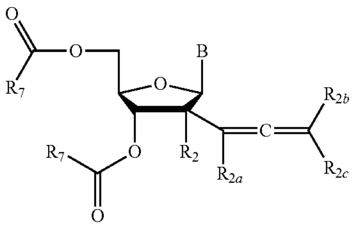
| Compound # | $R_{2a}$ | $R_{2b}$ | $R_{2c}$ | $R_2$ | $R_7$ | B |
|---|---|---|---|---|---|---|
| 205 | H | H | H | OH | i-Bu | 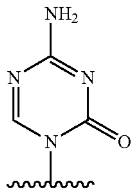 [SMILES: *n1cnc(N)nc1=O] |
| 206 | H | H | H | F | i-Bu | 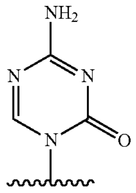 [SMILES: *n1cnc(N)nc1=O] |
| 207 | H | Me | Me | OH | i-Bu | 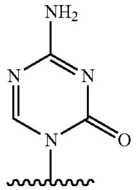 [SMILES: *n1cnc(N)nc1=O] |
| 208 | H | Me | Me | F | i-Bu | 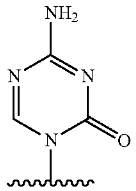 [SMILES: *n1cnc(N)nc1=O] |
| 209 | H | F | F | OH | i-Bu | 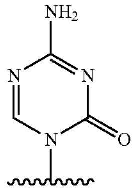 [SMILES: *n1cnc(N)nc1=O] |
| 210 | H | F | F | F | i-Bu | 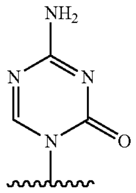 [SMILES: *n1cnc(N)nc1=O] |

TABLE 2-continued
(IV-1)
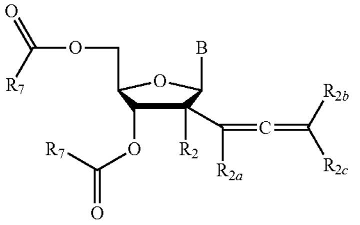
| Compound # | $R_{2a}$ | $R_{2b}$ | $R_{2c}$ | $R_2$ | $R_7$ | B |
|---|---|---|---|---|---|---|
| 211 | H | H | H | OH | i-Bu | 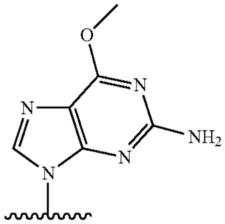 [SMILES: *n1cnc2c(OC)nc(N)nc21] |
| 212 | H | H | H | F | i-Bu | 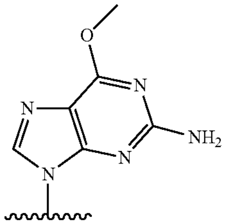 [SMILES: *n1cnc2c(OC)nc(N)nc21] |
| 213 | H | Me | Me | OH | i-Bu | 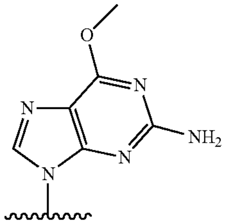 [SMILES: *n1cnc2c(OC)nc(N)nc21] |
| 214 | H | Me | Me | F | i-Bu | 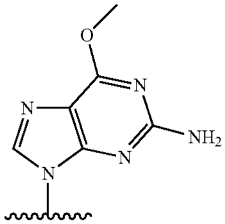 [SMILES: *n1cnc2c(OC)nc(N)nc21] |
| 215 | H | F | F | OH | i-Bu | 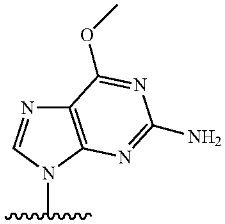 [SMILES: *n1cnc2c(OC)nc(N)nc21] |
TABLE 2-continued
(IV-1)
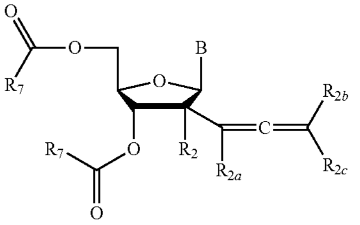
| Compound # | $R_{2a}$ | $R_{2b}$ | $R_{2c}$ | $R_2$ | $R_7$ | B |
|---|---|---|---|---|---|---|
| 216 | H | F | F | F | i-Bu | 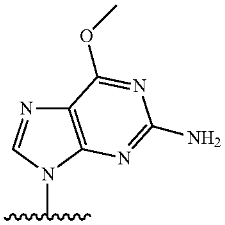 [SMILES: *n1cnc2c(OC)nc(N)nc21] |
| 217 | H | H | H | OH | i-Bu | 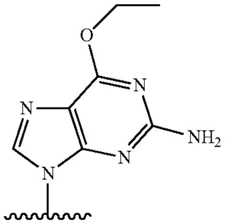 [SMILES: *n1cnc2c(OCC)nc(N)nc21] |
| 218 | H | H | H | F | i-Bu | 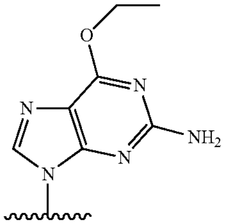 [SMILES: *n1cnc2c(OCC)nc(N)nc21] |
| 219 | H | Me | Me | OH | i-Bu | 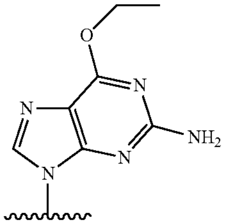 [SMILES: *n1cnc2c(OCC)nc(N)nc21] |
| 220 | H | Me | Me | F | i-Bu | 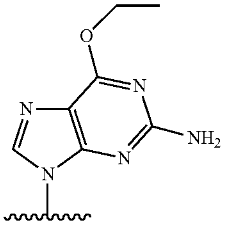 [SMILES: *n1cnc2c(OCC)nc(N)nc21] |

TABLE 2-continued
(IV-1)
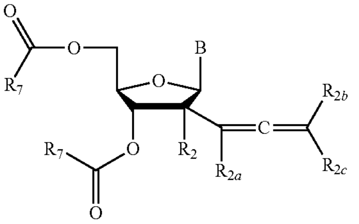
| Compound # | $R_{2a}$ | $R_{2b}$ | $R_{2c}$ | $R_2$ | $R_7$ | B |
|---|---|---|---|---|---|---|
| 221 | H | F | F | OH | i-Bu | 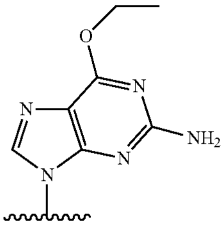 [SMILES: *n1cnc2c(OCC)nc(N)nc21] |
| 222 | H | F | F | F | i-Bu | 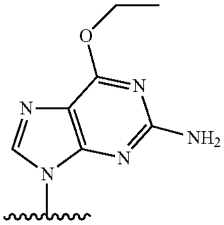 [SMILES: *n1cnc2c(OCC)nc(N)nc21] |
| 223 | H | H | H | OH | i-Bu | 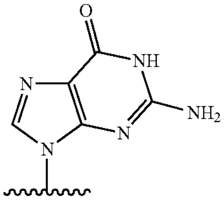 [SMILES: *n1cnc2c(=O)[nH]c(N)nc21] |
| 224 | H | H | H | F | i-Bu | 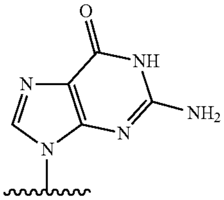 [SMILES: *n1cnc2c(=O)[nH]c(N)nc21] |
| 225 | H | Me | Me | OH | i-Bu | 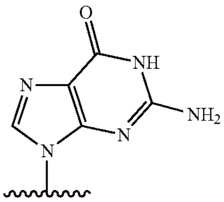 [SMILES: *n1cnc2c(=O)[nH]c(N)nc21] |
| 226 | H | Me | Me | F | i-Bu | 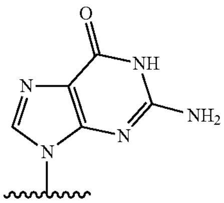 [SMILES: *n1cnc2c(=O)[nH]c(N)nc21] |
TABLE 2-continued
(IV-1)
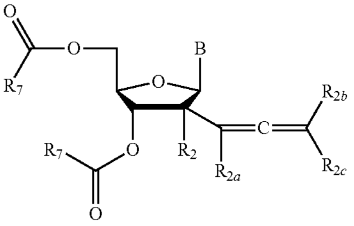
| Compound # | $R_{2a}$ | $R_{2b}$ | $R_{2c}$ | $R_2$ | $R_7$ | B |
|---|---|---|---|---|---|---|
| 227 | H | F | F | OH | i-Bu | 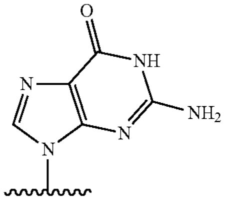 [SMILES: *n1cnc2c(=O)[nH]c(N)nc21] |
| 228 | H | F | F | F | i-Bu | 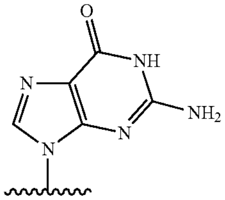 [SMILES: *n1cnc2c(=O)[nH]c(N)nc21] |
| 229 | H | H | H | OH | i-Bu | 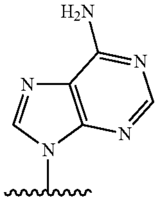 [SMILES: *n1cnc2c(N)ncnc21] |
| 230 | H | H | H | F | i-Bu | 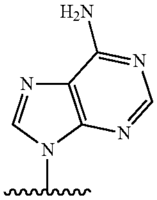 |
| 231 | H | Me | Me | OH | i-Bu | 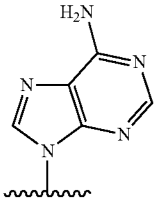 |
| 232 | H | Me | Me | F | i-Bu | 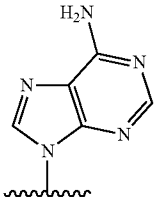 [SMILES: *n1cnc2c(N)ncnc21] |

TABLE 2-continued
(IV-1)
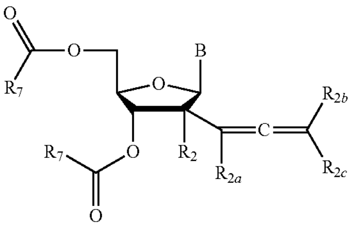
| Compound # | $R_{2a}$ | $R_{2b}$ | $R_{2c}$ | $R_2$ | $R_7$ | B |
|---|---|---|---|---|---|---|
| 233 | H | F | F | OH | i-Bu | 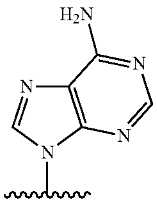 |
| 234 | H | F | F | F | i-Bu | 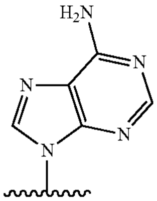 [SMILES: *n1cnc2c(N)ncnc21] |
| 235 | H | H | H | OH | i-Bu | 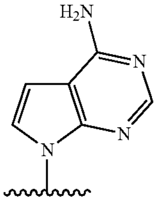 [SMILES: *n1ccc2c(N)ncnc21] |
| 236 | H | H | H | F | i-Bu | 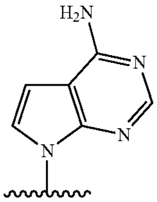 [SMILES: *n1ccc2c(N)ncnc21] |
| 237 | H | Me | Me | OH | i-Bu | 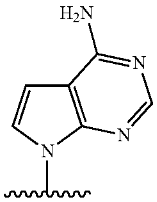 [SMILES: *n1ccc2c(N)ncnc21] |
| 238 | H | Me | Me | F | i-Bu | 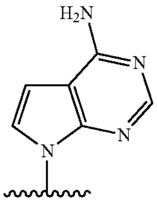 [SMILES: *n1ccc2c(N)ncnc21] |
TABLE 2-continued
(IV-1)
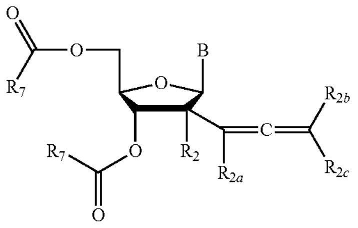
| Compound # | $R_{2a}$ | $R_{2b}$ | $R_{2c}$ | $R_2$ | $R_7$ | B |
|---|---|---|---|---|---|---|
| 239 | H | F | F | OH | i-Bu | 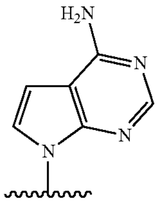 [SMILES: *n1ccc2c(N)ncnc21] |
| 240 | H | F | F | F | i-Bu | 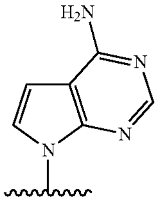 [SMILES: *n1ccc2c(N)ncnc21] |
(c) compounds represented by Formula (V-1) wherein $R_2$, $R_9$, $R_{12}$, $R_{13}$, and B are delineated for each compound in Table 3
TABLE 3
(V-1)
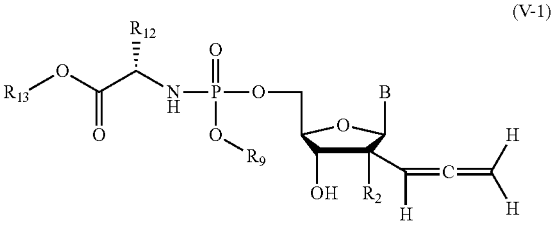
| Compound # | $R_2$ | $R_9$ | $R_{12}$ | $R_{13}$ | B |
|---|---|---|---|---|---|
| 241 | OH | Ph | Me | Me | 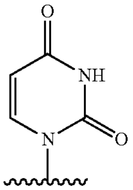 |
| 242 | F | Ph | Me | Me | 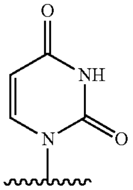 |

TABLE 3-continued
(V-1)
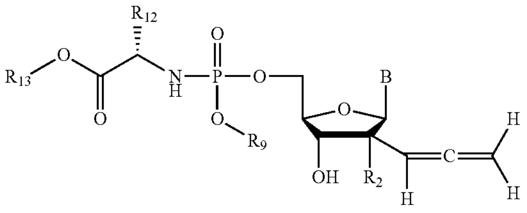
| Compound # | $R_2$ | $R_9$ | $R_{12}$ | $R_{13}$ | B |
|---|---|---|---|---|---|
| 243 | OH | Ph | Me | Me | 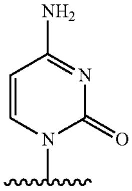 [SMILES: *n1ccc(N)nc1=O] |
| 244 | F | Ph | Me | Me | 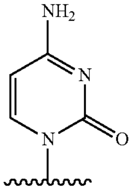 [SMILES: *n1ccc(N)nc1=O] |
| 245 | OH | Ph | Me | Me | 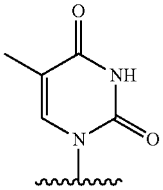 |
| 246 | F | Ph | Me | Me | 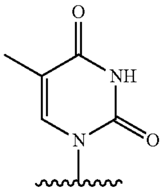 [SMILES: *n1cc(C)c(=O)[nH]c1=O] |
| 247 | OH | Ph | Me | Me | 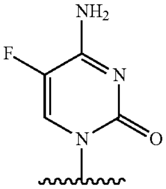 |
| 248 | F | Ph | Me | Me | 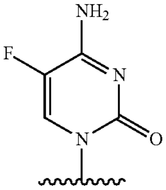 |
TABLE 3-continued
(V-1)
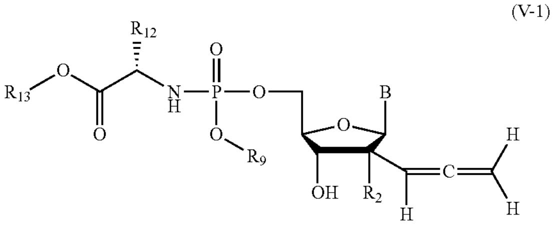
| Compound # | $R_2$ | $R_9$ | $R_{12}$ | $R_{13}$ | B |
|---|---|---|---|---|---|
| 249 | OH | Ph | Me | Me | 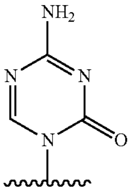 [SMILES: *n1cnc(N)nc1=O] |
| 250 | F | Ph | Me | Me | 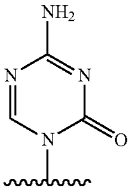 [SMILES: *n1cnc(N)nc1=O] |
| 251 | OH | Ph | Me | Me | 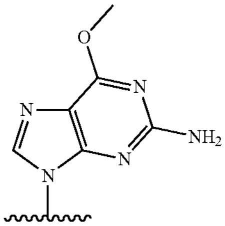 [SMILES: *n1cnc2c(OC)nc(N)nc21] |
| 252 | F | Ph | Me | Me | 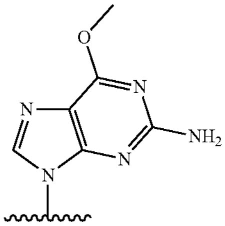 [SMILES: *n1cnc2c(OC)nc(N)nc21] |
| 253 | OH | Ph | Me | Me | 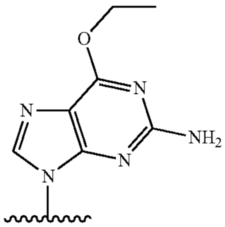 [SMILES: *n1cnc2c(OCC)nc(N)nc21] |
| 254 | F | Ph | Me | Me | 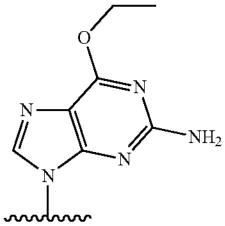 [SMILES: *n1cnc2c(OCC)nc(N)nc21] |

TABLE 3-continued
(V-1)
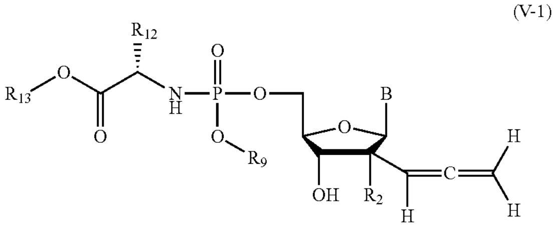
| Compound # | $R_2$ | $R_9$ | $R_{12}$ | $R_{13}$ | B |
|---|---|---|---|---|---|
| 255 | OH | Ph | Me | Me | 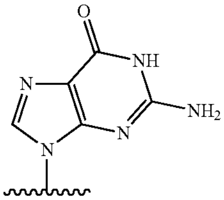 [SMILES: *n1cnc2c(=O)[nH]c(N)nc21] |
| 256 | F | Ph | Me | Me | 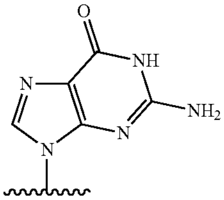 [SMILES: *n1cnc2c(=O)[nH]c(N)nc21] |
| 257 | OH | Ph | Me | Me | 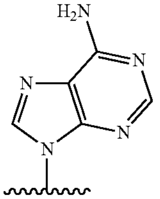 |
| 258 | F | Ph | Me | Me | 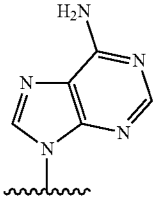 [SMILES: *n1cnc2c(N)ncnc21] |
| 259 | OH | Ph | Me | Me | 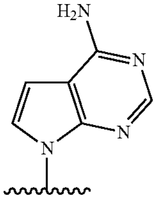 |
| 260 | F | Ph | Me | Me | 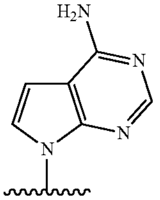 |
TABLE 3-continued
(V-1)
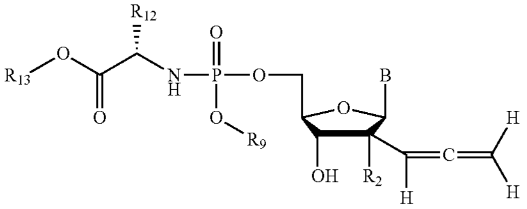
| Compound # | $R_2$ | $R_9$ | $R_{12}$ | $R_{13}$ | B |
|---|---|---|---|---|---|
| 261 | OH | 1-Naphthyl | Me | Me | 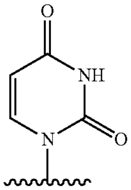 |
| 262 | F | 1-Naphthyl | Me | Me | 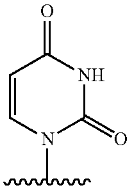 |
| 263 | OH | 1-Naphthyl | Me | Me | 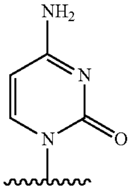 |
| 264 | F | 1-Naphthyl | Me | Me | 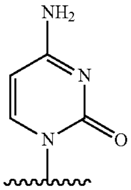 |
| 265 | OH | 1-Naphthyl | Me | Me | 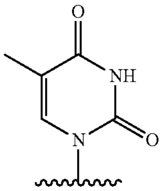 [SMILES: *n1cc(C)c(=O)[nH]c1=O] |
| 266 | F | 1-Naphthyl | Me | Me | 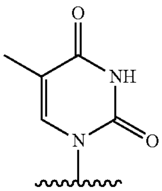 [SMILES: *n1cc(C)c(=O)[nH]c1=O] |

TABLE 3-continued
(V-1)
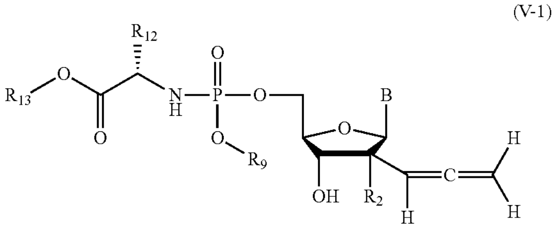
| Compound # | $R_2$ | $R_9$ | $R_{12}$ | $R_{13}$ | B |
|---|---|---|---|---|---|
| 267 | OH | 1-Naphthyl | Me | Me | 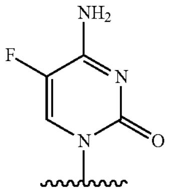 |
| 268 | F | 1-Naphthyl | Me | Me | 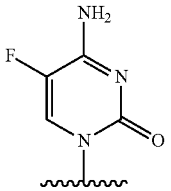 |
| 269 | OH | 1-Naphthyl | Me | Me | 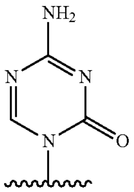 [SMILES: *n1cnc(N)nc1=O] |
| 270 | F | 1-Naphthyl | Me | Me | 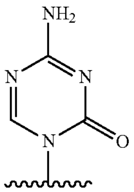 [SMILES: *n1cnc(N)nc1=O] |
| 271 | OH | 1-Naphthyl | Me | Me | 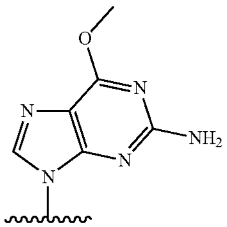 [SMILES: *n1cnc2c(OC)nc(N)nc21] |
| 272 | F | 1-Naphthyl | Me | Me | 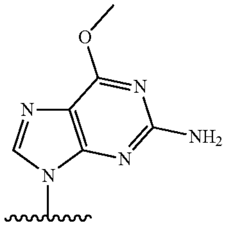 [SMILES: *n1cnc2c(OC)nc(N)nc21] |
TABLE 3-continued
(V-1)
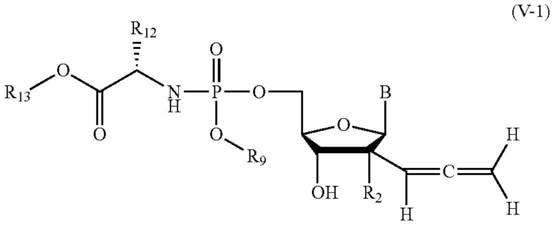
| Compound # | $R_2$ | $R_9$ | $R_{12}$ | $R_{13}$ | B |
|---|---|---|---|---|---|
| 273 | OH | 1-Naphthyl | Me | Me | 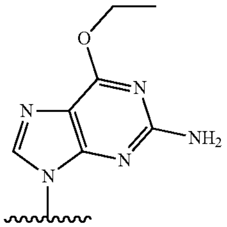 [SMILES: *n1cnc2c(OCC)nc(N)nc21] |
| 274 | F | 1-Naphthyl | Me | Me | 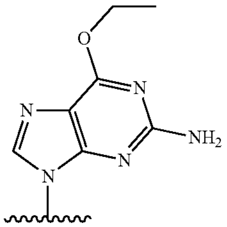 [SMILES: *n1cnc2c(OCC)nc(N)nc21] |
| 275 | OH | 1-Naphthyl | Me | Me | 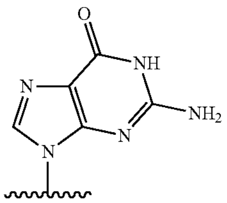 [SMILES: *n1cnc2c(=O)[nH]c(N)nc21] |
| 276 | F | 1-Naphthyl | Me | Me | 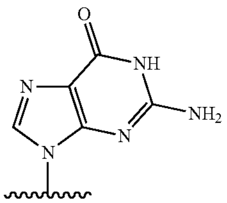 [SMILES: *n1cnc2c(=O)[nH]c(N)nc21] |
| 277 | OH | 1-Naphthyl | Me | Me | 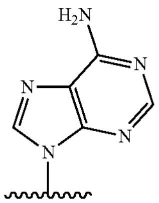 |
| 278 | F | 1-Naphthyl | Me | Me | 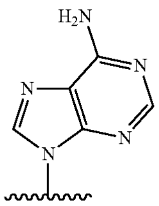 |

TABLE 3-continued
(V-1)
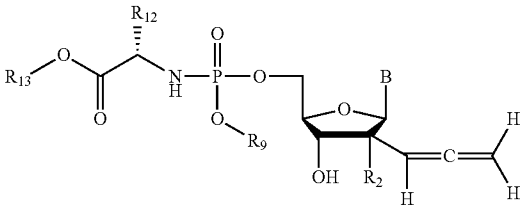
| Compound # | $R_2$ | $R_9$ | $R_{12}$ | $R_{13}$ | B |
|---|---|---|---|---|---|
| 279 | OH | 1-Naphthyl | Me | Me | 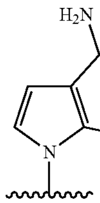 |
| 280 | F | 1-Naphthyl | Me | Me | 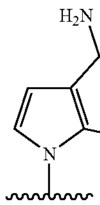 |
| 281 | OH | Ph | H | Me | 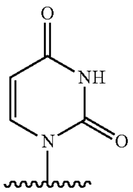 [SMILES: *n1ccc(=O)[nH]c1=O] |
| 282 | F | Ph | H | Me | 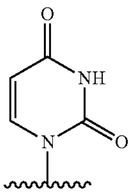 [SMILES: *n1ccc(=O)[nH]c1=O] |
| 283 | OH | Ph | H | Me | 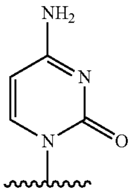 |
| 284 | F | Ph | H | Me | 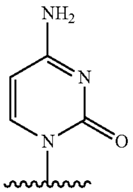 [SMILES: *n1ccc(N)nc1=O] |
TABLE 3-continued
(V-1)
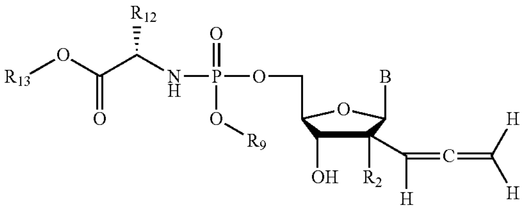
| Compound # | $R_2$ | $R_9$ | $R_{12}$ | $R_{13}$ | B |
|---|---|---|---|---|---|
| 285 | OH | Ph | H | Me | 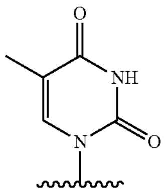 [SMILES: *n1cc(C)c(=O)[nH]c1=O] |
| 286 | F | Ph | H | Me | 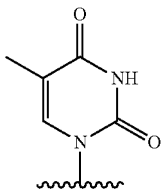 [SMILES: *n1cc(C)c(=O)[nH]c1=O] |
| 287 | OH | Ph | H | Me | 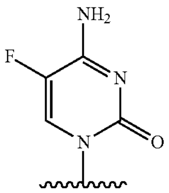 |
| 288 | F | Ph | H | Me | 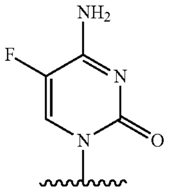 |
| 289 | OH | Ph | H | Me | 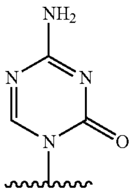 [SMILES: *n1cnc(N)nc1=O] |
| 290 | F | Ph | H | Me | 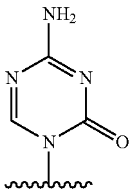 [SMILES: *n1cnc(N)nc1=O] |

TABLE 3-continued
(V-1)
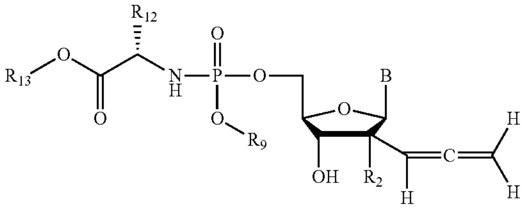
| Compound # | $R_2$ | $R_9$ | $R_{12}$ | $R_{13}$ | B |
|---|---|---|---|---|---|
| 291 | OH | Ph | H | Me | 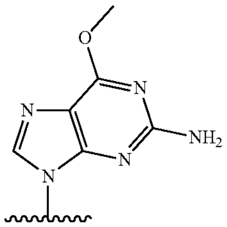 [SMILES: *n1cnc2c(OC)nc(N)nc21] |
| 292 | F | Ph | H | Me | 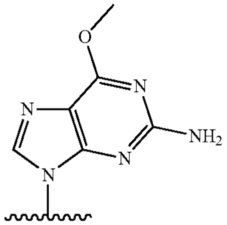 [SMILES: *n1cnc2c(OC)nc(N)nc21] |
| 293 | OH | Ph | H | Me | 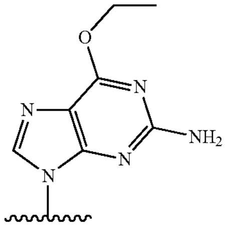 [SMILES: *n1cnc2c(OCC)nc(N)nc21] |
| 294 | F | Ph | H | Me | 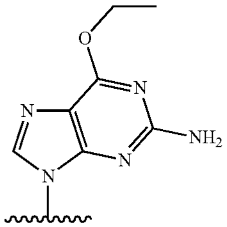 [SMILES: *n1cnc2c(OCC)nc(N)nc21] |
| 295 | OH | Ph | H | Me | 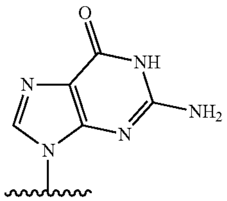 [SMILES: *n1cnc2c(=O)[nH]c(N)nc21] |
TABLE 3-continued
(V-1)
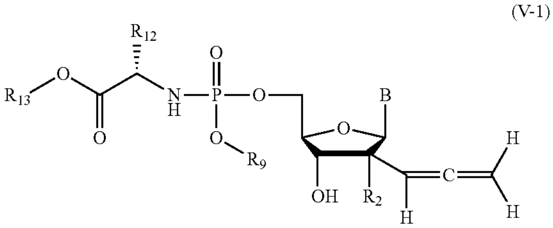
| Compound # | $R_2$ | $R_9$ | $R_{12}$ | $R_{13}$ | B |
|---|---|---|---|---|---|
| 296 | F | Ph | H | Me | 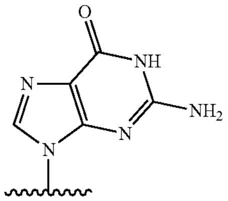 [SMILES: *n1cnc2c(=O)[nH]c(N)nc21] |
| 297 | OH | Ph | H | Me | 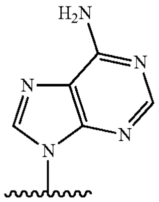 |
| 298 | F | Ph | H | Me | 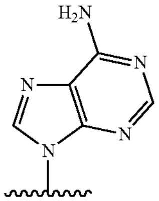 |
| 299 | OH | Ph | H | Me | 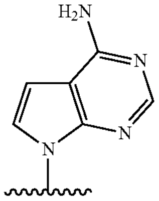 |
| 300 | F | Ph | H | Me | 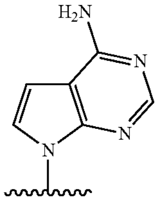 |
| 301 | OH | 1-Naphthyl | H | Me | 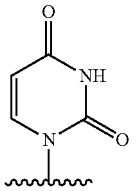 |

TABLE 3-continued
(V-1)
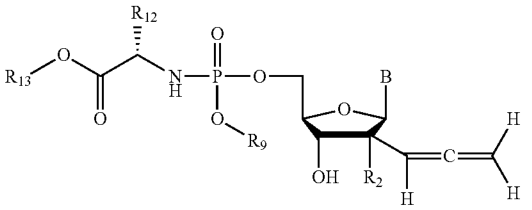
| Compound # | $R_2$ | $R_9$ | $R_{12}$ | $R_{13}$ | B |
|---|---|---|---|---|---|
| 302 | F | 1-Naphthyl | H | Me | 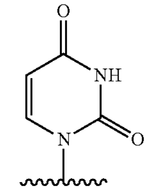 [SMILES: *n1ccc(=O)[nH]c1=O] |
| 303 | OH | 1-Naphthyl | H | Me | 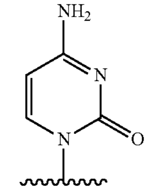 [SMILES: *n1ccc(N)nc1=O] |
| 304 | F | 1-Naphthyl | H | Me | 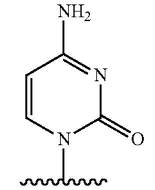 [SMILES: *n1ccc(N)nc1=O] |
| 305 | OH | 1-Naphthyl | H | Me | 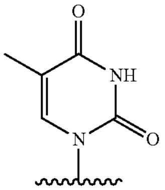 |
| 306 | F | 1-Naphthyl | H | Me | 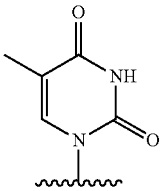 [SMILES: *n1cc(C)c(=O)[nH]c1=O] |
| 307 | OH | 1-Naphthyl | H | Me | 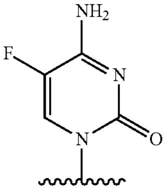 |
TABLE 3-continued
(V-1)
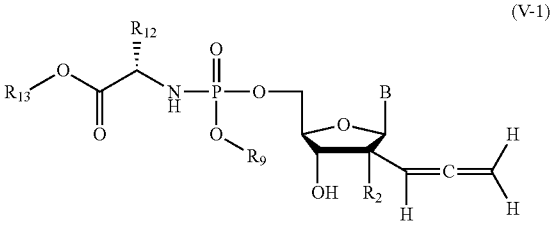
| Compound # | $R_2$ | $R_9$ | $R_{12}$ | $R_{13}$ | B |
|---|---|---|---|---|---|
| 308 | F | 1-Naphthyl | H | Me | 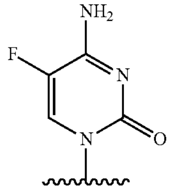 |
| 309 | OH | 1-Naphthyl | H | Me | 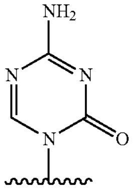 [SMILES: *n1cnc(N)nc1=O] |
| 310 | F | 1-Naphthyl | H | Me | 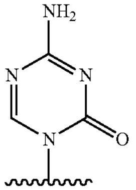 [SMILES: *n1cnc(N)nc1=O] |
| 311 | OH | 1-Naphthyl | H | Me | 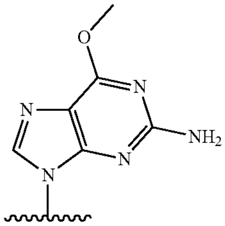 [SMILES: *n1cnc2c(OC)nc(N)nc21] |
| 312 | F | 1-Naphthyl | H | Me | 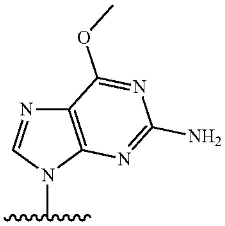 [SMILES: *n1cnc2c(OC)nc(N)nc21] |
| 313 | OH | 1-Naphthyl | H | Me | 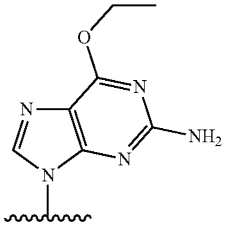 [SMILES: *n1cnc2c(OCC)nc(N)nc21] |

TABLE 3-continued
(V-1)
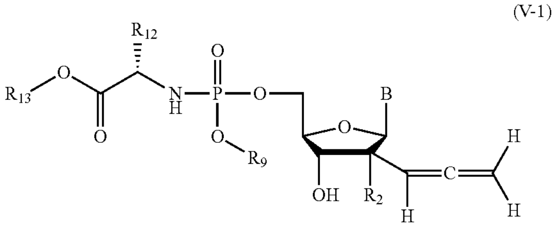
| Compound # | $R_2$ | $R_9$ | $R_{12}$ | $R_{13}$ | B |
|---|---|---|---|---|---|
| 314 | F | 1-Naphthyl | H | Me | 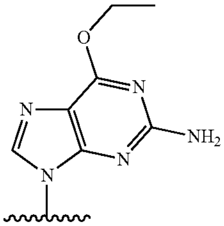 [SMILES: *n1cnc2c(OCC)nc(N)nc21] |
| 315 | OH | 1-Naphthyl | H | Me | 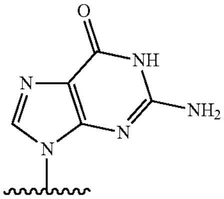 [SMILES: *n1cnc2c(=O)[nH]c(N)nc21] |
| 316 | F | 1-Naphthyl | H | Me | 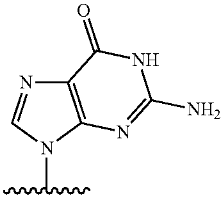 [SMILES: *n1cnc2c(=O)[nH]c(N)nc21] |
| 317 | OH | 1-Naphthyl | H | Me | 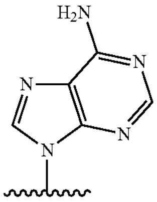 [SMILES: *n1cnc2c(N)ncnc21] |
| 318 | F | 1-Naphthyl | H | Me | 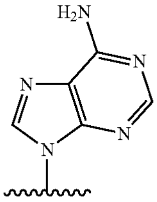 |
| 319 | OH | 1-Naphthyl | H | Me | 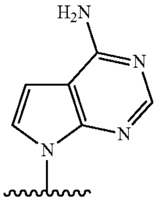 |
TABLE 3-continued
(V-1)
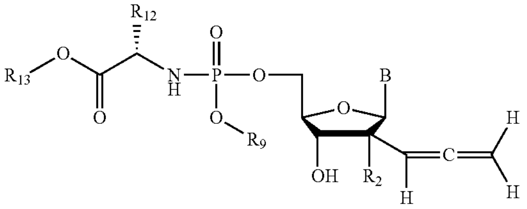
| Compound # | $R_2$ | $R_9$ | $R_{12}$ | $R_{13}$ | B |
|---|---|---|---|---|---|
| 320 | F | 1-Naphthyl | H | Me | 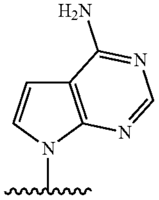 |
| 321 | OH | Ph | Me | n-Pentyl | 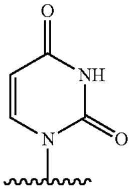 |
| 322 | F | Ph | Me | n-Pentyl | 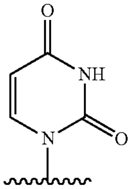 |
| 323 | OH | Ph | Me | n-Pentyl | 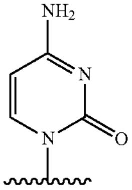 |
| 324 | F | Ph | Me | n-Pentyl | 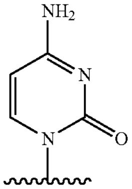 |
| 325 | OH | Ph | Me | n-Pentyl | 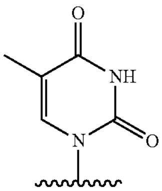 [SMILES: *n1cc(C)c(=O)[nH]c1=O] |

TABLE 3-continued
(V-1)
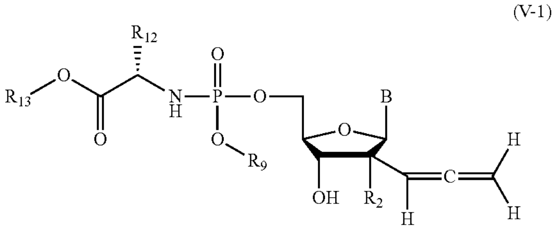
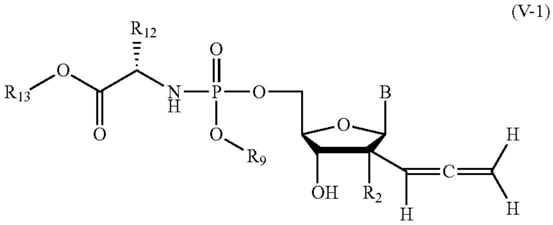
| Compound # | $R_2$ | $R_9$ | $R_{12}$ | $R_{13}$ | B |
|---|---|---|---|---|---|
| 326 | F | Ph | Me | n-Pentyl | 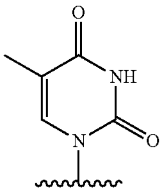 |
| 327 | OH | Ph | Me | n-Pentyl | 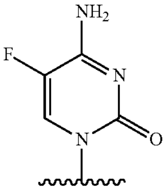 |
| 328 | F | Ph | Me | n-Pentyl | 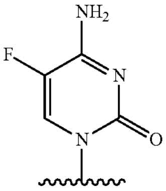 |
| 329 | OH | Ph | Me | n-Pentyl | 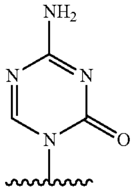 [SMILES: *n1cnc(N)nc1=O] |
| 330 | F | Ph | Me | n-Pentyl | 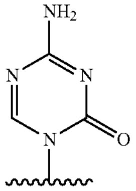 [SMILES: *n1cnc(N)nc1=O] |
| 331 | OH | Ph | Me | n-Pentyl | 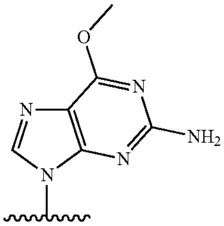 [SMILES: *n1cnc2c(OC)nc(N)nc21] |
| 332 | F | Ph | Me | n-Pentyl | 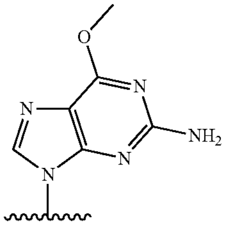 [SMILES: *n1cnc2c(OC)nc(N)nc21] |
| 333 | OH | Ph | Me | n-Pentyl | 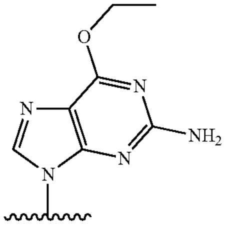 [SMILES: *n1cnc2c(OCC)nc(N)nc21] |
| 334 | F | Ph | Me | n-Pentyl | 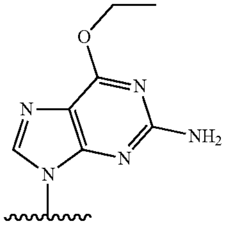 [SMILES: *n1cnc2c(OCC)nc(N)nc21] |
| 335 | OH | Ph | Me | n-Pentyl | 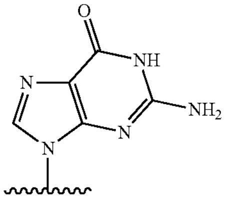 [SMILES: *n1cnc2c(=O)[nH]c(N)nc21] |
| 336 | F | Ph | Me | n-Pentyl | 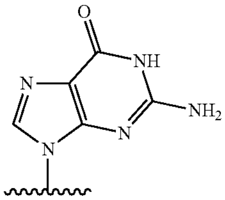 [SMILES: *n1cnc2c(=O)[nH]c(N)nc21] |
| 337 | OH | Ph | Me | n-Pentyl | 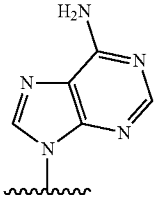 |

TABLE 3-continued
(V-1)
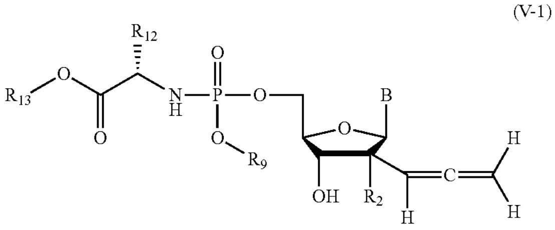
| Compound # | $R_2$ | $R_9$ | $R_{12}$ | $R_{13}$ | B |
|---|---|---|---|---|---|
| 338 | F | Ph | Me | n-Pentyl | 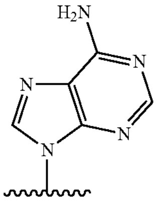 |
| 339 | OH | Ph | Me | n-Pentyl | 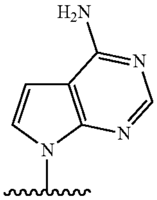 [SMILES: *n1ccc2c(N)ncnc21] |
| 340 | F | Ph | Me | n-Pentyl | 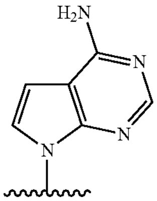 |
| 341 | OH | 1-Naphthyl | Me | n-Pentyl | 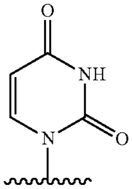 [SMILES: *n1ccc(=O)[nH]c1=O] |
| 342 | F | 1-Naphthyl | Me | n-Pentyl | 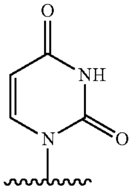 [SMILES: *n1ccc(=O)[nH]c1=O] |
| 343 | OH | 1-Naphthyl | Me | n-Pentyl | 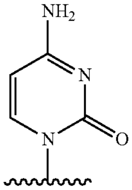 |
TABLE 3-continued
(V-1)
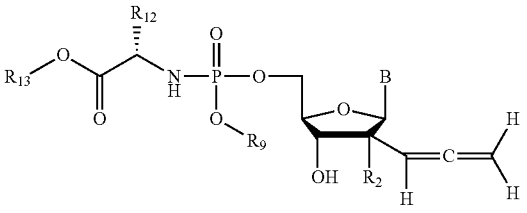
| Compound # | $R_2$ | $R_9$ | $R_{12}$ | $R_{13}$ | B |
|---|---|---|---|---|---|
| 344 | F | 1-Naphthyl | Me | n-Pentyl | 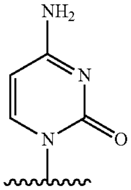 |
| 345 | OH | 1-Naphthyl | Me | n-Pentyl | 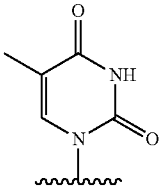 [SMILES: *n1cc(C)c(=O)[nH]c1=O] |
| 346 | F | 1-Naphthyl | Me | n-Pentyl | 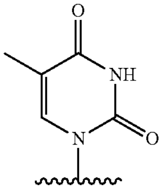 [SMILES: *n1cc(C)c(=O)[nH]c1=O] |
| 347 | OH | 1-Naphthyl | Me | n-Pentyl | 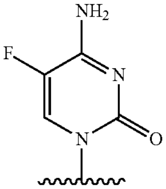 |
| 348 | F | 1-Naphthyl | Me | n-Pentyl | 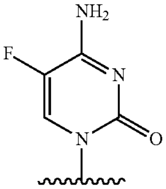 |
| 349 | OH | 1-Naphthyl | Me | n-Pentyl | 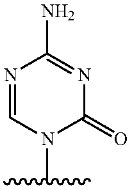 [SMILES: *n1cnc(N)nc1=O] |

TABLE 3-continued
(V-1)
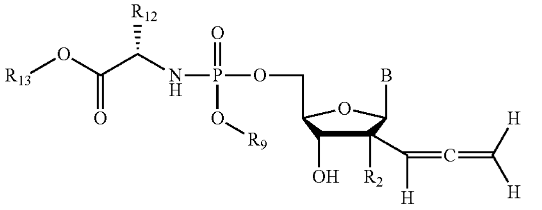
| Compound # | $R_2$ | $R_9$ | $R_{12}$ | $R_{13}$ | B |
|---|---|---|---|---|---|
| 350 | F | 1-Naphthyl | Me | n-Pentyl | 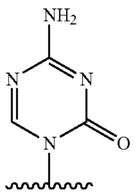 [SMILES: *n1cnc(N)nc1=O] |
| 351 | OH | 1-Naphthyl | Me | n-Pentyl | 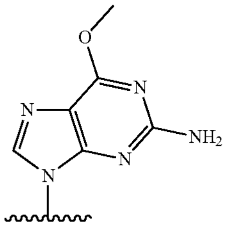 [SMILES: *n1cnc2c(OC)nc(N)nc21] |
| 352 | F | 1-Naphthyl | Me | n-Pentyl | 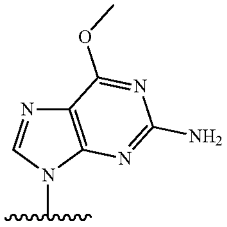 [SMILES: *n1cnc2c(OC)nc(N)nc21] |
| 353 | OH | 1-Naphthyl | Me | n-Pentyl | 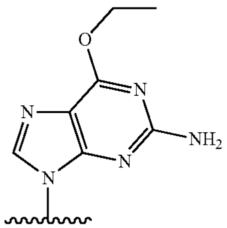 [SMILES: *n1cnc2c(OCC)nc(N)nc21] |
| 354 | F | 1-Naphthyl | Me | n-Pentyl | 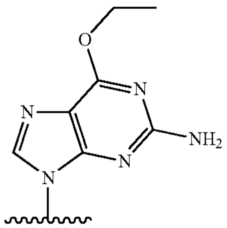 [SMILES: *n1cnc2c(OCC)nc(N)nc21] |
TABLE 3-continued
(V-1)
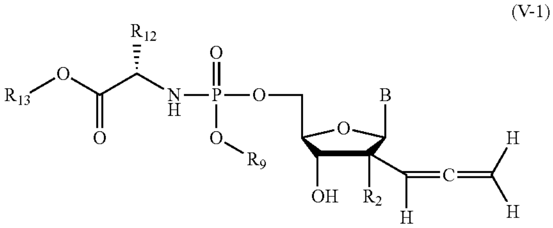
| Compound # | $R_2$ | $R_9$ | $R_{12}$ | $R_{13}$ | B |
|---|---|---|---|---|---|
| 355 | OH | 1-Naphthyl | Me | n-Pentyl | 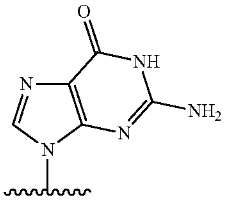 [SMILES: *n1cnc2c(=O)[nH]c(N)nc21] |
| 356 | F | 1-Naphthyl | Me | n-Pentyl | 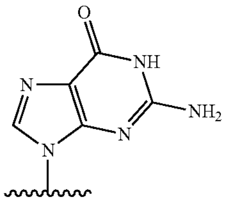 [SMILES: *n1cnc2c(=O)[nH]c(N)nc21] |
| 357 | OH | 1-Naphthyl | Me | n-Pentyl | 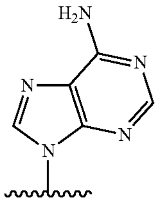 |
| 358 | F | 1-Naphthyl | Me | n-Pentyl | 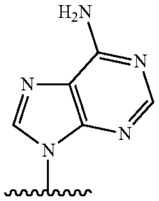 |
| 359 | OH | 1-Naphthyl | Me | n-Pentyl | 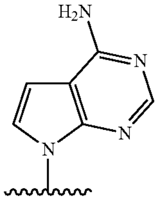 |
| 360 | F | 1-Naphthyl | Me | n-Pentyl | 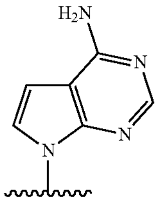 |

TABLE 3-continued
(V-1)
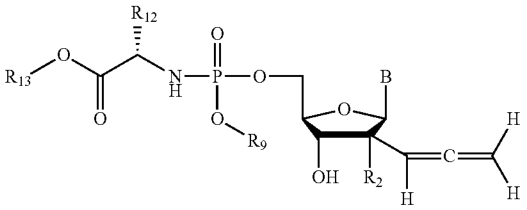
| Compound # | $R_2$ | $R_9$ | $R_{12}$ | $R_{13}$ | B |
|---|---|---|---|---|---|
| 361 | OH | Ph | H | n-Pentyl | 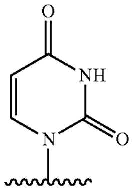 [SMILES: *n1ccc(=O)[nH]c1=O] |
| 362 | F | Ph | H | n-Pentyl | 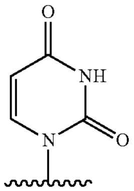 [SMILES: *n1ccc(=O)[nH]c1=O] |
| 363 | OH | Ph | H | n-Pentyl | 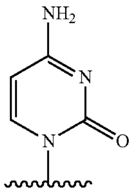 [SMILES: *n1ccc(N)nc1=O] |
| 364 | F | Ph | H | n-Pentyl | 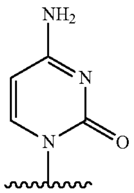 [SMILES: *n1ccc(N)nc1=O] |
| 365 | OH | Ph | H | n-Pentyl | 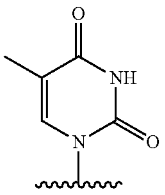 [SMILES: *n1cc(C)c(=O)[nH]c1=O] |
| 366 | F | Ph | H | n-Pentyl | 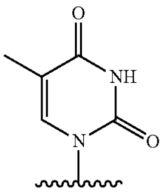 |
TABLE 3-continued
(V-1)
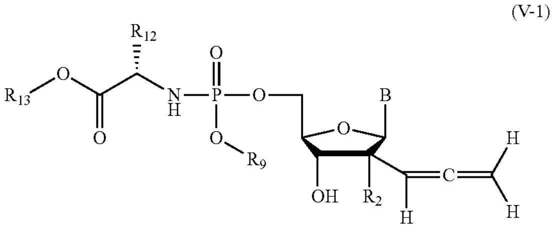
| Compound # | $R_2$ | $R_9$ | $R_{12}$ | $R_{13}$ | B |
|---|---|---|---|---|---|
| 367 | OH | Ph | H | n-Pentyl | 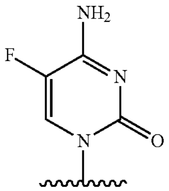 |
| 368 | F | Ph | H | n-Pentyl | 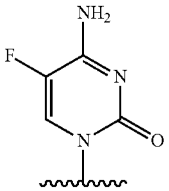 |
| 369 | OH | Ph | H | n-Pentyl | 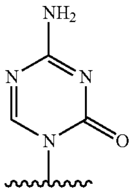 [SMILES: *n1cnc(N)nc1=O] |
| 370 | F | Ph | H | n-Pentyl | 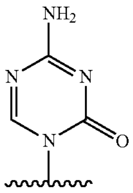 [SMILES: *n1cnc(N)nc1=O] |
| 371 | OH | Ph | H | n-Pentyl | 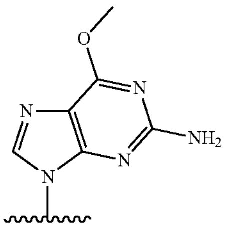 [SMILES: *n1cnc2c(OC)nc(N)nc21] |
| 372 | F | Ph | H | n-Pentyl | 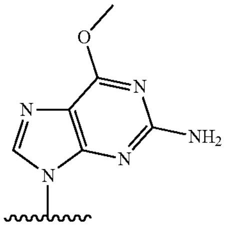 [SMILES: *n1cnc2c(OC)nc(N)nc21] |

TABLE 3-continued
(V-1)
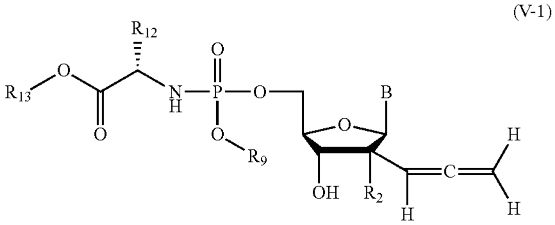
| Compound # | $R_2$ | $R_9$ | $R_{12}$ | $R_{13}$ | B |
|---|---|---|---|---|---|
| 373 | OH | Ph | H | n-Pentyl | 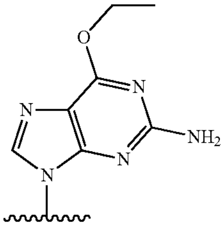 [SMILES: *n1cnc2c(OCC)nc(N)nc21] |
| 374 | F | Ph | H | n-Pentyl | 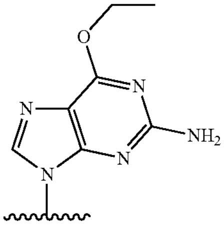 [SMILES: *n1cnc2c(OCC)nc(N)nc21] |
| 375 | OH | Ph | H | n-Pentyl | 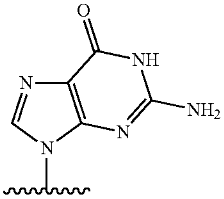 [SMILES: *n1cnc2c(=O)[nH]c(N)nc21] |
| 376 | F | Ph | H | n-Pentyl | 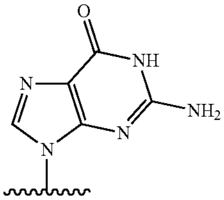 [SMILES: *n1cnc2c(=O)[nH]c(N)nc21] |
| 377 | OH | Ph | H | n-Pentyl | 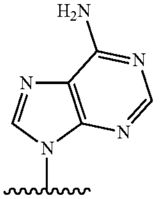 |
| 378 | F | Ph | H | n-Pentyl | 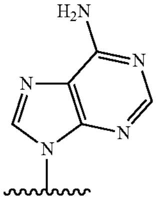 |
TABLE 3-continued
(V-1)
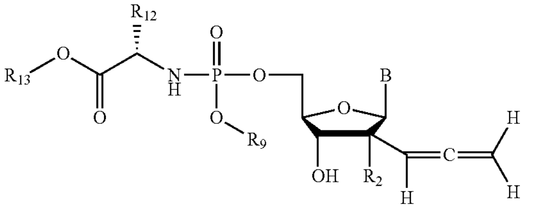
| Compound # | $R_2$ | $R_9$ | $R_{12}$ | $R_{13}$ | B |
|---|---|---|---|---|---|
| 379 | OH | Ph | H | n-Pentyl | 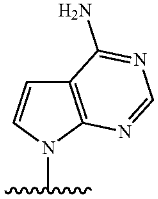 |
| 380 | F | Ph | H | n-Pentyl | 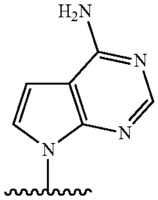 |
| 381 | OH | 1-Naphthyl | H | n-Pentyl | 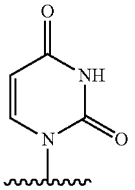 |
| 382 | F | 1-Naphthyl | H | n-Pentyl | 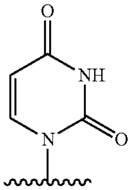 |
| 383 | OH | 1-Naphthyl | H | n-Pentyl | 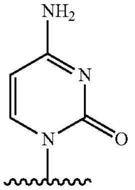 |
| 384 | F | 1-Naphthyl | H | n-Pentyl | 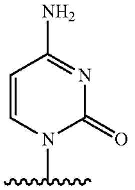 |

TABLE 3-continued
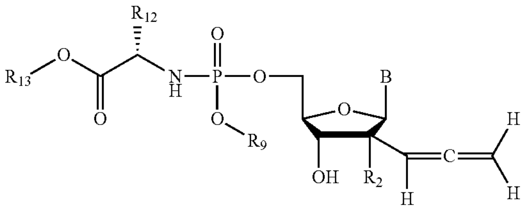
(V-1)
| Compound # | $R_2$ | $R_9$ | $R_{12}$ | $R_{13}$ | B |
|---|---|---|---|---|---|
| 385 | OH | 1-Naphthyl | H | n-Pentyl | 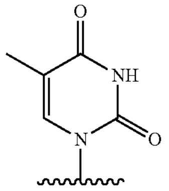 [SMILES: *n1cc(C)c(=O)[nH]c1=O] |
| 386 | F | 1-Naphthyl | H | n-Pentyl | 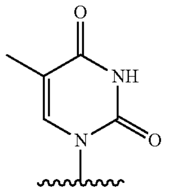 |
| 387 | OH | 1-Naphthyl | H | n-Pentyl | 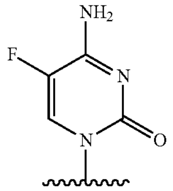 |
| 388 | F | 1-Naphthyl | H | n-Pentyl | 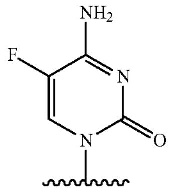 |
| 389 | OH | 1-Naphthyl | H | n-Pentyl | 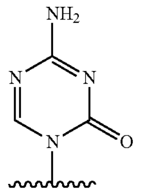 [SMILES: *n1cnc(N)nc1=O] |
| 390 | F | 1-Naphthyl | H | n-Pentyl | 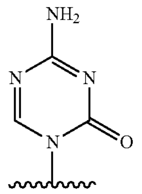 |
TABLE 3-continued
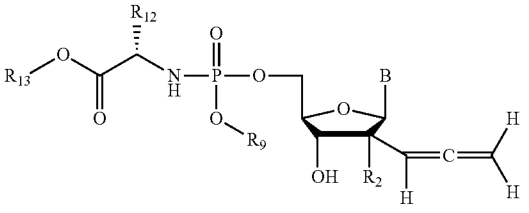
(V-1)
| Compound # | $R_2$ | $R_9$ | $R_{12}$ | $R_{13}$ | B |
|---|---|---|---|---|---|
| 391 | OH | 1-Naphthyl | H | n-Pentyl | 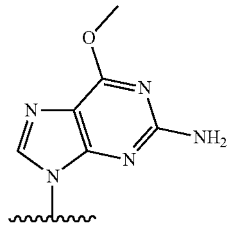 [SMILES: *n1cnc2c(OC)nc(N)nc21] |
| 392 | F | 1-Naphthyl | H | n-Pentyl | 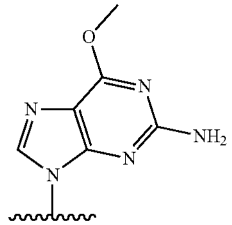 [SMILES: *n1cnc2c(OC)nc(N)nc21] |
| 393 | OH | 1-Naphthyl | H | n-Pentyl | 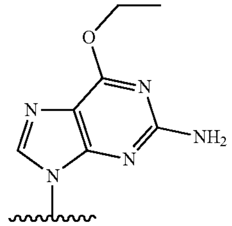 [SMILES: *n1cnc2c(OCC)nc(N)nc21] |
| 394 | F | 1-Naphthyl | H | n-Pentyl | 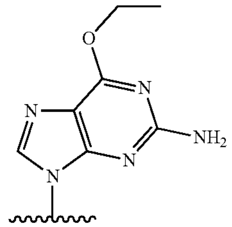 [SMILES: *n1cnc2c(OCC)nc(N)nc21] |
| 395 | OH | 1-Naphthyl | H | n-Pentyl | 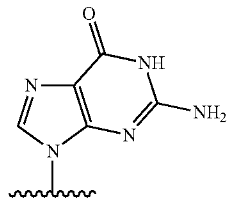 [SMILES: *n1cnc2c(=O)[nH]c(N)nc21] |

TABLE 3-continued
(V-1)
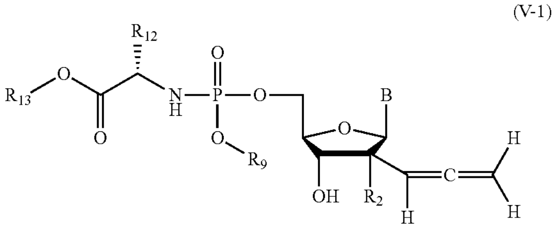
| Compound # | $R_2$ | $R_9$ | $R_{12}$ | $R_{13}$ | B |
|---|---|---|---|---|---|
| 396 | F | 1-Naphthyl | H | n-Pentyl | 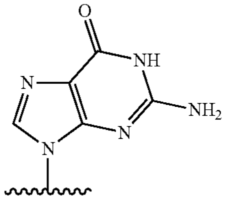 [SMILES: *n1cnc2c(=O)[nH]c(N)nc21] |
| 397 | OH | 1-Naphthyl | H | n-Pentyl | 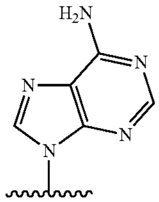 |
| 398 | F | 1-Naphthyl | H | n-Pentyl | 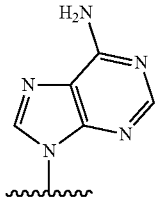 |
| 399 | OH | 1-Naphthyl | H | n-Pentyl | 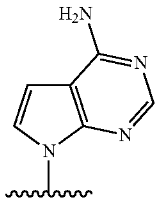 |
| 400 | F | 1-Naphthyl | H | n-Pentyl | 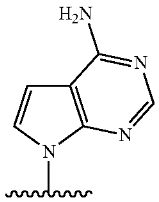 |
| 401 | OH | Ph | Me | i-Pr | 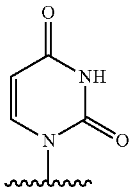 [SMILES: *n1ccc(=O)[nH]c1=O] |
TABLE 3-continued
(V-1)
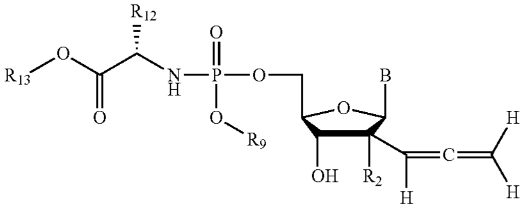
| Compound # | $R_2$ | $R_9$ | $R_{12}$ | $R_{13}$ | B |
|---|---|---|---|---|---|
| 402 | F | Ph | Me | i-Pr | 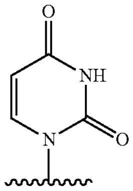 |
| 403 | OH | Ph | Me | i-Pr | 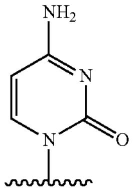 |
| 404 | F | Ph | Me | i-Pr | 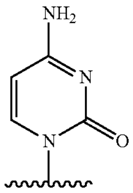 |
| 405 | OH | Ph | Me | i-Pr | 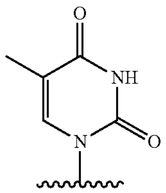 [SMILES: *n1cc(C)c(=O)[nH]c1=O] |
| 406 | F | Ph | Me | i-Pr | 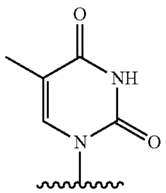 [SMILES: *n1cc(C)c(=O)[nH]c1=O] |
| 407 | OH | Ph | Me | i-Pr | 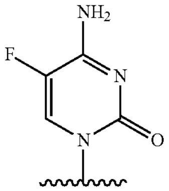 |

TABLE 3-continued
(V-1)
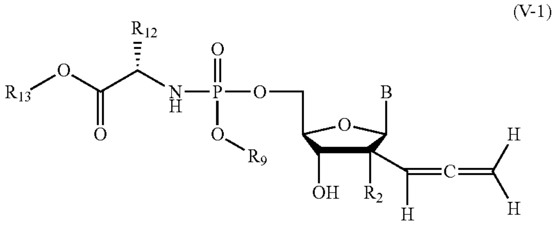
| Compound # | $R_2$ | $R_9$ | $R_{12}$ | $R_{13}$ | B |
|---|---|---|---|---|---|
| 408 | F | Ph | Me | i-Pr | 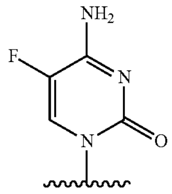 |
| 409 | OH | Ph | Me | i-Pr | 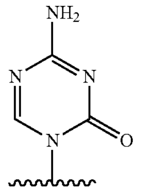 [SMILES: *n1cnc(N)nc1=O] |
| 410 | F | Ph | Me | i-Pr | 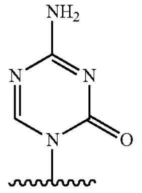 [SMILES: *n1cnc(N)nc1=O] |
| 411 | OH | Ph | Me | i-Pr | 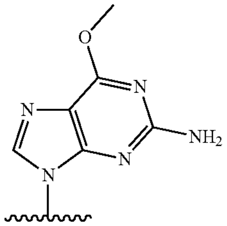 [SMILES: *n1cnc2c(OC)nc(N)nc21] |
| 412 | F | Ph | Me | i-Pr | 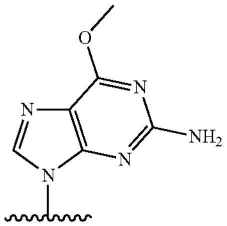 [SMILES: *n1cnc2c(OC)nc(N)nc21] |
| 413 | OH | Ph | Me | i-Pr | 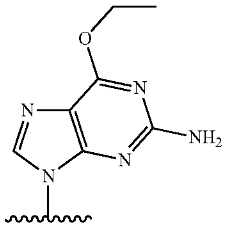 [SMILES: *n1cnc2c(OCC)nc(N)nc21] |
TABLE 3-continued
(V-1)
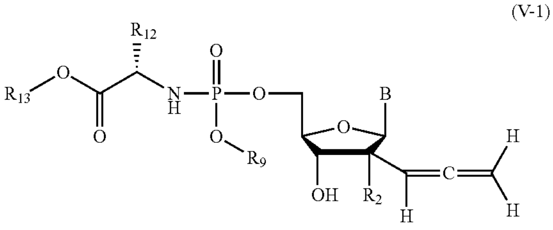
| Compound # | $R_2$ | $R_9$ | $R_{12}$ | $R_{13}$ | B |
|---|---|---|---|---|---|
| 414 | F | Ph | Me | i-Pr | 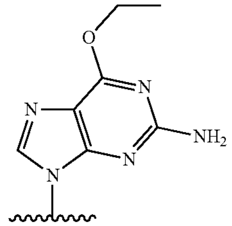 [SMILES: *n1cnc2c(OCC)nc(N)nc21] |
| 415 | OH | Ph | Me | i-Pr | 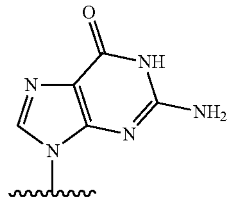 [SMILES: *n1cnc2c(=O)[nH]c(N)nc21] |
| 416 | F | Ph | Me | i-Pr | 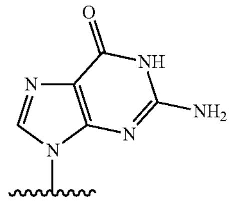 [SMILES: *n1cnc2c(=O)[nH]c(N)nc21] |
| 417 | OH | Ph | Me | i-Pr | 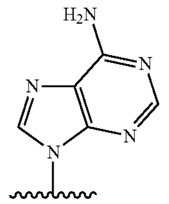 |
| 418 | F | Ph | Me | i-Pr | 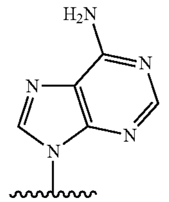 |
| 419 | OH | Ph | Me | i-Pr | 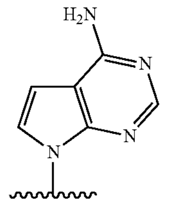 |

TABLE 3-continued
(V-1)
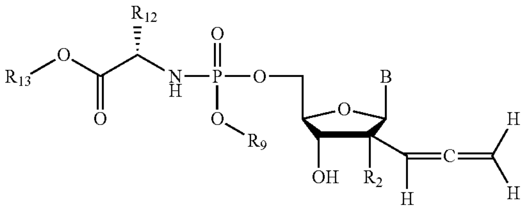
| Compound # | $R_2$ | $R_9$ | $R_{12}$ | $R_{13}$ | B |
|---|---|---|---|---|---|
| 420 | F | Ph | Me | i-Pr | 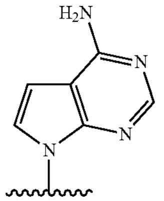 |
| 421 | OH | 1-Naphthyl | Me | i-Pr | 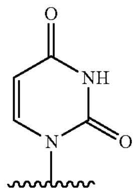 [SMILES: *n1ccc(=O)[nH]c1=O] |
| 422 | F | 1-Naphthyl | Me | i-Pr | 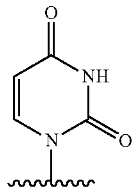 [SMILES: *n1ccc(=O)[nH]c1=O] |
| 423 | OH | 1-Naphthyl | Me | i-Pr | 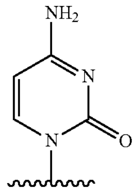 [SMILES: *n1ccc(N)nc1=O] |
| 424 | F | 1-Naphthyl | Me | i-Pr | 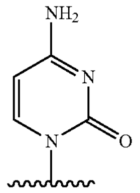 [SMILES: *n1ccc(N)nc1=O] |
| 425 | OH | 1-Naphthyl | Me | i-Pr | 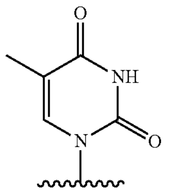 |
TABLE 3-continued
(V-1)
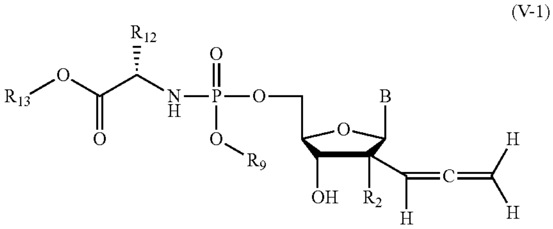
| Compound # | $R_2$ | $R_9$ | $R_{12}$ | $R_{13}$ | B |
|---|---|---|---|---|---|
| 426 | F | 1-Naphthyl | Me | i-Pr | 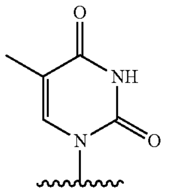 [SMILES: *n1cc(C)c(=O)[nH]c1=O] |
| 427 | OH | 1-Naphthyl | Me | i-Pr | 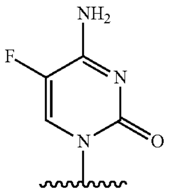 |
| 428 | F | 1-Naphthyl | Me | i-Pr | 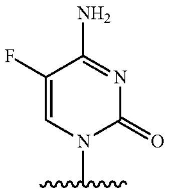 |
| 429 | OH | 1-Naphthyl | Me | i-Pr | 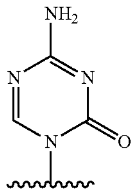 [SMILES: *n1cnc(N)nc1=O] |
| 430 | F | 1-Naphthyl | Me | i-Pr | 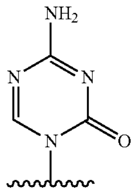 [SMILES: *n1cnc(N)nc1=O] |
| 431 | OH | 1-Naphthyl | Me | i-Pr | 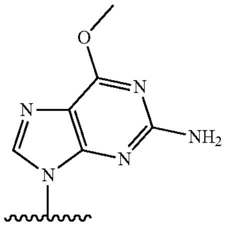 [SMILES: *n1cnc2c(OC)nc(N)nc21] |

TABLE 3-continued
(V-1)
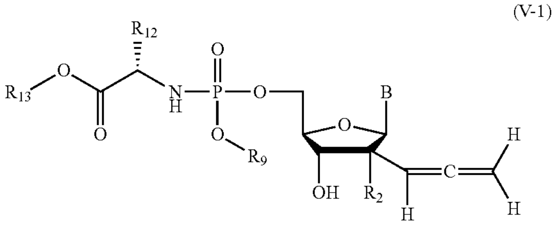
| Compound # | $R_2$ | $R_9$ | $R_{12}$ | $R_{13}$ | B |
|---|---|---|---|---|---|
| 432 | F | 1-Naphthyl | Me | i-Pr | 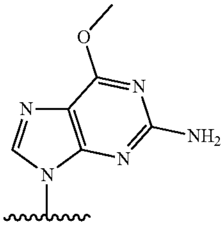 [SMILES: *n1cnc2c(OC)nc(N)nc21] |
| 433 | OH | 1-Naphthyl | Me | i-Pr | 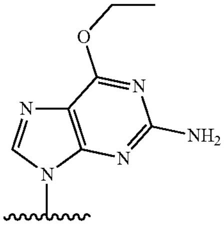 [SMILES: *n1cnc2c(OCC)nc(N)nc21] |
| 434 | F | 1-Naphthyl | Me | i-Pr | 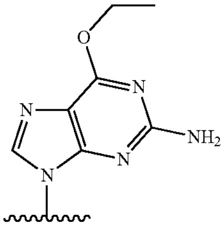 [SMILES: *n1cnc2c(OCC)nc(N)nc21] |
| 435 | OH | 1-Naphthyl | Me | i-Pr | 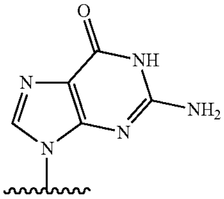 [SMILES: *n1cnc2c(=O)[nH]c(N)nc21] |
| 436 | F | 1-Naphthyl | Me | i-Pr | 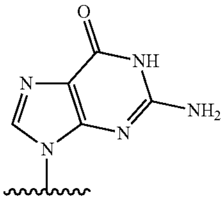 [SMILES: *n1cnc2c(=O)[nH]c(N)nc21] |
| 437 | OH | 1-Naphthyl | Me | i-Pr | 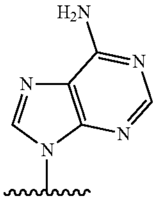 |
TABLE 3-continued
(V-1)
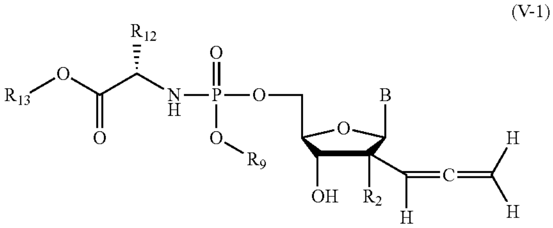
| Compound # | $R_2$ | $R_9$ | $R_{12}$ | $R_{13}$ | B |
|---|---|---|---|---|---|
| 438 | F | 1-Naphthyl | Me | i-Pr | 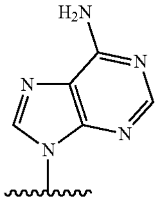 |
| 439 | OH | 1-Naphthyl | Me | i-Pr | 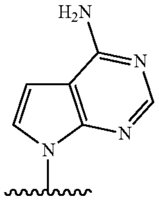 |
| 440 | F | 1-Naphthyl | Me | i-Pr | 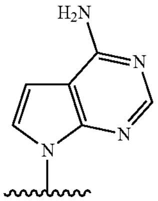 |
| 441 | OH | Ph | H | i-Pr | 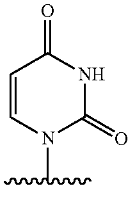 |
| 442 | F | Ph | H | i-Pr | 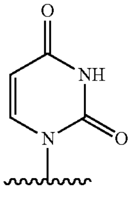 |
| 443 | OH | Ph | H | i-Pr | 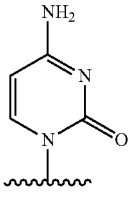 |

TABLE 3-continued
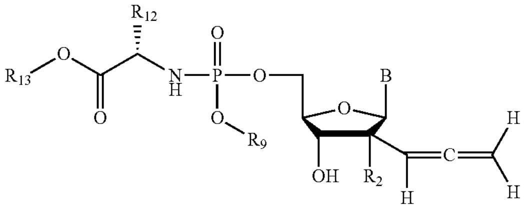
(V-1)
| Compound # | $R_2$ | $R_9$ | $R_{12}$ | $R_{13}$ | B |
|---|---|---|---|---|---|
| 444 | F | Ph | H | i-Pr | 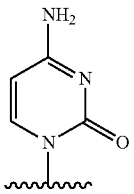 [SMILES: *n1ccc(N)nc1=O] |
| 445 | OH | Ph | H | i-Pr | 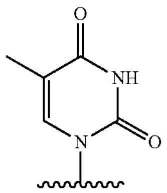 [SMILES: *n1cc(C)c(=O)[nH]c1=O] |
| 446 | F | Ph | H | i-Pr | 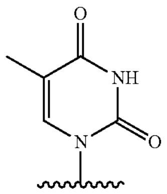 [SMILES: *n1cc(C)c(=O)[nH]c1=O] |
| 447 | OH | Ph | H | i-Pr | 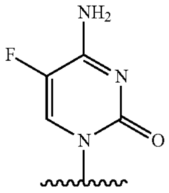 |
| 448 | F | Ph | H | i-Pr | 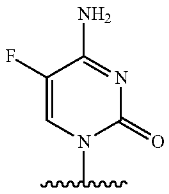 |
| 449 | OH | Ph | H | i-Pr | 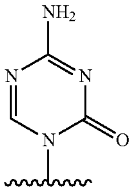 |
TABLE 3-continued
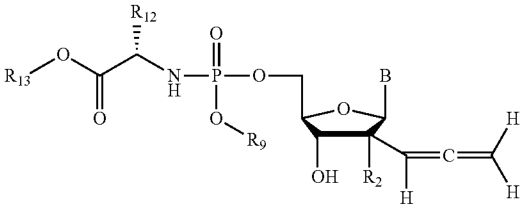
(V-1)
| Compound # | $R_2$ | $R_9$ | $R_{12}$ | $R_{13}$ | B |
|---|---|---|---|---|---|
| 450 | F | Ph | H | i-Pr | 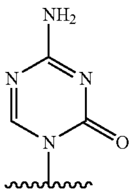 [SMILES: *n1cnc(N)nc1=O] |
| 451 | OH | Ph | H | i-Pr | 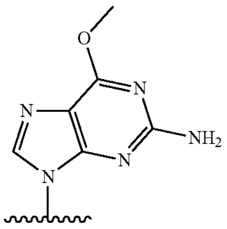 [SMILES: *n1cnc2c(OC)nc(N)nc21] |
| 452 | F | Ph | H | i-Pr | 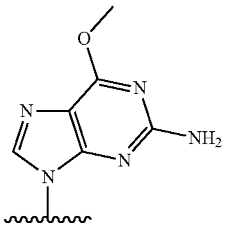 [SMILES: *n1cnc2c(OC)nc(N)nc21] |
| 453 | OH | Ph | H | i-Pr | 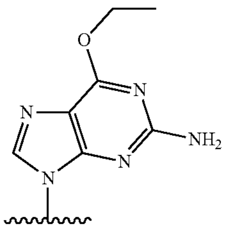 [SMILES: *n1cnc2c(OCC)nc(N)nc21] |
| 454 | F | Ph | H | i-Pr | 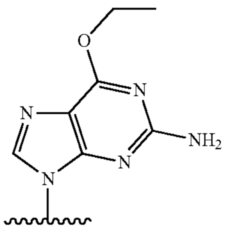 [SMILES: *n1cnc2c(OCC)nc(N)nc21] |

TABLE 3-continued
(V-1)
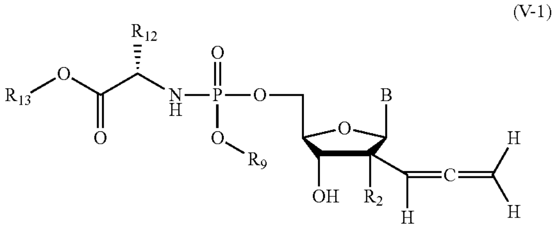
| Compound # | $R_2$ | $R_9$ | $R_{12}$ | $R_{13}$ | B |
|---|---|---|---|---|---|
| 455 | OH | Ph | H | i-Pr | 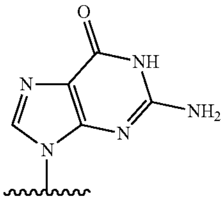 [SMILES: *n1cnc2c(=O)[nH]c(N)nc21] |
| 456 | F | Ph | H | i-Pr | 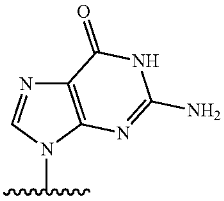 [SMILES: *n1cnc2c(=O)[nH]c(N)nc21] |
| 457 | OH | Ph | H | i-Pr | 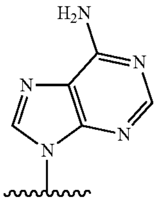 |
| 458 | F | Ph | H | i-Pr | 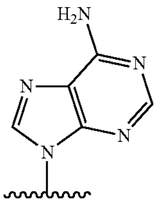 |
| 459 | OH | Ph | H | i-Pr | 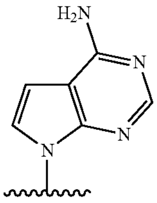 |
| 460 | F | Ph | H | i-Pr | 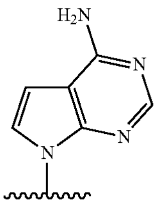 |
TABLE 3-continued
(V-1)
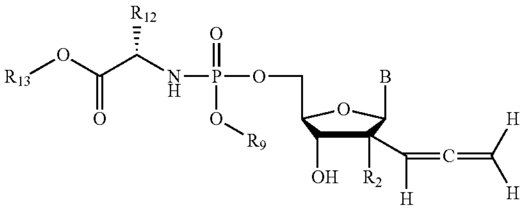
| Compound # | $R_2$ | $R_9$ | $R_{12}$ | $R_{13}$ | B |
|---|---|---|---|---|---|
| 461 | OH | 1-Naphthyl | H | i-Pr | 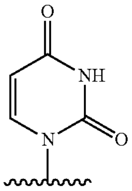 |
| 462 | F | 1-Naphthyl | H | i-Pr | 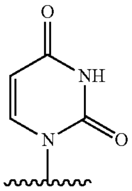 |
| 463 | OH | 1-Naphthyl | H | i-Pr | 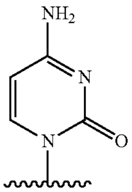 |
| 464 | F | 1-Naphthyl | H | i-Pr | 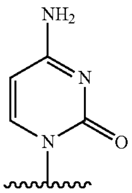 |
| 465 | OH | 1-Naphthyl | H | i-Pr | 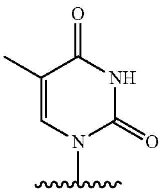 [SMILES: *n1cc(C)c(=O)[nH]c1=O] |
| 466 | F | 1-Naphthyl | H | i-Pr | 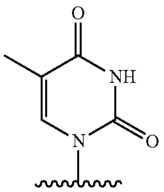 [SMILES: *n1cc(C)c(=O)[nH]c1=O] |

TABLE 3-continued
(V-1)
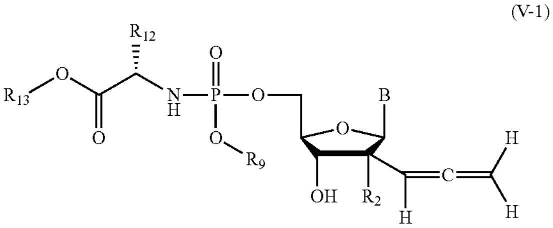
| Compound # | $R_2$ | $R_9$ | $R_{12}$ | $R_{13}$ | B |
|---|---|---|---|---|---|
| 467 | OH | 1-Naphthyl | H | i-Pr | 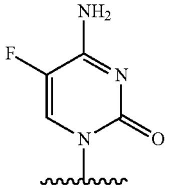 |
| 468 | F | 1-Naphthyl | H | i-Pr | 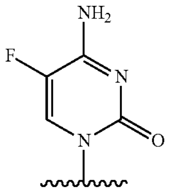 |
| 469 | OH | 1-Naphthyl | H | i-Pr | 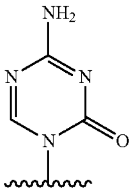 [SMILES: *n1cnc(N)nc1=O] |
| 470 | F | 1-Naphthyl | H | i-Pr | 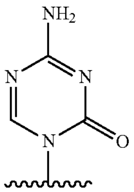 [SMILES: *n1cnc(N)nc1=O] |
| 471 | OH | 1-Naphthyl | H | i-Pr | 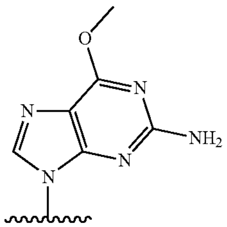 [SMILES: *n1cnc2c(OC)nc(N)nc21] |
| 472 | F | 1-Naphthyl | H | i-Pr | 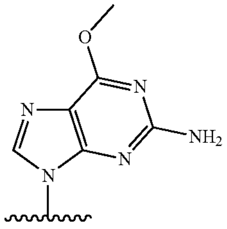 [SMILES: *n1cnc2c(OC)nc(N)nc21] |
TABLE 3-continued
(V-1)
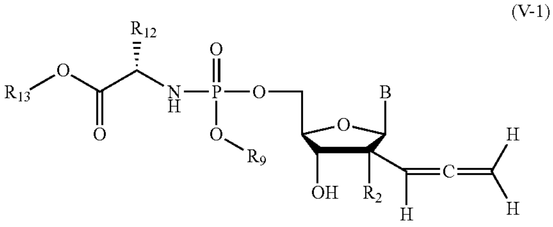
| Compound # | $R_2$ | $R_9$ | $R_{12}$ | $R_{13}$ | B |
|---|---|---|---|---|---|
| 473 | OH | 1-Naphthyl | H | i-Pr | 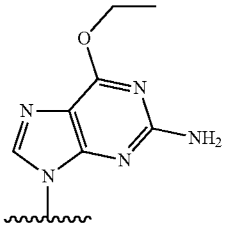 [SMILES: *n1cnc2c(OCC)nc(N)nc21] |
| 474 | F | 1-Naphthyl | H | i-Pr | 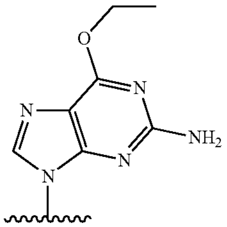 [SMILES: *n1cnc2c(OCC)nc(N)nc21] |
| 475 | OH | 1-Naphthyl | H | i-Pr | 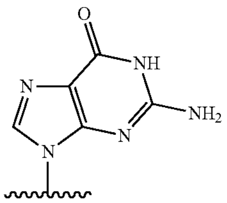 [SMILES: *n1cnc2c(=O)[nH]c(N)nc21] |
| 476 | F | 1-Naphthyl | H | i-Pr | 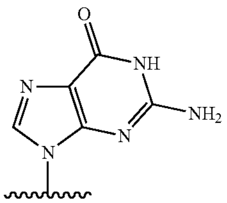 [SMILES: *n1cnc2c(=O)[nH]c(N)nc21] |
| 477 | OH | 1-Naphthyl | H | i-Pr | 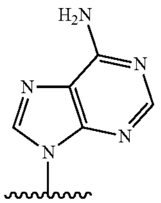 |
| 478 | F | 1-Naphthyl | H | i-Pr | 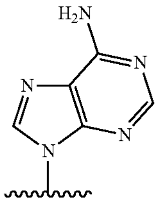 |

TABLE 3-continued
(V-1)
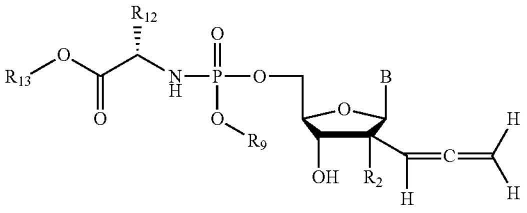
| Compound # | $R_2$ | $R_9$ | $R_{12}$ | $R_{13}$ | B |
|---|---|---|---|---|---|
| 479 | OH | 1-Naphthyl | H | i-Pr | 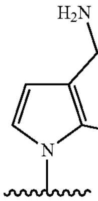 |
| 480 | F | 1-Naphthyl | H | i-Pr | 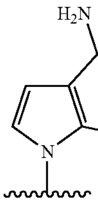 |
| 481 | OH | Ph | Me | Benzyl | 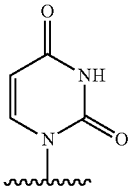 [SMILES: *n1ccc(=O)[nH]c1=O] |
| 482 | F | Ph | Me | Benzyl | 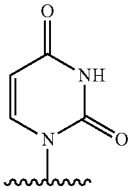 [SMILES: *n1ccc(=O)[nH]c1=O] |
| 483 | OH | Ph | Me | Benzyl | 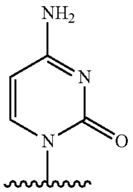 |
| 484 | F | Ph | Me | Benzyl | 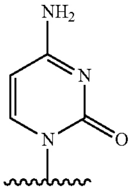 [SMILES: *n1ccc(N)nc1=O] |
TABLE 3-continued
(V-1)
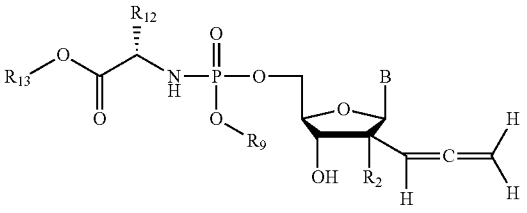
| Compound # | $R_2$ | $R_9$ | $R_{12}$ | $R_{13}$ | B |
|---|---|---|---|---|---|
| 485 | OH | Ph | Me | Benzyl | 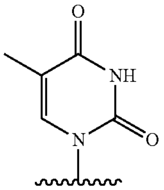 [SMILES: *n1cc(C)c(=O)[nH]c1=O] |
| 486 | F | Ph | Me | Benzyl | 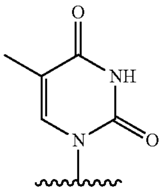 [SMILES: *n1cc(C)c(=O)[nH]c1=O] |
| 487 | OH | Ph | Me | Benzyl | 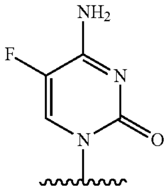 |
| 488 | F | Ph | Me | Benzyl | 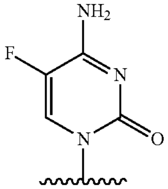 |
| 489 | OH | Ph | Me | Benzyl | 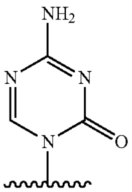 [SMILES: *n1cnc(N)nc1=O] |
| 490 | F | Ph | Me | Benzyl | 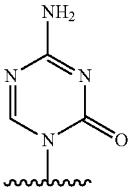 [SMILES: *n1cnc(N)nc1=O] |

TABLE 3-continued
(V-1)
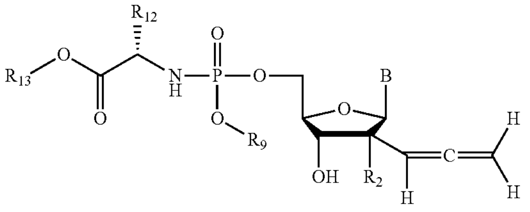
| Compound # | $R_2$ | $R_9$ | $R_{12}$ | $R_{13}$ | B |
|---|---|---|---|---|---|
| 491 | OH | Ph | Me | Benzyl | 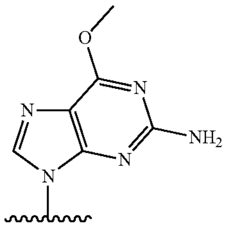 [SMILES: *n1cnc2c(OC)nc(N)nc21] |
| 492 | F | Ph | Me | Benzyl | 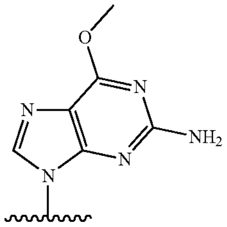 [SMILES: *n1cnc2c(OC)nc(N)nc21] |
| 493 | OH | Ph | Me | Benzyl | 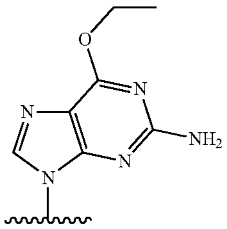 [SMILES: *n1cnc2c(OCC)nc(N)nc21] |
| 494 | F | Ph | Me | Benzyl | 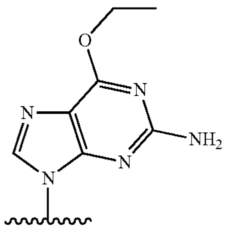 [SMILES: *n1cnc2c(OCC)nc(N)nc21] |
| 495 | OH | Ph | Me | Benzyl | 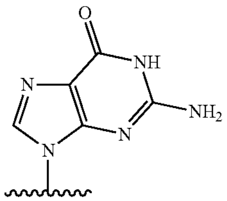 [SMILES: *n1cnc2c(=O)[nH]c(N)nc21] |
TABLE 3-continued
(V-1)
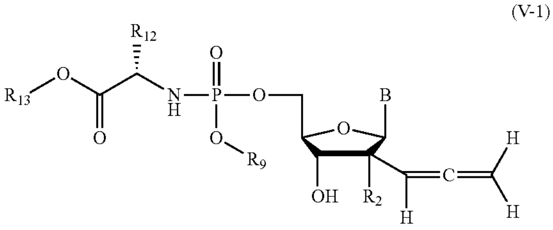
| Compound # | $R_2$ | $R_9$ | $R_{12}$ | $R_{13}$ | B |
|---|---|---|---|---|---|
| 496 | F | Ph | Me | Benzyl | 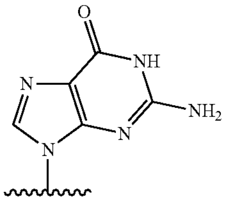 [SMILES: *n1cnc2c(=O)[nH]c(N)nc21] |
| 497 | OH | Ph | Me | Benzyl | 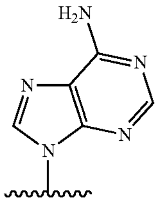 |
| 498 | F | Ph | Me | Benzyl | 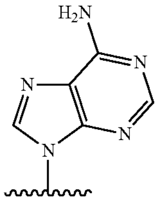 |
| 499 | OH | Ph | Me | Benzyl | 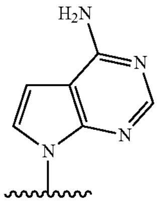 |
| 500 | F | Ph | Me | Benzyl | 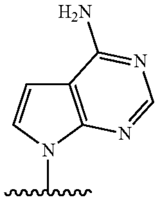 |
| 501 | OH | 1-Naphthyl | Me | Benzyl | 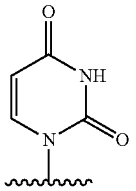 |

TABLE 3-continued
(V-1)
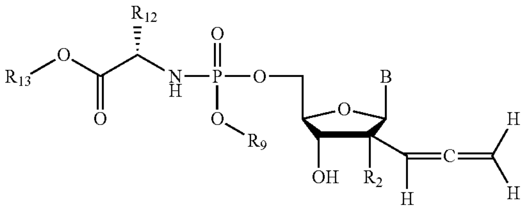
TABLE 3-continued
(V-1)
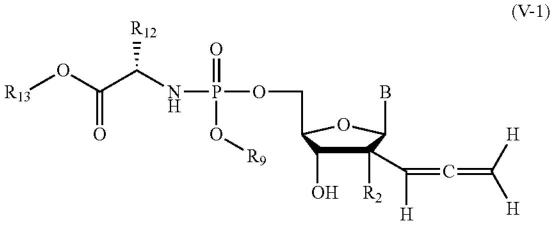
| Compound # | $R_2$ | $R_9$ | $R_{12}$ | $R_{13}$ | B |
|---|---|---|---|---|---|
| 502 | F | 1-Naphthyl | Me | Benzyl | 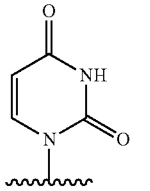 [SMILES: *n1ccc(=O)[nH]c1=O] |
| 503 | OH | 1-Naphthyl | Me | Benzyl | 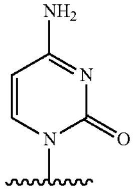 [SMILES: *n1ccc(N)nc1=O] |
| 504 | F | 1-Naphthyl | Me | Benzyl | 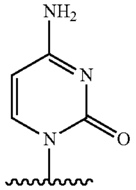 [SMILES: *n1ccc(N)nc1=O] |
| 505 | OH | 1-Naphthyl | Me | Benzyl | 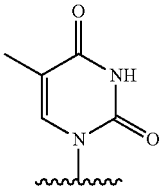 |
| 506 | F | 1-Naphthyl | Me | Benzyl | 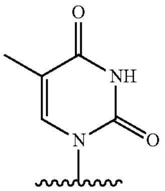 [SMILES: *n1cc(C)c(=O)[nH]c1=O] |
| 507 | OH | 1-Naphthyl | Me | Benzyl | 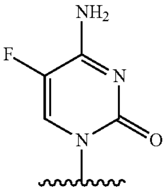 |
| 508 | F | 1-Naphthyl | Me | Benzyl | 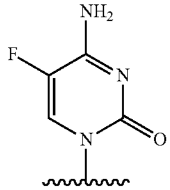 |
| 509 | OH | 1-Naphthyl | Me | Benzyl | 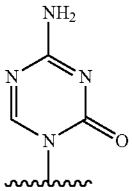 [SMILES: *n1cnc(N)nc1=O] |
| 510 | F | 1-Naphthyl | Me | Benzyl | 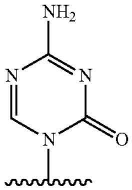 [SMILES: *n1cnc(N)nc1=O] |
| 511 | OH | 1-Naphthyl | Me | Benzyl | 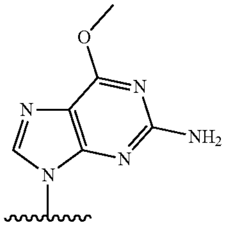 [SMILES: *n1cnc2c(OC)nc(N)nc21] |
| 512 | F | 1-Naphthyl | Me | Benzyl | 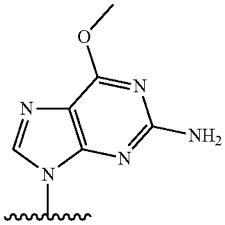 [SMILES: *n1cnc2c(OC)nc(N)nc21] |
| 513 | OH | 1-Naphthyl | Me | Benzyl | 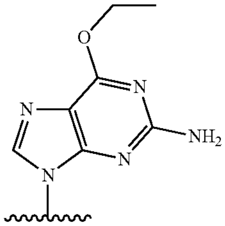 [SMILES: *n1cnc2c(OCC)nc(N)nc21] |

TABLE 3-continued
(V-1)
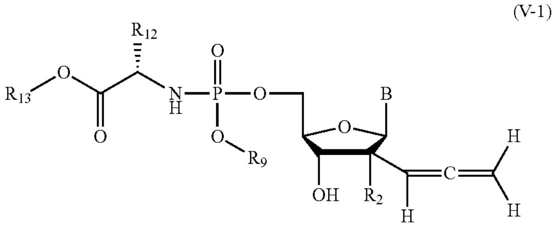
| Compound # | $R_2$ | $R_9$ | $R_{12}$ | $R_{13}$ | B |
|---|---|---|---|---|---|
| 514 | F | 1-Naphthyl | Me | Benzyl | 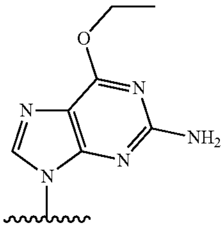 [SMILES: *n1cnc2c(OCC)nc(N)nc21] |
| 515 | OH | 1-Naphthyl | Me | Benzyl | 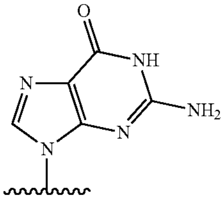 [SMILES: *n1cnc2c(=O)[nH]c(N)nc21] |
| 516 | F | 1-Naphthyl | Me | Benzyl | 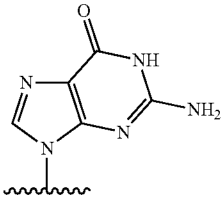 [SMILES: *n1cnc2c(=O)[nH]c(N)nc21] |
| 517 | OH | 1-Naphthyl | Me | Benzyl | 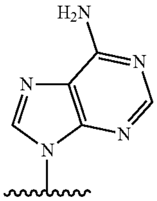 [SMILES: *n1cnc2c(N)ncnc21] |
| 518 | F | 1-Naphthyl | Me | Benzyl | 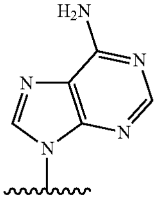 |
| 519 | OH | 1-Naphthyl | Me | Benzyl | 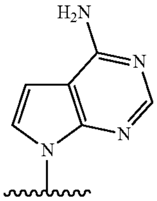 |
TABLE 3-continued
(V-1)
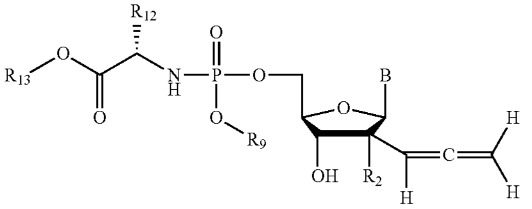
| Compound # | $R_2$ | $R_9$ | $R_{12}$ | $R_{13}$ | B |
|---|---|---|---|---|---|
| 520 | F | 1-Naphthyl | Me | Benzyl | 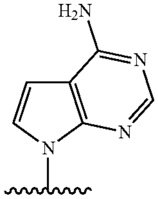 |
| 521 | OH | Ph | H | Benzyl | 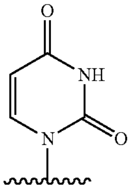 |
| 522 | F | Ph | H | Benzyl | 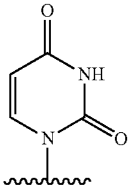 |
| 523 | OH | Ph | H | Benzyl | 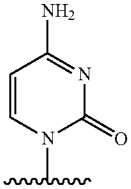 |
| 524 | F | Ph | H | Benzyl | 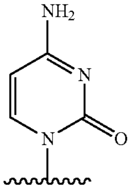 |
| 525 | OH | Ph | H | Benzyl | 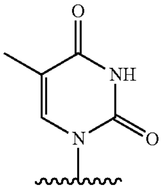 [SMILES: *n1cc(C)c(=O)[nH]c1=O] |

TABLE 3-continued
(V-1)
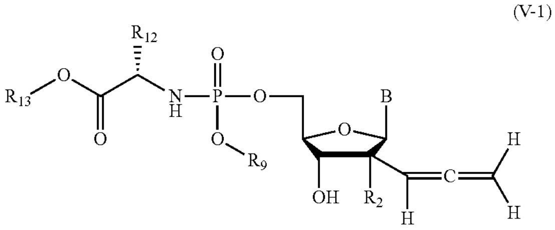
| Compound # | $R_2$ | $R_9$ | $R_{12}$ | $R_{13}$ | B |
|---|---|---|---|---|---|
| 526 | F | Ph | H | Benzyl | 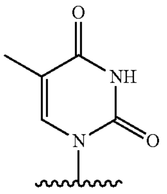 |
| 527 | OH | Ph | H | Benzyl | 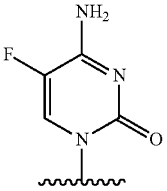 |
| 528 | F | Ph | H | Benzyl | 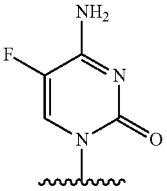 |
| 529 | OH | Ph | H | Benzyl | 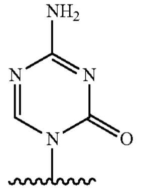 [SMILES: *n1cnc(N)nc1=O] |
| 530 | F | Ph | H | Benzyl | 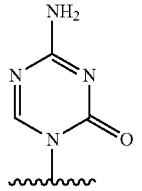 [SMILES: *n1cnc(N)nc1=O] |
| 531 | OH | Ph | H | Benzyl | 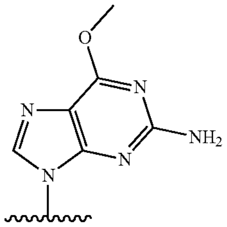 [SMILES: *n1cnc2c(OC)nc(N)nc21] |
TABLE 3-continued
(V-1)
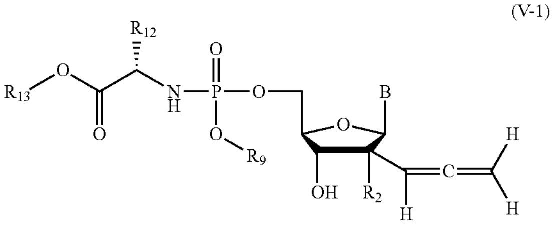
| Compound # | $R_2$ | $R_9$ | $R_{12}$ | $R_{13}$ | B |
|---|---|---|---|---|---|
| 532 | F | Ph | H | Benzyl | 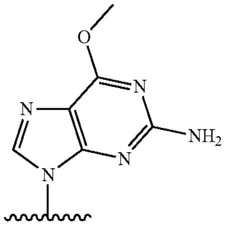 [SMILES: *n1cnc2c(OC)nc(N)nc21] |
| 533 | OH | Ph | H | Benzyl | 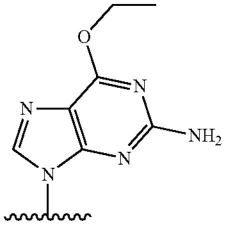 [SMILES: *n1cnc2c(OCC)nc(N)nc21] |
| 534 | F | Ph | H | Benzyl | 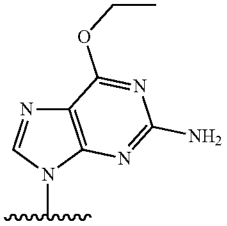 [SMILES: *n1cnc2c(OCC)nc(N)nc21] |
| 535 | OH | Ph | H | Benzyl | 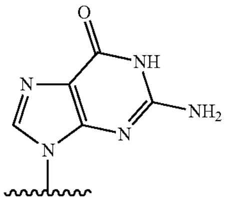 [SMILES: *n1cnc2c(=O)[nH]c(N)nc21] |
| 536 | F | Ph | H | Benzyl | 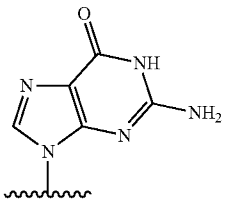 [SMILES: *n1cnc2c(=O)[nH]c(N)nc21] |
| 537 | OH | Ph | H | Benzyl | 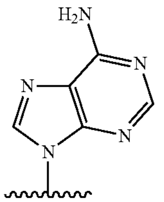 |

TABLE 3-continued
(V-1)
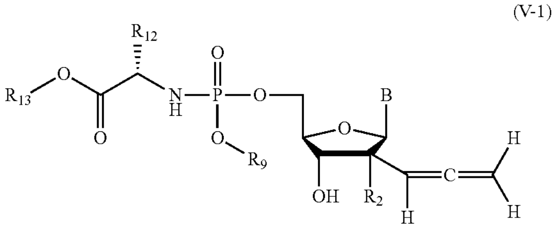
| Compound # | $R_2$ | $R_9$ | $R_{12}$ | $R_{13}$ | B |
|---|---|---|---|---|---|
| 538 | F | Ph | H | Benzyl | 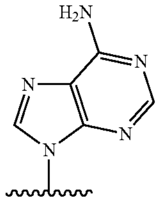 |
| 539 | OH | Ph | H | Benzyl | 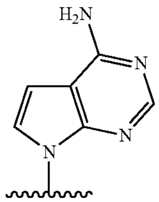 [SMILES: *n1ccc2c(N)ncnc21] |
| 540 | F | Ph | H | Benzyl | 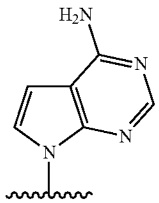 |
| 541 | OH | 1-Naphthyl | H | Benzyl | 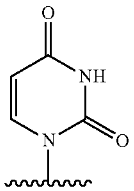 [SMILES: *n1ccc(=O)[nH]c1=O] |
| 542 | F | 1-Naphthyl | H | Benzyl | 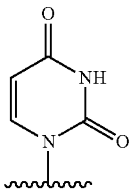 [SMILES: *n1ccc(=O)[nH]c1=O] |
| 543 | OH | 1-Naphthyl | H | Benzyl | 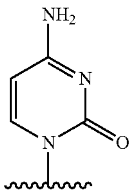 |
TABLE 3-continued
(V-1)
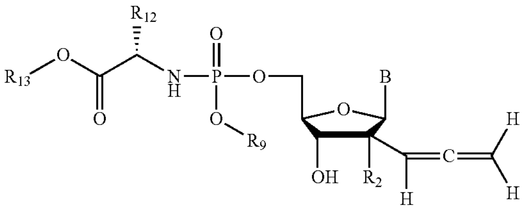
| Compound # | $R_2$ | $R_9$ | $R_{12}$ | $R_{13}$ | B |
|---|---|---|---|---|---|
| 544 | F | 1-Naphthyl | H | Benzyl | 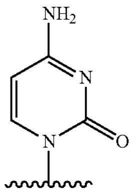 |
| 545 | OH | 1-Naphthyl | H | Benzyl | 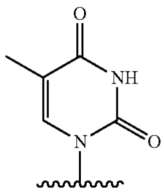 [SMILES: *n1cc(C)c(=O)[nH]c1=O] |
| 546 | F | 1-Naphthyl | H | Benzyl | 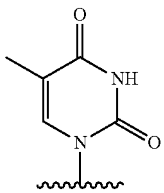 [SMILES: *n1cc(C)c(=O)[nH]c1=O] |
| 547 | OH | 1-Naphthyl | H | Benzyl | 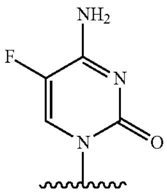 |
| 548 | F | 1-Naphthyl | H | Benzyl | 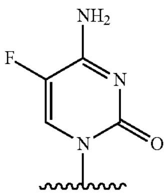 |
| 549 | OH | 1-Naphthyl | H | Benzyl | 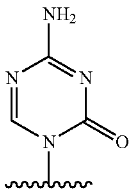 [SMILES: *n1cnc(N)nc1=O] |

TABLE 3-continued
(V-1)
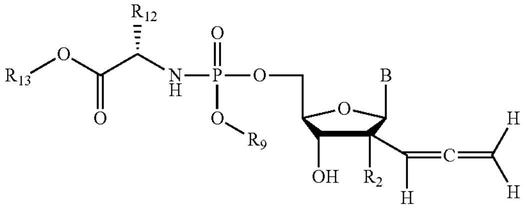
| Compound # | $R_2$ | $R_9$ | $R_{12}$ | $R_{13}$ | B |
|---|---|---|---|---|---|
| 550 | F | 1-Naphthyl | H | Benzyl | 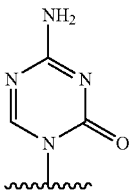 [SMILES: *n1cnc(N)nc1=O] |
| 551 | OH | 1-Naphthyl | H | Benzyl | 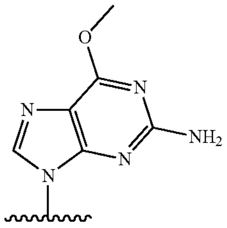 [SMILES: *n1cnc2c(OC)nc(N)nc21] |
| 552 | F | 1-Naphthyl | H | Benzyl | 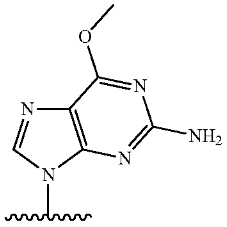 [SMILES: *n1cnc2c(OC)nc(N)nc21] |
| 553 | OH | 1-Naphthyl | H | Benzyl | 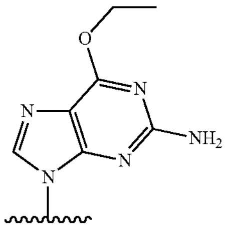 [SMILES: *n1cnc2c(OCC)nc(N)nc21] |
| 554 | F | 1-Naphthyl | H | Benzyl | 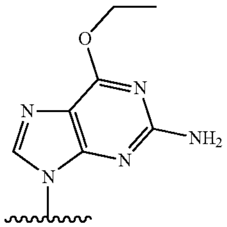 [SMILES: *n1cnc2c(OCC)nc(N)nc21] |
TABLE 3-continued
(V-1)
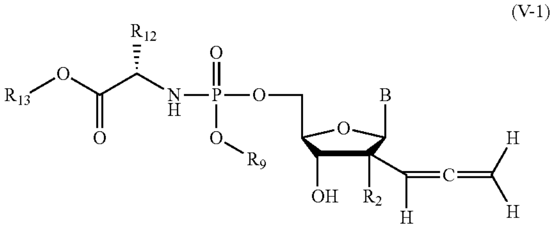
| Compound # | $R_2$ | $R_9$ | $R_{12}$ | $R_{13}$ | B |
|---|---|---|---|---|---|
| 555 | OH | 1-Naphthyl | H | Benzyl | 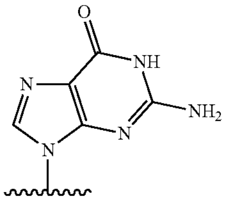 [SMILES: *n1cnc2c(=O)[nH]c(N)nc21] |
| 556 | F | 1-Naphthyl | H | Benzyl | 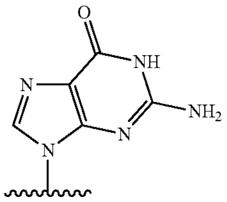 [SMILES: *n1cnc2c(=O)[nH]c(N)nc21] |
| 557 | OH | 1-Naphthyl | H | Benzyl | 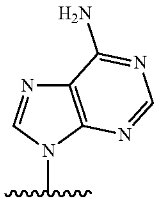 |
| 558 | F | 1-Naphthyl | H | Benzyl | 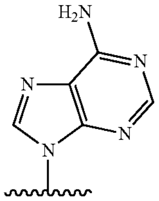 |
| 559 | OH | 1-Naphthyl | H | Benzyl | 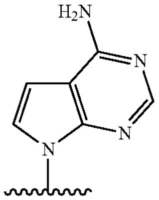 |
| 560 | F | 1-Naphthyl | H | Benzyl | 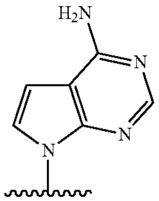 |

TABLE 3-continued
(V-1)
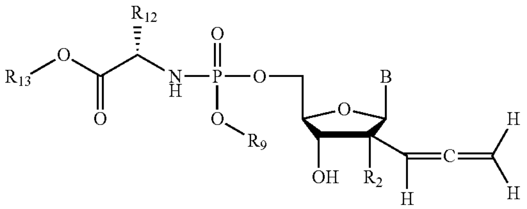
| Compound # | $R_2$ | $R_9$ | $R_{12}$ | $R_{13}$ | B |
|---|---|---|---|---|---|
| 561 | OH | Ph | Me | t-Bu$CH_2$— | 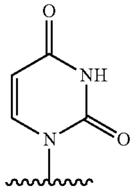 [SMILES: *n1ccc(=O)[nH]c1=O] |
| 562 | F | Ph | Me | t-Bu$CH_2$— | 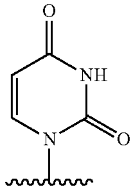 [SMILES: *n1ccc(=O)[nH]c1=O] |
| 563 | OH | Ph | Me | t-Bu$CH_2$— | 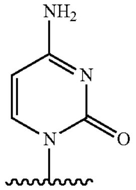 [SMILES: *n1ccc(N)nc1=O] |
| 564 | F | Ph | Me | t-Bu$CH_2$— | 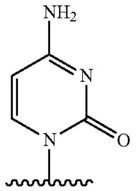 [SMILES: *n1ccc(N)nc1=O] |
| 565 | OH | Ph | Me | t-Bu$CH_2$— | 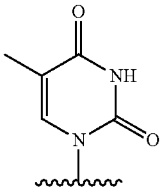 [SMILES: *n1cc(C)c(=O)[nH]c1=O] |
| 566 | F | Ph | Me | t-Bu$CH_2$— | 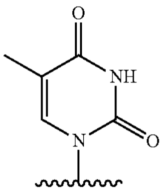 |
TABLE 3-continued
(V-1)
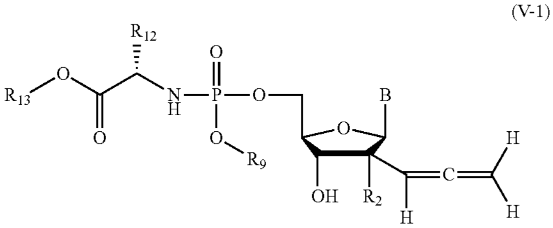
| Compound # | $R_2$ | $R_9$ | $R_{12}$ | $R_{13}$ | B |
|---|---|---|---|---|---|
| 567 | OH | Ph | Me | t-Bu$CH_2$— | 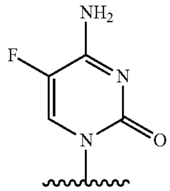 |
| 568 | F | Ph | Me | t-Bu$CH_2$— | 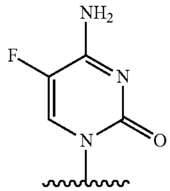 |
| 569 | OH | Ph | Me | t-Bu$CH_2$— | 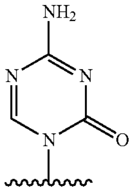 [SMILES: *n1cnc(N)nc1=O] |
| 570 | F | Ph | Me | t-Bu$CH_2$— | 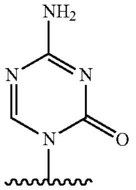 [SMILES: *n1cnc(N)nc1=O] |
| 571 | OH | Ph | Me | t-Bu$CH_2$— | 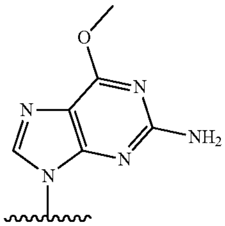 [SMILES: *n1cnc2c(OC)nc(N)nc21] |
| 572 | F | Ph | Me | t-Bu$CH_2$— | 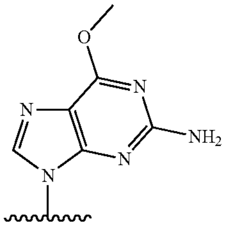 [SMILES: *n1cnc2c(OC)nc(N)nc21] |

TABLE 3-continued
(V-1)
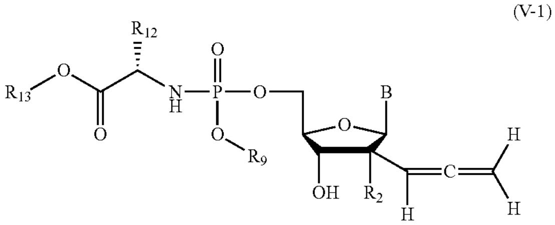
| Compound # | $R_2$ | $R_9$ | $R_{12}$ | $R_{13}$ | B |
|---|---|---|---|---|---|
| 573 | OH | Ph | Me | t-BuCH$_2$— | 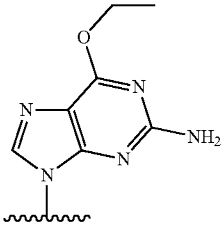 [SMILES: *n1cnc2c(OCC)nc(N)nc21] |
| 574 | F | Ph | Me | t-BuCH$_2$— | 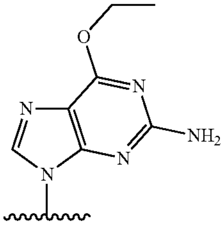 [SMILES: *n1cnc2c(OCC)nc(N)nc21] |
| 575 | OH | Ph | Me | t-BuCH$_2$— | 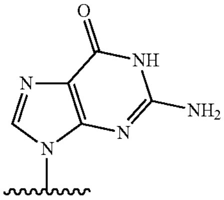 [SMILES: *n1cnc2c(=O)[nH]c(N)nc21] |
| 576 | F | Ph | Me | t-BuCH$_2$— | 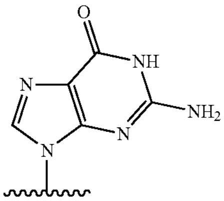 [SMILES: *n1cnc2c(=O)[nH]c(N)nc21] |
| 577 | OH | Ph | Me | t-BuCH$_2$— | 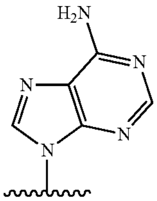 |
| 578 | F | Ph | Me | t-BuCH$_2$— | 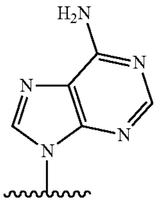 |
TABLE 3-continued
(V-1)
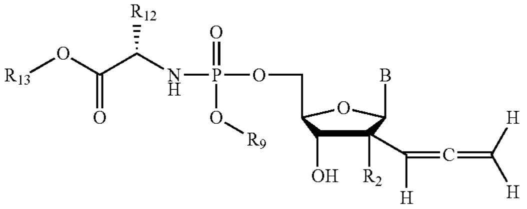
| Compound # | $R_2$ | $R_9$ | $R_{12}$ | $R_{13}$ | B |
|---|---|---|---|---|---|
| 579 | OH | Ph | Me | t-BuCH$_2$— | 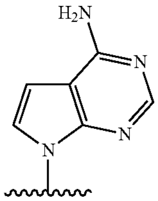 |
| 580 | F | Ph | Me | t-BuCH$_2$— | 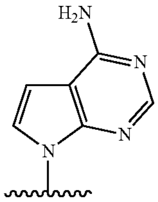 |
| 581 | OH | 1-Naphthyl | Me | t-BuCH$_2$— | 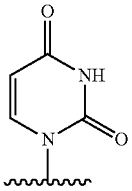 |
| 582 | F | 1-Naphthyl | Me | t-BuCH$_2$— | 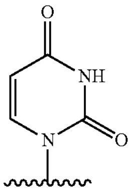 |
| 583 | OH | 1-Naphthyl | Me | t-BuCH$_2$— | 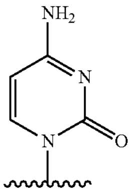 |
| 584 | F | 1-Naphthyl | Me | t-BuCH$_2$— | 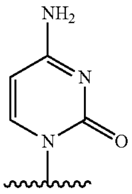 |

TABLE 3-continued
(V-1)
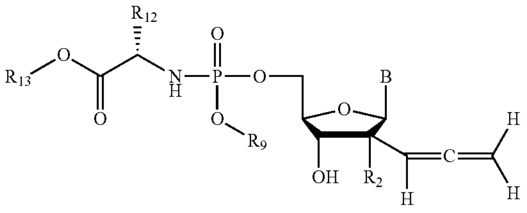
| Compound # | $R_2$ | $R_9$ | $R_{12}$ | $R_{13}$ | B |
|---|---|---|---|---|---|
| 585 | OH | 1-Naphthyl | Me | t-BuCH$_2$— | 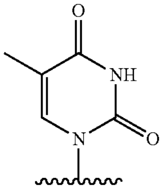 [SMILES: *n1cc(C)c(=O)[nH]c1=O] |
| 586 | F | 1-Naphthyl | Me | t-BuCH$_2$— | 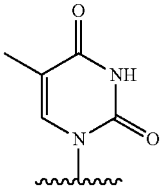 [SMILES: *n1cc(C)c(=O)[nH]c1=O] |
| 587 | OH | 1-Naphthyl | Me | t-BuCH$_2$— | 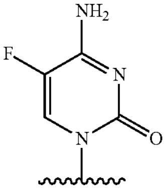 |
| 588 | F | 1-Naphthyl | Me | t-BuCH$_2$— | 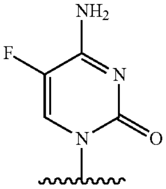 |
| 589 | OH | 1-Naphthyl | Me | t-BuCH$_2$— | 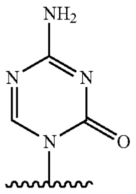 [SMILES: *n1cnc(N)nc1=O] |
| 590 | F | 1-Naphthyl | Me | t-BuCH$_2$— | 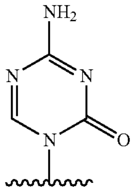 |
TABLE 3-continued
(V-1)
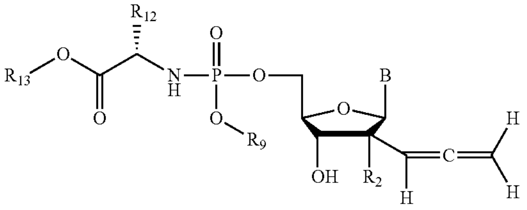
| Compound # | $R_2$ | $R_9$ | $R_{12}$ | $R_{13}$ | B |
|---|---|---|---|---|---|
| 591 | OH | 1-Naphthyl | Me | t-BuCH$_2$— | 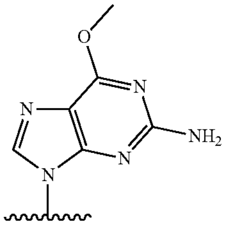 [SMILES: *n1cnc2c(OC)nc(N)nc21] |
| 592 | F | 1-Naphthyl | Me | t-BuCH$_2$— | 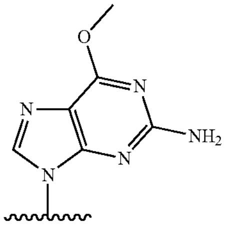 [SMILES: *n1cnc2c(OC)nc(N)nc21] |
| 593 | OH | 1-Naphthyl | Me | t-BuCH$_2$— | 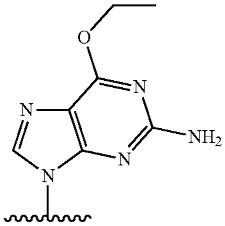 [SMILES: *n1cnc2c(OCC)nc(N)nc21] |
| 594 | F | 1-Naphthyl | Me | t-BuCH$_2$— | 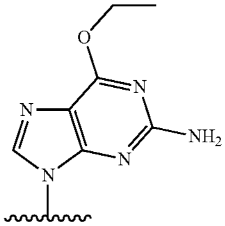 [SMILES: *n1cnc2c(OCC)nc(N)nc21] |
| 595 | OH | 1-Naphthyl | Me | t-BuCH$_2$— | 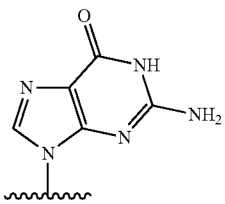 [SMILES: *n1cnc2c(=O)[nH]c(N)nc21] |

TABLE 3-continued
(V-1)
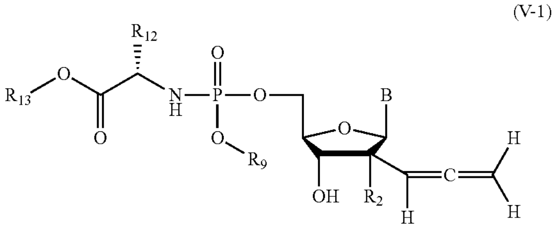
| Compound # | $R_2$ | $R_9$ | $R_{12}$ | $R_{13}$ | B |
|---|---|---|---|---|---|
| 596 | F | 1-Naphthyl | Me | t-$BuCH_2$— | 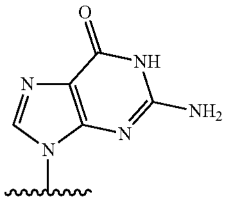 [SMILES: *n1cnc2c(=O)[nH]c(N)nc21] |
| 597 | OH | 1-Naphthyl | Me | t-$BuCH_2$— | 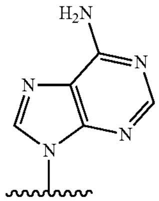 |
| 598 | F | 1-Naphthyl | Me | t-$BuCH_2$— | 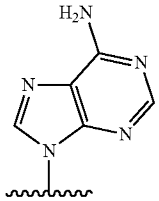 |
| 599 | OH | 1-Naphthyl | Me | t-$BuCH_2$— | 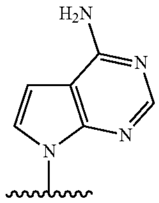 |
| 600 | F | 1-Naphthyl | Me | t-$BuCH_2$— | 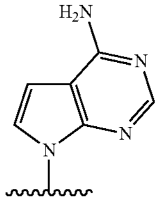 |
| 601 | OH | Ph | H | t-$BuCH_2$— | 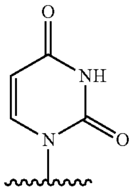 [SMILES: *n1ccc(=O)[nH]c1=O] |
TABLE 3-continued
(V-1)
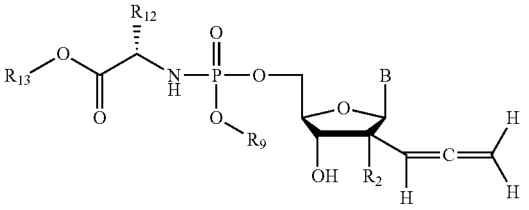
| Compound # | $R_2$ | $R_9$ | $R_{12}$ | $R_{13}$ | B |
|---|---|---|---|---|---|
| 602 | F | Ph | H | t-$BuCH_2$— | 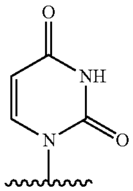 |
| 603 | OH | Ph | H | t-$BuCH_2$— | 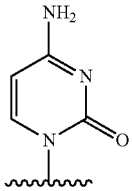 |
| 604 | F | Ph | H | t-$BuCH_2$— | 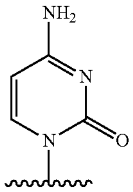 |
| 605 | OH | Ph | H | t-$BuCH_2$— | 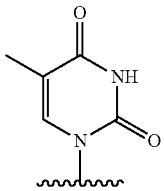 [SMILES: *n1cc(C)c(=O)[nH]c1=O] |
| 606 | F | Ph | H | t-$BuCH_2$— | 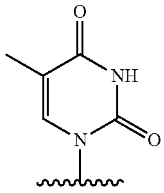 [SMILES: *n1cc(C)c(=O)[nH]c1=O] |
| 607 | OH | Ph | H | t-$BuCH_2$— | 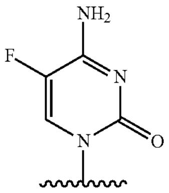 |

TABLE 3-continued
(V-1)
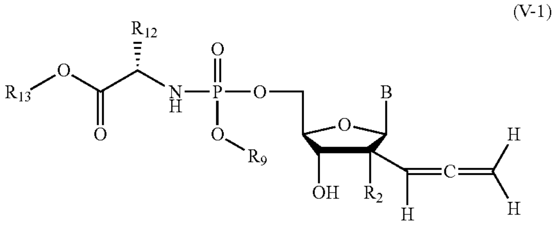
| Compound # | $R_2$ | $R_9$ | $R_{12}$ | $R_{13}$ | B |
|---|---|---|---|---|---|
| 608 | F | Ph | H | t-BuCH$_2$— | 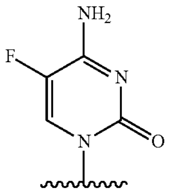 |
| 609 | OH | Ph | H | t-BuCH$_2$— | 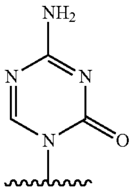 [SMILES: *n1cnc(N)nc1=O] |
| 610 | F | Ph | H | t-BuCH$_2$— | 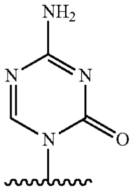 [SMILES: *n1cnc(N)nc1=O] |
| 611 | OH | Ph | H | t-BuCH$_2$— | 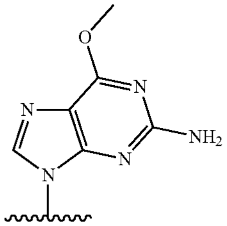 [SMILES: *n1cnc2c(OC)nc(N)nc21] |
| 612 | F | Ph | H | t-BuCH$_2$— | 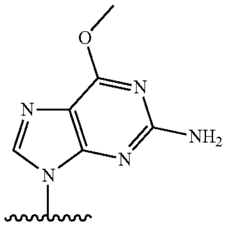 [SMILES: *n1cnc2c(OC)nc(N)nc21] |
| 613 | OH | Ph | H | t-BuCH$_2$— | 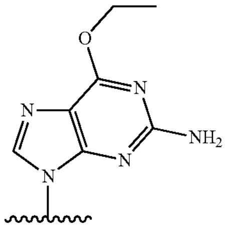 [SMILES: *n1cnc2c(OCC)nc(N)nc21] |
TABLE 3-continued
(V-1)
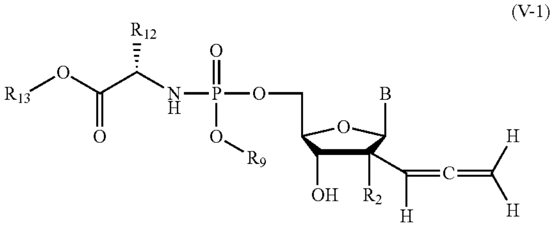
| Compound # | $R_2$ | $R_9$ | $R_{12}$ | $R_{13}$ | B |
|---|---|---|---|---|---|
| 614 | F | Ph | H | t-BuCH$_2$— | 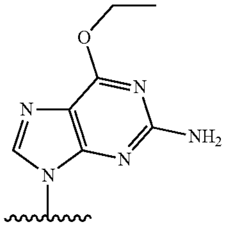 [SMILES: *n1cnc2c(OCC)nc(N)nc21] |
| 615 | OH | Ph | H | t-BuCH$_2$— | 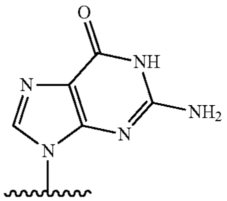 [SMILES: *n1cnc2c(=O)[nH]c(N)nc21] |
| 616 | F | Ph | H | t-BuCH$_2$— | 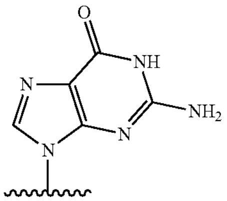 [SMILES: *n1cnc2c(=O)[nH]c(N)nc21] |
| 617 | OH | Ph | H | t-BuCH$_2$— | 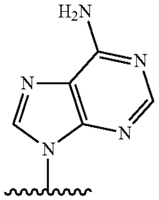 |
| 618 | F | Ph | H | t-BuCH$_2$— | 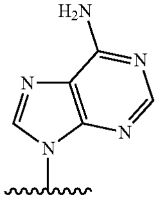 |
| 619 | OH | Ph | H | t-BuCH$_2$— | 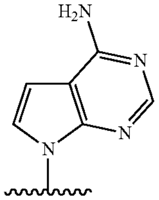 |

TABLE 3-continued
(V-1)
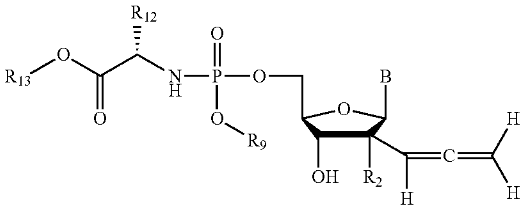
| Compound # | $R_2$ | $R_9$ | $R_{12}$ | $R_{13}$ | B |
|---|---|---|---|---|---|
| 620 | F | Ph | H | t-$BuCH_2$— | 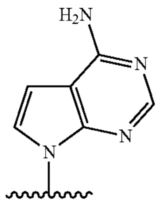 |
| 621 | OH | 1-Naphthyl | H | t-$BuCH_2$— | 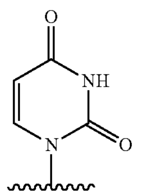 [SMILES: *n1ccc(=O)[nH]c1=O] |
| 622 | F | 1-Naphthyl | H | t-$BuCH_2$— | 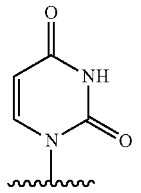 [SMILES: *n1ccc(=O)[nH]c1=O] |
| 623 | OH | 1-Naphthyl | H | t-$BuCH_2$— | 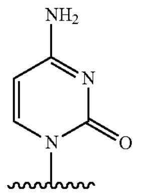 [SMILES: *n1ccc(N)nc1=O] |
| 624 | F | 1-Naphthyl | H | t-$BuCH_2$— | 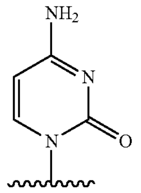 [SMILES: *n1ccc(N)nc1=O] |
| 625 | OH | 1-Naphthyl | H | t-$BuCH_2$— | 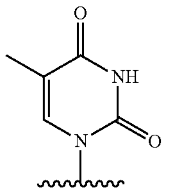 |
TABLE 3-continued
(V-1)
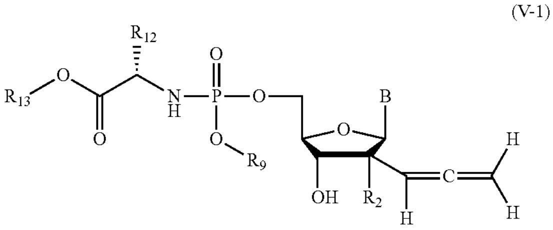
| Compound # | $R_2$ | $R_9$ | $R_{12}$ | $R_{13}$ | B |
|---|---|---|---|---|---|
| 626 | F | 1-Naphthyl | H | t-$BuCH_2$— | 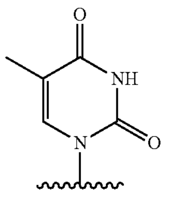 [SMILES: *n1cc(C)c(=O)[nH]c1=O] |
| 627 | OH | 1-Naphthyl | H | t-$BuCH_2$— | 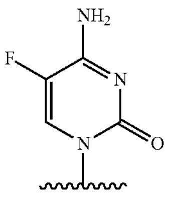 |
| 628 | F | 1-Naphthyl | H | t-$BuCH_2$— | 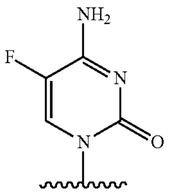 |
| 629 | OH | 1-Naphthyl | H | t-$BuCH_2$— | 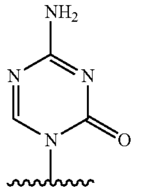 [SMILES: *n1cnc(N)nc1=O] |
| 630 | F | 1-Naphthyl | H | t-$BuCH_2$— | 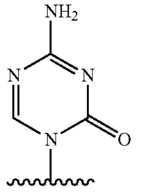 [SMILES: *n1cnc(N)nc1=O] |
| 631 | OH | 1-Naphthyl | H | t-$BuCH_2$— | 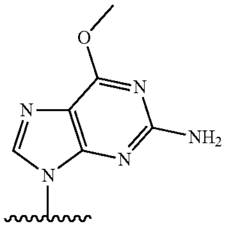 [SMILES: *n1cnc2c(OC)nc(N)nc21] |

TABLE 3-continued

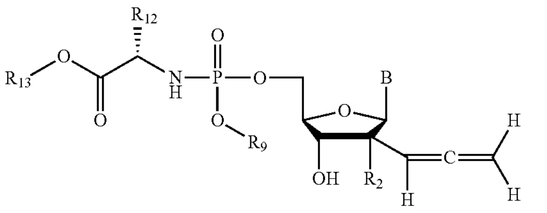

(V-1)

| Compound # | $R_2$ | $R_9$ | $R_{12}$ | $R_{13}$ | B |
|---|---|---|---|---|---|
| 632 | F | 1-Naphthyl | H | t-BuCH$_2$— | 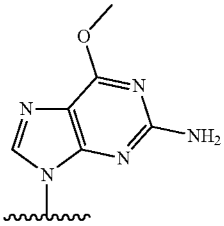 [SMILES: *n1cnc2c(OC)nc(N)nc21] |
| 633 | OH | 1-Naphthyl | H | t-BuCH$_2$— | 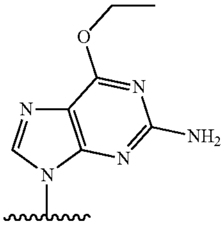 [SMILES: *n1cnc2c(OCC)nc(N)nc21] |
| 634 | F | 1-Naphthyl | H | t-BuCH$_2$— | 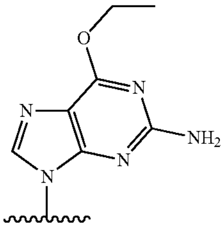 [SMILES: *n1cnc2c(OCC)nc(N)nc21] |
| 635 | OH | 1-Naphthyl | H | t-BuCH$_2$— | 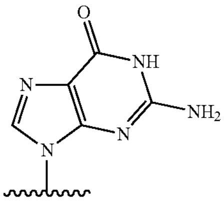 [SMILES: *n1cnc2c(=O)[nH]c(N)nc21] |
| 636 | F | 1-Naphthyl | H | t-BuCH$_2$— | 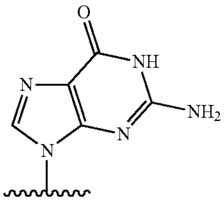 [SMILES: *n1cnc2c(=O)[nH]c(N)nc21] |

TABLE 3-continued

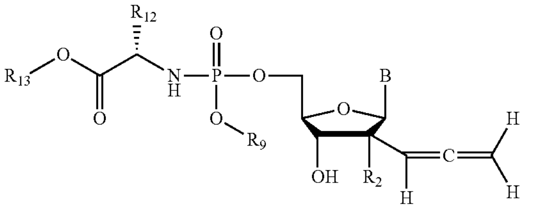

(V-1)

| Compound # | $R_2$ | $R_9$ | $R_{12}$ | $R_{13}$ | B |
|---|---|---|---|---|---|
| 637 | OH | 1-Naphthyl | H | t-BuCH$_2$— | 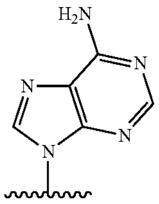 |
| 638 | F | 1-Naphthyl | H | t-BuCH$_2$— | 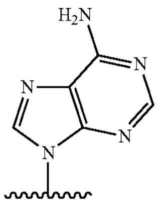 |
| 639 | OH | 1-Naphthyl | H | t-BuCH$_2$— | 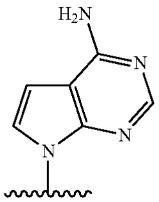 |
| 640 | F | 1-Naphthyl | H | t-BuCH$_2$— | 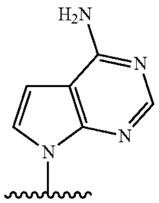 |

(d) compounds represented by Formula (VI-1) wherein $R_2$, $R_9$, $R_{12}$, $R_{13}$, and B are delineated for each compound in Table 4

TABLE 4
(VI-1)
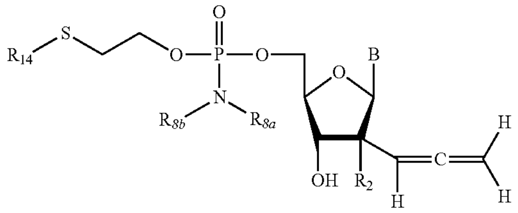
| Compound # | $R_2$ | $R_{14}$ | $NR_{8a}R_{8b}$ | B |
|---|---|---|---|---|
| 641 | OH | 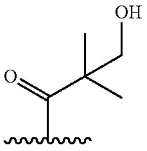 [SMILES: *C(=O)C(C)(C)CO] | 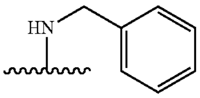 [SMILES: *NCc1ccccc1] | 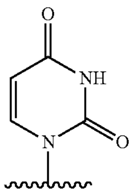 [SMILES: *n1ccc(=O)[nH]c1=O] |
| 642 | F | 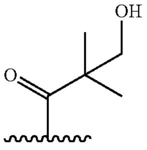 [SMILES: *C(=O)C(C)(C)CO] | 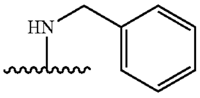 [SMILES: *NCc1ccccc1] | 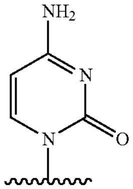 [SMILES: *n1ccc(N)nc1=O] |
| 643 | OH | 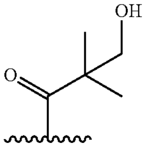 [SMILES: *C(=O)C(C)(C)CO] | 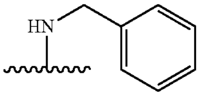 [SMILES: *NCc1ccccc1] | 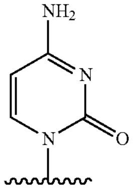 [SMILES: *n1ccc(N)nc1=O] |
| 644 | F | 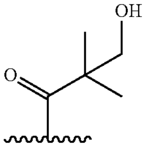 [SMILES: *C(=O)C(C)(C)CO] | 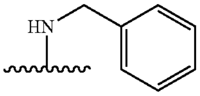 | 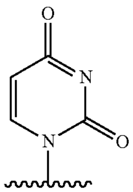 |
| 645 | OH | 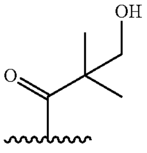 [SMILES: *C(=O)C(C)(C)CO] | 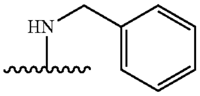 [SMILES: *NCc1ccccc1] | 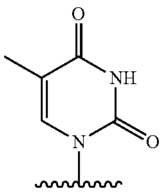 [SMILES: *n1cc(C)c(=O)[nH]c1=O] |
| 646 | F | 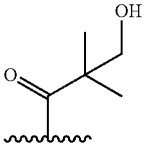 [SMILES: *C(=O)C(C)(C)CO] | 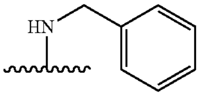 | 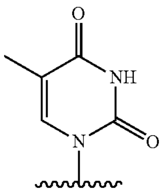 [SMILES: *n1cc(C)c(=O)[nH]c1=O] |

TABLE 4-continued
(VI-1)
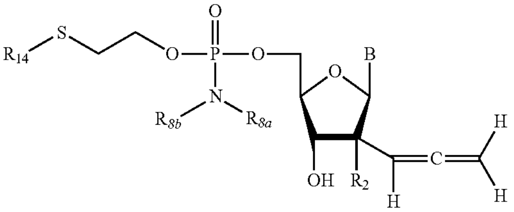
| Compound # | $R_2$ | $R_{14}$ | $NR_{8a}R_{8b}$ | B |
|---|---|---|---|---|
| 647 | OH | 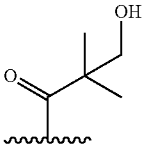 [SMILES: *C(=O)C(C)(C)CO] | 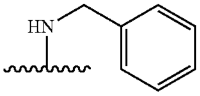 [SMILES: *NCc1ccccc1] | 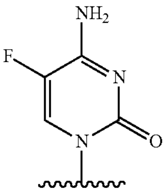 [SMILES: *n1cc(F)c(N)nc1=O] |
| 648 | F | 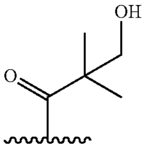 [SMILES: *C(=O)C(C)(C)CO] | 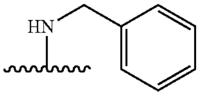 [SMILES: *NCc1ccccc1] | 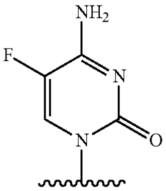 [SMILES: *n1cc(F)c(N)nc1=O] |
| 649 | OH | 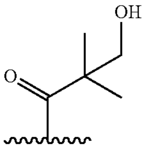 [SMILES: *C(=O)C(C)(C)CO] | 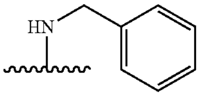 [SMILES: *NCc1ccccc1] | 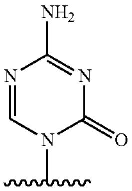 [SMILES: *n1cnc(N)nc1=O] |
| 650 | F | 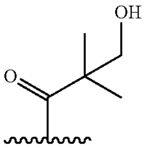 [SMILES: *C(=O)C(C)(C)CO] | 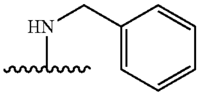 | 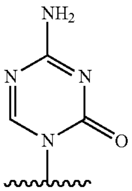 [SMILES: *n1cnc(N)nc1=O] |
| 651 | OH | 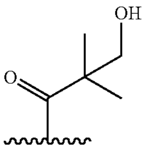 [SMILES: *C(=O)C(C)(C)CO] | 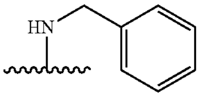 [SMILES: *NCc1ccccc1] | 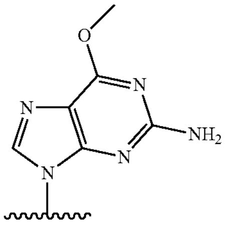 [SMILES: *n1cnc2c(OC)nc(N)nc21] |
| 652 | F | 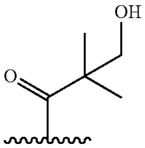 [SMILES: *C(=O)C(C)(C)CO] | 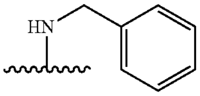 [SMILES: *NCc1ccccc1] | 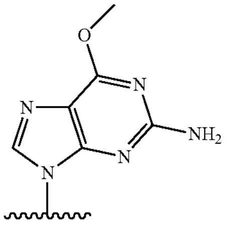 [SMILES: *n1cnc2c(OC)nc(N)nc21] |

TABLE 4-continued
(VI-1)
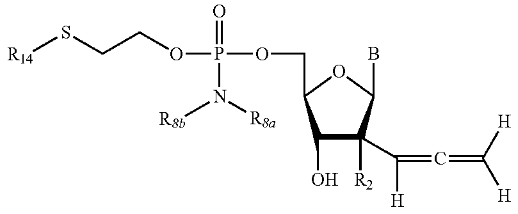
| Compound # | $R_2$ | $R_{14}$ | $NR_{8a}R_{8b}$ | B |
|---|---|---|---|---|
| 653 | OH | 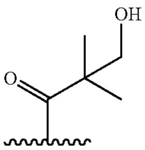 [SMILES: *C(=O)C(C)(C)CO] | 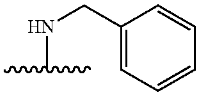 [SMILES: *NCc1ccccc1] | 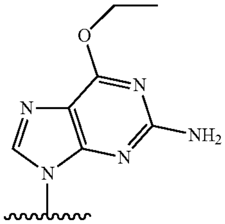 [SMILES: *n1cnc2c(OCC)nc(N)nc21] |
| 654 | F | 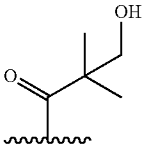 [SMILES: *C(=O)C(C)(C)CO] | 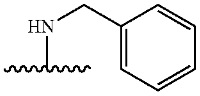 | 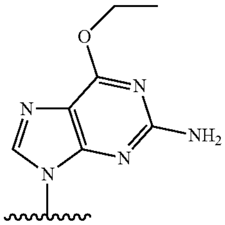 [SMILES: *n1cnc2c(OCC)nc(N)nc21] |
| 655 | OH | 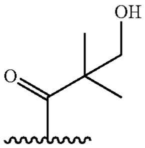 [SMILES: *C(=O)C(C)(C)CO] | 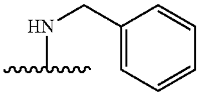 [SMILES: *NCc1ccccc1] | 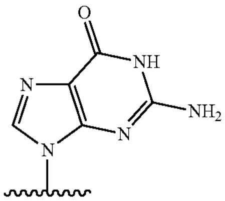 [SMILES: *n1cnc2c(=O)[nH]c(N)nc21] |
| 656 | F | 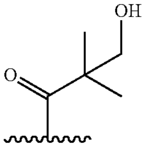 [SMILES: *C(=O)C(C)(C)CO] | 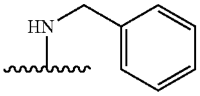 | 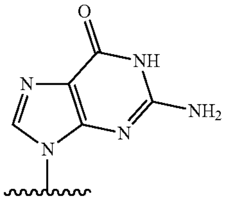 [SMILES: *n1cnc2c(=O)[nH]c(N)nc21] |
| 657 | OH | 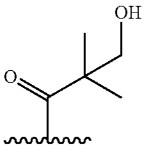 [SMILES: *C(=O)C(C)(C)CO] | 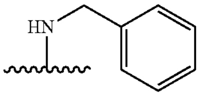 [SMILES: *NCc1ccccc1] | 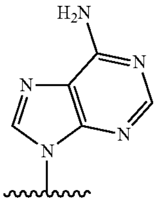 [SMILES: *n1cnc2c(N)ncnc21] |
| 658 | F | 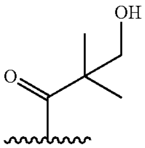 [SMILES: *C(=O)C(C)(C)CO] | 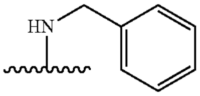 [SMILES: *NCc1ccccc1] | 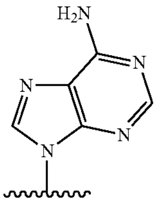 [SMILES: *n1cnc2c(N)ncnc21] |

TABLE 4-continued
(VI-1)
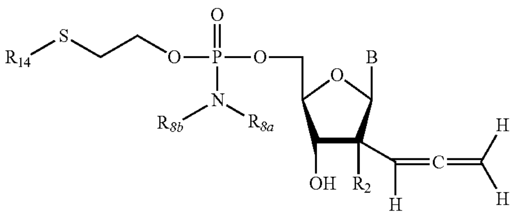
| Compound # | $R_2$ | $R_{14}$ | $NR_{8a}R_{8b}$ | B |
|---|---|---|---|---|
| 659 | OH | 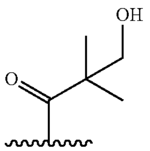 [SMILES: *C(=O)C(C)(C)CO] | 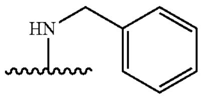 | 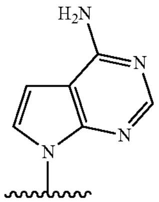 [SMILES: *n1ccc2c(N)ncnc21] |
| 660 | F | 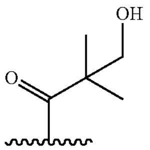 [SMILES: *C(=O)C(C)(C)CO] | 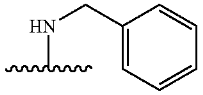 [SMILES: *NCc1ccccc1] | 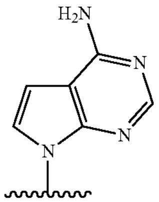 [SMILES: *n1ccc2c(N)ncnc21] |
| 661 | OH | 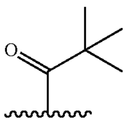 [SMILES: *C(=O)C(C)(C)C] | 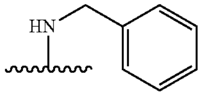 [SMILES: *NCc1ccccc1] | 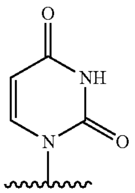 [SMILES: *n1ccc(=O)[nH]c1=O] |
| 662 | F | 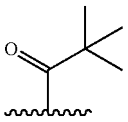 [SMILES: *C(=O)C(C)(C)C] | 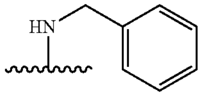 [SMILES: *NCc1ccccc1] | 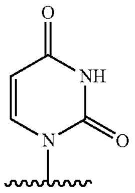 [SMILES: *n1ccc(=O)[nH]c1=O] |
| 663 | OH | 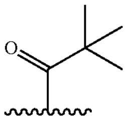 [SMILES: *C(=O)C(C)(C)C] | 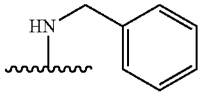 [SMILES: *NCc1ccccc1] | 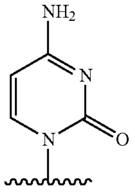 [SMILES: *n1ccc(N)nc1=O] |
| 664 | F | 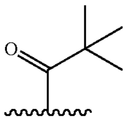 [SMILES: *C(=O)C(C)(C)C] | 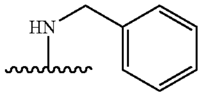 [SMILES: *NCc1ccccc1] | 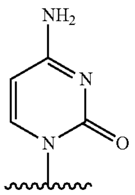 [SMILES: *n1ccc(N)nc1=O] |

TABLE 4-continued
(VI-1)
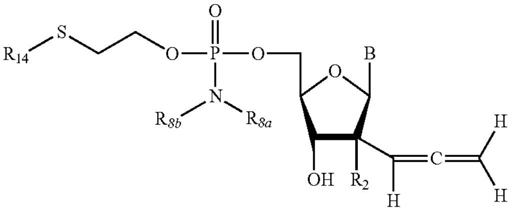
| Compound # | $R_2$ | $R_{14}$ | $NR_{8a}R_{8b}$ | B |
|---|---|---|---|---|
| 665 | OH | 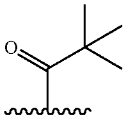 [SMILES: *C(=O)C(C)(C)C] | 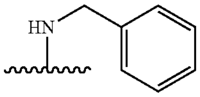 | 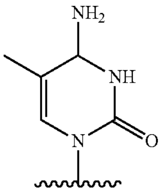 [SMILES: *N1C=C(C)C(N)NC1=O] |
| 666 | F | 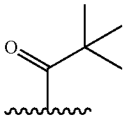 [SMILES: *C(=O)C(C)(C)C] | 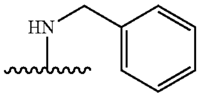 [SMILES: *NCc1ccccc1] | 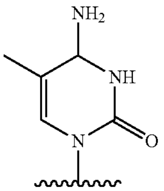 [SMILES: *N1C=C(C)C(N)NC1=O] |
| 667 | OH | 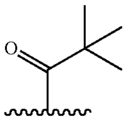 [SMILES: *C(=O)C(C)(C)C] | 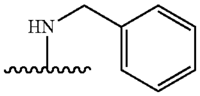 [SMILES: *NCc1ccccc1] | 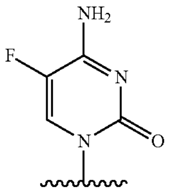 [SMILES: *n1cc(F)c(N)nc1=O] |
| 668 | F | 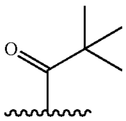 [SMILES: *C(=O)C(C)(C)C] | 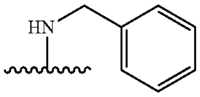 [SMILES: *NCc1ccccc1] | 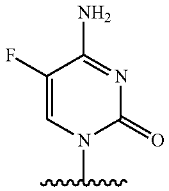 [SMILES: *n1cc(F)c(N)nc1=O] |
| 669 | OH | 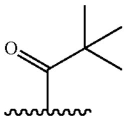 [SMILES: *C(=O)C(C)(C)C] | 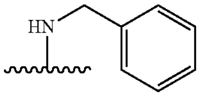 [SMILES: *NCc1ccccc1] | 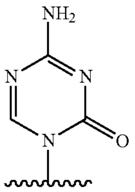 [SMILES: *n1cnc(N)nc1=O] |
| 670 | F | 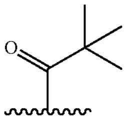 [SMILES: *C(=O)C(C)(C)C] | 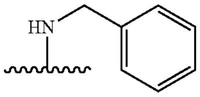 [SMILES: *NCc1ccccc1] | 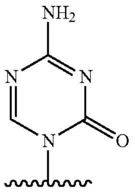 [SMILES: *n1cnc(N)nc1=O] |

TABLE 4-continued
(VI-1)
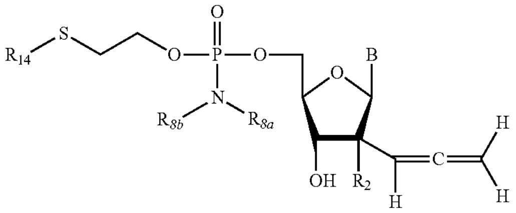
| Compound # | $R_2$ | $R_{14}$ | $NR_{8a}R_{8b}$ | B |
|---|---|---|---|---|
| 671 | OH | 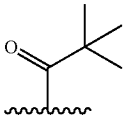 | 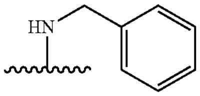 [SMILES: *NCc1ccccc1] | 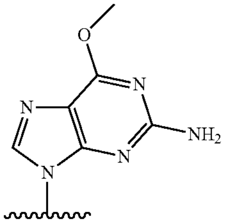 [SMILES: *n1cnc2c(OC)nc(N)nc21] |
| 672 | F | 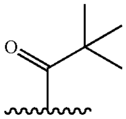 [SMILES: *C(=O)C(C)(C)C] | 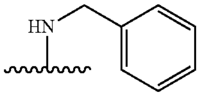 [SMILES: *NCc1ccccc1] | 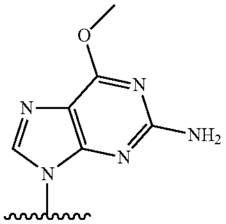 [SMILES: *n1cnc2c(OC)nc(N)nc21] |
| 673 | OH | 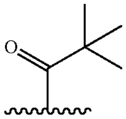 [SMILES: *C(=O)C(C)(C)C] | 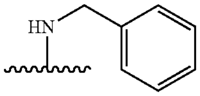 [SMILES: *NCc1ccccc1] | 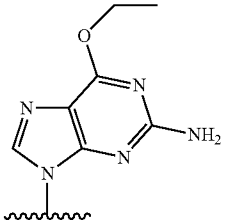 [SMILES: *n1cnc2c(OCC)nc(N)nc21] |
| 674 | F | 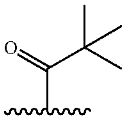 | 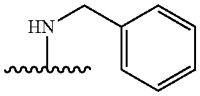 [SMILES: *NCc1ccccc1] | 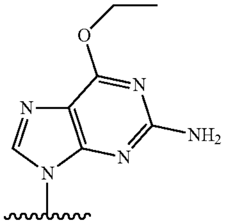 [SMILES: *n1cnc2c(OCC)nc(N)nc21] |
| 675 | OH | 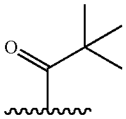 [SMILES: *C(=O)C(C)(C)C] | 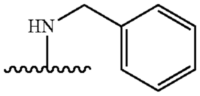 [SMILES: *NCc1ccccc1] | 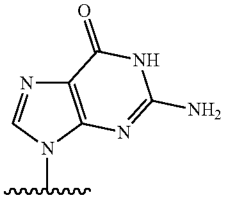 [SMILES: *n1cnc2c(=O)[nH]c(N)nc21] |
| 676 | F | 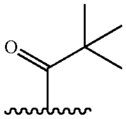 [SMILES: *C(=O)C(C)(C)C] | 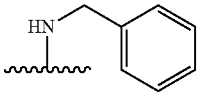 [SMILES: *NCc1ccccc1] | 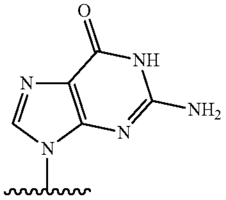 [SMILES: *n1cnc2c(=O)[nH]c(N)nc21] |

TABLE 4-continued
(VI-1)
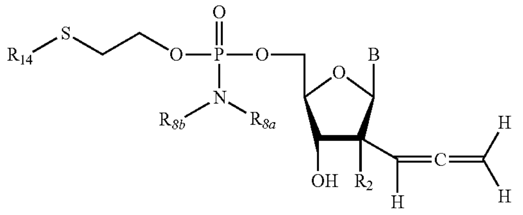
| Compound # | $R_2$ | $R_{14}$ | $NR_{8a}R_{8b}$ | B |
|---|---|---|---|---|
| 677 | OH | 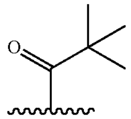 [SMILES: *C(=O)C(C)(C)C] | 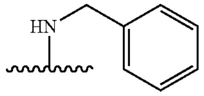 [SMILES: *NCc1ccccc1] | 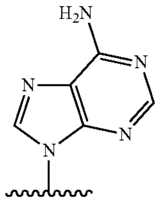 [SMILES: *n1cnc2c(N)ncnc21] |
| 678 | F | 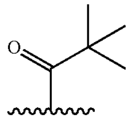 [SMILES: *C(=O)C(C)(C)C] | 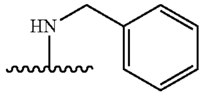 [SMILES: *NCc1ccccc1] | 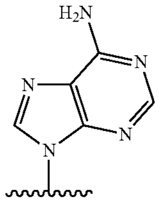 [SMILES: *n1cnc2c(N)ncnc21] |
| 679 | OH | 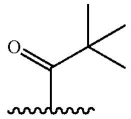 | 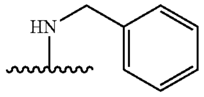 [SMILES: *NCc1ccccc1] | 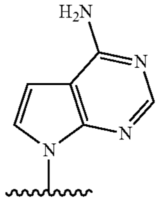 [SMILES: *n1ccc2c(N)ncnc21] |
| 680 | F | 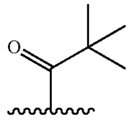 [SMILES: *C(=O)C(C)(C)C] | 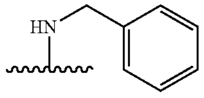 [SMILES: *NCc1ccccc1] | 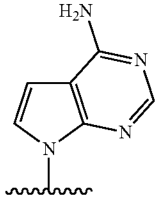 [SMILES: *n1ccc2c(N)ncnc21] |
| 681 | OH | 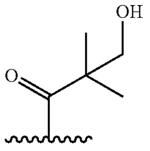 [SMILES: *C(=O)C(C)(C)CO] | 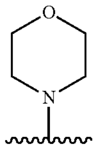 | 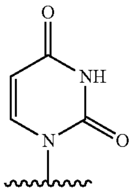 [SMILES: *n1ccc(=O)[nH]c1=O] |
| 682 | F | 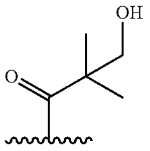 [SMILES: *C(=O)C(C)(C)CO] | 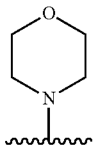 | 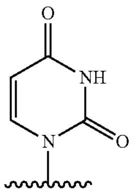 [SMILES: *n1ccc(=O)[nH]c1=O] |

TABLE 4-continued
(VI-1)
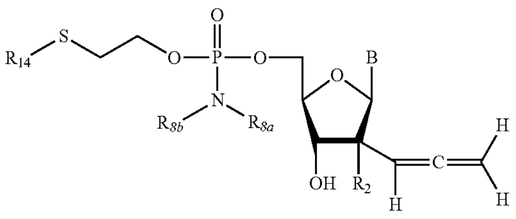
| Compound # | $R_2$ | $R_{14}$ | $NR_{8a}R_{8b}$ | B |
|---|---|---|---|---|
| 683 | OH | 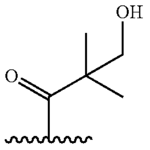 [SMILES: *C(=O)C(C)(C)CO] | 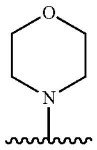 | 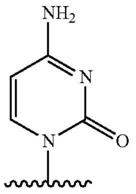 |
| 684 | F | 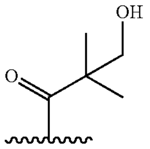 [SMILES: *C(=O)C(C)(C)CO] | 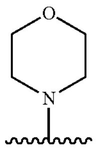 | 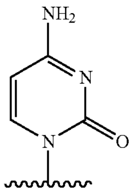 [SMILES: *n1ccc(N)nc1=O] |
| 685 | OH | 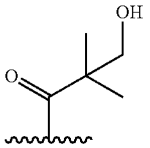 [SMILES: *C(=O)C(C)(C)CO] | 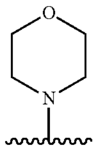 | 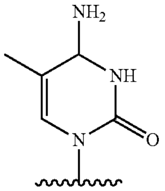 [SMILES: *N1C=C(C)C(N)NC1=O] |
| 686 | F | 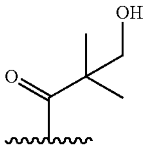 [SMILES: *C(=O)C(C)(C)CO] | 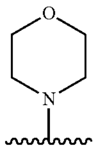 | 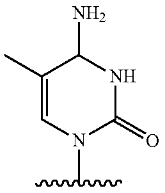 [SMILES: *N1C=C(C)C(N)NC1=O] |
| 687 | OH | 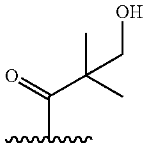 [SMILES: *C(=O)C(C)(C)CO] | 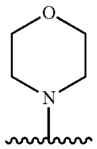 | 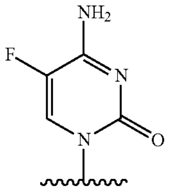 [SMILES: *n1cc(F)c(N)nc1=O] |
| 688 | F | 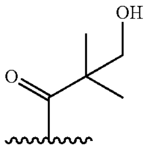 [SMILES: *C(=O)C(C)(C)CO] | 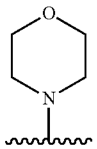 | 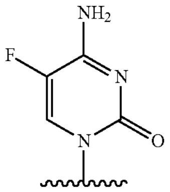 [SMILES: *n1cc(F)c(N)nc1=O] |

TABLE 4-continued
(VI-1)
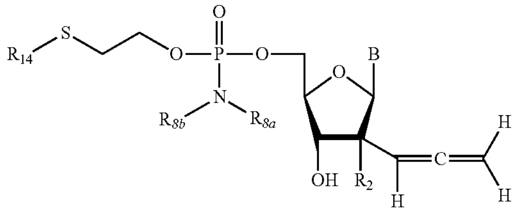
| Compound # | $R_2$ | $R_{14}$ | $NR_{8a}R_{8b}$ | B |
| --- | --- | --- | --- | --- |
| 689 | OH | 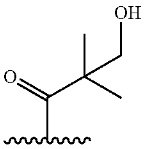 [SMILES: *C(=O)C(C)(C)CO] | 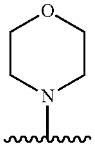 | 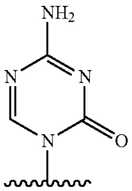 [SMILES: *n1cnc(N)nc1=O] |
| 690 | F | 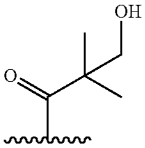 [SMILES: *C(=O)C(C)(C)CO] | 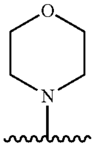 | 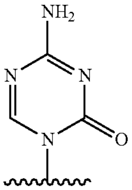 [SMILES: *n1cnc(N)nc1=O] |
| 691 | OH | 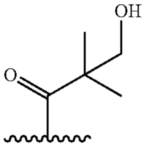 [SMILES: *C(=O)C(C)(C)CO] | 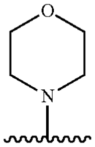 | 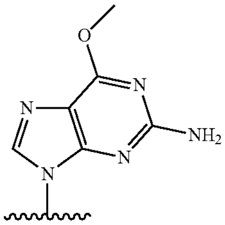 [SMILES: *n1cnc2c(OC)nc(N)nc21] |
| 692 | F | 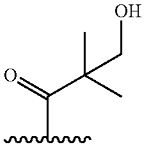 [SMILES: *C(=O)C(C)(C)CO] | 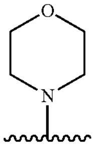 | 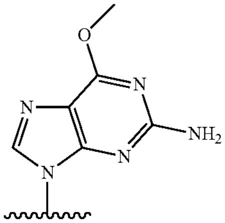 [SMILES: *n1cnc2c(OC)nc(N)nc21] |
| 693 | OH | 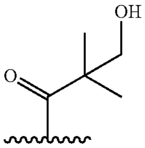 [SMILES: *C(=O)C(C)(C)CO] | 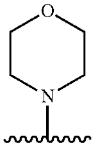 | 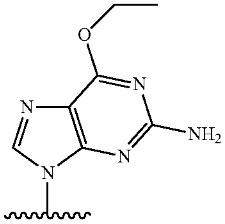 [SMILES: *n1cnc2c(OCC)nc(N)nc21] |
| 694 | F | 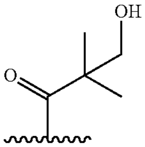 [SMILES: *C(=O)C(C)(C)CO] | 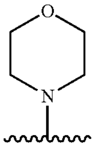 | 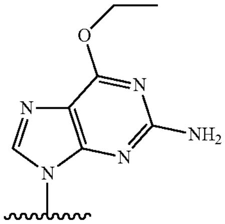 [SMILES: *n1cnc2c(OCC)nc(N)nc21] |

TABLE 4-continued
(VI-1)
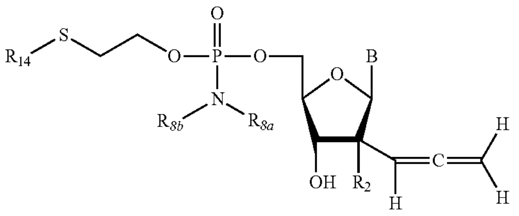
| Compound # | $R_2$ | $R_{14}$ | $NR_{8a}R_{8b}$ | B |
|---|---|---|---|---|
| 695 | OH | 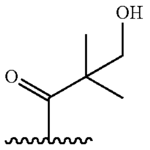 [SMILES: *C(=O)C(C)(C)CO] | 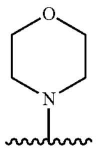 | 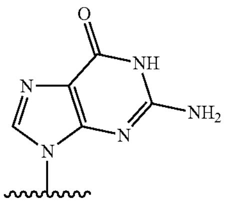 [SMILES: *n1cnc2c(=O)[nH]c(N)nc21] |
| 696 | F | 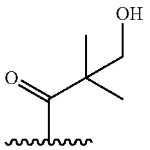 [SMILES: *C(=O)C(C)(C)CO] | 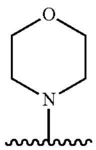 | 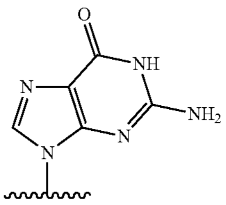 [SMILES: *n1cnc2c(=O)[nH]c(N)nc21] |
| 697 | OH | 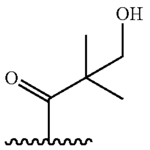 [SMILES: *C(=O)C(C)(C)CO] | 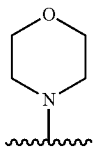 | 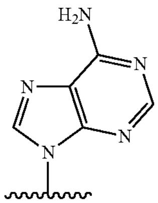 [SMILES: *n1cnc2c(N)ncnc21] |
| 698 | F | 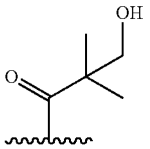 [SMILES: *C(=O)C(C)(C)CO] | 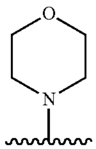 | 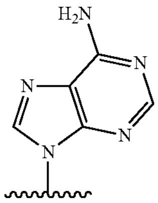 [SMILES: *n1cnc2c(N)ncnc21] |
| 699 | OH | 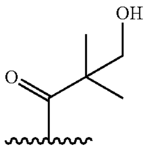 [SMILES: *C(=O)C(C)(C)CO] | 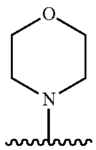 | 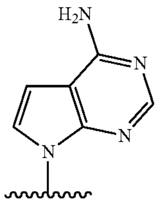 [SMILES: *n1ccc2c(N)ncnc21] |
| 700 | F | 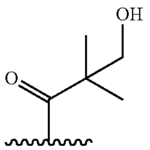 [SMILES: *C(=O)C(C)(C)CO] | 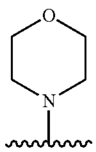 | 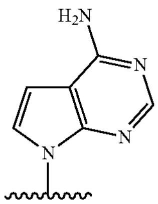 [SMILES: *n1ccc2c(N)ncnc21] |

TABLE 4-continued
(VI-1)
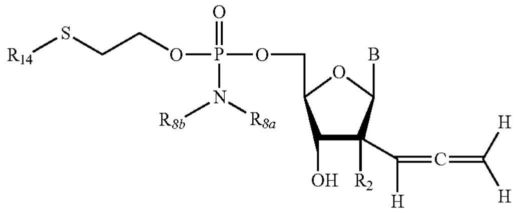
| Compound # | $R_2$ | $R_{14}$ | $NR_{8a}R_{8b}$ | B |
|---|---|---|---|---|
| 701 | OH | 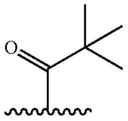 [SMILES: *C(=O)C(C)(C)C] | 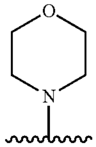 | 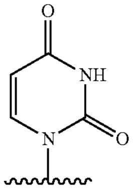 [SMILES: *n1ccc(=O)[nH]c1=O] |
| 702 | F | 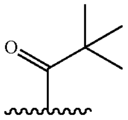 [SMILES: *C(=O)C(C)(C)C] | 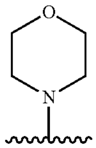 | 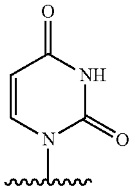 [SMILES: *n1ccc(=O)[nH]c1=O] |
| 703 | OH | 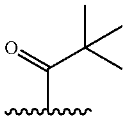 | 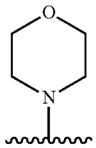 | 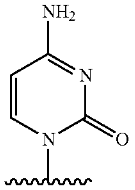 [SMILES: *n1ccc(N)nc1=O] |
| 704 | F | 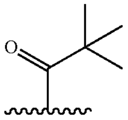 [SMILES: *C(=O)C(C)(C)C] | 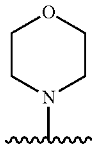 | 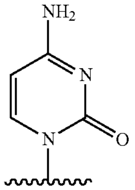 [SMILES: *n1ccc(N)nc1=O] |
| 705 | OH | 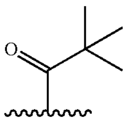 [SMILES: *C(=O)C(C)(C)C] | 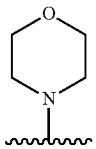 | 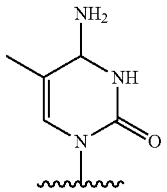 [SMILES: *N1C=C(C)C(N)NC1=O] |
| 706 | F | 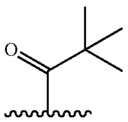 [SMILES: *C(=O)C(C)(C)C] | 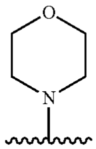 | 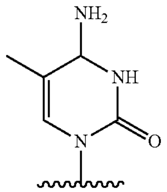 [SMILES: *N1C=C(C)C(N)NC1=O] |

TABLE 4-continued
(VI-1)
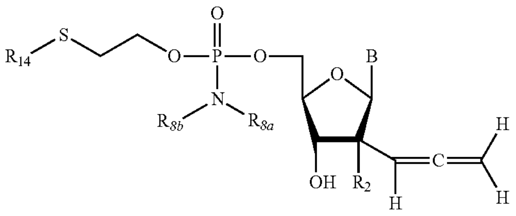
| Compound # | $R_2$ | $R_{14}$ | $NR_{8a}R_{8b}$ | B |
|---|---|---|---|---|
| 707 | OH | 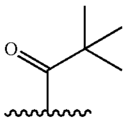 [SMILES: *C(=O)C(C)(C)C] | 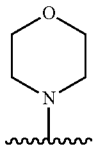 | 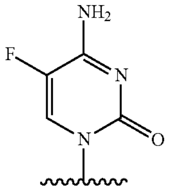 [SMILES: *n1cc(F)c(N)nc1=O] |
| 708 | F | 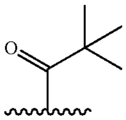 [SMILES: *C(=O)C(C)(C)C] | 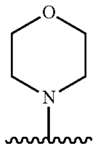 | 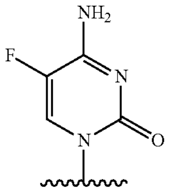 [SMILES: *n1cc(F)c(N)nc1=O] |
| 709 | OH | 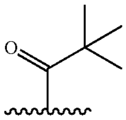 [SMILES: *C(=O)C(C)(C)C] | 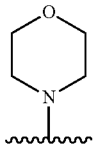 | 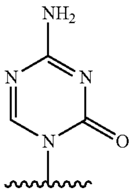 [SMILES: *n1cnc(N)nc1=O] |
| 710 | F | 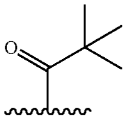 [SMILES: *C(=O)C(C)(C)C] | 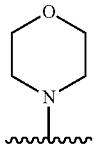 | 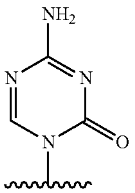 [SMILES: *n1cnc(N)nc1=O] |
| 711 | OH | 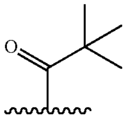 [SMILES: *C(=O)C(C)(C)C] | 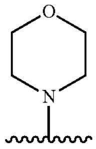 | 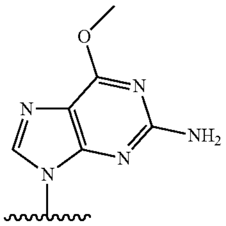 [SMILES: *n1cnc2c(OC)nc(N)nc21] |
| 712 | F | 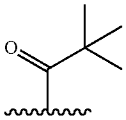 [SMILES: *C(=O)C(C)(C)C] | 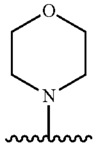 | 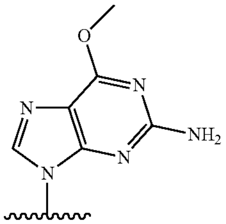 [SMILES: *n1cnc2c(OC)nc(N)nc21] |

TABLE 4-continued
(VI-1)
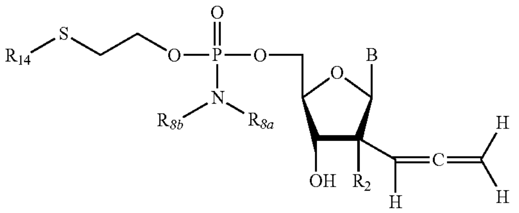
| Compound # | $R_2$ | $R_{14}$ | $NR_{8a}R_{8b}$ | B |
|---|---|---|---|---|
| 713 | OH | 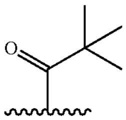 [SMILES: *C(=O)C(C)(C)C] | 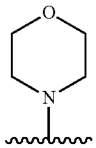 | 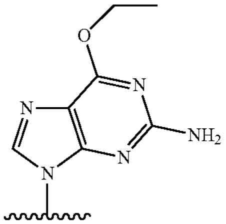 [SMILES: *n1cnc2c(OCC)nc(N)nc21] |
| 714 | F | 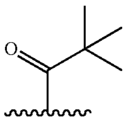 [SMILES: *C(=O)C(C)(C)C] | 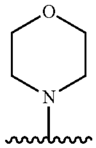 | 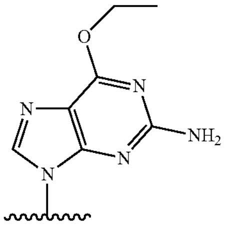 [SMILES: *n1cnc2c(OCC)nc(N)nc21] |
| 715 | OH | 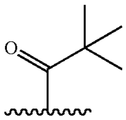 [SMILES: *C(=O)C(C)(C)C] | 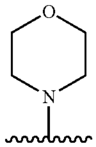 | 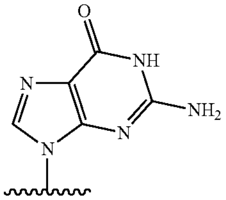 [SMILES: *n1cnc2c(=O)[nH]c(N)nc21] |
| 716 | F | 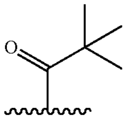 [SMILES: *C(=O)C(C)(C)C] | 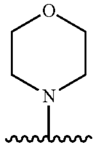 | 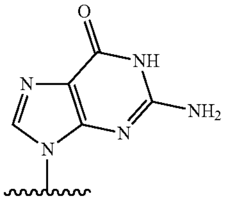 [SMILES: *n1cnc2c(=O)[nH]c(N)nc21] |
| 717 | OH | 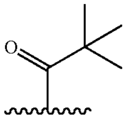 [SMILES: *C(=O)C(C)(C)C] | 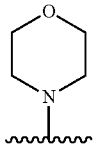 | 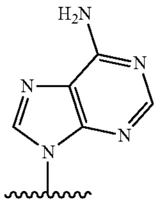 [SMILES: *n1cnc2c(N)ncnc21] |
| 718 | F | 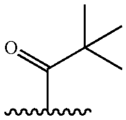 [SMILES: *C(=O)C(C)(C)C] | 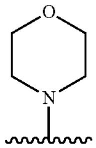 | 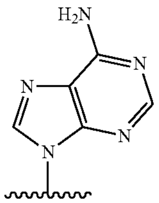 [SMILES: *n1cnc2c(N)ncnc21] |

TABLE 4-continued
(VI-1)
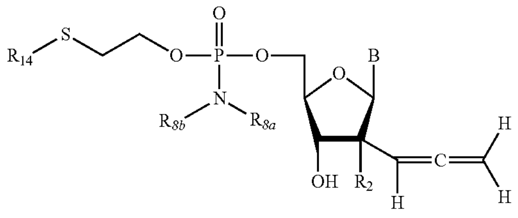
| Compound # | $R_2$ | $R_{14}$ | $NR_{8a}R_{8b}$ | B |
|---|---|---|---|---|
| 719 | OH | 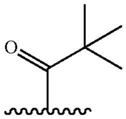 [SMILES: *C(=O)C(C)(C)C] | 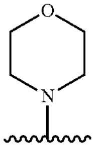 | 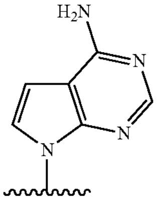 [SMILES: *n1ccc2c(N)ncnc21] |
| 720 | F | 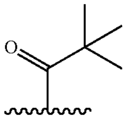 [SMILES: *C(=O)C(C)(C)C] | 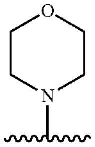 | 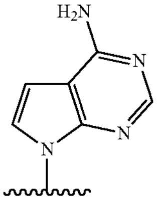 [SMILES: *n1ccc2c(N)ncnc21] |
| 721 | OH | 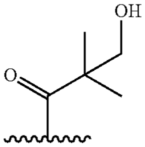 [SMILES: *C(=O)C(C)(C)CO] | 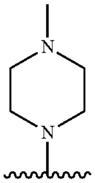 | 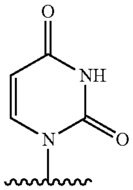 [SMILES: *n1ccc(=O)[nH]c1=O] |
| 722 | F | 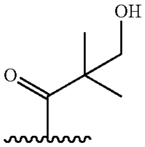 [SMILES: *C(=O)C(C)(C)CO] | 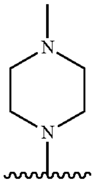 | 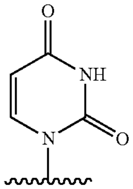 [SMILES: *n1ccc(=O)[nH]c1=O] |
| 723 | OH | 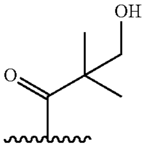 [SMILES: *C(=O)C(C)(C)CO] | 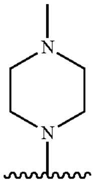 | 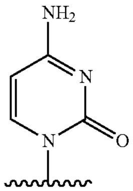 [SMILES: *n1ccc(N)nc1=O] |
| 724 | F | 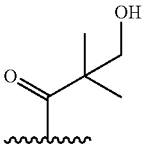 [SMILES: *C(=O)C(C)(C)CO] | 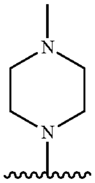 | 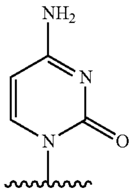 [SMILES: *n1ccc(N)nc1=O] |

TABLE 4-continued
(VI-1)
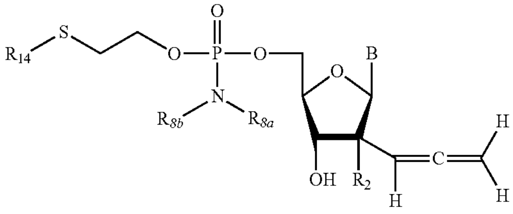
| Compound # | $R_2$ | $R_{14}$ | $NR_{8a}R_{8b}$ | B |
|---|---|---|---|---|
| 725 | OH | 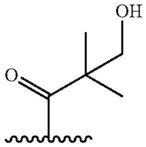 [SMILES: *C(=O)C(C)(C)CO] | 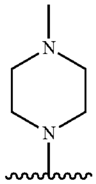 | 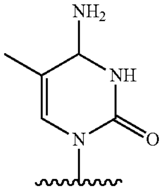 [SMILES: *N1C=C(C)C(N)NC1=O] |
| 726 | F | 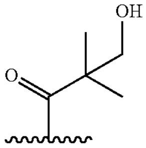 [SMILES: *C(=O)C(C)(C)CO] | 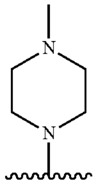 | 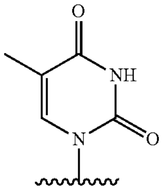 [SMILES: *n1cc(C)c(=O)[nH]c1=O] |
| 727 | OH | 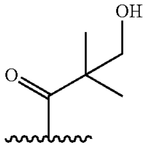 [SMILES: *C(=O)C(C)(C)CO] | 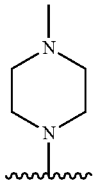 | 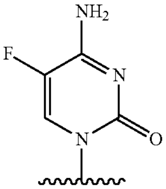 [SMILES: *n1cc(F)c(N)nc1=O] |
| 728 | F | 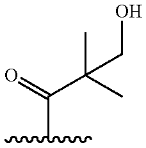 [SMILES: *C(=O)C(C)(C)CO] | 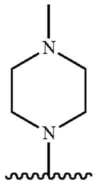 | 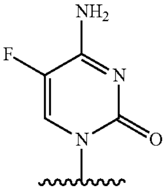 [SMILES: *n1cc(F)c(N)nc1=O] |
| 729 | OH | 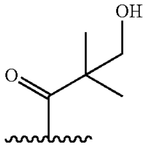 [SMILES: *C(=O)C(C)(C)CO] | 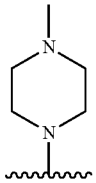 | 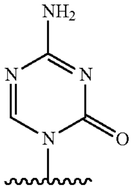 [SMILES: *n1cnc(N)nc1=O] |
| 730 | F | 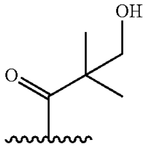 [SMILES: *C(=O)C(C)(C)CO] | 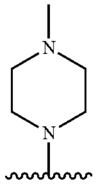 | 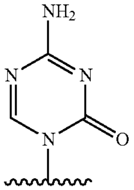 [SMILES: *n1cnc(N)nc1=O] |

TABLE 4-continued
(VI-1)
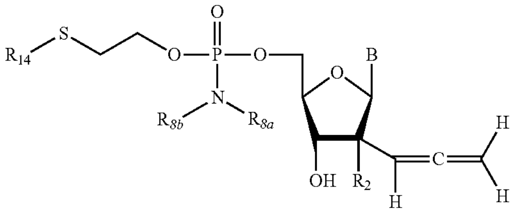
| Compound # | $R_2$ | $R_{14}$ | $NR_{8a}R_{8b}$ | B |
|---|---|---|---|---|
| 731 | OH | 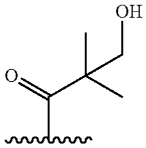 [SMILES: *C(=O)C(C)(C)CO] | 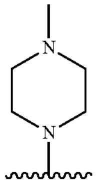 | 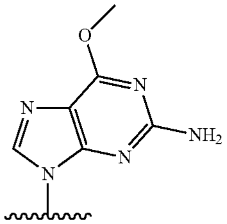 [SMILES: *n1cnc2c(OC)nc(N)nc21] |
| 732 | F | 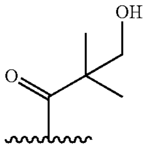 [SMILES: *C(=O)C(C)(C)CO] | 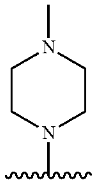 | 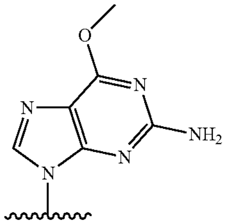 [SMILES: *n1cnc2c(OC)nc(N)nc21] |
| 733 | OH | 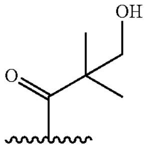 [SMILES: *C(=O)C(C)(C)CO] | 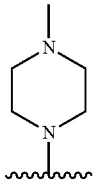 | 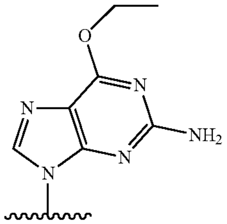 [SMILES: *n1cnc2c(OCC)nc(N)nc21] |
| 734 | F | 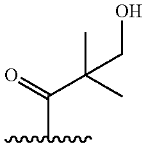 [SMILES: *C(=O)C(C)(C)CO] | 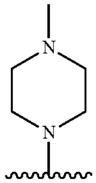 | 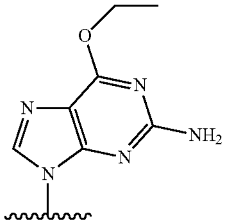 [SMILES: *n1cnc2c(OCC)nc(N)nc21] |
| 735 | OH | 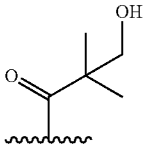 [SMILES: *C(=O)C(C)(C)CO] | 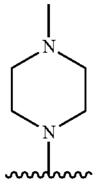 | 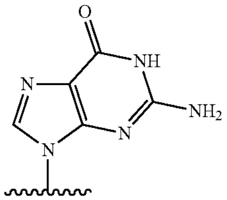 [SMILES: *n1cnc2c(=O)[nH]c(N)nc21] |
| 736 | F | 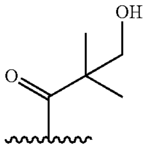 [SMILES: *C(=O)C(C)(C)CO] | 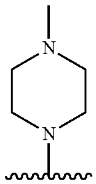 | 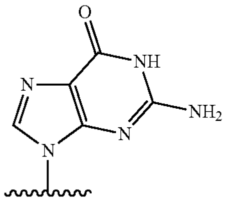 [SMILES: *n1cnc2c(=O)[nH]c(N)nc21] |

TABLE 4-continued
(VI-1)
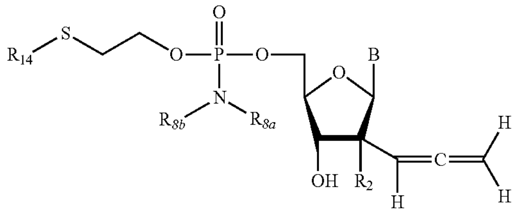
| Compound # | $R_2$ | $R_{14}$ | $NR_{8a}R_{8b}$ | B |
|---|---|---|---|---|
| 737 | OH | 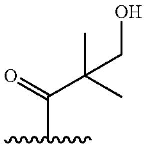 [SMILES: *C(=O)C(C)(C)CO] | 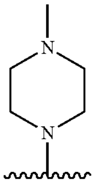 | 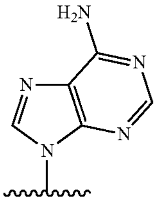 [SMILES: *n1cnc2c(N)ncnc21] |
| 738 | F | 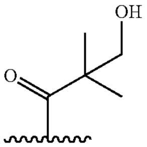 [SMILES: *C(=O)C(C)(C)CO] | 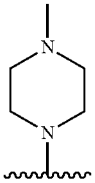 | 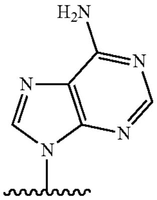 [SMILES: *n1cnc2c(N)ncnc21] |
| 739 | OH | 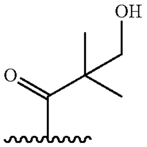 [SMILES: *C(=O)C(C)(C)CO] | 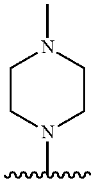 | 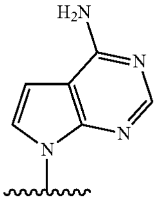 [SMILES: *n1ccc2c(N)ncnc21] |
| 740 | F | 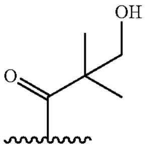 [SMILES: *C(=O)C(C)(C)CO] | 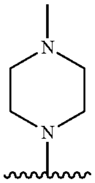 | 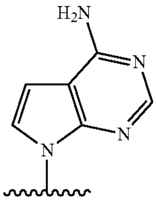 [SMILES: *n1ccc2c(N)ncnc21] |
| 741 | OH | 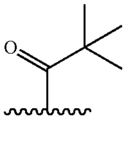 [SMILES: *C(=O)C(C)(C)C] | 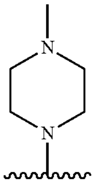 | 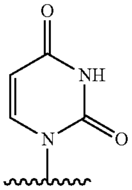 [SMILES: *n1ccc(=O)[nH]c1=O] |
| 742 | F | 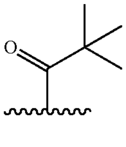 [SMILES: *C(=O)C(C)(C)C] | 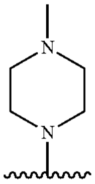 | 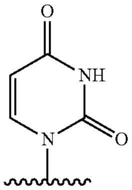 [SMILES: *n1ccc(=O)[nH]c1=O] |

TABLE 4-continued
(VI-1)
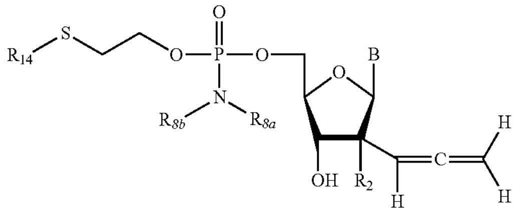
| Compound # | $R_2$ | $R_{14}$ | $NR_{8a}R_{8b}$ | B |
|---|---|---|---|---|
| 743 | OH | 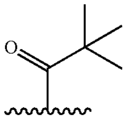 [SMILES: *C(=O)C(C)(C)C] | 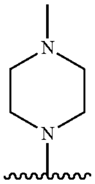 | 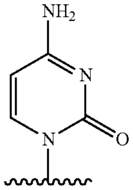 [SMILES: *n1ccc(N)nc1=O] |
| 744 | F | 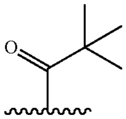 [SMILES: *C(=O)C(C)(C)C] | 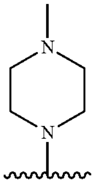 | 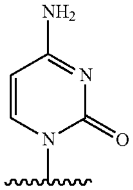 [SMILES: *n1ccc(N)nc1=O] |
| 745 | OH | 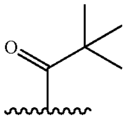 [SMILES: *C(=O)C(C)(C)C] | 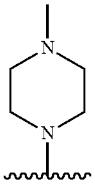 | 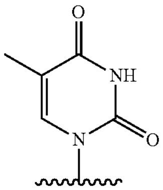 [SMILES: *n1cc(C)c(=O)[nH]c1=O] |
| 746 | F | 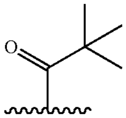 [SMILES: *C(=O)C(C)(C)C] | 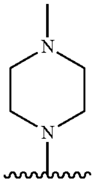 | 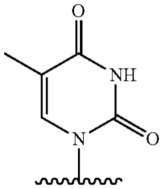 [SMILES: *n1cc(C)c(=O)[nH]c1=O] |
| 747 | OH | 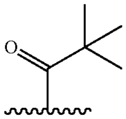 [SMILES: *C(=O)C(C)(C)C] | 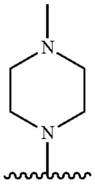 | 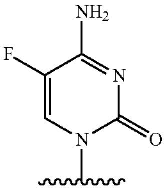 [SMILES: *n1cc(F)c(N)nc1=O] |
| 748 | F | 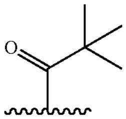 [SMILES: *C(=O)C(C)(C)C] | 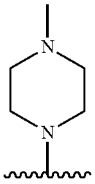 | 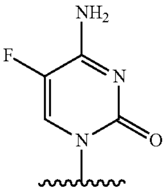 [SMILES: *n1cc(F)c(N)nc1=O] |

TABLE 4-continued
(VI-1)
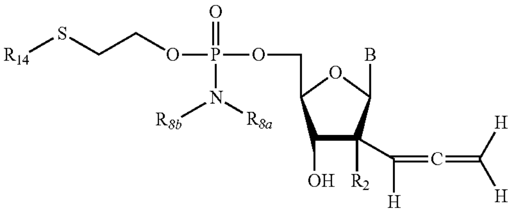
| Compound # | $R_2$ | $R_{14}$ | $NR_{8a}R_{8b}$ | B |
|---|---|---|---|---|
| 749 | OH | 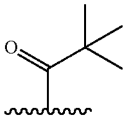 [SMILES: *C(=O)C(C)(C)C] | 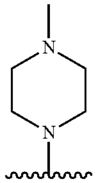 | 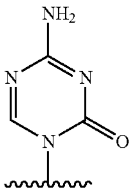 [SMILES: *n1cnc(N)nc1=O] |
| 750 | F | 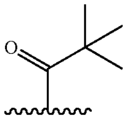 [SMILES: *C(=O)C(C)(C)C] | 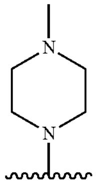 | 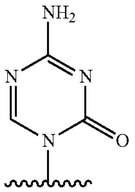 [SMILES: *n1cnc(N)nc1=O] |
| 751 | OH | 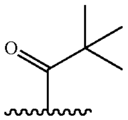 [SMILES: *C(=O)C(C)(C)C] | 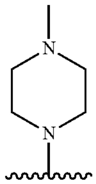 | 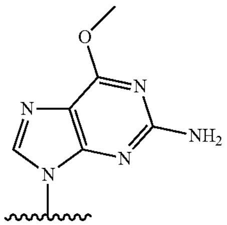 [SMILES: *n1cnc2c(OC)nc(N)nc21] |
| 752 | F | 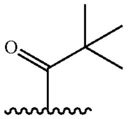 [SMILES: *C(=O)C(C)(C)C] | 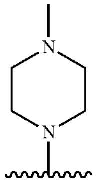 | 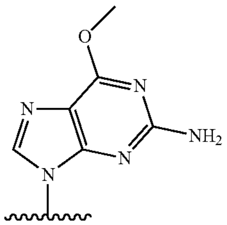 [SMILES: *n1cnc2c(OC)nc(N)nc21] |
| 753 | OH | 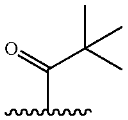 [SMILES: *C(=O)C(C)(C)C] | 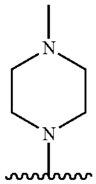 | 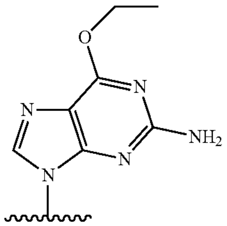 [SMILES: *n1cnc2c(OCC)nc(N)nc21] |
| 754 | F | 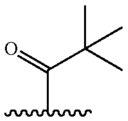 [SMILES: *C(=O)C(C)(C)C] | 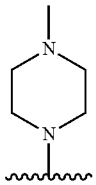 | 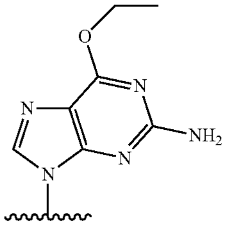 [SMILES: *n1cnc2c(OCC)nc(N)nc21] |

TABLE 4-continued
(VI-1)
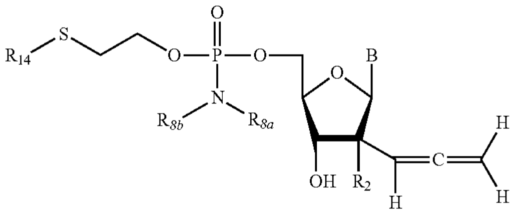
| Compound # | $R_2$ | $R_{14}$ | $NR_{8a}R_{8b}$ | B |
|---|---|---|---|---|
| 755 | OH | 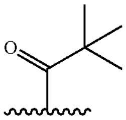 [SMILES: *C(=O)C(C)(C)C] | 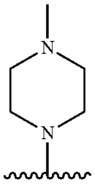 | 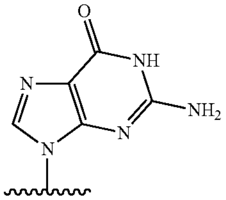 [SMILES: *n1cnc2c(=O)[nH]c(N)nc21] |
| 756 | F | 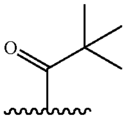 [SMILES: *C(=O)C(C)(C)C] | 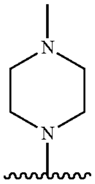 | 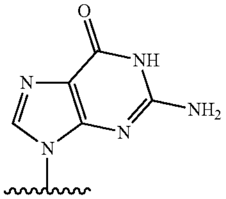 [SMILES: *n1cnc2c(=O)[nH]c(N)nc21] |
| 757 | OH | 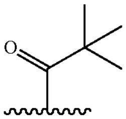 [SMILES: *C(=O)C(C)(C)C] | 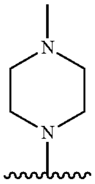 | 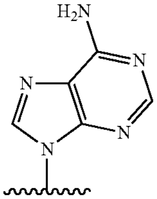 [SMILES: *n1cnc2c(N)ncnc21] |
| 758 | F | 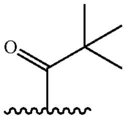 [SMILES: *C(=O)C(C)(C)C] | 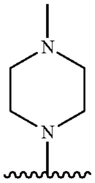 | 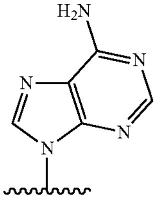 [SMILES: *n1cnc2c(N)ncnc21] |
| 759 | OH | 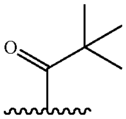 [SMILES: *C(=O)C(C)(C)C] | 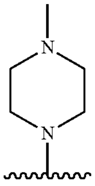 | 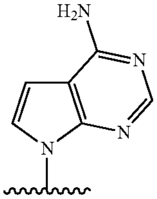 [SMILES: *n1ccc2c(N)ncnc21] |
| 760 | F | 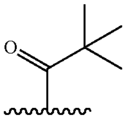 [SMILES: *C(=O)C(C)(C)C] | 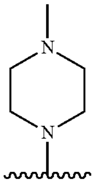 | 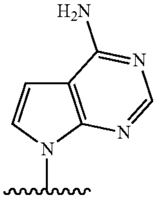 [SMILES: *n1ccc2c(N)ncnc21] |

TABLE 4-continued
(VI-1)
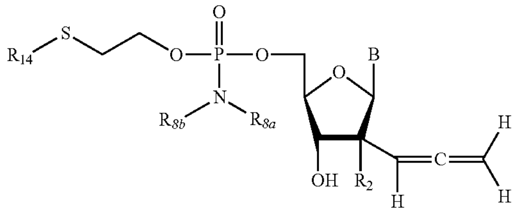
| Compound # | $R_2$ | $R_{14}$ | $NR_{8a}R_{8b}$ | B |
|---|---|---|---|---|
| 761 | OH | 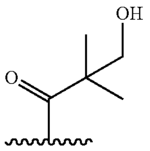 [SMILES: *C(=O)C(C)(C)CO] | 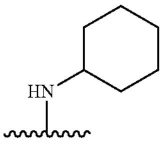 [SMILES: *NC1CCCCC1] | 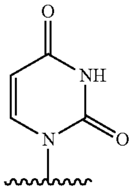 [SMILES: *n1ccc(=O)[nH]c1=O] |
| 762 | F | 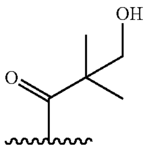 [SMILES: *C(=O)C(C)(C)CO] | 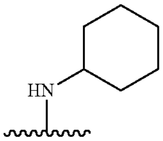 [SMILES: *NC1CCCCC1] | 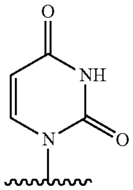 [SMILES: *n1ccc(=O)[nH]c1=O] |
| 763 | OH | 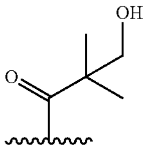 [SMILES: *C(=O)C(C)(C)CO] | 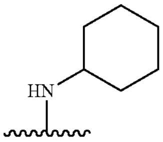 [SMILES: *NC1CCCCC1] | 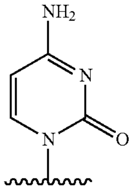 [SMILES: *n1ccc(N)nc1=O] |
| 764 | F | 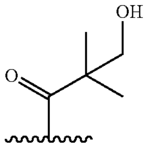 [SMILES: *C(=O)C(C)(C)CO] | 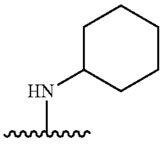 [SMILES: *NC1CCCCC1] | 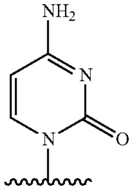 [SMILES: *n1ccc(N)nc1=O] |
| 765 | OH | 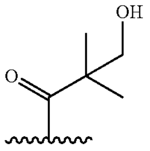 [SMILES: *C(=O)C(C)(C)CO] | 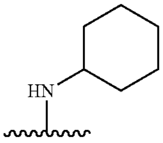 [SMILES: *NC1CCCCC1] | 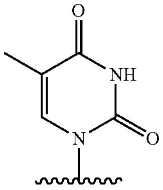 [SMILES: *n1cc(C)c(=O)[nH]c1=O] |
| 766 | F | 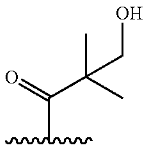 [SMILES: *C(=O)C(C)(C)CO] | 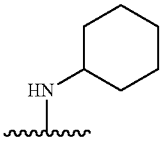 [SMILES: *NC1CCCCC1] | 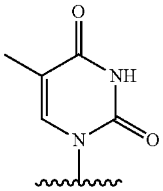 [SMILES: *n1cc(C)c(=O)[nH]c1=O] |

TABLE 4-continued
(VI-1)
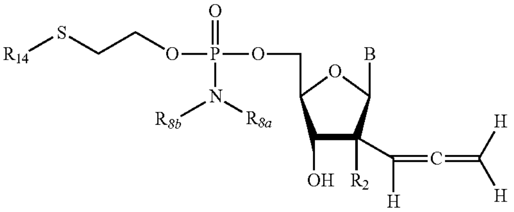
| Compound # | $R_2$ | $R_{14}$ | $NR_{8a}R_{8b}$ | B |
| --- | --- | --- | --- | --- |
| 767 | OH | 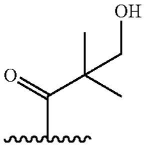 [SMILES: *C(=O)C(C)(C)CO] | 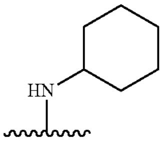 [SMILES: *NC1CCCCC1] | 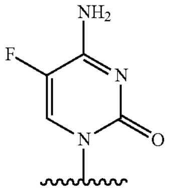 [SMILES: *n1cc(F)c(N)nc1=O] |
| 768 | F | 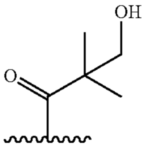 [SMILES: *C(=O)C(C)(C)CO] | 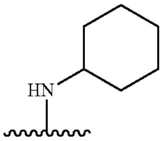 [SMILES: *NC1CCCCC1] | 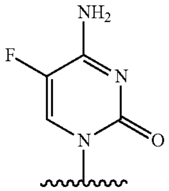 [SMILES: *n1cc(F)c(N)nc1=O] |
| 769 | OH | 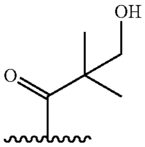 [SMILES: *C(=O)C(C)(C)CO] | 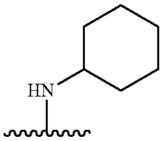 [SMILES: *NC1CCCCC1] | 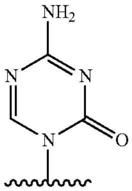 [SMILES: *n1cnc(N)nc1=O] |
| 770 | F | 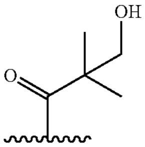 [SMILES: *C(=O)C(C)(C)CO] | 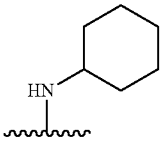 [SMILES: *NC1CCCCC1] | 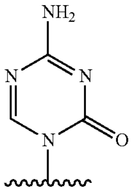 [SMILES: *n1cnc(N)nc1=O] |
| 771 | OH | 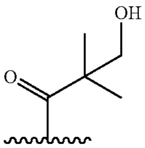 [SMILES: *C(=O)C(C)(C)CO] | 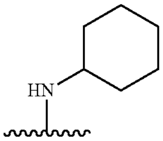 [SMILES: *NC1CCCCC1] | 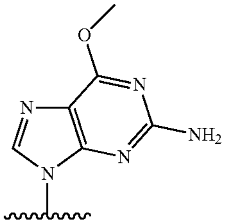 [SMILES: *n1cnc2c(OC)nc(N)nc21] |
| 772 | F | 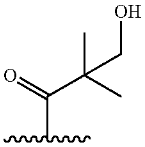 [SMILES: *C(=O)C(C)(C)CO] | 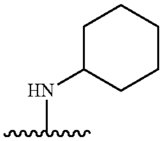 [SMILES: *NC1CCCCC1] | 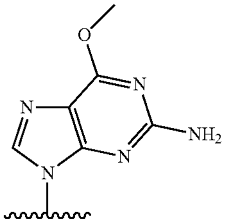 [SMILES: *n1cnc2c(OC)nc(N)nc21] |

TABLE 4-continued
(VI-1)
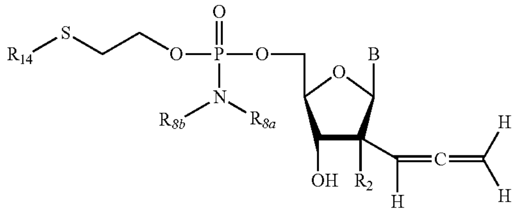
| Compound # | $R_2$ | $R_{14}$ | $NR_{8a}R_{8b}$ | B |
|---|---|---|---|---|
| 773 | OH | 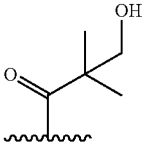 [SMILES: *C(=O)C(C)(C)CO] | 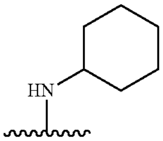 [SMILES: *NC1CCCCC1] | 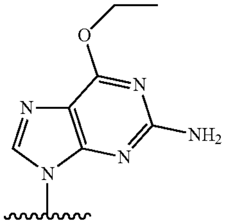 [SMILES: *n1cnc2c(OCC)nc(N)nc21] |
| 774 | F | 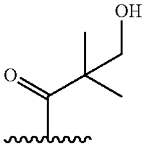 [SMILES: *C(=O)C(C)(C)CO] | 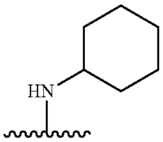 [SMILES: *NC1CCCCC1] | 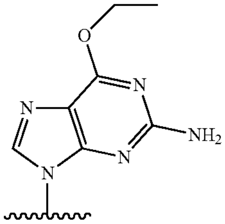 [SMILES: *n1cnc2c(OCC)nc(N)nc21] |
| 775 | OH | 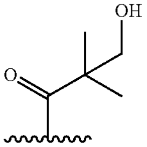 [SMILES: *C(=O)C(C)(C)CO] | 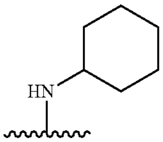 [SMILES: *NC1CCCCC1] | 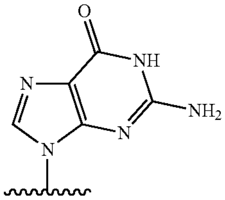 [SMILES: *n1cnc2c(=O)[nH]c(N)nc21] |
| 776 | F | 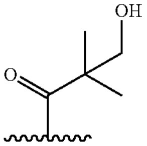 [SMILES: *C(=O)C(C)(C)CO] | 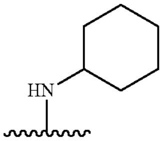 [SMILES: *NC1CCCCC1] | 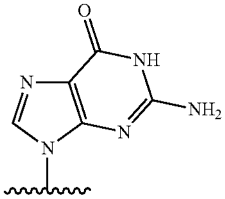 [SMILES: *n1cnc2c(=O)[nH]c(N)nc21] |
| 777 | OH | 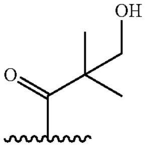 [SMILES: *C(=O)C(C)(C)CO] | 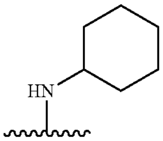 [SMILES: *NC1CCCCC1] | 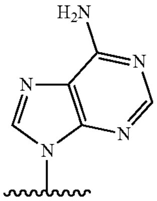 [SMILES: *n1cnc2c(N)ncnc21] |
| 778 | F | 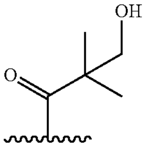 [SMILES: *C(=O)C(C)(C)CO] | 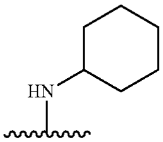 [SMILES: *NC1CCCCC1] | 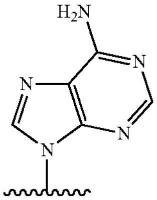 [SMILES: *n1cnc2c(N)ncnc21] |

TABLE 4-continued
(VI-1)
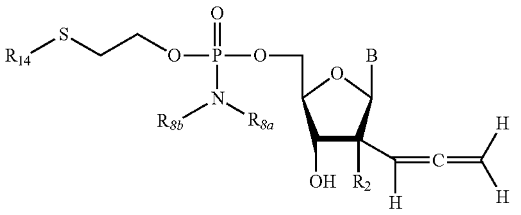
| Compound # | $R_2$ | $R_{14}$ | $NR_{8a}R_{8b}$ | B |
|---|---|---|---|---|
| 779 | OH | 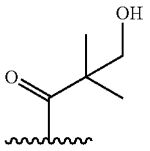 [SMILES: *C(=O)C(C)(C)CO] | 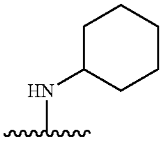 [SMILES: *NC1CCCCC1] | 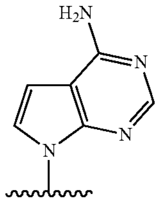 [SMILES: *n1ccc2c(N)ncnc21] |
| 780 | F | 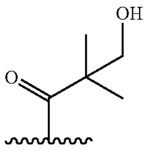 [SMILES: *C(=O)C(C)(C)CO] | 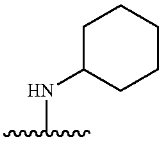 [SMILES: *NC1CCCCC1] | 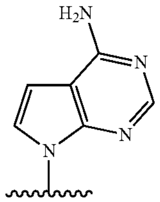 [SMILES: *n1ccc2c(N)ncnc21] |
| 781 | OH | 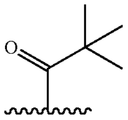 [SMILES: *C(=O)C(C)(C)C] | 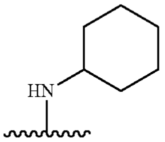 [SMILES: *NC1CCCCC1] | 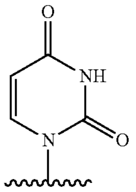 [SMILES: *n1ccc(=O)[nH]c1=O] |
| 782 | F | 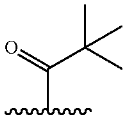 [SMILES: *C(=O)C(C)(C)C] | 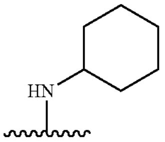 [SMILES: *NC1CCCCC1] | 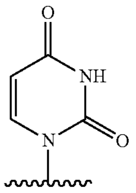 [SMILES: *n1ccc(=O)[nH]c1=O] |
| 783 | OH | 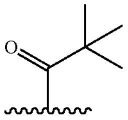 [SMILES: *C(=O)C(C)(C)C] | 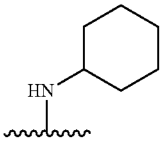 [SMILES: *NC1CCCCC1] | 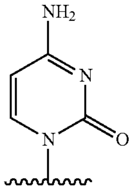 [SMILES: *n1ccc(N)nc1=O] |
| 784 | F | 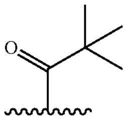 [SMILES: *C(=O)C(C)(C)C] | 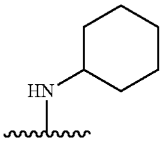 [SMILES: *NC1CCCCC1] | 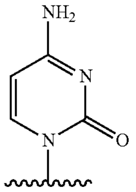 [SMILES: *n1ccc(N)nc1=O] |

TABLE 4-continued
(VI-1)
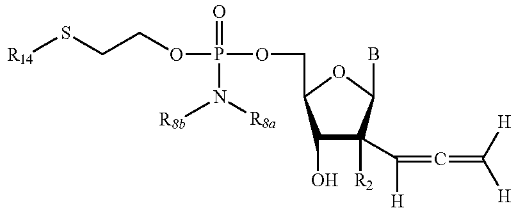
| Compound # | $R_2$ | $R_{14}$ | $NR_{8a}R_{8b}$ | B |
|---|---|---|---|---|
| 785 | OH | 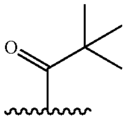 [SMILES: *C(=O)C(C)(C)C] | 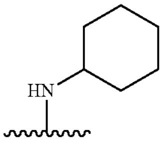 [SMILES: *NC1CCCCC1] | 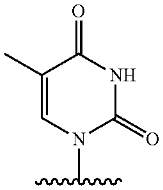 [SMILES: *n1cc(C)c(=O)[nH]c1=O] |
| 786 | F | 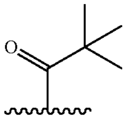 [SMILES: *C(=O)C(C)(C)C] | 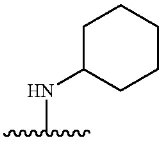 [SMILES: *NC1CCCCC1] | 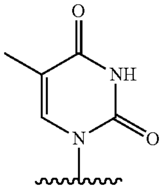 [SMILES: *n1cc(C)c(=O)[nH]c1=O] |
| 787 | OH | 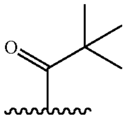 [SMILES: *C(=O)C(C)(C)C] | 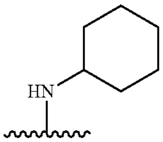 [SMILES: *NC1CCCCC1] | 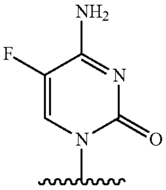 [SMILES: *n1cc(F)c(N)nc1=O] |
| 788 | F | 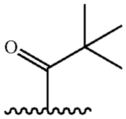 [SMILES: *C(=O)C(C)(C)C] | 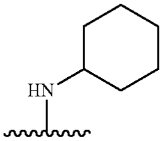 [SMILES: *NC1CCCCC1] | 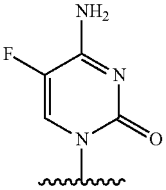 [SMILES: *n1cc(F)c(N)nc1=O] |
| 789 | OH | 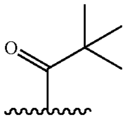 [SMILES: *C(=O)C(C)(C)C] | 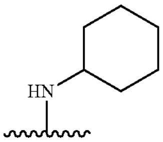 [SMILES: *NC1CCCCC1] | 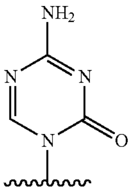 [SMILES: *n1cnc(N)nc1=O] |
| 790 | F | 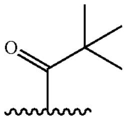 [SMILES: *C(=O)C(C)(C)C] | 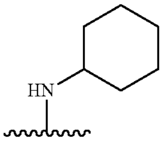 [SMILES: *NC1CCCCC1] | 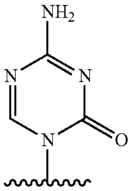 [SMILES: *n1cnc(N)nc1=O] |

TABLE 4-continued
(VI-1)
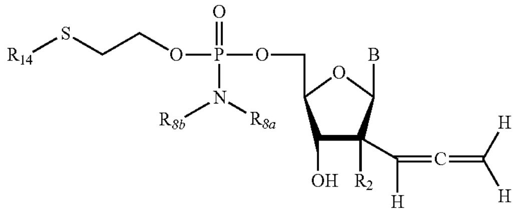
| Compound # | $R_2$ | $R_{14}$ | $NR_{8a}R_{8b}$ | B |
|---|---|---|---|---|
| 791 | OH | 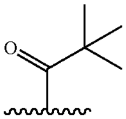 [SMILES: *C(=O)C(C)(C)C] | 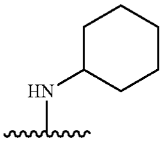 [SMILES: *NC1CCCCC1] | 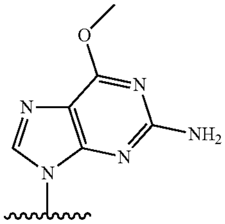 [SMILES: *n1cnc2c(OC)nc(N)nc21] |
| 792 | F | 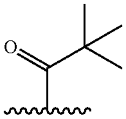 [SMILES: *C(=O)C(C)(C)C] | 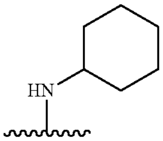 [SMILES: *NC1CCCCC1] | 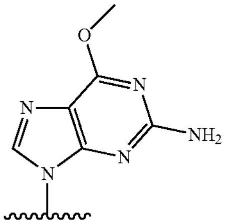 [SMILES: *n1cnc2c(OC)nc(N)nc21] |
| 793 | OH | 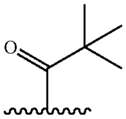 [SMILES: *C(=O)C(C)(C)C] | 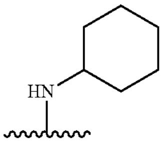 [SMILES: *NC1CCCCC1] | 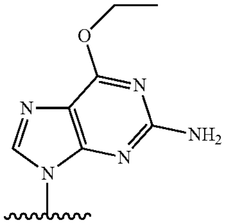 [SMILES: *n1cnc2c(OCC)nc(N)nc21] |
| 794 | F | 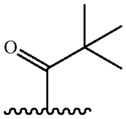 [SMILES: *C(=O)C(C)(C)C] | 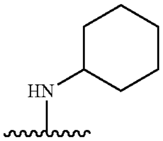 [SMILES: *NC1CCCCC1] | 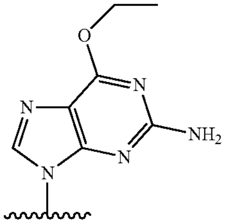 [SMILES: *n1cnc2c(OCC)nc(N)nc21] |
| 795 | OH | 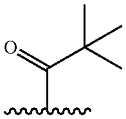 [SMILES: *C(=O)C(C)(C)C] | 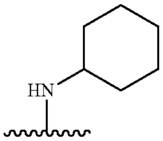 [SMILES: *NC1CCCCC1] | 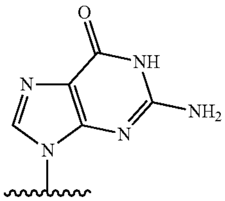 [SMILES: *n1cnc2c(=O)[nH]c(N)nc21] |
| 796 | F | 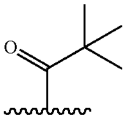 [SMILES: *C(=O)C(C)(C)C] | 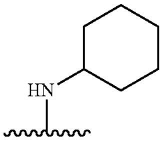 [SMILES: *NC1CCCCC1] | 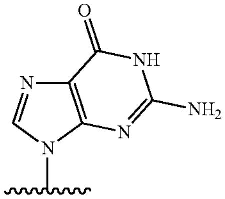 [SMILES: *n1cnc2c(=O)[nH]c(N)nc21] |

TABLE 4-continued
(VI-1)
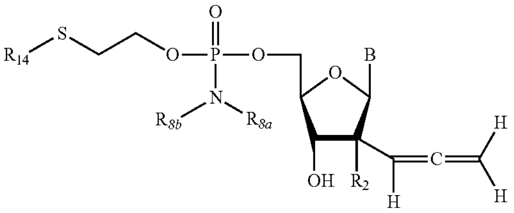
| Compound # | $R_2$ | $R_{14}$ | $NR_{8a}R_{8b}$ | B |
|---|---|---|---|---|
| 797 | OH | 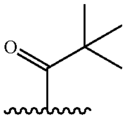 | 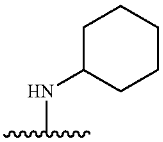 [SMILES: *NC1CCCCC1] | 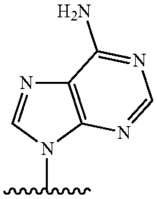 [SMILES: *n1cnc2c(N)ncnc21] |
| 798 | F | 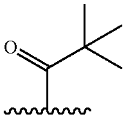 [SMILES: *C(=O)C(C)(C)C] | 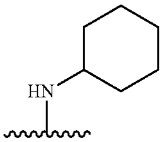 [SMILES: *NC1CCCCC1] | 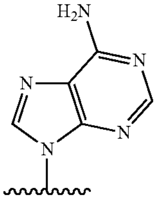 [SMILES: *n1cnc2c(N)ncnc21] |
| 799 | OH | 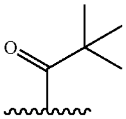 [SMILES: *C(=O)C(C)(C)C] | 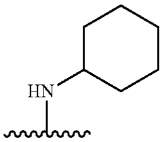 [SMILES: *NC1CCCCC1] | 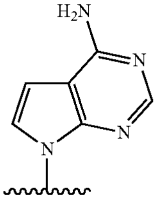 [SMILES: *n1ccc2c(N)ncnc21] |
| 800 | F | 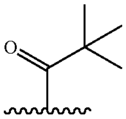 [SMILES: *C(=O)C(C)(C)C] | 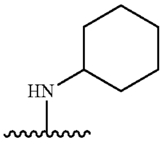 [SMILES: *NC1CCCCC1] | 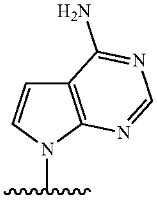 [SMILES: *n1ccc2c(N)ncnc21] |
and
(e) compounds represented by Formula (VII-1) wherein $R_2$, $R_{2b}$, $R_{2c}$, $R_6$, and B are delineated for each compound in Table 5

TABLE 5
(VII-1)
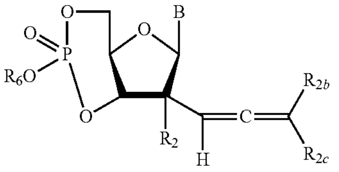
| Compound # | $R_6$ | $R_{2b}$ | $R_{2c}$ | $R_2$ | B |
|---|---|---|---|---|---|
| 801 | i-Pr | H | H | OH | 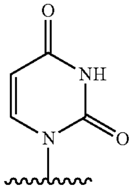 [SMILES: *n1ccc(=O)[nH]c1=O] |
| 802 | i-Pr | H | H | F | 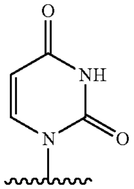 [SMILES: *n1ccc(=O)[nH]c1=O] |
| 803 | i-Pr | Me | Me | OH | 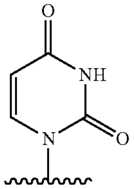 [SMILES: *n1ccc(=O)[nH]c1=O] |
| 804 | i-Pr | Me | Me | F | 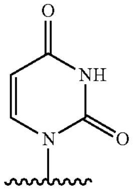 [SMILES: *n1ccc(=O)[nH]c1=O] |
| 805 | i-Pr | F | F | OH | 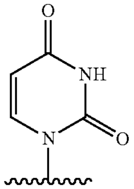 [SMILES: *n1ccc(=O)[nH]c1=O] |
| 806 | i-Pr | F | F | F | 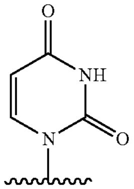 [SMILES: *n1ccc(=O)[nH]c1=O] |
| 807 | i-Pr | H | H | OH | 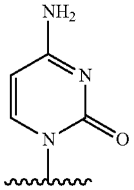 [SMILES: *n1ccc(N)nc1=O] |
TABLE 5-continued
(VII-1)
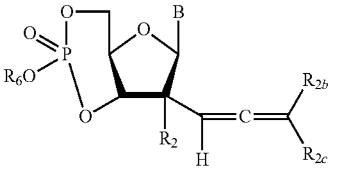
| Compound # | $R_6$ | $R_{2b}$ | $R_{2c}$ | $R_2$ | B |
|---|---|---|---|---|---|
| 808 | i-Pr | H | H | F | 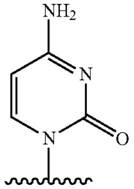 |
| 809 | i-Pr | Me | Me | OH | 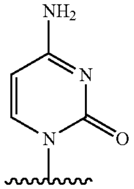 [SMILES: *n1ccc(N)nc1=O] |
| 810 | i-Pr | Me | Me | F | 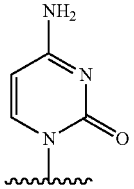 [SMILES: *n1ccc(N)nc1=O] |
| 811 | i-Pr | F | F | OH | 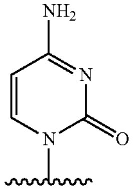 [SMILES: *n1ccc(N)nc1=O] |
| 812 | i-Pr | F | F | F | 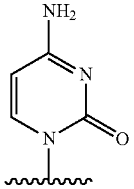 [SMILES: *n1ccc(N)nc1=O] |
| 813 | i-Pr | H | H | OH | 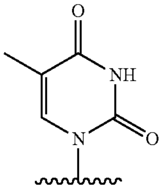 [SMILES: *n1cc(C)c(=O)[nH]c1=O] |
| 814 | i-Pr | H | H | F | 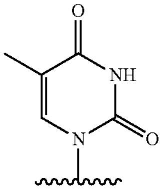 |

TABLE 5-continued
(VII-1)
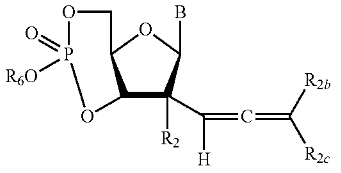
| Compound # | $R_6$ | $R_{2b}$ | $R_{2c}$ | $R_2$ | B |
|---|---|---|---|---|---|
| 815 | i-Pr | Me | Me | OH | 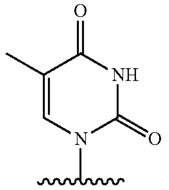 [SMILES: *n1cc(C)c(=O)[nH]c1=O] |
| 816 | i-Pr | Me | Me | F | 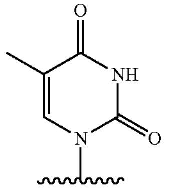 [SMILES: *n1cc(C)c(=O)[nH]c1=O] |
| 817 | i-Pr | F | F | OH | 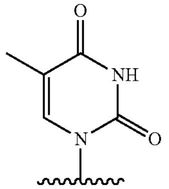 [SMILES: *n1cc(C)c(=O)[nH]c1=O] |
| 818 | i-Pr | F | F | F | 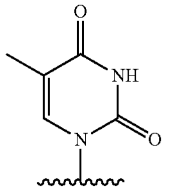 [SMILES: *n1cc(C)c(=O)[nH]c1=O] |
| 819 | i-Pr | H | H | OH | 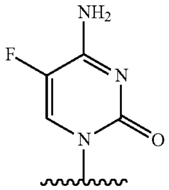 |
| 820 | i-Pr | H | H | F | 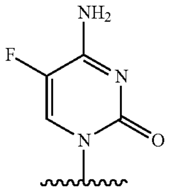 |
| 821 | i-Pr | Me | Me | OH | 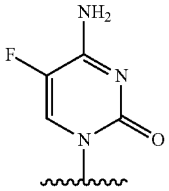 |
TABLE 5-continued
(VII-1)
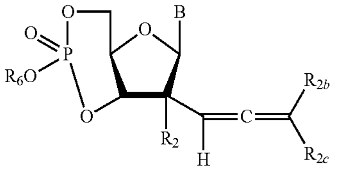
| Compound # | $R_6$ | $R_{2b}$ | $R_{2c}$ | $R_2$ | B |
|---|---|---|---|---|---|
| 822 | i-Pr | Me | Me | F | 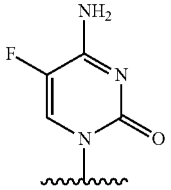 |
| 823 | i-Pr | F | F | OH | 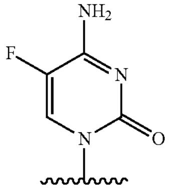 |
| 824 | i-Pr | F | F | F | 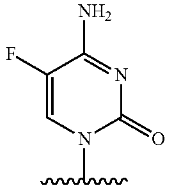 |
| 825 | i-Pr | H | H | OH | 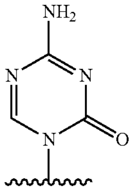 [SMILES: *n1cnc(N)nc1=O] |
| 826 | i-Pr | H | H | F | 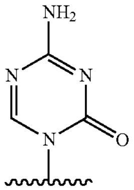 [SMILES: *n1cnc(N)nc1=O] |
| 827 | i-Pr | Me | Me | OH | 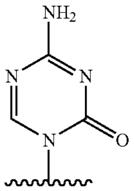 [SMILES: *n1cnc(N)nc1=O] |
| 828 | i-Pr | Me | Me | F | 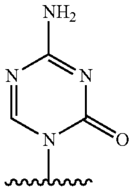 [SMILES: *n1cnc(N)nc1=O] |

TABLE 5-continued
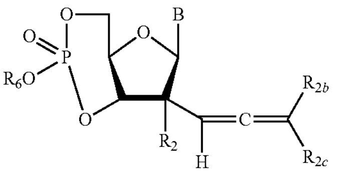
(VII-1)
| Compound # | $R_6$ | $R_{2b}$ | $R_{2c}$ | $R_2$ | B |
|---|---|---|---|---|---|
| 829 | i-Pr | F | F | OH | 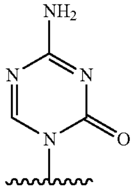 [SMILES: *n1cnc(N)nc1=O] |
| 830 | i-Pr | F | F | F | 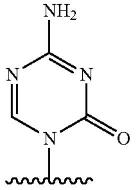 [SMILES: *n1cnc(N)nc1=O] |
| 831 | i-Pr | H | H | OH | 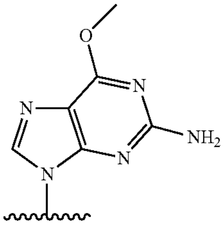 [SMILES: *n1cnc2c(OC)nc(N)nc21] |
| 832 | i-Pr | H | H | F | 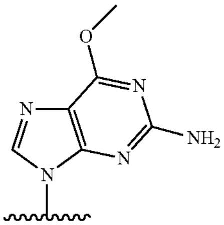 [SMILES: *n1cnc2c(OC)nc(N)nc21] |
| 833 | i-Pr | Me | Me | OH | 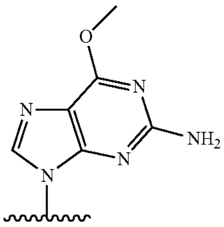 [SMILES: *n1cnc2c(OC)nc(N)nc21] |
| 834 | i-Pr | Me | Me | F | 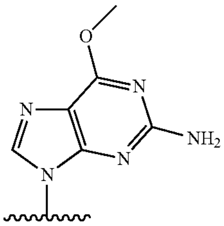 [SMILES: *n1cnc2c(OC)nc(N)nc21] |
TABLE 5-continued
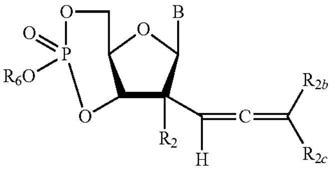
(VII-1)
| Compound # | $R_6$ | $R_{2b}$ | $R_{2c}$ | $R_2$ | B |
|---|---|---|---|---|---|
| 835 | i-Pr | F | F | OH | 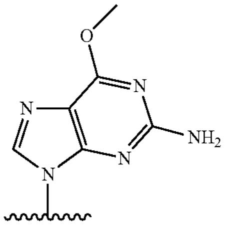 [SMILES: *n1cnc2c(OC)nc(N)nc21] |
| 836 | i-Pr | F | F | F | 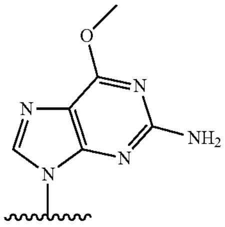 [SMILES: *n1cnc2c(OC)nc(N)nc21] |
| 837 | i-Pr | H | H | OH | 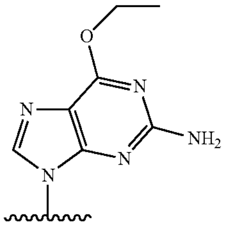 [SMILES: *n1cnc2c(OCC)nc(N)nc21] |
| 838 | i-Pr | H | H | F | 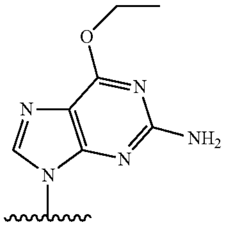 [SMILES: *n1cnc2c(OCC)nc(N)nc21] |
| 839 | i-Pr | Me | Me | OH | 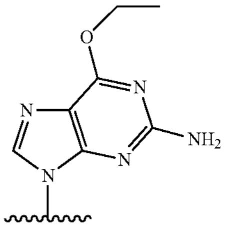 [SMILES: *n1cnc2c(OCC)nc(N)nc21] |
| 840 | i-Pr | Me | Me | F | 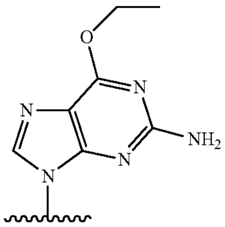 |

TABLE 5-continued
(VII-1)
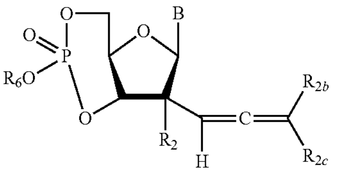
| Compound # | $R_6$ | $R_{2b}$ | $R_{2c}$ | $R_2$ | B |
|---|---|---|---|---|---|
| 841 | i-Pr | F | F | OH | 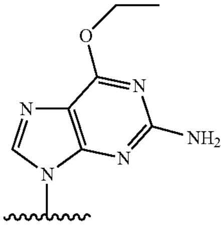 [SMILES: *n1cnc2c(OCC)nc(N)nc21] |
| 842 | i-Pr | F | F | F | 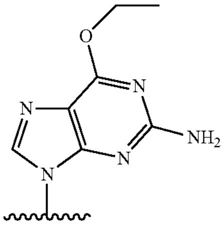 [SMILES: *n1cnc2c(OCC)nc(N)nc21] |
| 843 | i-Pr | H | H | OH | 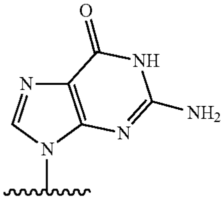 [SMILES: *n1cnc2c(=O)[nH]c(N)nc21] |
| 844 | i-Pr | H | H | F | 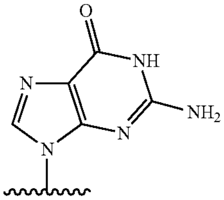 [SMILES: *n1cnc2c(=O)[nH]c(N)nc21] |
| 845 | i-Pr | Me | Me | OH | 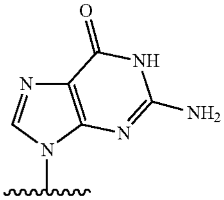 [SMILES: *n1cnc2c(=O)[nH]c(N)nc21] |
| 846 | i-Pr | Me | Me | F | 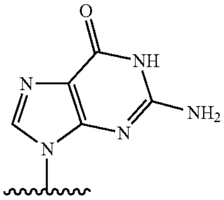 [SMILES: *n1cnc2c(=O)[nH]c(N)nc21] |
TABLE 5-continued
(VII-1)
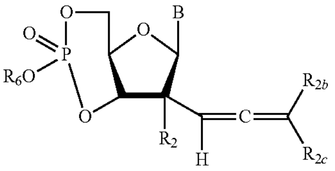
| Compound # | $R_6$ | $R_{2b}$ | $R_{2c}$ | $R_2$ | B |
|---|---|---|---|---|---|
| 847 | i-Pr | F | F | OH | 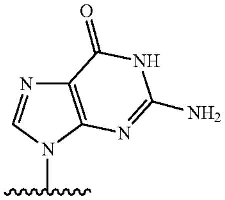 [SMILES: *n1cnc2c(=O)[nH]c(N)nc21] |
| 848 | i-Pr | F | F | F | 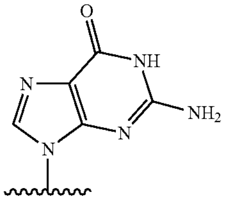 [SMILES: *n1cnc2c(=O)[nH]c(N)nc21] |
| 849 | i-Pr | H | H | OH | 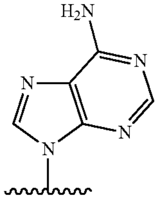 [SMILES: *n1cnc2c(N)ncnc21] |
| 850 | i-Pr | H | H | F | 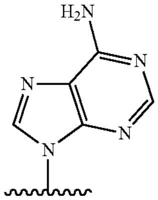 [SMILES: *n1cnc2c(N)ncnc21] |
| 851 | i-Pr | Me | Me | OH | 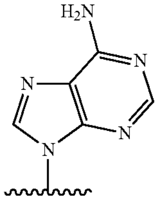 [SMILES: *n1cnc2c(N)ncnc21] |
| 852 | i-Pr | Me | Me | F | 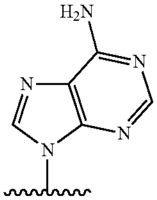 |

TABLE 5-continued
(VII-1)
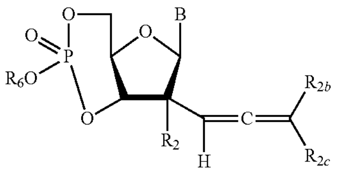
| Compound # | $R_6$ | $R_{2b}$ | $R_{2c}$ | $R_2$ | B |
|---|---|---|---|---|---|
| 853 | i-Pr | F | F | OH | 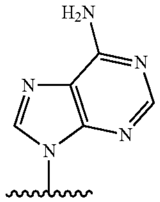 [SMILES: *n1cnc2c(N)ncnc21] |
| 854 | i-Pr | F | F | F | 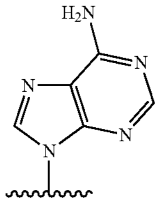 [SMILES: *n1cnc2c(N)ncnc21] |
| 855 | i-Pr | H | H | OH | 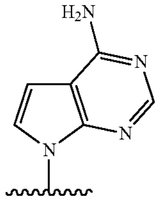 [SMILES: *n1ccc2c(N)ncnc21] |
| 856 | i-Pr | H | H | F | 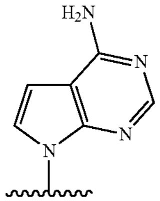 [SMILES: *n1ccc2c(N)ncnc21] |
| 857 | i-Pr | Me | Me | OH | 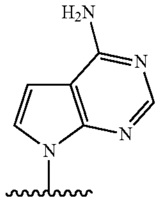 [SMILES: *n1ccc2c(N)ncnc21] |
| 858 | i-Pr | Me | Me | F | 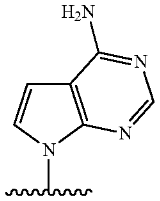 [SMILES: *n1ccc2c(N)ncnc21] |
TABLE 5-continued
(VII-1)
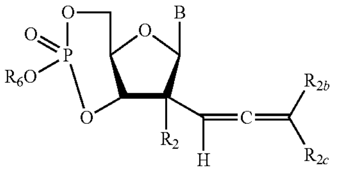
| Compound # | $R_6$ | $R_{2b}$ | $R_{2c}$ | $R_2$ | B |
|---|---|---|---|---|---|
| 859 | i-Pr | F | F | OH | 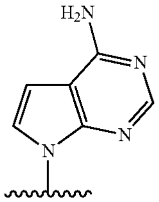 [SMILES: *n1ccc2c(N)ncnc21] |
| 860 | i-Pr | F | F | F | 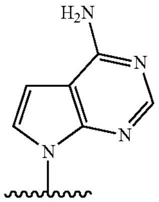 [SMILES: *n1ccc2c(N)ncnc21] |
| 861 | Et | H | H | OH | 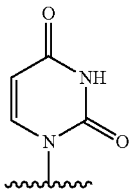 [SMILES: *n1ccc(=O)[nH]c1=O] |
| 862 | Et | H | H | F | 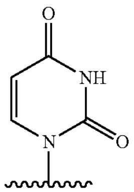 [SMILES: *n1ccc(=O)[nH]c1=O] |
| 863 | Et | Me | Me | OH | 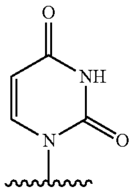 [SMILES: *n1ccc(=O)[nH]c1=O] |
| 864 | Et | Me | Me | F | 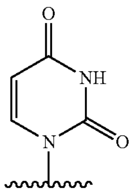 [SMILES: *n1ccc(=O)[nH]c1=O] |

TABLE 5-continued
(VII-1)
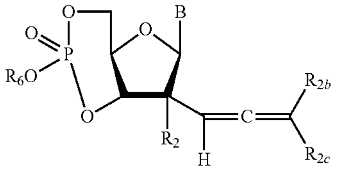
| Compound # | $R_6$ | $R_{2b}$ | $R_{2c}$ | $R_2$ | B |
|---|---|---|---|---|---|
| 865 | Et | F | F | OH | 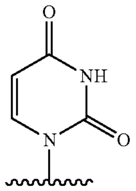 [SMILES: *n1ccc(=O)[nH]c1=O] |
| 866 | Et | F | F | F | 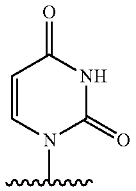 [SMILES: *n1ccc(=O)[nH]c1=O] |
| 867 | Et | H | H | OH | 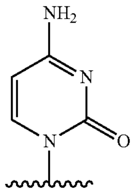 [SMILES: *n1ccc(N)nc1=O] |
| 868 | Et | H | H | F | 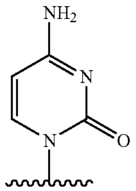 [SMILES: *n1ccc(N)nc1=O] |
| 869 | Et | Me | Me | OH | 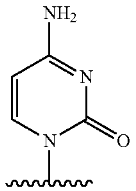 [SMILES: *n1ccc(N)nc1=O] |
| 870 | Et | Me | Me | F | 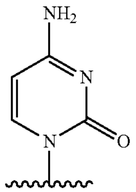 [SMILES: *n1ccc(N)nc1=O] |
| 871 | Et | F | F | OH | 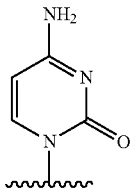 [SMILES: *n1ccc(N)nc1=O] |
TABLE 5-continued
(VII-1)
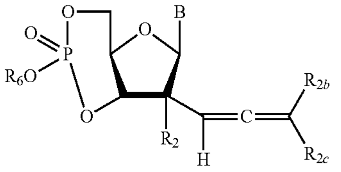
| Compound # | $R_6$ | $R_{2b}$ | $R_{2c}$ | $R_2$ | B |
|---|---|---|---|---|---|
| 872 | Et | F | F | F | 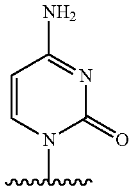 [SMILES: *n1ccc(N)nc1=O] |
| 873 | Et | H | H | OH | 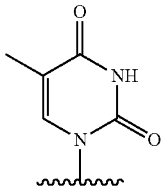 [SMILES: *n1cc(C)c(=O)[nH]c1=O] |
| 874 | Et | H | H | F | 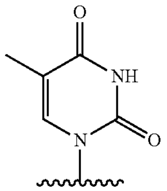 [SMILES: *n1cc(C)c(=O)[nH]c1=O] |
| 875 | Et | Me | Me | OH | 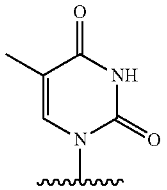 [SMILES: *n1cc(C)c(=O)[nH]c1=O] |
| 876 | Et | Me | Me | F | 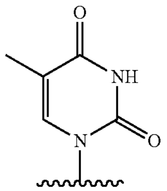 [SMILES: *n1cc(C)c(=O)[nH]c1=O] |
| 877 | Et | F | F | OH | 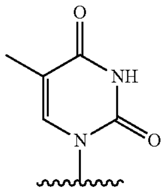 [SMILES: *n1cc(C)c(=O)[nH]c1=O] |
| 878 | Et | F | F | F | 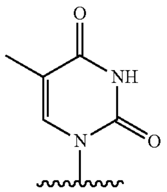 [SMILES: *n1cc(C)c(=O)[nH]c1=O] |

TABLE 5-continued
(VII-1)
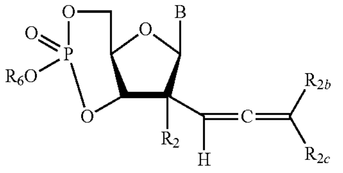
| Compound # | $R_6$ | $R_{2b}$ | $R_{2c}$ | $R_2$ | B |
|---|---|---|---|---|---|
| 879 | Et | H | H | OH | 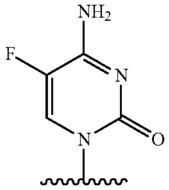 |
| 880 | Et | H | H | F | 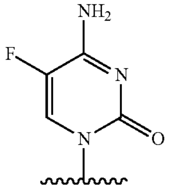 |
| 881 | Et | Me | Me | OH | 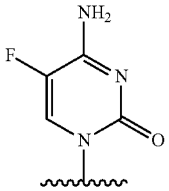 |
| 882 | Et | Me | Me | F | 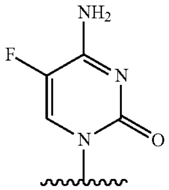 |
| 883 | Et | F | F | OH | 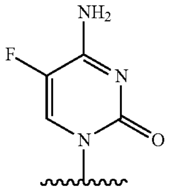 |
| 884 | Et | F | F | F | 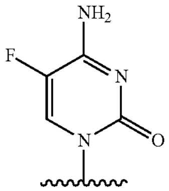 |
| 885 | Et | H | H | OH | 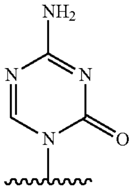 [SMILES: *n1cnc(N)nc1=O] |
TABLE 5-continued
(VII-1)
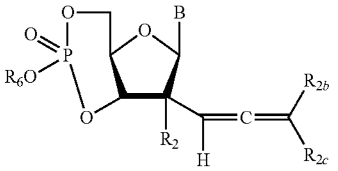
| Compound # | $R_6$ | $R_{2b}$ | $R_{2c}$ | $R_2$ | B |
|---|---|---|---|---|---|
| 886 | Et | H | H | F | 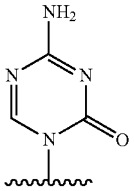 [SMILES: *n1cnc(N)nc1=O] |
| 887 | Et | Me | Me | OH | 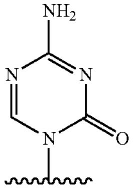 [SMILES: *n1cnc(N)nc1=O] |
| 888 | Et | Me | Me | F | 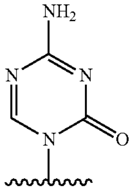 [SMILES: *n1cnc(N)nc1=O] |
| 889 | Et | F | F | OH | 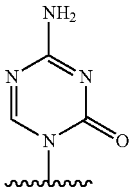 [SMILES: *n1cnc(N)nc1=O] |
| 890 | Et | F | F | F | 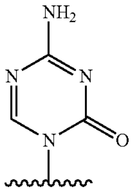 [SMILES: *n1cnc(N)nc1=O] |
| 891 | Et | H | H | OH | 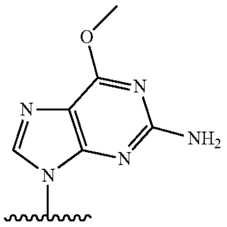 [SMILES: *n1cnc2c(OC)nc(N)nc21] |

TABLE 5-continued
(VII-1)
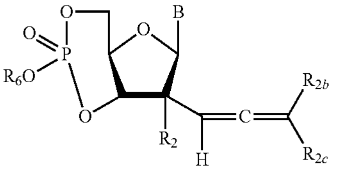
| Compound # | $R_6$ | $R_{2b}$ | $R_{2c}$ | $R_2$ | B |
|---|---|---|---|---|---|
| 892 | Et | H | H | F | 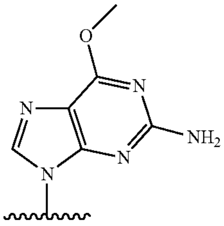 |
| 893 | Et | Me | Me | OH | 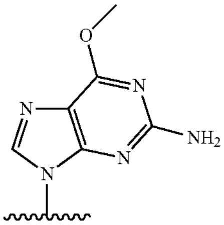 [SMILES: *n1cnc2c(OC)nc(N)nc21] |
| 894 | Et | Me | Me | F | 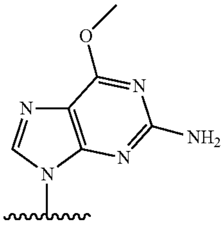 [SMILES: *n1cnc2c(OC)nc(N)nc21] |
| 895 | Et | F | F | OH | 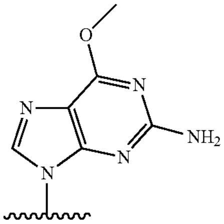 [SMILES: *n1cnc2c(OC)nc(N)nc21] |
| 896 | Et | F | F | F | 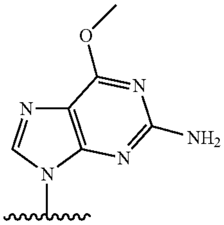 [SMILES: *n1cnc2c(OC)nc(N)nc21] |
| 897 | Et | H | H | OH | 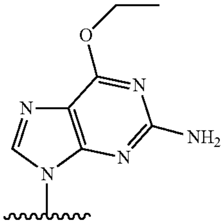 [SMILES: *n1cnc2c(OCC)nc(N)nc21] |
TABLE 5-continued
(VII-1)
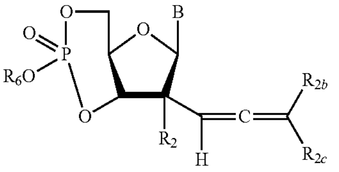
| Compound # | $R_6$ | $R_{2b}$ | $R_{2c}$ | $R_2$ | B |
|---|---|---|---|---|---|
| 898 | Et | H | H | F | 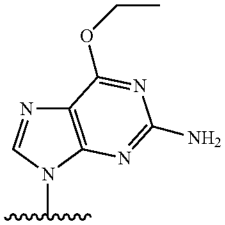 [SMILES: *n1cnc2c(OCC)nc(N)nc21] |
| 899 | Et | Me | Me | OH | 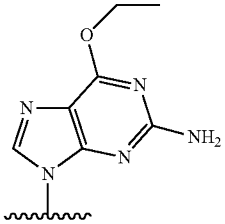 [SMILES: *n1cnc2c(OCC)nc(N)nc21] |
| 900 | Et | Me | Me | F | 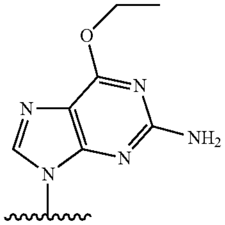 [SMILES: *n1cnc2c(OCC)nc(N)nc21] |
| 901 | Et | F | F | OH | 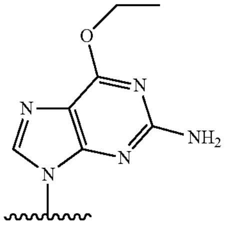 [SMILES: *n1cnc2c(OCC)nc(N)nc21] |
| 902 | Et | F | F | F | 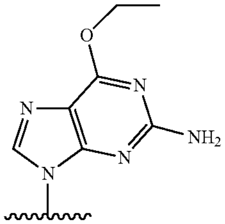 [SMILES: *n1cnc2c(OCC)nc(N)nc21] |
| 903 | Et | H | H | OH | 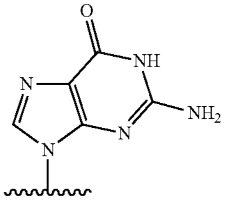 [SMILES: *n1cnc2c(=O)[nH]c(N)nc21] |

TABLE 5-continued
(VII-1)
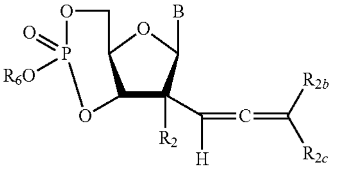
| Compound # | $R_6$ | $R_{2b}$ | $R_{2c}$ | $R_2$ | B |
|---|---|---|---|---|---|
| 904 | Et | H | H | F | 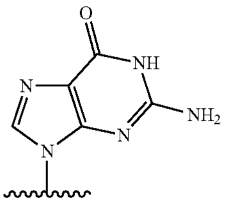 [SMILES: *n1cnc2c(=O)[nH]c(N)nc21] |
| 905 | Et | Me | Me | OH | 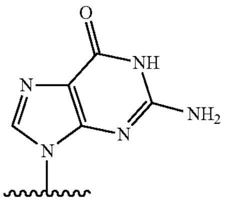 [SMILES: *n1cnc2c(=O)[nH]c(N)nc21] |
| 906 | Et | Me | Me | F | 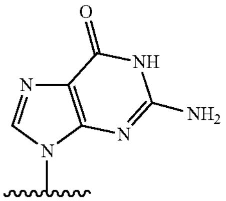 [SMILES: *n1cnc2c(=O)[nH]c(N)nc21] |
| 907 | Et | F | F | OH | 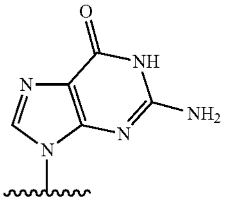 [SMILES: *n1cnc2c(=O)[nH]c(N)nc21] |
| 908 | Et | F | F | F | 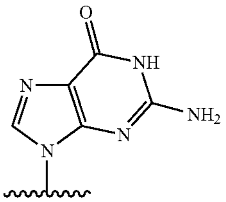 [SMILES: *n1cnc2c(=O)[nH]c(N)nc21] |
| 909 | Et | H | H | OH | 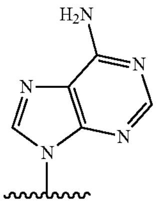 [SMILES: *n1cnc2c(N)ncnc21] |
TABLE 5-continued
(VII-1)
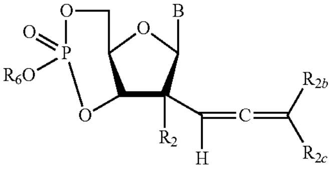
| Compound # | $R_6$ | $R_{2b}$ | $R_{2c}$ | $R_2$ | B |
|---|---|---|---|---|---|
| 910 | Et | H | H | F | 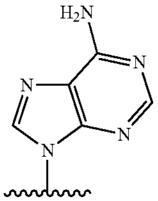 [SMILES: *n1cnc2c(N)ncnc21] |
| 911 | Et | Me | Me | OH | 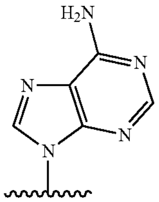 [SMILES: *n1cnc2c(N)ncnc21] |
| 912 | Et | Me | Me | F | 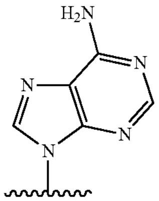 [SMILES: *n1cnc2c(N)ncnc21] |
| 913 | Et | F | F | OH | 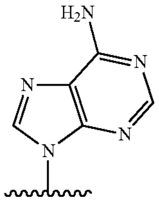 [SMILES: *n1cnc2c(N)ncnc21] |
| 914 | Et | F | F | F | 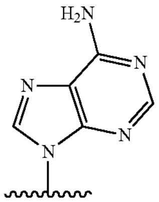 [SMILES: *n1cnc2c(N)ncnc21] |
| 915 | Et | H | H | OH | 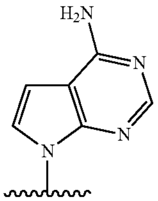 [SMILES: *n1ccc2c(N)ncnc21] |

TABLE 5-continued (VII-1)

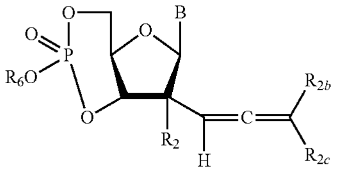

| Compound # | $R_6$ | $R_{2b}$ | $R_{2c}$ | $R_2$ | B |
|---|---|---|---|---|---|
| 916 | Et | H | H | F | 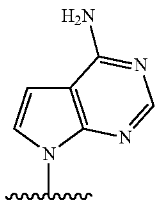 [SMILES: *n1ccc2c(N)ncnc21] |
| 917 | Et | Me | Me | OH | 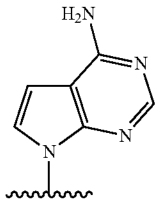 [SMILES: *n1ccc2c(N)ncnc21] |
| 918 | Et | Me | Me | F | 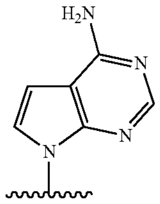 [SMILES: *n1ccc2c(N)ncnc21] |
| 919 | Et | F | F | OH | 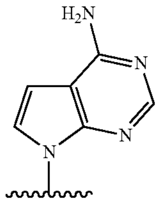 [SMILES: *n1ccc2c(N)ncnc21] |

TABLE 5-continued (VII-1)

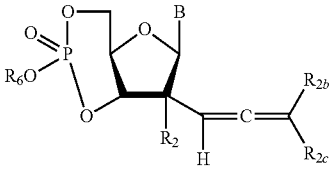

| Compound # | $R_6$ | $R_{2b}$ | $R_{2c}$ | $R_2$ | B |
|---|---|---|---|---|---|
| 920 | Et | F | F | F | 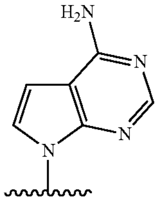 |

or a pharmaceutically acceptable salt thereof.

9. A pharmaceutical composition comprising a compound according to claim 1 or a pharmaceutically acceptable salt or ester thereof, in combination with a pharmaceutically acceptable carrier or excipient.

10. A method of treating a hepatitis C virus infection in a subject, comprising administering to the subject a therapeutically effective amount of the compound of claim 1.

11. A method of inhibiting the replication of hepatitis C virus, the method comprising contacting said virus with an effective amount of the compound of claim 1.

12. The method of claim 10 further comprising administering concurrently an additional anti-hepatitis C virus agent.

13. The method of claim 12, wherein said additional anti-hepatitis C virus agent is selected from the group consisting of α-interferon, β-interferon, ribavarin, and adamantine.

14. The method of claim 12, wherein said additional anti-hepatitis C virus agent is an inhibitor of hepatitis C virus helicase, polymerase, metalloprotease, or internal ribosome entry site.

15. The pharmaceutical composition of claim 9, further comprising another anti-hepatitis C virus agent.

16. The pharmaceutical composition of claim 9, further comprising an agent selected from the group consisting of interferon, ribavirin, amantadine, another hepatitis C virus protease inhibitor, an hepatitis C virus polymerase inhibitor, an hepatitis C virus helicase inhibitor, or an internal ribosome entry site inhibitor.

17. The pharmaceutical composition of claim 9, further comprising pegylated interferon.

18. The pharmaceutical composition of claim 9, further comprising another anti-viral, anti-bacterial, anti-fungal or anti-cancer agent, or an immune modulator.

19. The pharmaceutical composition of claim 9, further comprising a cytochrome P450 monooxygenase inhibitor or a pharmaceutically acceptable salt thereof.

20. The pharmaceutical composition of claim 19, wherein the cytochrome P450 mooxygenase inhibitor is ritonavir.

21. A method of treating a hepatitis C viral infection in a subject in need thereof comprising administering to the subject a cytochrome P450 monooxygenase inhibitor or a pharmaceutically acceptable salt thereof and a compound as set forth in claim 1 or a pharmaceutically acceptable salt thereof.

* * * * *